US012570671B2

(12) United States Patent
Degnan et al.

(10) Patent No.: US 12,570,671 B2
(45) **Date of Patent: *Mar. 10, 2026**

(54) SUBSTITUTED OXOISOINDOLINE COMPOUNDS FOR THE TREATMENT OF CANCER

(71) Applicant: BRISTOL-MYERS SQUIBB COMPANY, Princeton, NJ (US)

(72) Inventors: Andrew P. Degnan, Jamison, PA (US); Godwin Kwame Kumi, Morrisville, PA (US); Andrew J. Tebben, Morrisville, PA (US); Audris Huang, New Hope, PA (US); Peter Kinam Park, New York, NY (US); Donna M. Bilder, Lambertville, NJ (US); Emily Charlotte Cherney, Newtown, PA (US); Ashok Vinayak Purandare, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 658 days.

This patent is subject to a terminal disclaimer.

(21) Appl. No.: 17/913,206

(22) PCT Filed: Mar. 22, 2021

(86) PCT No.: PCT/US2021/023382

§ 371 (c)(1),
(2) Date: Sep. 21, 2022

(87) PCT Pub. No.: WO2021/194914

PCT Pub. Date: Sep. 30, 2021

(65) Prior Publication Data

US 2023/0322803 A1 Oct. 12, 2023

Related U.S. Application Data

(60) Provisional application No. 62/993,144, filed on Mar. 23, 2020.

(51) Int. Cl.

*C07D 498/04* (2006.01)
*C07D 401/14* (2006.01)
*C07D 471/04* (2006.01)

(52) U.S. Cl.

CPC ......... *C07D 498/04* (2013.01); *C07D 401/14* (2013.01); *C07D 471/04* (2013.01)

(58) Field of Classification Search

CPC ............................ C07D 498/04; C07D 401/14

See application file for complete search history.

(56) References Cited

U.S. PATENT DOCUMENTS 9,523,126 B2 12/2016 Drake et al.
10,040,804 B2 8/2018 Chan et al.
10,669,260 B2 6/2020 Chan et al.
2018/0015087 A1 1/2018 Liu et al.
2018/0099940 A1 4/2018 Crew et al.
2018/0125821 A1 5/2018 Crew et al.
2019/0017998 A1 1/2019 Cathers et al.
2020/0016143 A1 1/2020 Beckwith et al.
2020/0017461 A1 1/2020 Adcock et al.
2020/0148663 A1 5/2020 Chan et al.
2021/0147383 A1* 5/2021 Degnan ................ C07D 413/14

FOREIGN PATENT DOCUMENTS

CN 104230787 A 12/2014
JP 2011012014 A2 1/2011
WO 199803502 A1 1/1998
WO 2002059106 A1 8/2002
WO 2003014315 A2 2/2003
WO 2015107196 A1 7/2015
WO 2016197032 A1 12/2016
WO 2017046036 A1 3/2017
WO 2017161119 A1 9/2017
WO 2017176957 A1 10/2017
WO 2017185034 A1 10/2017
WO 2017197051 A1 11/2017

(Continued)

OTHER PUBLICATIONS

International Preliminary Report on Patentability for PCT Application PCT/US2021/023382, mailed Sep. 22, 2022.

Kronke et al., "Lenalidomide Causes Selective Degradaton of IKZF1 and IKZF3 in Multiple Myeloma Cells", Science 343 301-305 (2014).

Lu et al, "The Myeloma Drug Lenalidomide Promotes Cereblon-Dependent Destruction of Ikaros Proteins", Science 343 305-309 (2014).

(Continued)

*Primary Examiner* — Sarah Pihonak
*Assistant Examiner* — Mikhail O'Donnel Robinson
(74) *Attorney, Agent, or Firm* — Gary Greenblatt

(57) ABSTRACT

Disclosed are compounds of Formula (I) or a salt thereof, wherein Ring A is a carbon-linked ring; and Ring A, $R_1$, and n are defined herein. Also disclosed are methods of using such compounds to inhibit Helios protein, and pharmaceutical compositions comprising such compounds. These compounds are useful in the treatment of viral infections and proliferative disorders, such as cancer.

(I)

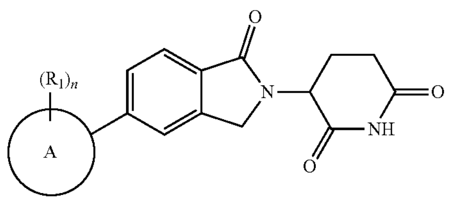

18 Claims, No Drawings

Specification includes a Sequence Listing.

(56) References Cited

FOREIGN PATENT DOCUMENTS

| | | | |
|---|---|---|---|
| WO | 2017197055 | A1 | 11/2017 |
| WO | 2017197056 | A1 | 11/2017 |
| WO | 2018052945 | A1 | 3/2018 |
| WO | 2018102725 | A1 | 6/2018 |
| WO | 2018118598 | A1 | 6/2018 |
| WO | 2018119441 | A9 | 6/2018 |
| WO | 2018119448 | A1 | 6/2018 |
| WO | 2019038717 | A1 | 2/2019 |
| WO | 2019079569 | A1 | 4/2019 |
| WO | 2019148055 | A9 | 8/2019 |
| WO | 2019191112 | A1 | 10/2019 |
| WO | 2019241271 | A1 | 12/2019 |
| WO | 2020012334 | A1 | 1/2020 |
| WO | 2020012337 | A1 | 1/2020 |
| WO | 2020128972 | A1 | 6/2020 |
| WO | 2021101919 | A1 | 5/2021 |

OTHER PUBLICATIONS

Petzold et al., Structural basis of lenalidomide-induced CK1α degradation by the CRL4CRBN ubiquitin ligase, Nature 532, 127-130 (2016).

Stewart et al., "New thalidomide analogues derived through Sonogashira or Suzuki reactions and their TNF expression inhibition profiles" Bioorganic & Medicinal Chemistry, 18(2) 650-662 (2010).

Stewart et al., "Synthesis and TNF expression inhibitory properties of new thalidomide analogues derived via Heck cross coupling" Bioorganic & Medicinal Chemistry Letters, 17 5819-5624 (2007).

Thornton et al., "CD4+CD25+ Immunoregulatory T Cells Suppress Polyclonal T Cell Activation In Vitro by Inhibiting Interleukin 2 Production" J Experimental Medicine 188(2) 287-296 (1998).

Yu et al., "Intratumor depletion of CD4+ cells unmasks tumor immunogenicity leading to the rejection of late-stage tumors" J. Experimental Medicine, vol. 201(5) 779-791 (2005).

* cited by examiner

SEQUENCE LISTING

<160> NUMBER OF SEQ ID NOS: 8

<210> SEQ ID NO 1
<211> LENGTH: 526
<212> TYPE: PRT
<213> ORGANISM: Homo sapiens

<400> SEQUENCE: 1

Met Glu Thr Glu Ala Ile Asp Gly Tyr Ile Thr Cys Asp Asn Glu Leu
1 5 10 15

Ser Pro Glu Arg Glu His Ser Asn Met Ala Ile Asp Leu Thr Ser Ser
20 25 30

Thr Pro Asn Gly Gln His Ala Ser Pro Ser His Met Thr Ser Thr Asn
35 40 45

Ser Val Lys Leu Glu Met Gln Ser Asp Glu Glu Cys Asp Arg Lys Pro
50 55 60

Leu Ser Arg Glu Asp Glu Ile Arg Gly His Asp Glu Gly Ser Ser Leu
65 70 75 80

Glu Glu Pro Leu Ile Glu Ser Ser Glu Val Ala Asp Asn Arg Lys Val
85 90 95

Gln Glu Leu Gln Gly Glu Gly Gly Ile Arg Leu Pro Asn Gly Lys Leu
100 105 110

Lys Cys Asp Val Cys Gly Met Val Cys Ile Gly Pro Asn Val Leu Met
115 120 125

Val His Lys Arg Ser His Thr Gly Glu Arg Pro Phe His Cys Asn Gln
130 135 140

Cys Gly Ala Ser Phe Thr Gln Lys Gly Asn Leu Leu Arg His Ile Lys
145 150 155 160

Leu His Ser Gly Glu Lys Pro Phe Lys Cys Pro Phe Cys Ser Tyr Ala
165 170 175

Cys Arg Arg Arg Asp Ala Leu Thr Gly His Leu Arg Thr His Ser Val
180 185 190

Gly Lys Pro His Lys Cys Asn Tyr Cys Gly Arg Ser Tyr Lys Gln Arg
195 200 205

Ser Ser Leu Glu Glu His Lys Glu Arg Cys His Asn Tyr Leu Gln Asn
210 215 220

Val Ser Met Glu Ala Ala Gly Gln Val Met Ser His His Val Pro Pro
225 230 235 240

Met Glu Asp Cys Lys Glu Gln Glu Pro Ile Met Asp Asn Asn Ile Ser
245 250 255

Leu Val Pro Phe Glu Arg Pro Ala Val Ile Glu Lys Leu Thr Gly Asn
260 265 270

```
Met Gly Lys Arg Lys Ser Ser Thr Pro Gln Lys Phe Val Gly Glu Lys
        275                 280                 285

Leu Met Arg Phe Ser Tyr Pro Asp Ile His Phe Asp Met Asn Leu Thr
    290                 295                 300

Tyr Glu Lys Glu Ala Glu Leu Met Gln Ser His Met Met Asp Gln Ala
305                 310                 315                 320

Ile Asn Asn Ala Ile Thr Tyr Leu Gly Ala Glu Ala Leu His Pro Leu
                325                 330                 335

Met Gln His Pro Pro Ser Thr Ile Ala Glu Val Ala Pro Val Ile Ser
            340                 345                 350

Ser Ala Tyr Ser Gln Val Tyr His Pro Asn Arg Ile Glu Arg Pro Ile
        355                 360                 365

Ser Arg Glu Thr Ala Asp Ser His Glu Asn Asn Met Asp Gly Pro Ile
    370                 375                 380

Ser Leu Ile Arg Pro Lys Ser Arg Pro Gln Glu Arg Glu Ala Ser Pro
385                 390                 395                 400

Ser Asn Ser Cys Leu Asp Ser Thr Asp Ser Glu Ser Ser His Asp Asp
                405                 410                 415

His Gln Ser Tyr Gln Gly His Pro Ala Leu Asn Pro Lys Arg Lys Gln
            420                 425                 430

Ser Pro Ala Tyr Met Lys Glu Asp Val Lys Ala Leu Asp Thr Thr Lys
        435                 440                 445

Ala Pro Lys Gly Ser Leu Lys Asp Ile Tyr Lys Val Phe Asn Gly Glu
    450                 455                 460

Gly Glu Gln Ile Arg Ala Phe Lys Cys Glu His Cys Arg Val Leu Phe
465                 470                 475                 480

Leu Asp His Val Met Tyr Thr Ile His Met Gly Cys His Gly Tyr Arg
                485                 490                 495

Asp Pro Leu Glu Cys Asn Ile Cys Gly Tyr Arg Ser Gln Asp Arg Tyr
            500                 505                 510

Glu Phe Ser Ser His Ile Val Arg Gly Glu His Thr Phe His
        515                 520                 525


<210> SEQ ID NO 2
<211> LENGTH: 500
<212> TYPE: PRT
<213> ORGANISM: Homo sapiens

<400> SEQUENCE: 2

Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Glu Arg
            100                 105                 110

Pro Phe His Cys Asn Gln Cys Gly Ala Ser Phe Thr Gln Lys Gly Asn
```

```
        115                 120                 125

Leu Leu Arg His Ile Lys Leu His Ser Gly Glu Lys Pro Phe Lys Cys
    130                 135                 140

Pro Phe Cys Ser Tyr Ala Cys Arg Arg Arg Asp Ala Leu Thr Gly His
145                 150                 155                 160

Leu Arg Thr His Ser Val Gly Lys Pro His Lys Cys Asn Tyr Cys Gly
                165                 170                 175

Arg Ser Tyr Lys Gln Arg Ser Ser Leu Glu Glu His Lys Glu Arg Cys
            180                 185                 190

His Asn Tyr Leu Gln Asn Val Ser Met Glu Ala Ala Gly Gln Val Met
        195                 200                 205

Ser His His Val Pro Pro Met Glu Asp Cys Lys Glu Gln Glu Pro Ile
    210                 215                 220

Met Asp Asn Asn Ile Ser Leu Val Pro Phe Glu Arg Pro Ala Val Ile
225                 230                 235                 240

Glu Lys Leu Thr Gly Asn Met Gly Lys Arg Lys Ser Ser Thr Pro Gln
                245                 250                 255

Lys Phe Val Gly Glu Lys Leu Met Arg Phe Ser Tyr Pro Asp Ile His
            260                 265                 270

Phe Asp Met Asn Leu Thr Tyr Glu Lys Glu Ala Glu Leu Met Gln Ser
        275                 280                 285

His Met Met Asp Gln Ala Ile Asn Asn Ala Ile Thr Tyr Leu Gly Ala
    290                 295                 300

Glu Ala Leu His Pro Leu Met Gln His Pro Pro Ser Thr Ile Ala Glu
305                 310                 315                 320

Val Ala Pro Val Ile Ser Ser Ala Tyr Ser Gln Val Tyr His Pro Asn
                325                 330                 335

Arg Ile Glu Arg Pro Ile Ser Arg Glu Thr Ala Asp Ser His Glu Asn
            340                 345                 350

Asn Met Asp Gly Pro Ile Ser Leu Ile Arg Pro Lys Ser Arg Pro Gln
        355                 360                 365

Glu Arg Glu Ala Ser Pro Ser Asn Ser Cys Leu Asp Ser Thr Asp Ser
    370                 375                 380

Glu Ser Ser His Asp Asp His Gln Ser Tyr Gln Gly His Pro Ala Leu
385                 390                 395                 400

Asn Pro Lys Arg Lys Gln Ser Pro Ala Tyr Met Lys Glu Asp Val Lys
                405                 410                 415

Ala Leu Asp Thr Thr Lys Ala Pro Lys Gly Ser Leu Lys Asp Ile Tyr
            420                 425                 430

Lys Val Phe Asn Gly Glu Gly Glu Gln Ile Arg Ala Phe Lys Cys Glu
        435                 440                 445

His Cys Arg Val Leu Phe Leu Asp His Val Met Tyr Thr Ile His Met
    450                 455                 460

Gly Cys His Gly Tyr Arg Asp Pro Leu Glu Cys Asn Ile Cys Gly Tyr
465                 470                 475                 480

Arg Ser Gln Asp Arg Tyr Glu Phe Ser Ser His Ile Val Arg Gly Glu
                485                 490                 495

His Thr Phe His
            500


<210> SEQ ID NO 3
<211> LENGTH: 452
<212> TYPE: PRT
<213> ORGANISM: Homo sapiens
```

<400> SEQUENCE: 3

```
Met Glu Thr Glu Ala Ile Asp Gly Tyr Ile Thr Cys Asp Asn Glu Leu
1               5                   10                  15

Ser Pro Glu Arg Glu His Ser Asn Met Ala Ile Asp Leu Thr Ser Ser
            20                  25                  30

Thr Pro Asn Gly Gln His Ala Ser Pro Ser His Met Thr Ser Thr Asn
        35                  40                  45

Ser Val Lys Leu Glu Met Gln Ser Asp Glu Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Glu Arg
            100                 105                 110

Pro Phe His Cys Asn Gln Cys Gly Ala Ser Phe Thr Gln Lys Gly Asn
        115                 120                 125

Leu Leu Arg His Ile Lys Leu His Ser Gly Glu Lys Pro Phe Lys Cys
    130                 135                 140

Pro Phe Cys Ser Tyr Ala Cys Arg Arg Arg Asp Ala Leu Thr Gly His
145                 150                 155                 160

Leu Arg Thr His Ser Val Gly Lys Pro His Lys Cys Asn Tyr Cys Gly
                165                 170                 175

Arg Ser Tyr Lys Gln Arg Ser Ser Leu Glu Glu His Lys Glu Arg Cys
            180                 185                 190

His Asn Tyr Leu Gln Asn Val Ser Met Glu Ala Ala Gly Gln Val Met
        195                 200                 205

Ser His His Gly Glu Lys Leu Met Arg Phe Ser Tyr Pro Asp Ile His
    210                 215                 220

Phe Asp Met Asn Leu Thr Tyr Glu Lys Glu Ala Glu Leu Met Gln Ser
225                 230                 235                 240

His Met Met Asp Gln Ala Ile Asn Asn Ala Ile Thr Tyr Leu Gly Ala
                245                 250                 255

Glu Ala Leu His Pro Leu Met Gln His Pro Pro Ser Thr Ile Ala Glu
            260                 265                 270

Val Ala Pro Val Ile Ser Ser Ala Tyr Ser Gln Val Tyr His Pro Asn
        275                 280                 285

Arg Ile Glu Arg Pro Ile Ser Arg Glu Thr Ala Asp Ser His Glu Asn
    290                 295                 300

Asn Met Asp Gly Pro Ile Ser Leu Ile Arg Pro Lys Ser Arg Pro Gln
305                 310                 315                 320

Glu Arg Glu Ala Ser Pro Ser Asn Ser Cys Leu Asp Ser Thr Asp Ser
                325                 330                 335

Glu Ser Ser His Asp Asp His Gln Ser Tyr Gln Gly His Pro Ala Leu
            340                 345                 350

Asn Pro Lys Arg Lys Gln Ser Pro Ala Tyr Met Lys Glu Asp Val Lys
        355                 360                 365

Ala Leu Asp Thr Thr Lys Ala Pro Lys Gly Ser Leu Lys Asp Ile Tyr
    370                 375                 380

Lys Val Phe Asn Gly Glu Gly Glu Gln Ile Arg Ala Phe Lys Cys Glu
385                 390                 395                 400

His Cys Arg Val Leu Phe Leu Asp His Val Met Tyr Thr Ile His Met
```

405 410 415

Gly Cys His Gly Tyr Arg Asp Pro Leu Glu Cys Asn Ile Cys Gly Tyr
420 425 430

Arg Ser Gln Asp Arg Tyr Glu Phe Ser Ser His Ile Val Arg Gly Glu
435 440 445

His Thr Phe His
450

<210> SEQ ID NO 4
<211> LENGTH: 239
<212> TYPE: PRT
<213> ORGANISM: Homo sapiens

<400> SEQUENCE: 4

Met Glu Thr Glu Ala Ile Asp Gly Tyr Ile Thr Cys Asp Asn Glu Leu
1 5 10 15

Ser Pro Glu Arg Glu His Ser Asn Met Ala Ile Asp Leu Thr Ser Ser
20 25 30

Thr Pro Asn Gly Gln His Ala Ser Pro Ser His Met Thr Ser Thr Asn
35 40 45

Ser Val Lys Leu Glu Met Gln Ser Asp Glu Glu Cys Asp Arg Lys Pro
50 55 60

Leu Ser Arg Glu Asp Glu Ile Arg Gly His Asp Glu Gly Ser Ser Leu
65 70 75 80

Glu Glu Pro Leu Ile Glu Ser Ser Glu Val Ala Asp Asn Arg Lys Val
85 90 95

Gln Glu Leu Gln Gly Glu Gly Gly Ile Arg Leu Pro Asn Gly Lys Leu
100 105 110

Lys Cys Asp Val Cys Gly Met Val Cys Ile Gly Pro Asn Val Leu Met
115 120 125

Val His Lys Arg Ser His Thr Gly Glu Arg Pro Phe His Cys Asn Gln
130 135 140

Cys Gly Ala Ser Phe Thr Gln Lys Gly Asn Leu Leu Arg His Ile Lys
145 150 155 160

Leu His Ser Gly Glu Lys Pro Phe Lys Cys Pro Phe Cys Ser Tyr Ala
165 170 175

Cys Arg Arg Arg Asp Ala Leu Thr Gly His Leu Arg Thr His Ser Val
180 185 190

Gly Lys Pro His Lys Cys Asn Tyr Cys Gly Arg Ser Tyr Lys Gln Arg
195 200 205

Ser Ser Leu Glu Glu His Lys Glu Arg Cys His Asn Tyr Leu Gln Asn
210 215 220

Val Ser Met Glu Ala Ala Gly Gln Val Met Ser His His Asp Ser
225 230 235

<210> SEQ ID NO 5
<211> LENGTH: 454
<212> TYPE: PRT
<213> ORGANISM: Homo sapiens

<400> SEQUENCE: 5

Met Glu Thr Glu Ala Ile Asp Gly Tyr Ile Thr Cys Asp Asn Glu Leu
1 5 10 15

Ser Pro Glu Arg Glu His Ser Asn Met Ala Ile Asp Leu Thr Ser Ser
20 25 30

Thr Pro Asn Gly Gln His Ala Ser Pro Ser His Met Thr Ser Thr Asn

```
        35                  40                  45

Ser Val Lys Leu Glu Met Gln Ser Asp Glu Glu Cys Asp Arg Lys Pro
    50                  55                  60

Leu Ser Arg Glu Asp Glu Ile Arg Gly His Asp Glu Gly Ser Ser Leu
65                  70                  75                  80

Glu Glu Pro Leu Ile Glu Ser Ser Glu Val Ala Asp Asn Arg Lys Val
                85                  90                  95

Gln Glu Leu Gln Gly Glu Gly Gly Ile Arg Leu Pro Asn Gly Glu Arg
            100                 105                 110

Pro Phe His Cys Asn Gln Cys Gly Ala Ser Phe Thr Gln Lys Gly Asn
        115                 120                 125

Leu Leu Arg His Ile Lys Leu His Ser Gly Glu Lys Pro Phe Lys Cys
    130                 135                 140

Pro Phe Cys Ser Tyr Ala Cys Arg Arg Arg Asp Ala Leu Thr Gly His
145                 150                 155                 160

Leu Arg Thr His Ser Val Pro Pro Met Glu Asp Cys Lys Glu Gln Glu
                165                 170                 175

Pro Ile Met Asp Asn Asn Ile Ser Leu Val Pro Phe Glu Arg Pro Ala
            180                 185                 190

Val Ile Glu Lys Leu Thr Gly Asn Met Gly Lys Arg Lys Ser Ser Thr
        195                 200                 205

Pro Gln Lys Phe Val Gly Glu Lys Leu Met Arg Phe Ser Tyr Pro Asp
    210                 215                 220

Ile His Phe Asp Met Asn Leu Thr Tyr Glu Lys Glu Ala Glu Leu Met
225                 230                 235                 240

Gln Ser His Met Met Asp Gln Ala Ile Asn Asn Ala Ile Thr Tyr Leu
                245                 250                 255

Gly Ala Glu Ala Leu His Pro Leu Met Gln His Pro Pro Ser Thr Ile
            260                 265                 270

Ala Glu Val Ala Pro Val Ile Ser Ser Ala Tyr Ser Gln Val Tyr His
        275                 280                 285

Pro Asn Arg Ile Glu Arg Pro Ile Ser Arg Glu Thr Ala Asp Ser His
    290                 295                 300

Glu Asn Asn Met Asp Gly Pro Ile Ser Leu Ile Arg Pro Lys Ser Arg
305                 310                 315                 320

Pro Gln Glu Arg Glu Ala Ser Pro Ser Asn Ser Cys Leu Asp Ser Thr
                325                 330                 335

Asp Ser Glu Ser Ser His Asp Asp His Gln Ser Tyr Gln Gly His Pro
            340                 345                 350

Ala Leu Asn Pro Lys Arg Lys Gln Ser Pro Ala Tyr Met Lys Glu Asp
        355                 360                 365

Val Lys Ala Leu Asp Thr Thr Lys Ala Pro Lys Gly Ser Leu Lys Asp
    370                 375                 380

Ile Tyr Lys Val Phe Asn Gly Glu Gly Glu Gln Ile Arg Ala Phe Lys
385                 390                 395                 400

Cys Glu His Cys Arg Val Leu Phe Leu Asp His Val Met Tyr Thr Ile
                405                 410                 415

His Met Gly Cys His Gly Tyr Arg Asp Pro Leu Glu Cys Asn Ile Cys
            420                 425                 430

Gly Tyr Arg Ser Gln Asp Arg Tyr Glu Phe Ser Ser His Ile Val Arg
        435                 440                 445

Gly Glu His Thr Phe His
    450
```

-continued

<210> SEQ ID NO 6
<211> LENGTH: 23
<212> TYPE: PRT
<213> ORGANISM: Homo sapiens

<400> SEQUENCE: 6

Phe His Cys Asn Gln Cys Gly Ala Ser Phe Thr Gln Lys Gly Asn Leu
1 5 10 15

Leu Arg His Ile Lys Leu His
20

<210> SEQ ID NO 7
<211> LENGTH: 585
<212> TYPE: PRT
<213> ORGANISM: Homo sapiens

<400> SEQUENCE: 7

Met His Thr Pro Pro Ala Leu Pro Arg Arg Phe Gln Gly Gly Gly Arg
1 5 10 15

Val Arg Thr Pro Gly Ser His Arg Gln Gly Lys Asp Asn Leu Glu Arg
20 25 30

Asp Pro Ser Gly Gly Cys Val Pro Asp Phe Leu Pro Gln Ala Gln Asp
35 40 45

Ser Asn His Phe Ile Met Glu Ser Leu Phe Cys Glu Ser Ser Gly Asp
50 55 60

Ser Ser Leu Glu Lys Glu Phe Leu Gly Ala Pro Val Gly Pro Ser Val
65 70 75 80

Ser Thr Pro Asn Ser Gln His Ser Ser Pro Ser Arg Ser Leu Ser Ala
85 90 95

Asn Ser Ile Lys Val Glu Met Tyr Ser Asp Glu Glu Ser Ser Arg Leu
100 105 110

Leu Gly Pro Asp Glu Arg Leu Leu Glu Lys Asp Asp Ser Val Ile Val
115 120 125

Glu Asp Ser Leu Ser Glu Pro Leu Gly Tyr Cys Asp Gly Ser Gly Pro
130 135 140

Glu Pro His Ser Pro Gly Gly Ile Arg Leu Pro Asn Gly Lys Leu Lys
145 150 155 160

Cys Asp Val Cys Gly Met Val Cys Ile Gly Pro Asn Val Leu Met Val
165 170 175

His Lys Arg Ser His Thr Gly Glu Arg Pro Phe His Cys Asn Gln Cys
180 185 190

Gly Ala Ser Phe Thr Gln Lys Gly Asn Leu Leu Arg His Ile Lys Leu
195 200 205

His Ser Gly Glu Lys Pro Phe Lys Cys Pro Phe Cys Asn Tyr Ala Cys
210 215 220

Arg Arg Arg Asp Ala Leu Thr Gly His Leu Arg Thr His Ser Val Ser
225 230 235 240

Ser Pro Thr Val Gly Lys Pro Tyr Lys Cys Asn Tyr Cys Gly Arg Ser
245 250 255

Tyr Lys Gln Gln Ser Thr Leu Glu Glu His Lys Glu Arg Cys His Asn
260 265 270

Tyr Leu Gln Ser Leu Ser Thr Glu Ala Gln Ala Leu Ala Gly Gln Pro
275 280 285

Gly Asp Glu Ile Arg Asp Leu Glu Met Val Pro Asp Ser Met Leu His
290 295 300

Ser Ser Ser Glu Arg Pro Thr Phe Ile Asp Arg Leu Ala Asn Ser Leu
305 310 315 320

Thr Lys Arg Lys Arg Ser Thr Pro Gln Lys Phe Val Gly Glu Lys Gln
325 330 335

Met Arg Phe Ser Leu Ser Asp Leu Pro Tyr Asp Val Asn Ser Gly Gly
340 345 350

Tyr Glu Lys Asp Val Glu Leu Val Ala His His Ser Leu Glu Pro Gly
355 360 365

Phe Gly Ser Ser Leu Ala Phe Val Gly Ala Glu His Leu Arg Pro Leu
370 375 380

Arg Leu Pro Pro Thr Asn Cys Ile Ser Glu Leu Thr Pro Val Ile Ser
385 390 395 400

Ser Val Tyr Thr Gln Met Gln Pro Leu Pro Gly Arg Leu Glu Leu Pro
405 410 415

Gly Ser Arg Glu Ala Gly Glu Gly Pro Glu Asp Leu Ala Asp Gly Gly
420 425 430

Pro Leu Leu Tyr Arg Pro Arg Gly Pro Leu Thr Asp Pro Gly Ala Ser
435 440 445

Pro Ser Asn Gly Cys Gln Asp Ser Thr Asp Thr Glu Ser Asn His Glu
450 455 460

Asp Arg Val Ala Gly Val Val Ser Leu Pro Gln Gly Pro Pro Pro Gln
465 470 475 480

Pro Pro Pro Thr Ile Val Val Gly Arg His Ser Pro Ala Tyr Ala Lys
485 490 495

Glu Asp Pro Lys Pro Gln Glu Gly Leu Leu Arg Gly Thr Pro Gly Pro
500 505 510

Ser Lys Glu Val Leu Arg Val Val Gly Glu Ser Gly Glu Pro Val Lys
515 520 525

Ala Phe Lys Cys Glu His Cys Arg Ile Leu Phe Leu Asp His Val Met
530 535 540

Phe Thr Ile His Met Gly Cys His Gly Phe Arg Asp Pro Phe Glu Cys
545 550 555 560

Asn Ile Cys Gly Tyr His Ser Gln Asp Arg Tyr Glu Phe Ser Ser His
565 570 575

Ile Val Arg Gly Glu His Lys Val Gly
580 585

<210> SEQ ID NO 8
<211> LENGTH: 544
<212> TYPE: PRT
<213> ORGANISM: Homo sapiens

<400> SEQUENCE: 8

Met Asp Ser Arg Tyr Leu Gln Leu Gln Leu Tyr Leu Pro Ser Cys Ser
1 5 10 15

Leu Leu Gln Gly Ser Gly Asp Ser Ser Leu Glu Lys Glu Phe Leu Gly
20 25 30

Ala Pro Val Gly Pro Ser Val Ser Thr Pro Asn Ser Gln His Ser Ser
35 40 45

Pro Ser Arg Ser Leu Ser Ala Asn Ser Ile Lys Val Glu Met Tyr Ser
50 55 60

Asp Glu Glu Ser Ser Arg Leu Leu Gly Pro Asp Glu Arg Leu Leu Glu
65 70 75 80

Lys Asp Asp Ser Val Ile Val Glu Asp Ser Leu Ser Glu Pro Leu Gly

-continued

```
                85                  90                  95

Tyr Cys Asp Gly Ser Gly Pro Glu Pro His Ser Pro Gly Gly Ile Arg
            100                 105                 110

Leu Pro Asn Gly Lys Leu Lys Cys Asp Val Cys Gly Met Val Cys Ile
        115                 120                 125

Gly Pro Asn Val Leu Met Val His Lys Arg Ser His Thr Gly Glu Arg
    130                 135                 140

Pro Phe His Cys Asn Gln Cys Gly Ala Ser Phe Thr Gln Lys Gly Asn
145                 150                 155                 160

Leu Leu Arg His Ile Lys Leu His Ser Gly Glu Lys Pro Phe Lys Cys
                165                 170                 175

Pro Phe Cys Asn Tyr Ala Cys Arg Arg Arg Asp Ala Leu Thr Gly His
            180                 185                 190

Leu Arg Thr His Ser Val Ser Ser Pro Thr Val Gly Lys Pro Tyr Lys
        195                 200                 205

Cys Asn Tyr Cys Gly Arg Ser Tyr Lys Gln Gln Ser Thr Leu Glu Glu
    210                 215                 220

His Lys Glu Arg Cys His Asn Tyr Leu Gln Ser Leu Ser Thr Glu Ala
225                 230                 235                 240

Gln Ala Leu Ala Gly Gln Pro Gly Asp Glu Ile Arg Asp Leu Glu Met
                245                 250                 255

Val Pro Asp Ser Met Leu His Ser Ser Ser Glu Arg Pro Thr Phe Ile
            260                 265                 270

Asp Arg Leu Ala Asn Ser Leu Thr Lys Arg Lys Arg Ser Thr Pro Gln
        275                 280                 285

Lys Phe Val Gly Glu Lys Gln Met Arg Phe Ser Leu Ser Asp Leu Pro
    290                 295                 300

Tyr Asp Val Asn Ser Gly Gly Tyr Glu Lys Asp Val Glu Leu Val Ala
305                 310                 315                 320

His His Ser Leu Glu Pro Gly Phe Gly Ser Ser Leu Ala Phe Val Gly
                325                 330                 335

Ala Glu His Leu Arg Pro Leu Arg Leu Pro Pro Thr Asn Cys Ile Ser
            340                 345                 350

Glu Leu Thr Pro Val Ile Ser Ser Val Tyr Thr Gln Met Gln Pro Leu
        355                 360                 365

Pro Gly Arg Leu Glu Leu Pro Gly Ser Arg Glu Ala Gly Glu Gly Pro
    370                 375                 380

Glu Asp Leu Ala Asp Gly Gly Pro Leu Leu Tyr Arg Pro Arg Gly Pro
385                 390                 395                 400

Leu Thr Asp Pro Gly Ala Ser Pro Ser Asn Gly Cys Gln Asp Ser Thr
                405                 410                 415

Asp Thr Glu Ser Asn His Glu Asp Arg Val Ala Gly Val Val Ser Leu
            420                 425                 430

Pro Gln Gly Pro Pro Pro Gln Pro Pro Pro Thr Ile Val Val Gly Arg
        435                 440                 445

His Ser Pro Ala Tyr Ala Lys Glu Asp Pro Lys Pro Gln Glu Gly Leu
    450                 455                 460

Leu Arg Gly Thr Pro Gly Pro Ser Lys Glu Val Leu Arg Val Val Gly
465                 470                 475                 480

Glu Ser Gly Glu Pro Val Lys Ala Phe Lys Cys Glu His Cys Arg Ile
                485                 490                 495

Leu Phe Leu Asp His Val Met Phe Thr Ile His Met Gly Cys His Gly
            500                 505                 510
```

-continued
```
Phe Arg Asp Pro Phe Glu Cys Asn Ile Cys Gly Tyr His Ser Gln Asp
        515                 520                 525

Arg Tyr Glu Phe Ser Ser His Ile Val Arg Gly Glu His Lys Val Gly
    530                 535                 540
```

SUBSTITUTED OXOISOINDOLINE COMPOUNDS FOR THE TREATMENT OF CANCER

CROSS REFERENCE

This application is a national phase application under 35 U.S.C. § 371 of International Patent Application No. PCT/US2021/023382, filed Mar. 22, 2021, which claims priority to U.S. Provisional Application Serial 62/993,144, filed Mar. 23, 2020, the contents of which are specifically incorporated fully herein by reference.

DESCRIPTION

The present invention generally relates to substituted oxoisoindoline compounds that inhibit Helios protein. Provided herein are substituted oxoisoindoline compounds, compositions comprising such compounds, and methods of their use. The invention further pertains to pharmaceutical compositions comprising at least one compound according to the invention that are useful for the treatment of proliferative disorders, such as cancer, and viral infections.

BACKGROUND OF THE INVENTION

Regulatory T cells (Tregs) play an essential role in controlling self-tolerance and immune homeostasis via maintenance of inhibitory activity and anergy in the face of vigorous immune and inflammatory responses. Through the preservation of a stable, anergic and suppressive phenotype, Tregs attenuate excessive immune responses and prevent or ameliorate autoimmunity. A number of reports have documented the presence of Tregs within human tumor tissues. Studies demonstrated a clear negative correlation between the number of Tregs and T cell infiltration into the tumor and survival (Curiel et al., 2004, *Nat. Med.* 10: 942-949; Viguier et al., 2004, *J Immuno.* 1173:1444-1453; Beyer et al., 2006, *Blood* 108: 804-811; Zou et al., 2006, *Nat. Rev. Immunol.* 6: 295-307), implying a potential critical role of Tregs in preventing the development of effective anti-tumor immunity. Accumulated evidence indicates that Foxp3+CD25+ CD4+Tregs dominantly infiltrate into tumors and apparently hinder immune responses to tumor cells in rodents and humans. Once activated by a specific antigen, Tregs suppress responder T cells in an antigen-nonspecific and bystander manner in vitro (Takahashi et al., 1998, *Int Immunol.* 10:1969-80; Thornton et al., 1998, *J Exp. Med.* 188:287-96). Foxp3+CD25+CD4+Tregs are apparently capable of suppressing a wide range of antitumor immune responses involving CD4+ helper T cells, CD8+ T cells, natural killer cells, and natural killer T cells (Tanaka et al., 2017, *Cell Research* 27:109-118). Intratumoral depletion of CD25+CD4+Tregs induced regression of established tumors with a change in the cytokine milieu at tumor sites (Yu et al., 2005, *J Exp Med.* 201: 779-91). In addition, transfer of Treg-depleted CD4+ T cells markedly augmented antitumor immune responses compared with Tregs containing T-cell transfer (Antony et al., 2005, *J Immunol* 174:2591-601). Tumor-infiltrating Tregs activated by either tumor-derived self-antigens or tumor-associated antigens can similarly suppress specific antitumor immune responses. Modulation of the activities of key factors to control Treg differentiation could represent a potential therapeutic strategy for the treatment of certain diseases, including cancer and viral infections.

FoxP3+CD4 Tregs are remarkably stable. Studies are still evolving to understand the genetic mechanisms that ensure their phenotypic stability after expansion during inflammation, infection or autoimmunity. Transcription factors (TF) responsible for maintaining the stable immunosuppressive phenotype of Tregs likely contribute to this process. The Helios (IKZF2) gene, a member of the Ikaros family of TFs, differs from other Ikaros family members based on its selective expression by thymocytes undergoing negative selection, as well as by regulatory lineages of CD4 and CD8 T cells. Helios is expressed by two regulatory T-cell lineages, FoxP3+CD4+ and Ly49+CD8+ Tregs, which are essential to maintain self-tolerance (Kim et al., 2015, *Science* 350:334-339; Sebastian et al., 2016, *J Immunol* 196: 144-155). Interestingly, recent studies suggest that although Helios is largely dispensable for Treg activity in the steady state, control of the genetic program of FoxP3+ CD4 Tregs by Helios in the context of inflammation is essential to maintain a stable phenotype and potentiate suppressive function (Thornton et al., 2010, *J Immunol.* 184:3433-3441; Kim et al., 2015). Helios expression by Tregs was demonstrated to be crucial in their capability to maintain a suppressive and anergic phenotype in the face of intense inflammatory responses. Activation of the IL-2Ra-STAT5 pathway was demonstrated to be a key contributor by ensuring Treg survival and stability (Kim et al., 2015). Helios plays an indispensable role in maintaining the phenotype of FoxP3+ CD4 Tregs by exerting dominant, lymphocyte-intrinsic inhibition to prevent autoimmune disease in the presence of highly activated self-reactive T cells from scurfy mice, which have no FoxP3 fork head domain. Bone marrow (BM) chimeras reconstituted with Helios−/−/Scurfy BM but not Helios+/+/Scurfy BM cells rapidly developed autoimmunity (Kim et al., 2015). These observations indicate the critical contribution of Helios to self-reactive T cell selection, differentiation, and function.

Immune suppression exerted by Tregs can impede antitumor immune responses. A selective deficiency of Helios in FoxP3+ CD4 Tregs results in increased Treg instability and conversion of intratumoral CD4 Treg to effector T cells (Teff). Instability of intratumoral Tregs may increase the numbers of Teff cells within tumors as a combined result of Treg conversion and reduced Treg suppressive activities. In addition, defective IL-2 responses were observed in Helios-deficient intratumoral Tregs, which results in decreased numbers of activated Tregs and may also contribute to the increased intratumoral Teff activities. Interaction between tumor cells and infiltrating immune cells leads to secretion of inflammatory mediators, including TNF-α, IL-6, IL-17, IL-1, and TGF-β, and the formation of a local inflammatory environment (Kim et al., 2015).

Lineage instability of Helios-deficient Tregs is also accompanied by diminished FoxP3 expression and results in the acquisition of an effector phenotype by producing proinflammatory cytokines. Effector cell conversion of Helios-deficient Tregs within the tumor-tissue microenvironment is associated with increased expression of genes that control Teff phenotype (Yates et al., 2018, *PNAS,* 2018, 115: 2162-2167). Acquisition of an unstable phenotype by Helios deficiency only occurs within the tumor microenvironment (TME), but not in peripheral lymphoid organs (Nakagawa et al., 2016, *PNAS* 113: 6248-6253). Within the chronic inflammatory TME, Helios deficiency in Tregs could drastically alleviate the repressed genetic programs associated with T helper cell differentiation by up-regulating T helper cell associated TFs and effector cytokines. These genetic changes of Helios-deficient Tregs are most apparent in a Treg subpopulation with high affinity for self-antigens, as shown by enhanced GITR/PD-1 expression and increased responsiveness to self-antigens. Their combined effects may promote a phenotype conversion of Tregs into Teff within the TME with increased T-cell receptor (TCR) engagement and costimulatory receptor expression by Tregs, suggesting that the alterations in gene expression, as a central feature of Treg conversion, are immune milieu dependent (Yates et al., 2018).

Reduced Helios expression in FoxP3+ CD4 Tregs may allow conversion of memory Tregs into Teff cells that express self-reactive T-cell receptors with specificity for tumor antigens. An altered Treg signature might be selectively induced within the chronic inflammatory conditions of growing tumor. Helios-deficient Tregs may display a TCR repertoire skewed toward high-affinity against self-peptides/MHC, which can promote robust activation in TME (Yates et al., 2018). In view of the increased self-reactivity of TCR in CD4 Tregs compared with conventional T cells, conversion of Tregs could generate highly potent effector CD4 T cells accompanied by attenuated Treg-mediated suppression within the TME. A more effective strategy may depend on approaches that selectively convert intratumoral Tregs into Teff cells without affecting the systemic Treg population. As a key player in the maintenance of Treg size and functional stability in response to diverse immunological perturbations, pharmacological intervention of Helios could be relevant to the strategies that strengthen current tumor immunotherapy. Since Treg to Teff conversion may be confined to inflammatory intratumoral microenvironments, antibody or small molecule-based approaches that target Helios may lead to improved Treg dependent cancer immunotherapy. Importantly, conversion of Helios-deficient Tregs only occurs within the local inflammatory environment of the tumor. This approach may not provoke the autoimmune side effects associated with systemic reduction of Tregs. Therefore, strategies that specifically harness Helios-dependent control of the intratumoral Treg phenotype represent a significant promise to improve cancer immunotherapy. Furthermore, removal of Foxp3+Tregs was also reported to enhance vaccine-induced antitumor T-cell responses (Nishikawa et al., 2010, *Int. J. Cancer* 127: 759-767), suggesting that decreasing Helios levels could be beneficial in boosting the efficacy of cancer vaccines.

Besides anti-tumor immunotherapy, during viral infections, Treg cells can limit the immunopathology resulting from excessive inflammation, yet potentially inhibit effective antiviral T cell responses and promote virus persistence (Schmitz et al., 2013, *PLOS Pathogens* 9: e1003362). Chronic, but not acute, infection of mice with lymphocytic choriomeningitis virus results in a marked expansion of Foxp3+Tregs, implying a potential mechanism that certain infectious agents could evade host immune responses by activation and expansion of Tregs (Punkosdy et al., 2011, *PNAS* 108: 3677-3682). Treatment benefits could be achieved by decreasing Helios levels in activated Tregs in the context relevant to chronic viral infections.

There is a need for compounds useful as inhibitors of Helios protein.

SUMMARY OF THE INVENTION

The present invention provides substituted oxoisoindoline compounds of Formula (I) or salts thereof, which are useful to decrease Helios protein levels, decrease Helios activity levels and/or inhibit Helios expression levels in the cells.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder by decreasing the activity of Helios protein, the method comprising administering to a patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament to decrease Helios protein levels, decrease Helios activity levels and/or inhibit Helios expression levels in cells to control Treg differentiation, for the treatment of certain diseases, including cancer and viral infections.

The compounds of Formula (I) and compositions comprising the compounds of Formula (I) may be used in treating, preventing, or curing viral infections and various proliferative disorders, such as cancer. Pharmaceutical compositions comprising these compounds are useful in treating, preventing, or slowing the progression of diseases or disorders in a variety of therapeutic areas, such as viral infections and cancer.

These and other features of the invention will be set forth in expanded form as the disclosure continues.

DETAILED DESCRIPTION

Applicants have found substituted oxoisoindoline compounds that inhibit Helios protein by facilitating the interaction of Helios protein and the corresponding E3 ubiquitin ligase complex (Cullin4-Cereblon, CUL4-CRBN). These compounds decrease Helios protein levels, decrease Helios activity levels and/or inhibit Helios expression levels in the cells to control Treg differentiation. These compounds are useful for the treatment of certain diseases, including cancer and viral infections. The compounds are provided to be useful as pharmaceuticals with desirable stability, bioavailability, therapeutic index, and toxicity values that are important to their drugability.

The first aspect of the present invention provides at least one compound of Formula (I):

(I)

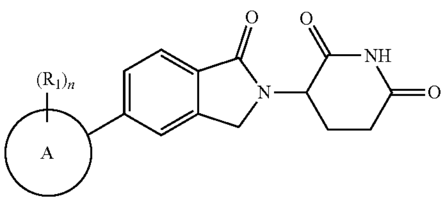

or a salt thereof, wherein:

Ring A is:

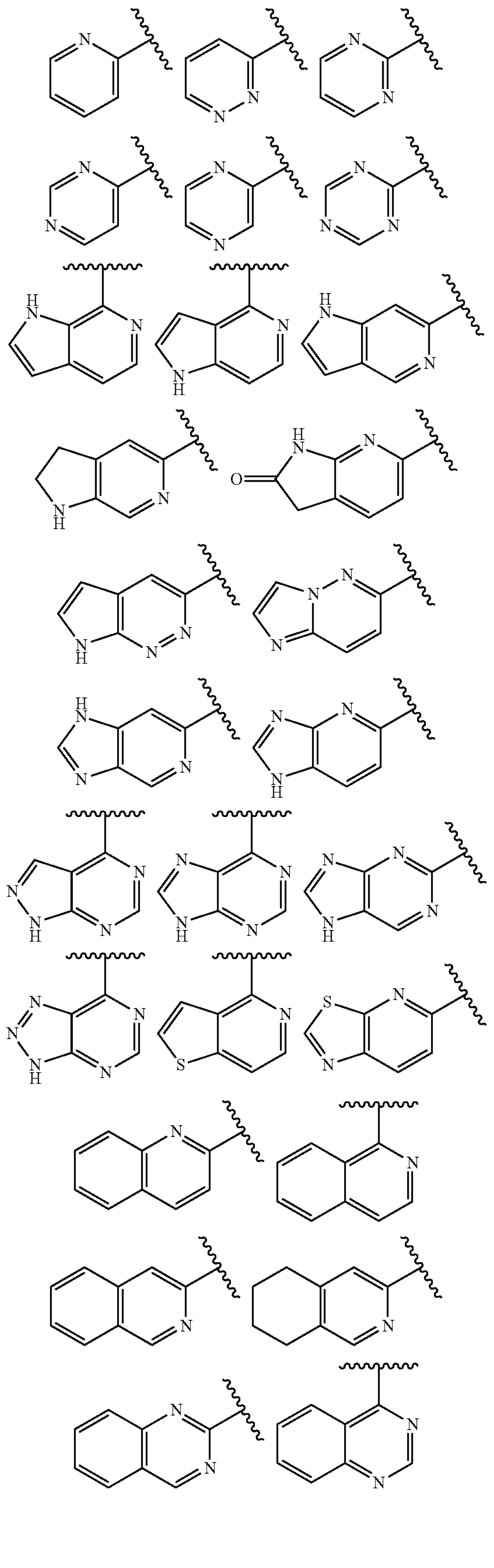

-continued

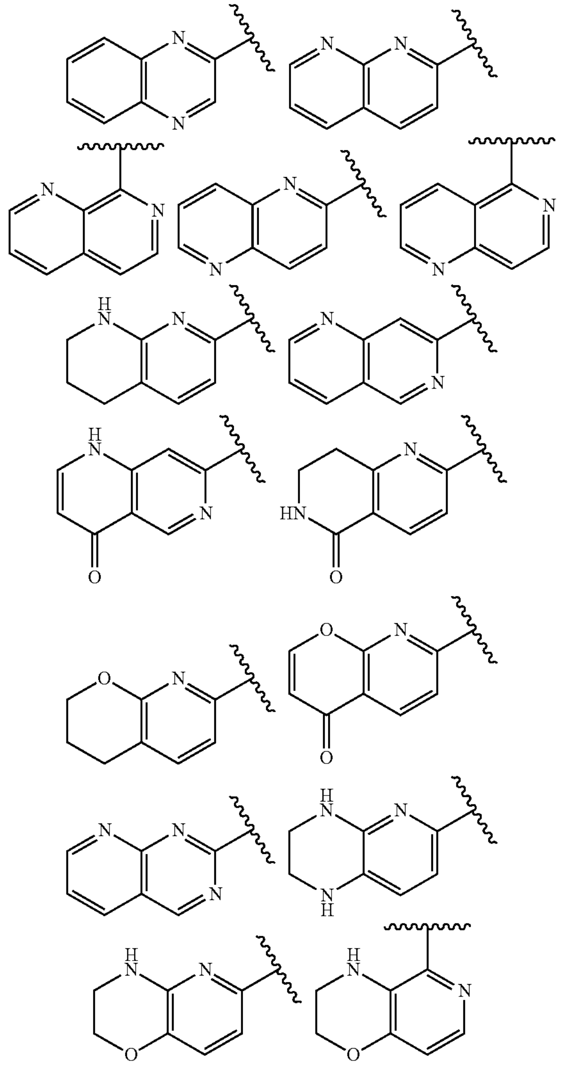

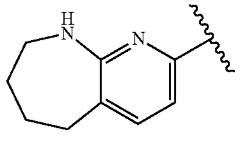

or

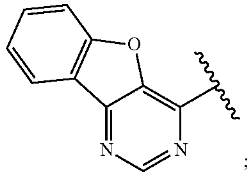

;

each $R_1$ is independently F, Cl, Br, —CN, —OH, —$NO_2$, $C_{1-6}$ alkyl substituted with zero to 6 $R_{1a}$, $C_{1-3}$ alkoxy substituted with zero to 6 $R_{1a}$, —$CR_xR_xOCR_xR_x$(phenyl), —$NR_yR_y$, —$NR_xC(O)H$, —$NR_xC(O)(C_{1-2}$ alkyl), —$NR_xC(O)NR_xR_x$, —C(O)H, —C(O)OH, —C(O)O($C_{1-3}$ alkyl), —$C(O)NR_xR_x$, —$C(O)NR_x(C_{3-6}$ cycloalkyl), —OC(O)($C_{1-3}$ alkyl), —$SO_2(C_{1-3}$ alkyl), —NHN($C_{1-2}$ alkyl)$_2$, —$CH_2CH_2Si(CH_3)_3$ or a cyclic group selected from $C_{3-6}$ cycloalkyl, phenyl, pyridinyl, piperidinyl, piperazinyl, pyrrolidinyl, morpholinyl, and dioxidothiomorpholinyl, wherein said cyclic group is substituted with zero to 4 $R_{1b}$;

each $R_{1a}$ is independently F, Cl, —CN, —OH, $C_{1-2}$ alkoxy, $C_{1-2}$ fluoroalkoxy, —$SO_2(C_{1-3}$ alkyl), or phenyl;

each $R_{1b}$ is independently F, Cl, $C_{1-2}$ alkyl, $C_{1-2}$ fluoroalkyl, $C_{1-2}$ alkoxy, $C_{1-2}$ fluoroalkoxy, —C(O)($C_{1-3}$ alkyl), or —$SO_2(C_{1-3}$ alkyl);

each $R_x$ is independently H or —$CH_3$;

each $R_y$ is independently H or $C_{1-6}$ alkyl; and n is zero, 1, 2, 3, or 4.

One embodiment provides a compound of Formula (I) or a salt thereof, wherein each $R_1$ is independently F, Cl, Br, —CN, —OH, —$NO_2$, $C_{1-5}$ alkyl substituted with zero to 6 $R_{1a}$, $C_{1-2}$ alkoxy substituted with zero to 5 $R_{1a}$, —$CR_xR_xOCH_2$(phenyl), —$NR_yR_y$, —$NR_xC(O)CH_3$, —$NR_xC(O)NR_xR_x$, —C(O)H, —C(O)OH, —C(O)O($C_{1-2}$ alkyl), —$C(O)NR_xR_x$, —$C(O)NR_x$(cyclopropyl), —OC(O)($C_{1-2}$ alkyl), —$SO_2$($C_{1-2}$ alkyl), —$NHN(CH_3)_2$, —$CH_2CH_2Si(CH_3)_3$, or a cyclic group selected from $C_{3-6}$ cycloalkyl, phenyl, pyridinyl, piperidinyl, piperazinyl, pyrrolidinyl, morpholinyl, and dioxidothiomorpholinyl, wherein said cyclic group is substituted with zero to 3 $R_{1b}$.

One embodiment provides a compound of Formula (I) or a salt thereof, wherein each $R_1$ is independently F, Cl, Br, —CN, —OH, —$NO_2$, $C_{1-5}$ alkyl substituted with zero to 6 $R_{1a}$, $C_{1-2}$ alkoxy substituted with zero to 5 $R_{1a}$, —$CR_xR_xOCH_2$(phenyl), —$NR_yR_y$, —$NR_xC(O)CH_3$, —$NR_xC(O)NR_xR_x$, —C(O)H, —C(O)OH, —C(O)O($C_{1-2}$ alkyl), —$C(O)NR_xR_x$, —$C(O)NR_x$(cyclopropyl), —OC(O)($C_{1-2}$ alkyl), —$SO_2$($C_{1-2}$ alkyl), —$NHN(CH_3)_2$, —$CH_2CH_2Si(CH_3)_3$, or a cyclic group selected from $C_{3-6}$ cycloalkyl, phenyl, pyridinyl, piperidinyl, piperazinyl, pyrrolidinyl, morpholinyl, and dioxidothiomorpholinyl, wherein said cyclic group is substituted with zero to 3 $R_{1b}$; each $R_{1b}$ is independently F, Cl, $C_{1-2}$ alkyl, —$CH_2F$, —$CHF_2$, —$CF_3$, $C_{1-2}$ alkoxy, —$OCF_3$, —C(O)($C_{1-2}$ alkyl), or —$SO_2$($C_{1-2}$ alkyl); and n is zero, 1, 2, or 3.

One embodiment provides a compound of Formula (I) or a salt thereof, wherein each $R_1$ is independently F, Cl, Br, —CN, —OH, —$NO_2$, —$CH_3$, —$CH_2CH_3$, —$CHCH_2CH_3$, —$CH(CH_3)_2$, —$CH_2C(CH_3)_3$, —$CF_3$, —$CH_2Cl$, —$CH_2CN$, —$CH_2$(phenyl), —$CH_2OH$, —$CH_2OCH_2$(phenyl), —$OCH_3$, —$OCH_2CH_3$, —$OCH_2$(phenyl), —$NH_2$, —$NH(CH_3)$, —$NH(CH_2CH_3)$, —$NH(CH(CH_3)CH_2CH_3)$, —$N(CH_3)_2$, —$N(CH_2CH_3)_2$, —$NHC(O)CH_3$, —$N(CH_3)C(O)CH_3$, —C(O)H, —$C(O)OCH_3$, —C(O)NH(cyclopropyl), —$C(O)NH_2$, —$C(O)N(CH_3)_2$, —$CH_2CH_2Si(CH_3)_3$, —$OC(O)CH_3$, —$NHN(CH_3)_2$, cyclopropyl, phenyl, pyridinyl, (benzyl)morpholinyl, (methylsulfonyl)piperazinyl, or acetylpiperazinyl; and n is zero, 1, 2, or 3.

One embodiment provides a compound of Formula (I) or a salt thereof, wherein each $R_1$ is independently F, Cl, Br, —CN, —OH, —$NO_2$, —$CH_3$, —$CH_2CH_3$, —$CH(CH_3)_2$, —$CH_2C(CH_3)_3$, —$CF_3$, —$CH_2Cl$, —$CH_2CN$, —$CH_2$(phenyl), —$CH_2OH$, —$CH_2OCH_2$(phenyl), —$OCH_3$, —$OCH_2CH_3$, —$OCH_2$(phenyl), —$NH_2$, —$NH(CH_3)$, —$NH(CH_2CH_3)$, —$NH(CH(CH_3)CH_2CH_3)$, —$N(CH_3)_2$, —$N(CH_2CH_3)_2$, —$NHC(O)CH_3$, —$N(CH_3)C(O)CH_3$, —C(O)H, —$C(O)OCH_3$, —C(O)NH(cyclopropyl), —$C(O)NH_2$, —$C(O)N(CH_3)_2$, —$CH_2CH_2Si(CH_3)_3$, —$OC(O)CH_3$, —$NHN(CH_3)_2$, cyclopropyl, phenyl, pyridinyl, or acetylpiperazinyl; and n is zero, 1, 2, or 3.

One embodiment provides a compound of Formula (I) or a salt thereof, wherein

Ring A is:

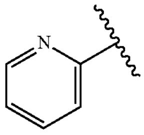
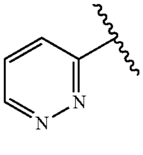
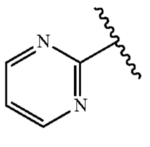

-continued

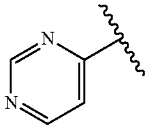
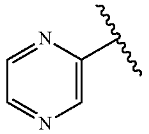
or
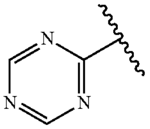
.

One embodiment provides a compound of Formula (I) or a salt thereof, wherein

Ring A is:

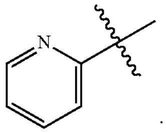 [SMILES: *c1ccccn1]
.

One embodiment provides a compound of Formula (I) or a salt thereof, wherein

Ring A is:

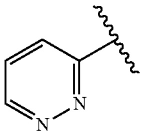
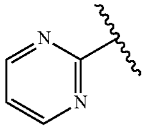
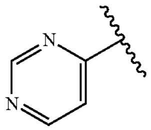
or
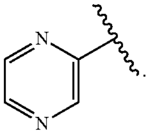
.

One embodiment provides a compound of Formula (I) or a salt thereof, wherein

Ring A is:

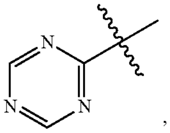 [SMILES: *c1ncncn1]
,

One embodiment provides a compound of Formula (I) or a salt thereof, wherein

Ring A is:

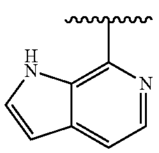
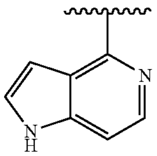
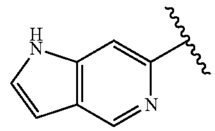
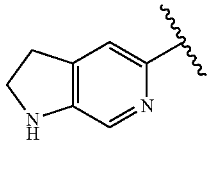
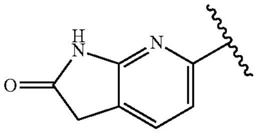

-continued
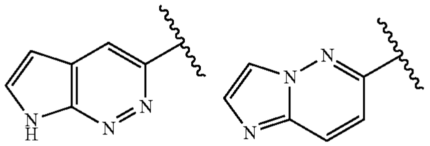
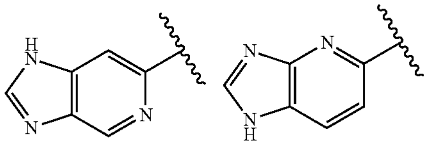
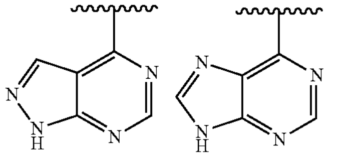
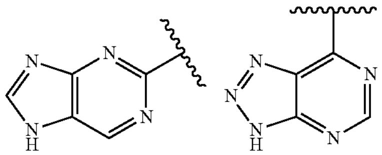
or
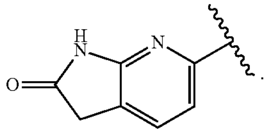
One embodiment provides a compound of Formula (I) or a salt thereof, wherein
Ring A is:
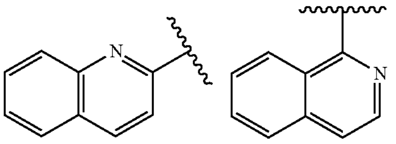
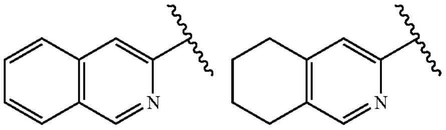
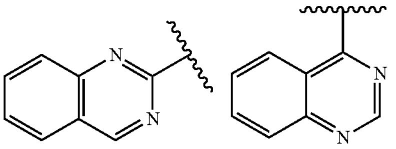
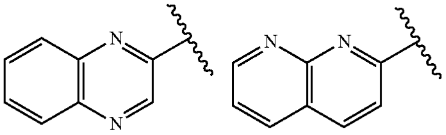
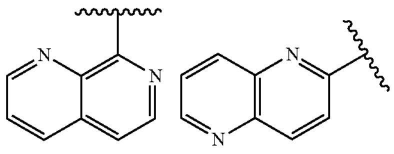
-continued
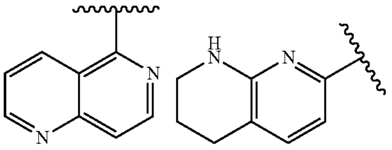
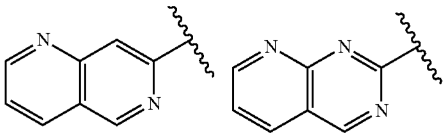
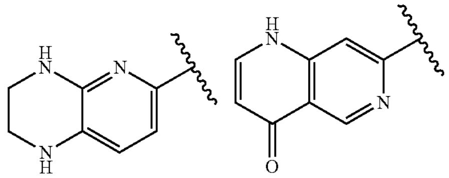
or
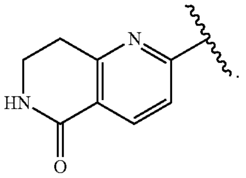
One embodiment provides a compound of Formula (I) or a salt thereof, wherein
Ring A is:
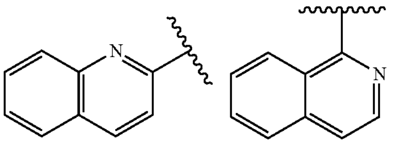
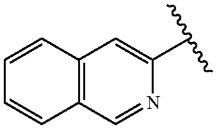
or
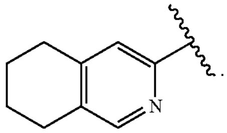
One embodiment provides a compound of Formula (I) or a salt thereof, wherein
Ring A is:
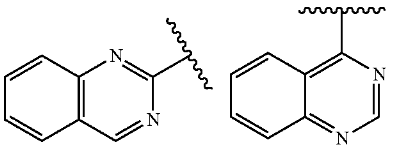
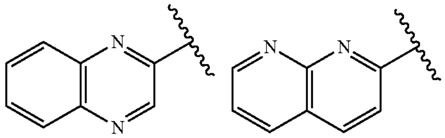
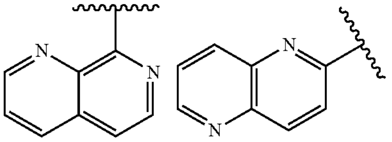

-continued

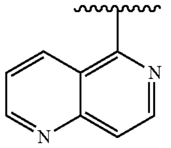 or 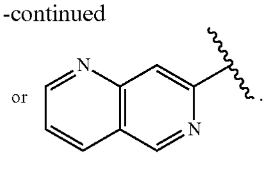

One embodiment provides a compound of Formula (I) or a salt thereof, wherein

Ring A is:

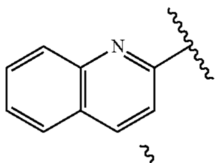 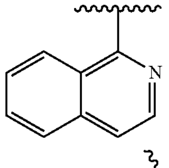

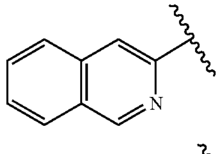 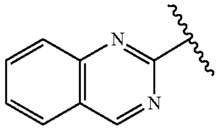

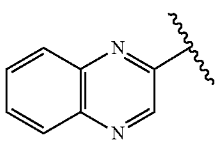 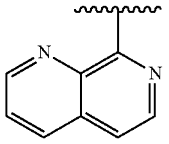

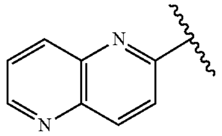 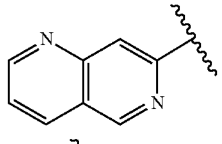 or

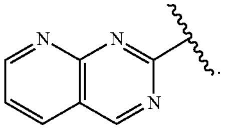

One embodiment provides a compound of Formula (I) or a salt thereof, wherein

Ring A is:

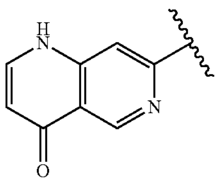 or 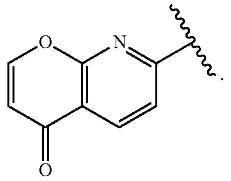

One embodiment provides a compound of Formula (I) or a salt thereof, wherein

Ring A is:

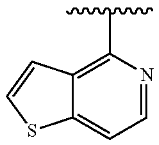 or 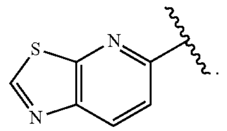

One embodiment provides a compound of Formula (I) or a salt thereof, wherein

Ring A is:

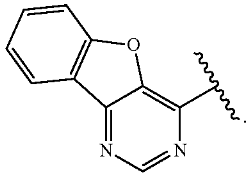 [SMILES: *c1ncnc2c1oc1ccccc12]

One embodiment provides a compound of Formula (I) or a salt thereof, wherein

Ring A is:

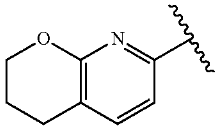 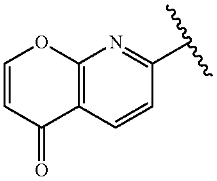

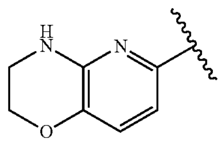 or 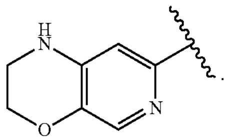

One embodiment provides a compound of Formula (I) or a salt thereof, wherein

Ring A is:

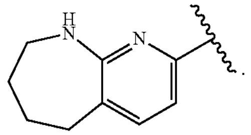 [SMILES: *c1ccc2c(n1)NCCCC2]

One embodiment provides a compound of Formula (I) or a salt thereof, wherein each $R_1$ is independently F, Cl, Br, —CN, —OH, —$NO_2$, $C_{1-6}$ alkyl substituted with zero to 6 $R_{1a}$, $C_{1-3}$ alkoxy substituted with zero to 6 $R_{1a}$, —$CR_xR_xOCR_xR_x$(phenyl), —$NR_yR_y$, —$NR_xC(O)H$, —$NR_xC(O)(C_{1-2}$ alkyl), —$NR_xC(O)NR_xR_x$, —C(O)H, —C(O)OH, —C(O)O($C_{1-3}$ alkyl), —$C(O)NR_xR_x$, —C(O)$NR_x(C_{3-6}$ cycloalkyl), —OC(O)($C_{1-3}$ alkyl), —$SO_2(C_{1-3}$ alkyl), or —NHN($C_{1-2}$ alkyl)$_2$. Included in this embodiment are compounds in which each $R_1$ is independently F, Cl, Br, —CN, —OH, —$NO_2$, $C_{1-5}$ alkyl substituted with zero to 6 $R_{1a}$, $C_{1-2}$ alkoxy substituted with zero to 5 $R_{1a}$, —$CR_xR_xOCH_2$(phenyl), —$NR_yR_y$, —$NR_xC(O)CH_3$, —$NR_xC(O)NR_xR_x$, —C(O)H, —C(O)OH, —C(O)O($C_{1-2}$ alkyl), —$C(O)NR_xR_x$, —$C(O)NR_x$(cyclopropyl), —OC(O)($C_{1-2}$ alkyl), —$SO_2(C_{1-2}$ alkyl), or —$NHN(CH_3)_2$. Also included in this embodiment are compounds in which each $R_1$ is independently F, Cl, Br, —CN, —OH, —$NO_2$, —$CH_3$, —$CH_2CH_3$, —$CH(CH_3)_2$, —$CH_2C(CH_3)_3$, —$CF_3$, —$CH_2Cl$, —$CH_2CN$, —$CH_2$(phenyl), —$CH_2OH$, —$CH_2OCH_2$(phenyl), —$OCH_3$, —$OCH_2CH_3$, —$OCH_2$(phenyl), —$NH_2$, —$NH(CH_3)$, —$NH(CH_2CH_3)$, —NH(CH($CH_3$)$CH_2CH_3$), —$N(CH_3)_2$, —$N(CH_2CH_3)_2$, —NHC(O)$CH_3$, —$N(CH_3)C(O)CH_3$, —C(O)H, —C(O)$OCH_3$, —C(O)NH(cyclopropyl), —$C(O)NH_2$, —C(O)$N(CH_3)_2$, —OC(O)$CH_3$, or —$NHN(CH_3)_2$.

One embodiment provides a compound of Formula (I) or a salt thereof, wherein each $R_1$ is independently a cyclic group selected from $C_{3-6}$ cycloalkyl, phenyl, pyridinyl, piperidinyl, piperazinyl, pyrrolidinyl, morpholinyl, and dioxidothiomorpholinyl, wherein said cyclic group is substituted with zero to 4 $R_{1b}$. Included in this embodiment are compounds in which each $R_1$ is independently a cyclic group selected from $C_{3-6}$ cycloalkyl, phenyl, pyridinyl, piperidinyl, piperazinyl, pyrrolidinyl, morpholinyl, and dioxidothiomorpholinyl, wherein said cyclic group is substituted with zero to 3 $R_{1b}$. Also included in this embodiment are compounds in which each $R_1$ is independently cyclopropyl, phenyl, pyridinyl, or acetylpiperazinyl.

One embodiment provides a compound of Formula (I) or a salt thereof, wherein n is zero, 1, 2, or 3. Included in this embodiment are compounds in which n is zero, 1, or 2.

Additionally, included in this embodiment are compounds in which n is 1 or 2.

One embodiment provides a compound of Formula (I) or a salt thereof, wherein

Ring A is

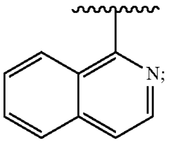 [SMILES: *c1nccc2ccccc12]

each $R_1$ is independently F, Cl, —CN, —OH, —$CH_3$, —$OCH_3$, —$OCH_2$(phenyl), —$NH_2$, —$N(CH_3)_2$, —$CH_2CH_3$, —$CH(CH_3)_2$, —$CH_2C(CH_3)_3$, —$CF_3$, —$CH_2Cl$, —$CH_2CN$, —$CH_2$(phenyl), —$CH_2OH$, —$CH_2OCH_2$(phenyl), —$OCH_2CH_3$, —$NH(CH_3)$, —$NH(CH_2CH_3)$, or —$NHC(O)CH_3$; and n is zero, 1, or 2.

One embodiment provides a compound of Formula (I) or a salt thereof, wherein

Ring A is

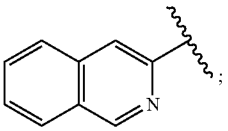 [SMILES: *c1cc2ccccc2cn1]

each $R_1$ is independently Cl, —CN, —$CH_3$, —$OCH_3$, —$OCH_2CH_3$, —$NH_2$, —$NH(CH_3)$, —$N(CH_3)_2$, —$NHC(O)CH_3$, —$N(CH_3)C(O)CH_3$, —$C(O)NH_2$, —$C(O)N(CH_3)_2$, or cyclopropyl; and n is zero, 1, or 2.

One embodiment provides a compound of Formula (I) or a salt thereof, wherein

Ring A is

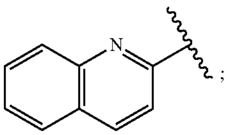 [SMILES: *c1ccc2ccccc2n1]

each $R_1$ is independently F, Cl, —OH, —$CH_3$, —$OCH_3$, —$NH_2$, —$C(O)OCH_3$, —C(O)NH(cyclopropyl), or phenyl; and n is zero, 1, or 2.

One embodiment provides a compound of Formula (I) or a salt thereof, wherein

Ring A is:

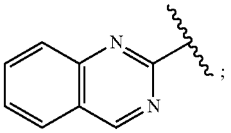 [SMILES: *c1ncc2ccccc2n1]

each $R_1$ is independently F, Cl, —$NH_2$, —$OCH_3$, —$N(CH_2CH_3)_2$, or —$C(O)OCH_3$; and n is zero, 1, 2, or 3.

One embodiment provides a compound of Formula (I) or a salt thereof, wherein

Ring A is:

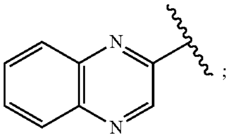 [SMILES: *c1cnc2ccccc2n1]

each $R_1$ is independently Cl, —OH, —$CH(CH_3)_2$, —$OCH_3$, —$NH_2$, —$NH(CH_2CH_3)$, —$C(O)OCH_3$, cyclopropyl, or One embodiment provides a compound of Formula (I) or a salt thereof, wherein Ring A is:

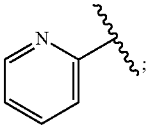 [SMILES: *c1ccccn1]

each $R_1$ is independently F, Cl, Br, —CN, —OH, —$NO_2$, —$CH_3$, —$OCH_3$, —$NH_2$, —$NH(CH_3)$, —$NH(CH_2CH_3)$, —$NHC(O)CH_3$, —$NHN(CH_3)_2$, cyclopropyl, phenyl, (benzyl)morpholinyl, (methylsulfonyl)piperazinyl, or acetylpiperazinyl; and n is zero, 1, 2, or 3.

One embodiment provides a compound of Formula (I) or a salt thereof, wherein

Ring A is:

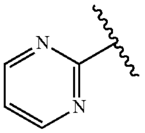 or 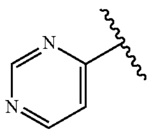 ;

each $R_1$ is independently —CN, —$NH_2$, —$C(O)NH_2$, phenyl, or pyridinyl; and n is zero, 1, or 2.

One embodiment provides a compound of Formula (I) or a salt thereof, wherein said compound is: 3-[1-oxo-5-(quinolin-2-yl)-2,3-dihydro-1H-isoindol-2-yl]piperidine-2,6-dione (1); 3-[5-(4-aminoisoquinolin-3-yl)-1-oxo-2,3-dihydro-1H-isoindol-2-yl]piperidine-2,6-dione (2); 3-(5-{8-oxa-3,5-diazatricyclo[7.4.0.0$^{2}$,7]trideca-1(9),2,4,6,10,12-hexaen-6-yl}-1-oxo-2,3-dihydro-1H-isoindol-2-yl)piperidine-2,6-dione (3); 3-[5-(1-aminoisoquinolin-3-yl)-1-oxo-2,3- dihydro-1H-isoindol-2-yl]piperidine-2,6-dione (4); 3-[5-(3-aminoquinoxalin-2-yl)-1-oxo-2,3-dihydro-1H-isoindol-2-yl]piperidine-2,6-dione (5); 3-(1-oxo-5-{7H-pyrrolo[2,3-c]pyridazin-3-yl}-2,3-dihydro-1H-isoindol-2-yl)piperidine-2,6-dione (6); 3-[1-oxo-5-(quinoxalin-2-yl)-2,3-dihydro-1H-isoindol-2-yl]piperidine-2,6-dione (7); 3-[5-(4-aminoquinolin-2-yl)-1-oxo-2,3-dihydro-1H-isoindol-2-yl]piperidine-2,6-dione (8); 3-[1-oxo-5-(quinazolin-2-yl)-2,3-dihydro-1H-isoindol-2-yl]piperidine-2,6-dione (9); 3-(5-{2-[(butan-2-yl)amino]-[1,3]thiazolo[5,4-b]pyridin-5-yl}-1-oxo-2,3-dihydro-1H-isoindol-2-yl)piperidine-2,6-dione (10); 3-(5-{7-fluoro-1H-pyrrolo[3,2-c]pyridin-4-yl}-1-oxo-2,3-dihydro-1H-isoindol-2-yl)piperidine-2,6-dione (11); 3-[5-(4-methoxyquinolin-2-yl)-1-oxo-2,3-dihydro-1H-isoindol-2-yl]piperidine-2,6-dione (12); 3-[1-oxo-5-(4-phenylquinolin-2-yl)-2,3-dihydro-1H-isoindol-2-yl]piperidine-2,6-dione (13); N-cyclopropyl-2-[2-(2,6-dioxopiperidin-3-yl)-1-oxo-2,3-dihydro-1H-isoindol-5-yl]quinoline-4-carboxamide (14); 3-{5-[6-chloro-4-(diethylamino)quinazolin-2-yl]-1-oxo-2,3-dihydro-1H-isoindol-2-yl}piperidine-2,6-dione (15); 3-[5-(4-amino-6,7-dimethoxyquinazolin-2-yl)-1-oxo-2,3-dihydro-1H-isoindol-2-yl]piperidine-2,6-dione (16); 3-[5-(6-methoxyisoquinolin-1-yl)-1-oxo-2,3-dihydro-1H-isoindol-2-yl]piperidine-2,6-dione (17); 3-[5-(6-chloroquinoxalin-2-yl)-1-oxo-2,3-dihydro-1H-isoindol-2-yl]piperidine-2,6-dione (18); 3-[5-(7-fluoroisoquinolin-1-yl)-1-oxo-2,3-dihydro-1H-isoindol-2-yl]piperidine-2,6-dione (19); 3-[5-(5-fluoroisoquinolin-1-yl)-1-oxo-2,3-dihydro-1H-isoindol-2-yl]piperidine-2,6-dione (20); 3-[5-(1,5-naphthyridin-2-yl)-1-oxo-2,3-dihydro-1H-isoindol-2-yl]piperidine-2,6-dione (21); 3-[5-(4-aminoquinazolin-2-yl)-1-oxo-2,3-dihydro-1H-isoindol-2-yl]piperidine-2,6-dione (22); 3-[5-(6-methylisoquinolin-1-yl)-1-oxo-2,3-dihydro-1H-isoindol-2-yl]piperidine-2,6-dione (23); 3-[5-(4-methylquinolin-2-yl)-1-oxo-2,3-dihydro-1H-isoindol-2-yl]piperidine-2,6-dione (24); 3-[5-(3-aminoisoquinolin-1-yl)-1-oxo-2,3-dihydro-1H-isoindol-2-yl]piperidine-2,6-dione (25); 3-[5-(6-fluoroquinoxalin-2-yl)-1-oxo-2,3-dihydro-1H-isoindol-2-yl]piperidine-2,6-dione (26); 3-[5-(6-chloroquinolin-2-yl)-1-oxo-2,3-dihydro-1H-isoindol-2-yl]piperidine-2,6-dione (27); 3-[5-(7-chloroquinolin-2-yl)-1-oxo-2,3-dihydro-1H-isoindol-2-yl]piperidine-2,6-dione (28); 3-[5-(6-methoxyquinolin-2-yl)-1-oxo-2,3-dihydro-1H-isoindol-2-yl]piperidine-2,6-dione (29); ethyl 3-[2-(2,6-dioxopiperidin-3-yl)-1-oxo-2,3-dihydro-1H-isoindol-5-yl]quinoxaline-2-carboxylate (30); methyl 2-[2-(2,6-dioxopiperidin-3-yl)-1-oxo-2,3-dihydro-1H-isoindol-5-yl]quinoline-6-carboxylate (31); 3-[5-(3-methylquinolin-2-yl)-1-oxo-2,3-dihydro-1H-isoindol-2-yl]piperidine-2,6-dione (32); 3-[5-(8-methoxyquinolin-2-yl)-1-oxo-2,3-dihydro-1H-isoindol-2-yl]piperidine-2,6-dione (33); 3-[5-(8-chloroquinolin-2-yl)-1-oxo-2,3-dihydro-1H-isoindol-2-yl]piperidine-2,6-dione (34); 3-[5-(6-fluoroquinazolin-2-yl)-1-oxo-2,3-dihydro-1H-isoindol-2-yl]piperidine-2,6-dione (35); 3-[5-(3-chloroquinolin-2-yl)-1-oxo-2,3-dihydro-1H-isoindol-2-yl]piperidine-2,6-dione (36); 3-[5-(4-hydroxyquinolin-2-yl)-1-oxo-2,3-dihydro-1H-isoindol-2-yl]piperidine-2,6-dione (37); 3-[5-(6-fluoroquinolin-2-yl)-1-oxo-2,3-dihydro-1H-isoindol-2-yl]piperidine-2,6-dione (38); 3-[5-(6-methylquinolin-2-yl)-1-oxo-2,3-dihydro-1H-isoindol-2-yl]piperidine-2,6-dione (39); 3-[5-(6-hydroxyquinolin-2-yl)-1-oxo-2,3-dihydro-1H-isoindol-2-yl]piperidine-2,6-dione (40); methyl 2-[2-(2,6-dioxopiperidin-3-yl)-1-oxo-2,3-dihydro-1H-isoindol-5-yl]quinazoline-7-carboxylate (41); 3-(5-{5-amino-3-[2-(trimethylsilyl)ethyl]-3H-[1,2,3]triazolo[4,5-d]pyrimidin-7-yl}-1-oxo-2,3-dihydro-1H-isoindol-2-yl)piperidine-2,6-dione (42); 3-[5-(2-amino-9H-purin-6-yl)-1-oxo-2,3-dihydro-1H-isoindol-2-yl]piperidine-2,6-dione (43); 3-[5-(6-amino-7H-purin-2-yl)-1-oxo-2,3-dihydro-1H-isoindol-2-yl]piperidine-2,6-dione (44); 3-(5-{6-amino-1-ethyl-1H-pyrazolo[3,4-d]pyrimidin-4-yl}-1-oxo-2,3-dihydro-1H-isoindol-2-yl)piperidine-2,6-dione (45); 3-{5-[5-amino-1-(2,2-dimethylpropyl)-4-oxo-1,4-dihydro-1,6-naphthyridin-7-yl]-1-oxo-2,3-dihydro-1H-isoindol-2-yl}piperidine-2,6-dione (46); 3-[5-(5-amino-4-oxo-1,4-dihydro-1,6-naphthyridin-7-yl)-1-oxo-2,3-dihydro-1H-isoindol-2-yl]piperidine-2,6-dione (47); N-{3-[2-(2,6-dioxopiperidin-3-yl)-1-oxo-2,3-dihydro-1H-isoindol-5-yl]isoquinolin-1-yl}acetamide (48); 3-{5-[1-(dimethylamino)isoquinolin-3-yl]-1-oxo-2,3-dihydro-1H-isoindol-2-yl}piperidine-2,6-dione (49); 3-{5-[1-(methylamino)isoquinolin-3-yl]-1-oxo-2,3-dihydro-1H-isoindol-2-yl}piperidine-2,6-dione (50); 3-{5-[5-(methylamino)-1,6-naphthyridin-7-yl]-1-oxo-2,3-dihydro-1H-isoindol-2-yl}piperidine-2,6-dione (51); N-{3-[2-(2,6-dioxopiperidin-3-yl)-1-oxo-2,3-dihydro-1H-isoindol-5-yl]isoquinolin-1-yl}-N-methylacetamide (52); 3-[5-(6-amino-1,7-naphthyridin-8-yl)-1-oxo-2,3-dihydro-1H-isoindol-2-yl]piperidine-2,6-dione (53); 3-[5-(3-amino-5-methoxyisoquinolin-1-yl)-1-oxo-2,3-dihydro-1H-isoindol-2-yl]piperidine-2,6-dione (54); 3-(5-(4-(4-acetylpiperazin-1-yl)pyrido[2,3-d]pyrimidin-2-yl)-1-oxoisoindolin-2-yl)piperidine-2,6-dione (55); 3-(5-{4-bromo-1H-pyrrolo[2,3-c]pyridin-7-yl}-1-oxo-2,3-dihydro-1H-isoindol-2-yl)piperidine-2,6-dione (56); 3-[5-(5-amino-1,6-naphthyridin-7-yl)-1-oxo-2,3-dihydro-1H-isoindol-2-yl]piperidine-2,6-dione (57); 3-[5-(3,6-dimethoxyisoquinolin-1-yl)-1-oxo-2,3-dihydro-1H-isoindol-2-yl]piperidine-2,6-dione (58); 1-[2-(2,6-dioxopiperidin-3-yl)-1-oxo-2,3-dihydro-1H-isoindol-5-yl]isoquinoline-3-carbonitrile (59); 4-[2-(2,6-dioxopiperidin-3-yl)-1-oxo-2,3-dihydro-1H-isoindol-5-yl]thieno[3,2-c]pyridine-2-carbaldehyde (60); 3-{5-[1-methyl-4-(methylamino)-1H-imidazo[4,5-c]pyridin-6-yl]-1-oxo-2,3-dihydro-1H-isoindol-2-yl}piperidine-2,6-dione (61); 3-(5-{2-methyl-4-oxo-4H-pyrano[2,3-b]pyridin-7-yl}-1-oxo-2,3-dihydro-1H-isoindol-2-yl)piperidine-2,6-dione (62); 3-{5-[5,7-dichloro-3-(dimethylamino)isoquinolin-1-yl]-1-oxo-2,3-dihydro-1H-isoindol-2-yl}piperidine-2,6-dione (63); 3-[5-(1,7-naphthyridin-8-yl)-1-oxo-2,3-dihydro-1H-isoindol-2-yl]piperidine-2,6-dione (64); 3-(5-{2-aminoimidazo[1,2-b]pyridazin-6-yl}-1-oxo-2,3-dihydro-1H-isoindol-2-yl)piperidine-2,6-dione (65); 3-[5-(isoquinolin-1-yl)-1-oxo-2,3-dihydro-1H-isoindol-2-yl]piperidine-2,6-dione (66); 3-[5-(isoquinolin-3-yl)-1-oxo-2,3-dihydro-1H-isoindol-2-yl]piperidine-2,6-dione (67); 3-(5-(2-amino-6-methoxypyrimidin-4-yl)-1-oxoisoindolin-2-yl)piperidine-2,6-dione (68); 3-(5-(6-aminopyridin-2-yl)-1-oxoisoindolin-2-yl)piperidine-2,6-dione (69); 3-(5-(2-aminopyrimidin-4-yl)-1-oxoisoindolin-2-yl)piperidine-2,6-dione (70); 3-(1-oxo-5-(4-phenylpyrimidin-2-yl)isoindolin-2-yl)piperidine-2,6-dione (71); 3-(1-oxo-5-(4-(pyridin-3-yl)pyrimidin-2-yl)isoindolin-2-yl)piperidine-2,6-dione (72); 3-(5-(4-amino-6-phenyl-1,3,5-triazin-2-yl)-1-oxoisoindolin-2-yl)piperidine-2,6-dione (73); 3-(1-oxo-5-(4-phenylpyridin-2-yl)isoindolin-2-yl)piperidine-2,6-dione (74); 3-(1-oxo-5-(4-(pyridin-2-yl)pyrimidin-2-yl)isoindolin-2-yl)piperidine-2,6-dione (75); 3-(2-(2,6-dioxopiperidin-3-yl)-1-oxoisoindolin-5-yl)pyridazine-4-carbonitrile (76); 6-[2-(2,6-dioxopiperidin-3-yl)-1-oxo-2,3-dihydro-1H-isoindol-5-yl]pyridazine-3-carbonitrile (77); 6-[2-(2,6-dioxopiperidin-3-yl)-1-oxo-2,3-dihydro-1H-isoindol-5-yl]pyridazine-3-carboxamide (78); 3-[5-(6-amino-3-nitropyridin-2-yl)-1-oxo-2,3-dihydro-1H-isoindol-2-yl]piperidine-2,6-dione (79); 4-amino-2-[2-(2,6-dioxopiperidin-3-yl)-1-oxo-2,3-dihydro-1H-isoindol-5-yl]pyrimidine-5-carbonitrile (80); 4-amino-2-[2-(2,6-dioxopiperidin-3-yl)-1-oxo-2,3-dihydro-1H-isoindol-5-yl]pyrimidine-5-carboxamide (81); (3S)-3-[5-(1-aminoisoquinolin-3-yl)-1-oxo-2,3-dihydro-1H-isoindol-2-yl]piperidine-2,6-dione (82); (3R)-3-[5-(1-aminoisoquinolin-3-yl)-1-oxo-2,3-dihydro-1H-isoindol-2-yl]piperidine-2,6-dione (83); (3S)-3-[5-(1-amino-4-ethoxyisoquinolin-3-yl)-1-oxo-2,3-dihydro-1H-isoindol-2-yl]piperidine-2,6-dione (84); 3-(5-(4-ethoxyisoquinolin-3-yl)-1-oxoisoindolin-2-yl)piperidine-2,6-dione (85); 3-(5-(1-chloro-4-ethoxyisoquinolin-3-yl)-1-oxoisoindolin-2-yl) piperidine-2,6-dione (86); 3-(5-(2,3-dihydro-1H-pyrido[3,4-b][1,4]oxazin-7-yl)-1-oxoisoindolin-2-yl)piperidine-2,6-dione (87); 3-(5-(1-methylisoquinolin-3-yl)-1-oxoisoindolin-2-yl)piperidine-2,6-dione (88); 3-(5-(1-cyclopropylisoquinolin-3-yl)-1-oxoisoindolin-2-yl) piperidine-2,6-dione (89); -(2-(2,6-dioxopiperidin-3-yl)-1-oxoisoindolin-5-yl)isoquinoline-4-carbonitrile (90); 3-(1-oxo-5-(quinazolin-4-yl) isoindolin-2-yl)piperidine-2,6-dione (91); 3-(5-(6-methyl-5-oxo-5,6,7,8-tetrahydro-1,6-naphthyridin-2-yl)-1-oxoisoindolin-2-yl)piperidine-2,6-dione (92); 3-(5-(3-chloroquinoxalin-2-yl)-1-oxoisoindolin-2-yl)piperidine-2,6-dione (93); 3-(5-(3-methoxyquinoxalin-2-yl)-1-oxoisoindolin-2-yl)piperidine-2,6-dione (94); 3-(5-(3-(ethylamino)quinoxalin-2-yl)-1-oxoisoindolin-2-yl) piperidine-2,6-dione (95); 3-(5-(3-hydroxyquinoxalin-2-yl)-1-oxoisoindolin-2-yl)piperidine-2,6-dione (96); 3-(5-(3-cyclopropylquinoxalin-2-yl)-1-oxoisoindolin-2-yl) piperidine-2,6-dione (97); 3-(5-(3-isopropylquinoxalin-2-yl)-1-oxoisoindolin-2-yl)piperidine-2,6-dione (98); 3-(1-oxo-5-(3-phenylquinoxalin-2-yl)isoindolin-2-yl)piperidine-2,6-dione (99); 3-(5-(1,6-naphthyridin-5-yl)-1-oxoisoindolin-2-yl)piperidine-2,6-dione (100); 3-(5-(6-amino-3-bromopyridin-2-yl)-1-oxoisoindolin-2-yl) piperidine-2,6-dione (101); 3-(5-(6-aminoisoquinolin-3-yl)-1-oxoisoindolin-2-yl)piperidine-2,6-dione (102); 3-(5-(4-methoxyisoquinolin-1-yl)-1-oxoisoindolin-2-yl)piperidine-2,6-dione (103); 3-(5-(3-methoxypyridin-2-yl)-1-oxoisoindolin-2-yl)piperidine-2,6-dione (104); 3-(5-(4-(benzyloxy)isoquinolin-1-yl)-1-oxoisoindolin-2-yl) piperidine-2,6-dione (105); 3-(5-(6-amino-3-methoxypyridin-2-yl)-1-oxoisoindolin-2-yl)piperidine-2,6-dione (106); 3-(5-(3-(hydroxymethyl)pyridin-2-yl)-1-oxoisoindolin-2-yl)piperidine-2,6-dione (107); 3-(5-(4-(hydroxymethyl)pyridin-2-yl)-1-oxoisoindolin-2-yl) piperidine-2,6-dione (108); 3-(1-oxo-5-(pyridin-2-yl) isoindolin-2-yl) piperidine-2,6-dione (109); 2-(2-(2,6-dioxopiperidin-3-yl)-1-oxoisoindolin-5-yl) isonicotinonitrile (110); 2-(2-(2-(2,6-dioxopiperidin-3-yl)-1-oxoisoindolin-5-yl)pyridin-4-yl)acetonitrile (111); 3-(5-(6-amino-4-(hydroxymethyl)pyridin-2-yl)-1-oxoisoindolin-2-yl)piperidine-2,6-dione (112); 3-(5-(2,3-dihydro-1H-pyrrolo[2,3-c]pyridin-5-yl)-1-oxoisoindolin-2-yl) piperidine-2,6-dione (113); 3-(1-oxo-5-(2-oxo-2,3-dihydro-1H-pyrrolo[2,3-b]pyridin-6-yl)isoindolin-2-yl)piperidine-2, 6-dione (114); 3-(1-oxo-5-(5,6,7,8-tetrahydroisoquinolin-3-yl)isoindolin-2-yl)piperidine-2,6-dione (115); 3-(5-(6-amino-5-methylpyridin-2-yl)-1-oxoisoindolin-2-yl) piperidine-2,6-dione (116); 3-(5-(5,6-diaminopyridin-2-yl)-1-oxoisoindolin-2-yl)piperidine-2,6-dione (117); 3-(1-oxo-5-(1,2,3,4-tetrahydropyrido[2,3-b]pyrazin-6-yl)isoindolin-2-yl)piperidine-2,6-dione (118); 3-(5-(5-amino-4,6-dimethylpyridin-2-yl)-1-oxoisoindolin-2-yl)piperidine-2,6-dione (119); 3-(5-(6-amino-4-(trifluoromethyl)pyridin-2-yl)-1-oxoisoindolin-2-yl)piperidine-2,6-dione (120); 3-(5-(4,5-dimethylpyridin-2-yl)-1-oxoisoindolin-2-yl)piperidine-2,6-dione (121); (3S)-3-[5-(1,8-naphthyridin-2-yl)-1-oxo-2,3-dihydro-1H-isoindol-2-yl]piperidine-2,6-dione (122); (S)-3-(5-(3-aminoisoquinolin-1-yl)-1-oxoisoindolin-2-yl) piperidine-2,6-dione (123); (S)—N-(1-(2-(2,6-dioxopiperidin-3-yl)-1-oxoisoindolin-5-yl) isoquinolin-3-yl)acetamide (124); 3-{2-[(3S)-2,6-dioxopiperidin-3-yl]-1-oxo-2,3-dihydro-1H-isoindol-5-yl}isoquinoline-1-carbonitrile (125); 3-{2-[(3S)-2,6-dioxopiperidin-3-yl]-1-oxo-2,3-dihydro-1H-isoindol-5-yl}isoquinoline-1-carboxamide (126); (4S)-7-{2-[(3S)-2,6-dioxopiperidin-3-yl]-1-oxo-2,3-dihydro-1H-isoindol-5-yl}-2H,3H,4H-pyrano[2,3-b]pyridin-4-yl acetate (127); (4R)-7-{2-[(3S)-2,6-dioxopiperidin-3-yl]-1-oxo-2,3-dihydro-1H-isoindol-5-yl}-2H,3H,4H-pyrano[2,3-b]pyridin-4-yl acetate (128); 3-{5-[7-chloro-4-(dimethylamino) isoquinolin-1-yl]-1-oxo-2,3-dihydro-1H-isoindol-2-yl}piperidine-2,6-dione (129); 1-amino-3-[2-(2,6-dioxopiperidin-3-yl)-1-oxo-2,3-dihydro-1H-isoindol-5-yl]-N,N-dimethylisoquinoline-4-carboxamide (130); 3-[5-(1-amino-4-methylisoquinolin-3-yl)-1-oxo-2,3-dihydro-1H-isoindol-2-yl]piperidine-2,6-dione (131); 3-[5-(6-amino-3-cyclopropylpyridin-2-yl)-1-oxo-2,3-dihydro-1H-isoindol-2-yl]piperidine-2,6-dione (132); 3-[5-(6-aminoisoquinolin-1-yl)-1-oxo-2,3-dihydro-1H-isoindol-2-yl]piperidine-2,6-dione (133); N-{1-[2-(2,6-dioxopiperidin-3-yl)-1-oxo-2,3-dihydro-1H-isoindol-5-yl]isoquinolin-6-yl}acetamide (134); 3-{5-[6-amino-4-(chloromethyl)pyridin-2-yl]-1-oxo-2,3-dihydro-1H-isoindol-2-yl}piperidine-2,6-dione (135); 3-(1-oxo-5-{5H,6H,7H,8H,9H-pyrido[2,3-b]azepin-2-yl}-2,3-dihydro-1H-isoindol-2-yl)piperidine-2,6-dione (136); 3-[1-oxo-5-(5,6,7,8-tetrahydro-1,8-naphthyridin-2-yl)-2,3-dihydro-1H-isoindol-2-yl]piperidine-2,6-dione (137); 3-{5-[6-(2,2-dimethylhydrazin-1-yl)pyridin-2-yl]-1-oxo-2,3-dihydro-1H-isoindol-2-yl}piperidine-2,6-dione (138); 3-(5-(1H-imidazo[4,5-b]pyridin-5-yl)-1-oxoisoindolin-2-yl) piperidine-2,6-dione (139); 3-(5-(6-amino-4-methylpyridin-2-yl)-1-oxoisoindolin-2-yl)piperidine-2,6-dione (140); 3-(5-(3,4-dihydro-2H-pyrido[3,2-b][1,4]oxazin-6-yl)-1-oxoisoindolin-2-yl)piperidine-2,6-dione (141); 3-(5-(6-aminopyrazin-2-yl)-1-oxoisoindolin-2-yl)piperidine-2,6-dione (142); 3-(5-(2-amino-6-methylpyrimidin-4-yl)-1-oxoisoindolin-2-yl)piperidine-2,6-dione (143); 3-(5-(4,6-dimethylpyridin-2-yl)-1-oxoisoindolin-2-yl)piperidine-2,6-dione (144); 3-(5-(5-chloro-3-hydroxyisoquinolin-1-yl)-1-oxoisoindolin-2-yl)piperidine-2,6-dione (145); 3-(5-(6-methoxy-4-methylpyridin-2-yl)-1-oxoisoindolin-2-yl) piperidine-2,6-dione (146); 3-(5-(6-hydroxy-4-methylpyridin-2-yl)-1-oxoisoindolin-2-yl)piperidine-2,6-dione (147); 2-amino-6-(2-(2,6-dioxopiperidin-3-yl)-1-oxoisoindolin-5-yl)-4-methylnicotinonitrile (148); 2-amino-6-(2-(2,6-dioxopiperidin-3-yl)-1-oxoisoindolin-5-yl) isonicotinonitrile (149); 3-(5-(1-amino-5,6,7,8-tetrahydroisoquinolin-3-yl)-1-oxoisoindolin-2-yl) piperidine-2,6-dione (150); 3-(5-(6-amino-4,5-dimethylpyridin-2-yl)-1-oxoisoindolin-2-yl) piperidine-2,6-dione (151); 6-(2-(2,6-dioxopiperidin-3-yl)-1-oxoisoindolin-5-yl)-4-methylnicotinonitrile (152); 3-(5-(6-amino-5-methoxy-4-methylpyridin-2-yl)-1-oxoisoindolin-2-yl)piperidine-2,6-dione (153); 3-(5-(6-amino-5-methoxy-4-methylpyridin-2-yl)-1-oxoisoindolin-2-yl)piperidine-2,6-dione (154); 3-[5-(6-methoxypyridin-2-yl)-1-oxo-2,3-dihydro-1H-isoindol-2-yl]piperidine-2,6-dione (155); 3-[5-(1-methoxyisoquinolin-3-yl)-1-oxo-2,3-dihydro-1H-isoindol-2-yl]piperidine-2,6-dione (156); 3-[1-oxo-5-(1-oxo-1,2-dihydroisoquinolin-3-yl)-2,3-dihydro-1H-isoindol-2-yl]piperidine-2,6-dione (157); 3-(5-{1-benzyl-1H-pyrrolo[3,2-c]pyridin-6-yl}-1-oxo-2,3-dihydro-1H-isoindol-2-yl) piperidine-2,6-dione (158); 3-(1-oxo-5-(1H-pyrrolo[3,2-c]pyridin-6-yl)isoindolin-2-yl)piperidine-2,6-dione (159);

3-(1-oxo-5-(1H-pyrrolo[3,2-c]pyridin-4-yl)isoindolin-2-yl) piperidine-2,6-dione (160); 3-(5-(1-benzyl-1H-pyrrolo[3,2-c]pyridin-4-yl)-1-oxoisoindolin-2-yl)piperidine-2,6-dione (161); 6-(2-(2,6-dioxopiperidin-3-yl)-1-oxoisoindolin-5-yl) picolinonitrile (162); 3-(5-(6-amino-4-(trifluoromethyl) pyridin-2-yl)-1-oxoisoindolin-2-yl)piperidine-2,6-dione (163); 3-(5-(6-amino-4-methoxypyridin-2-yl)-1-oxoisoindolin-2-yl)piperidine-2,6-dione (164); 3-(5-(6-amino-4-chloropyridin-2-yl)-1-oxoisoindolin-2-yl)piperidine-2,6-dione (165); 2-amino-6-(2-(2,6-dioxopiperidin-3-yl)-1-oxoisoindolin-5-yl)nicotinonitrile (166); 2-amino-6-(2-(2,6-dioxopiperidin-3-yl)-1-oxoisoindolin-5-yl)pyridine-3,5-dicarbonitrile (168); 2-amino-6-(2-(2,6-dioxopiperidin-3-yl)-1-oxoisoindolin-5-yl)-5-fluoronicotinonitrile (169); 3-(5-(6-amino-4-phenylpyridin-2-yl)-1-oxoisoindolin-2-yl) piperidine-2,6-dione (170); 6-amino-2-(2-(2,6-dioxopiperidin-3-yl)-1-oxoisoindolin-5-yl)-4-(trifluoromethyl)nicotinenitrile (171); 2-amino-6-(2-(2,6-dioxopiperidin-3-yl)-1-oxoisoindolin-5-yl)-4-propylnicotinonitrile (172); 6-amino-2-(2-(2,6-dioxopiperidin-3-yl)-1-oxoisoindolin-5-yl)-4-propylnicotinonitrile (173); 6-amino-4-(difluoromethyl)-2-(2-(2,6-dioxopiperidin-3-yl)-1-oxoisoindolin-5-yl) nicotinonitrile (174); 2-amino-6-(2-(2,6-dioxopiperidin-3-yl)-1-oxoisoindolin-5-yl)-5-(trifluoromethyl)nicotine-nitrile (175); 2-amino-4-(difluoromethyl)-6-(2-(2,6-dioxopiperidin-3-yl)-1-oxoisoindolin-5-yl) nicotinonitrile (176); 2-amino-6-(2-(2,6-dioxopiperidin-3-yl)-1-oxoisoindolin-5-yl)-4-(trifluoromethyl)nicotine-nitrile (177); 2-amino-6-(2-(2,6-dioxopiperidin-3-yl)-1-oxoisoindolin-5-yl)-4-isopropylnicotinonitrile (178); 6-amino-2-(2-(2,6-dioxopiperidin-3-yl)-1-oxoisoindolin-5-yl)-4-isopropylnicotinonitrile (179); 6-amino-2-(2-(2,6-dioxopiperidin-3-yl)-1-oxoisoindolin-5-yl)-5-methylnicotinonitrile (180); 2-amino-6-(2-(2,6-dioxopiperidin-3-yl)-1-oxoisoindolin-5-yl)-5-methoxynicotinonitrile (181); 6-amino-5-cyclopropyl-2-(2-(2,6-dioxopiperidin-3-yl)-1-oxoisoindolin-5-yl) nicotinonitrile (182); 2-amino-5-cyclopropyl-6-(2-(2,6-dioxopiperidin-3-yl)-1-oxoisoindolin-5-yl) nicotinonitrile (183); 3-(5-(6-amino-4-(4-benzylpiperazin-1-yl) pyridin-2-yl)-1-oxoisoindolin-2-yl) piperidine-2,6-dione (184); 3-(5-(6-amino-4-(4-(methylsulfonyl)piperazin-1-yl)pyridin-2-yl)-1-oxoisoindolin-2-yl) piperidine-2,6-dione (185); 3-(5-(4-(4-acetylpiperazin-1-yl)-6-aminopyridin-2-yl)-1-oxoisoindolin-2-yl)piperidine-2,6-dione (186); 3-(5-(4-methyl-6-(methylamino)pyridin-2-yl)-1-oxoisoindolin-2-yl) piperidine-2,6-dione (187); 3-(5-(6-(ethylamino)-4-methylpyridin-2-yl)-1-oxoisoindolin-2-yl)piperidine-2,6-dione (188); or 3-(5-(4,5-dimethyl-6-(methylamino)pyridin-2-yl)-1-oxoisoindolin-2-yl)piperidine-2,6-dione (189);

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group $—NH_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, $—CF_3$ and $—CH_2CF_3$.

The term "alkoxy," as used herein, refers to an alkyl group attached to the parent molecular moiety through an oxygen atom, for example, methoxy group ($—OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The compounds of the present invention include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salt(s) formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in Rautio, J. et al., *Nature Review DrugDiscovery,* 17, 559-587 (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

“Stable compound” and “stable structure” are meant to indicate a compound that is sufficiently robust to survive isolation to a useful degree of purity from a reaction mixture, and formulation into an efficacious therapeutic agent. The present invention is intended to embody stable compounds.

The term “Helios inhibitor” refers to an agent capable of decreasing Helios protein levels, decreasing Helios activity level and/or inhibiting Helios expression level in the cells to control Treg differentiation. The Helios inhibitor may be a reversible or irreversible inhibitor.

As used herein, “Helios” protein refers a protein that is a member of the Ikaros family of zinc finger proteins. In humans, Helios is encoded by the IKZF2 gene. Helios is also known as IKAROS family zinc finger 2, ANF1A2, ZNF1A2, ZNFN1A2, zinc finger protein, subfamily 1A, 2, and Ikaros family zinc finger protein 2. The members of this protein family include Ikaros, Helios, Aiolos, Eos, and Pegasus. As used herein Helios protein includes various isoform, which includes the isoforms 1-5 listed below.

Isoform 1 (UniProt Q9UKS7-1)

(SEQ ID NO: 1)

METEAIDGYITCDNELSPEREHSNMAIDLTSSTPNGQHASPSHMTSTNS
VKLEMQSDEECDRKPLSREDEIRGHDEGSSLEEPLIESSEVADNRKVQE
LQGEGGIRLPNGKLKCDVCGMVCIGPNVLMVHKRSHTGERPFHCNQCGA
SFTQKGNLLRHIKLHSGEKPFKCPFCSYACRRRDALTGHLRTHSVGKPH
KCNYCGRSYKQRSSLEEHKERCHNYLQNVSMEAAGQVMSHHVPPMEDCK
EQEPIMDNNISLVPFERPAVIEKLTGNMGKRKSSTPQKFVGEKLMRFSY
PDIHFDMNLTYEKEAELMQSHMMDQAINNAITYLGAEALHPLMQHPPST
IAEVAPVISSAYSQVYHPNRIERPISRETADSHENNMDGPISLIRPKSR
PQEREASPSNSCLDSTDSESSHDDHQSYQGHPALNPKRKQSPAYMKEDV
KALDTTKAPKGSLKDIYKVENGEGEQIRAFKCEHCRVLFLDHVMYTIHM
GCHGYRDPLECNICGYRSQDRYEFSSHIVRGEHTFH

Isoform 2 (UniProt Q9UKS7-2)

(SEQ ID NO: 2)

METEAIDGYITCDNELSPEREHSNMAIDLTSSTPNGQHASPSHMTSTNS
VKLEMQSDEECDRKPLSREDEIRGHDEGSSLEEPLIESSEVADNRKVQE
LQGEGGIRLPNGERPFHCNQCGASFTQKGNLLRHIKLHSGEKPFKCPFC
SYACRRRDALTGHLRTHSVGKPHKCNYCGRSYKQRSSLEEHKERCHNYL
QNVSMEAAGQVMSHHVPPMEDCKEQEPIMDNNISLVPFERPAVIEKLTG
NMGKRKSSTPQKFVGEKLMRFSYPDIHEDMNLTYEKEAELMQSHMMDQA
INNAITYLGAEALHPLMQHPPSTIAEVAPVISSAYSQVYHPNRIERPIS
RETADSHENNMDGPISLIRPKSRPQEREASPSNSCLDSTDSESSHDDHQ
SYQGHPALNPKRKQSPAYMKEDVKALDTTKAPKGSLKDIYKVENGEGEQ
IRAFKCEHCRVLFLDHVMYTIHMGCHGYRDPLECNICGYRSQDRYEFSS
HIVRGEHTFH

Isoform 4 (UniProt Q9UKS7-4)

(SEQ ID NO: 3)

METEAIDGYITCDNELSPEREHSNMAIDLTSSTPNGQHASPSHMTSTNS
VKLEMQSDEECDRKPLSREDEIRGHDEGSSLEEPLIESSEVADNRKVQE
LQGEGGIRLPNGERPFHCNQCGASFTQKGNLLRHIKLHSGEKPFKCPFC

-continued

SYACRRRDALTGHLRTHSVGKPHKCNYCGRSYKQRSSLEEHKERCHNYL
QNVSMEAAGQVMSHHGEKLMRFSYPDIHFDMNLTYEKEAELMQSHMMDQ
AINNAITYLGAEALHPLMQHPPSTIAEVAPVISSAYSQVYHPNRIERPI
SRETADSHENNMDGPISLIRPKSRPQEREASPSNSCLDSTDSESSHDDH
QSYQGHPALNPKRKQSPAYMKEDVKALDTTKAPKGSLKDIYKVENGEGE
QIRAFKCEHCRVLFLDHVMYTIHMGCHGYRDPLECNICGYRSQDRYEFS
SHIVRGEHTFH

Isoform 6 (UniProt Q9UKS7-6)

(SEQ ID NO: 4)

METEAIDGYITCDNELSPEREHSNMAIDLTSSTPNGQHASPSHMTSTNS
VKLEMQSDEECDRKPLSREDEIRGHDEGSSLEEPLIESSEVADNRKVQE
LQGEGGIRLPNGKLKCDVCGMVCIGPNVLMVHKRSHTGERPFHCNQCGA
SFTQKGNLLRHIKLHSGEKPFKCPFCSYACRRRDALTGHLRTHSVGKPH
KCNYCGRSYKQRSSLEEHKERCHNYLQNVSMEAAGQVMSHHDS

Isoform 7 (UniProt Q9UKS7-7)

(SEQ ID NO: 5)

METEAIDGYITCDNELSPEREHSNMAIDLTSSTPNGQHASPSHMTSTNS
VKLEMQSDEECDRKPLSREDEIRGHDEGSSLEEPLIESSEVADNRKVQE
LQGEGGIRLPNGERPFHCNQCGASFTQKGNLLRHIKLHSGEKPFKCPFC
SYACRRRDALTGHLRTHSVPPMEDCKEQEPIMDNNISLVPFERPAVIEK
LTGNMGKRKSSTPQKFVGEKLMRFSYPDIHFDMNLTYEKEAELMOSHMM
DQAINNAITYLGAEALHPLMQHPPSTIAEVAPVISSAYSQVYHPNRIER
PISRETADSHENNMDGPISLIRPKSRPQEREASPSNSCLDSTDSESSHD
DHQSYQGHPALNPKRKQSPAYMKEDVKALDTTKAPKGSLKDIYKVFNGE
GEQIRAFKCEHCRVLFLDHVMYTIHMGCHGYRDPLECNICGYRSQDRYE
FSSHIVRGEHTFH

The “Helios” isoforms 1, 2, 4, 6, and 7 listed above includes the degron FHCNQCGASFTQKGNLLRHIKLH (SEQ ID NO: 6)(bold and underlined). A degron is a portion of a protein that plays a role in regulating protein degradation rates.

As used herein, “Eos” protein is encoded by the IKZF4 gene, and is also known as IKAROS family zinc finger 4, ZNFN1A4, zinc finger protein, subfamily 1A, 4, Ikaros family zinc finger protein 4, and KIAA1782. “Eos” protein includes isoforms encoded by the following two human isoforms 1 (Q9H2S9-1) and 2 (Q9H2S9-2):

Isoform 1 (UniProt Q9H2S9-1)

(SEQ ID NO: 7)

MHTPPALPRRFQGGGRVRTPGSHRQGKDNLERDPSGGCVPDFLPQAQDS
NHFIMESLFCESSGDSSLEKEFLGAPVGPSVSTPNSQHSSPSRSLSANS
IKVEMYSDEESSRLLGPDERLLEKDDSVIVEDSLSEPLGYCDGSGPEPH
SPGGIRLPNGKLKCDVCGMVCIGPNVLMVHKRSHTGERPFHCNQCGASF
TQKGNLLRHIKLHSGEKPFKCPFCNYACRRRDALTGHLRTHSVSSPTVG
KPYKCNYCGRSYKQQSTLEEHKERCHNYLQSLSTEAQALAGQPGDEIRD
LEMVPDSMLHSSSERPTFIDRLANSLTKRKRSTPQKFVGEKQMRFSLSD
LPYDVNSGGYEKDVELVAHHSLEPGFGSSLAFVGAEHLRPLRLPPTNCI

-continued

SELTPVISSVYTQMQPLPGRLELPGSREAGEGPEDLADGGPLLYRPRGP

LTDPGASPSNGCQDSTDTESNHEDRVAGVVSLPQGPPPQPPPTIVVGRH

SPAYAKEDPKPQEGLLRGTPGPSKEVLRVVGESGEPVKAFKCEHCRILF

LDHVMFTIHMGCHGFRDPFECNICGYHSQDRYEFSSHIVRGEHKVG

Isoform 2 (UniProt Q9H2S9-2)

(SEQ ID NO: 8)

MDSRYLQLQLYLPSCSLLQGSGDSSLEKEFLGAPVGPSVSTPNSQHSSP

SRSLSANSIKVEMYSDEESSRLLGPDERLLEKDDSVIVEDSLSEPLGYC

DGSGPEPHSPGGIRLPNGKLKCDVCGMVCIGPNVLMVHKRSHTGERPFH

CNQCGASFTQKGNLLRHIKLHSGEKPFKCPFCNYACRRRDALTGHLRTH

SVSSPTVGKPYKCNYCGRSYKQQSTLEEHKERCHNYLQSLSTEAQALAG

QPGDEIRDLEMVPDSMLHSSSERPTFIDRLANSLTKRKRSTPQKFVGEK

QMRFSLSDLPYDVNSGGYEKDVELVAHHSLEPGFGSSLAFVGAEHLRPL

RLPPTNCISELTPVISSVYTQMQPLPGRLELPGSREAGEGPEDLADGGP

LLYRPRGPLTDPGASPSNGCQDSTDTESNHEDRVAGVVSLPQGPPPQPP

PTIVVGRHSPAYAKEDPKPQEGLLRGTPGPSKEVLRVVGESGEPVKAFK

CEHCRILFLDHVMFTIHMGCHGFRDPFECNICGYHSQDRYEFSSHIVRG

EHKVG

The "Eos" protein isoforms 1 and 2 listed above includes the degron FHCNQCGASFTQKGNLLRHIKLH (SEQ ID NO: 6) (bold and underlined), which is the same as the degron for the "Helios" protein.

As used herein, "Ikaros" protein is encoded by the IKZF1 gene. Ikaros is also known as TKAROS family zinc finger 1, ZNFN1A1, zinc finger protein, subfamily 1A, 1, Ikaros family zinc finger protein 1, IK1, lymphoid transcription factor LyF-1, Hs.54452, PPP1R92, protein phosphatase 1, regulatory subunit 92, PR00758, CVID13, and CLL-associated antigen KW-6. Ikaros protein includes isoforms encoded by amino acid sequences Q13422-1, Q13422-2, Q13422-3, Q13422-4, Q13422-7, and Q13422-8. Ikaros protein also includes isoforms encoded by amino acid sequences Q13422-5 and Q13422-6.

As used herein, "Aiolos" protein is encoded by the IKZF3 gene. Aiolos protein is also known as IKAROS family zinc finger 3, ZNFN1A3, zinc finger protein, subfamily 1A, 3, Ikaros family zinc finger protein 3, and AIO. Aiolos protein includes isoforms encoded by amino acid sequences Q9UKT9-1, Q9UKT9-3, Q9UKT9-4, Q9UKT9-6, Q9UKT9-7, Q9UKT9-8, Q9UKT9-9, and Q9UKT9-14. Aiolos protein also includes isoforms encoded by amino acid sequences Q9UKT9-2, Q9UKT9-5, Q9UKT9-10, Q9UKT9-11, Q9UKT9-12, and Q9UKT9-13, Q9UKT9-15, and Q9UKT9-16.

As used herein, "Pegasus" protein is also known as IKAROS family zinc finger 5, ZNFN1A5, zinc finger protein, subfamily 1A, 5, and Ikaros family zinc finger protein 5. Pegasus is encoded by the IKZF5 gene.

As used herein, the term "contacting" refers to the bringing together of indicated moieties in an in vitro system or an in vivo system. For example, "contacting" Helios protein with a compound of Formula (I) includes the administration of a compound of the present invention to an individual or patient, such as a human, having Helios protein, as well as, for example, introducing a compound of Formula (I) into a sample containing a cellular or purified preparation containing Helios protein.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. In contrast, "prophylaxis" or "prevention" refers to administration to a subject who does not have a disease to prevent the disease from occurring. "Treat," "treating," and "treatment" does not encompass prophylaxis or prevention.

"Therapeutically effective amount" is intended to include an amount of a compound of the present invention alone or an amount of the combination of compounds claimed or an amount of a compound of the present invention in combination with other active ingredients effective to decrease Helios protein levels, decrease Helios activity levels and/or inhibit Helios expression levels in the cells, or effective to treat or prevent viral infections and proliferative disorders, such as cancer.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

The term "patient" includes human and other mammalian subjects that receive either therapeutic or prophylactic treatment.

The term "subject" includes any human or non-human animal. For example, the methods and compositions herein disclosed can be used to treat a subject having cancer. A non-human animal includes all vertebrates, e.g., mammals and non-mammals, including non-human primates, sheep, dogs, cows, chickens, amphibians, reptiles, etc. In one embodiment, the subject is a human subject.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising a compound of the invention in combination with at least one additional pharmaceutically acceptable carrier.

Utility

The compounds of Formula (I) are useful for the treatment of cancer.

In one embodiment, the present invention provides a combined preparation of a compound of Formula (I), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the activity of Helios protein. The combined preparation can be used to decrease Helios protein level, Helios activity level and/or Helios expression level in the cells to control Treg differentiation.

The compounds for Formula (I) and pharmaceutical compositions comprising at least one compound of Formula (I) are useful in treating or preventing any diseases or conditions that are associated with the activity of Helios protein. These include viral and other infections (e.g., skin infections, GI infection, urinary tract infections, genito-urinary infections, systemic infections), and proliferative diseases (e.g., cancer). The compounds of Formula (I) and pharmaceutical compositions comprising in at least one compound of Formula (I) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of Formula (I) or pharmaceutical composition comprising at least compound of Formula (I) is administered orally. In other embodiments, the Formula (I) or pharmaceutical composition comprising at least compound of Formula (I) is administered parenterally.

The compounds of Formula (I) can selectively decrease Helios protein levels, decrease Helios activity levels and/or inhibit Helios expression levels in the cells to control Treg differentiation. For example, the compounds of Formula (I) can be used to selectively decrease Helios activity levels and/or inhibit Helios expression levels in the cells to control Treg differentiation in a cell or in an individual in need of a decrease in Helios protein levels, decrease in Helios activity levels and/or inhibition of Helios expression level by administering an inhibiting amount of a compound of Formula (I) or a salt thereof.

In one aspect, the compound(s) of Formula (I) are sequentially administered prior to administration of the immuno-oncology agent. In another aspect, compound(s) of Formula (I) are administered concurrently with the immuno-oncology agent. In yet another aspect, compound(s) of Formula (I) are sequentially administered after administration of the immuno-oncology agent.

In another aspect, compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fni4, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTOR, Lymphotoxin α 1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO207/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO206/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Types of cancers that may be treated with the compound of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of Formula (I) for treatment of Helios protein associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds of Formula (I) may also be combined with immunotherapy drugs, including cytokines such as interferon alpha, interleukin 2, and tumor necrosis factor (TNF) in the treatment of melanoma.

Compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-$\alpha$), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-10 or TGF-$\beta$).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.,* 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.,* 1(8):792-797 (1995)); (iv) inhibitors of Akt family kinases or the Akt pathway, such as, for example, rapamycin (see, for example, Sekulic et al., *Cancer Res.,* 60:3504-3513 (200)); (v) cell cycle kinase inhibitors such as, for example, flavopiridol and UCN-01 (see, for example, Sausville, *Curr. Med. Chem. Anti-Canc. Agents,* 3:47-56 (203)); and (vi) phosphatidyl inositol kinase inhibitors such as, for example, LY294002 (see, for example, Vlahos et al., *J. Biol. Chem.,* 269:5241-5248 (1994)). Alternatively, at least one STI and at least one compound of Formula (I) may be in separate pharmaceutical compositions. In a specific embodiment of the present invention, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present invention further provides a pharmaceutical composition for the treatment of a chronic viral infection in a patient comprising at least one compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, at least one compound of Formula (I) and at least one chemotherapeutic agent are administered to the patient concurrently or sequentially. In other words, at least one compound of Formula (I) may be administered first, at least one chemotherapeutic agent may be administered first, or at least one compound of Formula (I) and the at least one STI may be administered at the same time. Additionally, when more than one compound of Formula (I) and/or chemotherapeutic agent is used, the compounds may be administered in any order. Similarly, any antiviral agent or STI may also be administered at any point in comparison to the administration of the compound of Formula (I).

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV).

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH—

I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenyl-methyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions

The invention also provides pharmaceutically compositions which comprise a therapeutically effective amount of one or more of the compounds of Formula (I), formulated together with one or more pharmaceutically acceptable carriers (additives) and/or diluents, and optionally, one or more additional therapeutic agents described above.

The compounds of Formula (I) may be administered by any suitable route, preferably in the form of a pharmaceutical composition adapted to such a route, and in a dose effective for the treatment intended. The compounds and compositions of the compound of Formula (I) can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also includes pharmaceutical kits useful, for example, in the treatment or prevention of Helios protein-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of Formula (I) may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 200 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of Formula (I) (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of Formula (I) (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of Formula (I), alone or in combination with a pharmaceutical carrier. Optionally, compounds of Formula (I) can be used alone, in combination with other compounds of Formula (I), or in combination with one or more other therapeutic agent(s), e.g., an anticancer agent or other pharmaceutically active material.

Regardless of the route of administration selected, the compounds of Formula (I), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the therapeutic response for a particular patient, composition, and mode of administration, without being toxic to the patient.

The selected dosage level will depend upon a variety of factors including the activity of the particular compound of Formula (I) employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of Formula (I) employed in the pharmaceutical composition at levels lower than that required in order to achieve the therapeutic effect and gradually increase the dosage until the effect is achieved.

In general, a suitable daily dose of a compound of Formula (I) will be that amount of the compound which is the lowest dose effective to produce a therapeutic effect. Such an effective dose will generally depend upon the factors described above. Generally, oral, intravenous, intracerebroventricular and subcutaneous doses of the compounds of Formula (I) for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of Formula (I) to be administered alone, it is preferable to administer the compound as a pharmaceutical formulation (composition).

The above other therapeutic agents, when employed in combination with the compounds of Formula (I), may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 207).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

General routes to compounds described in the invention are illustrated in Schemes 1-5, where the $R_1$ and A substituents are defined previously in the text or a functional group that can be converted to the final substituent. The substituent L is a leaving group such as a halide (preferably I, Br, or Cl) or a triflate. The substituent M is a suitable coupling partner, such as boronic acid, boronic ester or stannane. The substituent R is a carboxylic acid protecting group such as tert-butyl, methyl, ethyl, or benzyl. As shown in Scheme 1, a general procedure for the preparation of compounds of the invention involves starting with a suitably substituted isoindolinone 1. The leaving group, L, of 1 can be converted a suitable coupling partner, M, using conditions well known to one of ordinary skill in the art or methods described herein to afford intermediate 2. Where M is a boronic acid or boronate ester, 2 can be united with a suitably substituted heterocycle 3 in a Suzuki-Miyaura coupling reaction using a suitable palladium catalyst (e.g. $Pd(PPh_3)_4$ or 1,1'-bis(diphenylphosphino)ferrocene]dichloropalladium(II)) in the presence of a suitable base (e.g. cesium carbonate, potassium phosphate, or sodium bicarbonate) to give 4. Where M is a stannane, 2 can be united with a suitably substituted heterocycle 3 in a Stille coupling reaction using a suitable catalyst system (e.g. $Pd(PPh_3)_4$ or bis(triphenylphosphine)dichloropalladium(II)/CuI) to give 4. Intermediate 4 can be converted to 5 via treatment with a protic acid such as benzenesulfonic acid. Alternately, in some cases, 4 can be converted to 5 by treatment with a base (e.g. $K_2CO_3$, $K_3PO_4$, or LiHMDS). In some cases, intermediate 4 may spontaneously cyclize to 5 under the Suzuki-Miyaura coupling or Stille coupling conditions employed to prepare it.

SCHEME 1

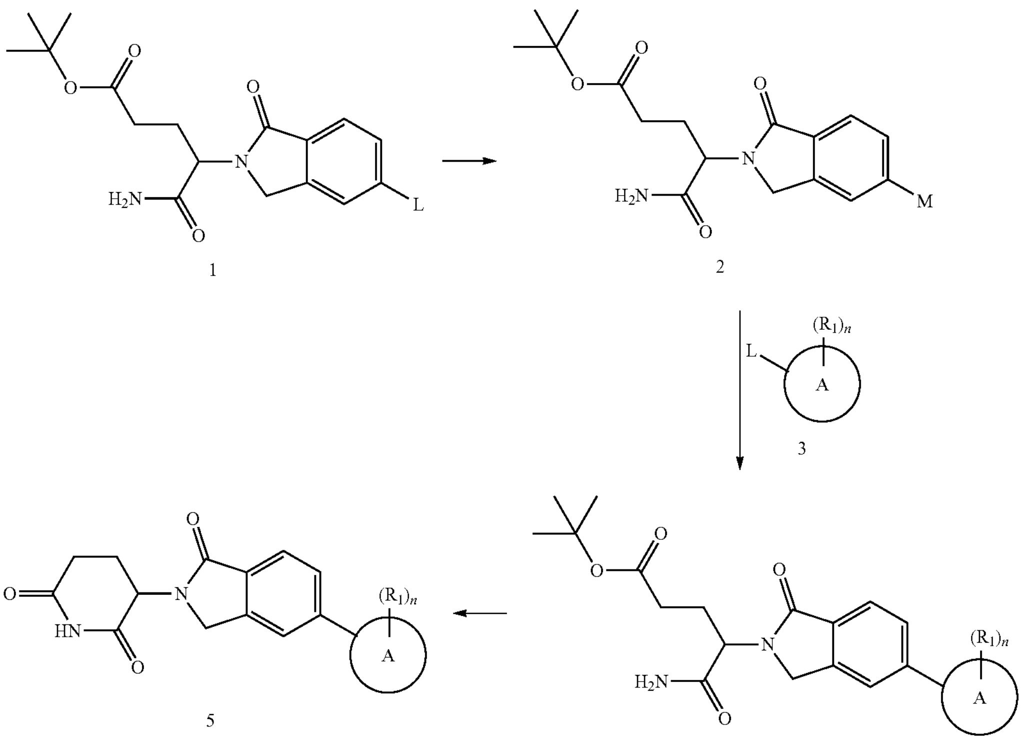

1 2 3 4 5

In some cases, it may be advantageous to couple heterocycle A earlier in the synthetic sequence. In such cases, the leaving group, L, of 6 can be converted a suitable coupling partner, M, using conditions well known to one of ordinary skill in the art or methods described herein to afford intermediate 7. Where M is a boronic acid or boronate ester, 7 can be united with a suitably substituted heterocycle 3 in a Suzuki-Miyaura coupling reaction using a suitable palladium catalyst (e.g. $Pd(PPh_3)_4$ or 1,1'-bis(diphenylphosphino)ferrocene]dichloropalladium(II)) in the presence of a suitable base (e.g. cesium carbonate, potassium phosphate, or sodium bicarbonate) to give 8. Where M is a stannane, 7 can be united with a suitably substituted heterocycle 3 in a Stille coupling reaction using a suitable catalyst system (e.g. $Pd(PPh_3)_4$ or bis(triphenylphosphine)dichloropalladium(II)/CuI) to give 8. The benzylic methyl group can be brominated through the action of NBS in the presence of a radical initiator such as light or AIBN to afford bromide 9. Bromide 9 can be condensed with 3-aminopiperidine-2,6-dione (10) in the presence of a base (e.g. diisopropylethylamine or triethylamine) to afford 5.

SCHEME 2

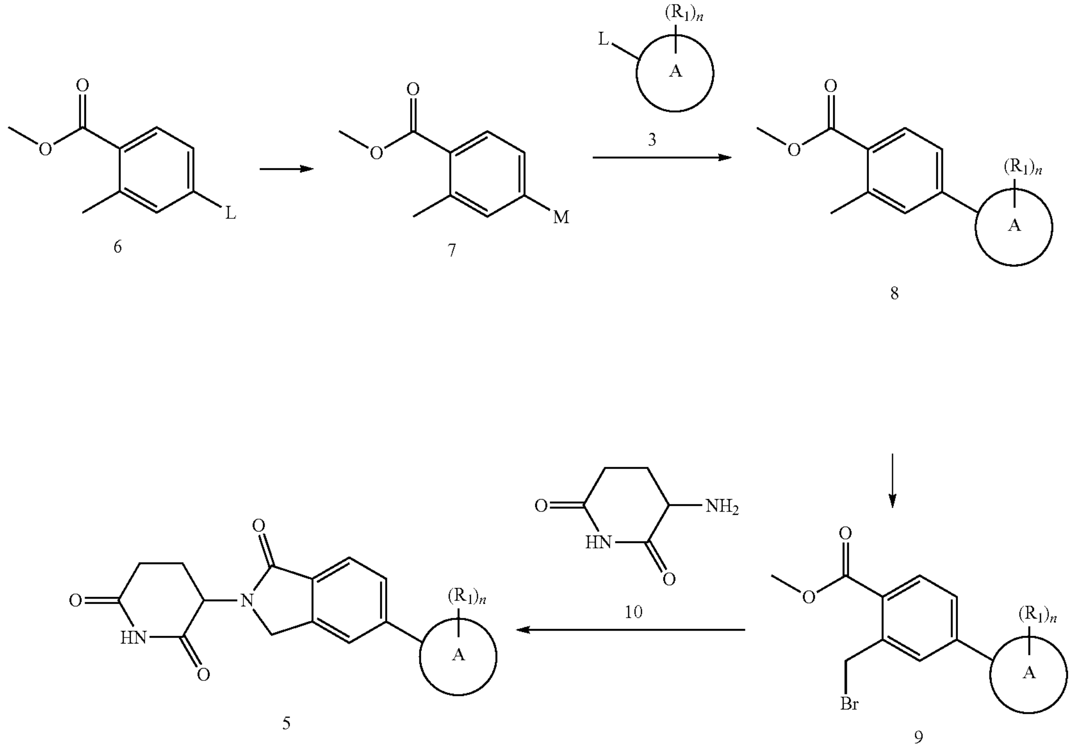

6 7 8 9 5

Alternately, bromide 9 can be condensed with 11 (where R=tert-butyl, methyl, ethyl, or benzyl) in the presence of a base (e.g. diisopropylethylamine or triethylamine) to afford intermediate 12 as shown in Scheme 3. Where R=tert-butyl, intermediate 12 can be further elaborated to compound 5 by methods described in Scheme 1.

SCHEME 3

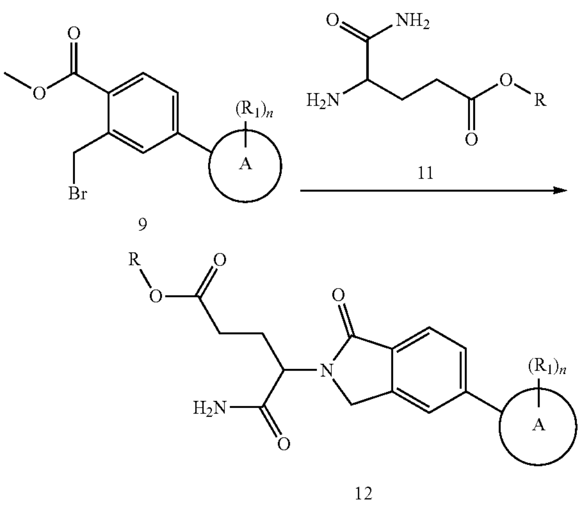

9 12

Depending on the specific selection of acid protecting group R in intermediate 12, different conditions may be required to convert it into compound 5 (Scheme 4). For instance where R=methyl, ethyl, or benzyl, base-induced cyclization of 12 may be preferred for the direct conversion 12 to 5 using a suitable base (e.g. LiHMDS) in a suitable solvent (e.g. tetrahydrofuran). Where R=tert-butyl, acid-induced cyclization of 12 may be preferred for direct conversion of 12 to 5 using a suitable acid (e.g. benzenesulfonic acid) in a suitable solvent (e.g. acetonitrile). In some cases, it may be preferable to use a twostep procedure, first liberating free carboxylic acid 13 using conditions which are appropriate to the specific acid protecting group R. Such methods are well known to one of ordinary skill in the art of organic synthesis. For instance where R=tert-butyl, acid hydrolysis using a suitable acid (e.g. trifluoroacetic acid or hydrochloric acid) may be preferred. Where R=methyl, ethyl, or benzyl, basic hydrolysis using a suitable base (e.g. LiOH) may be preferred. In other cases, where R=benzyl, it may be advantageous to deprotect by the action of palladium-catalyzed hydrogenolysis.

Once liberated, the carboxylic acid of 13 can be activated toward intramolecular attack by the pendant primary amide by the action of thionyl chloride/dimethylformamide or carbonyldiimidazole/dimethylaminopyridine to afford 5.

SCHEME 4

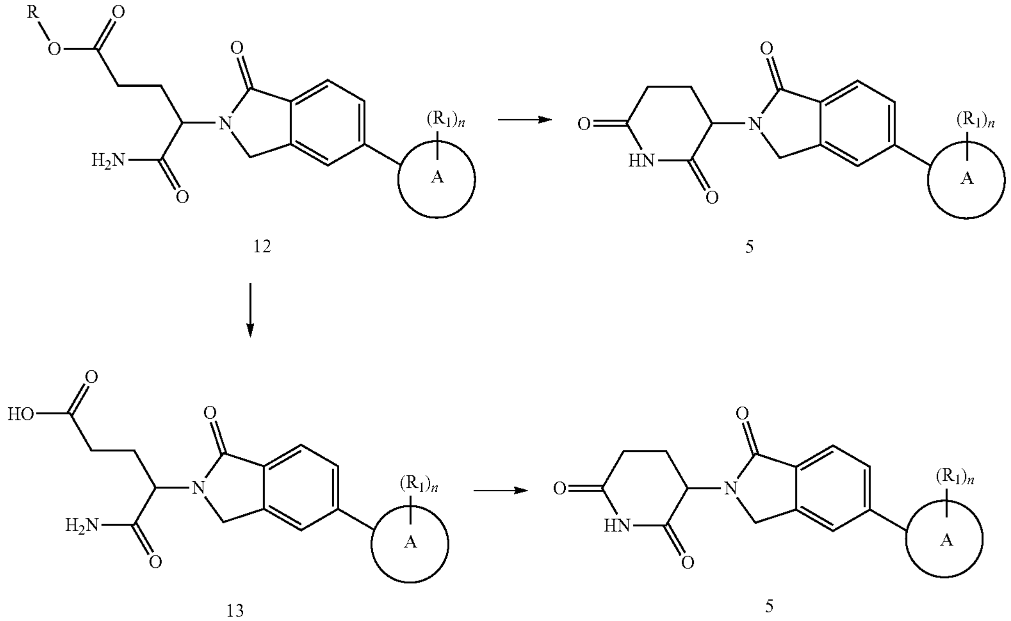

12 5

13 5

As shown in the previous schemes, isoindolinones substituted with a suitable leaving group L are useful intermediates in the synthesis of Formula (I) compounds. They may be prepared as outlined in Scheme 5 where L is a leaving group such as halide. To begin, the benzylic methyl group of intermediate 6 can be brominated through the action of NBS in the presence of a radical initiator such as light or AIBN to afford bromide 14. Bromide 14 can be condensed with 3-aminopiperidine-2,6-dione (10) in the presence of a base (e.g. diisopropylethylamine or triethylamine) to afford 15. In some cases, it may be possible to convert intermediate 15 to 5 by methods analogous to the conversion of 1 to 4 (Scheme 1). In other cases, it may be preferable to condense bromide 14 with intermediate 11 to afford 16. Intermediate 16 can be converted to 5 by methods analogous to those described in Scheme 1 and Scheme 4.

SCHEME 5

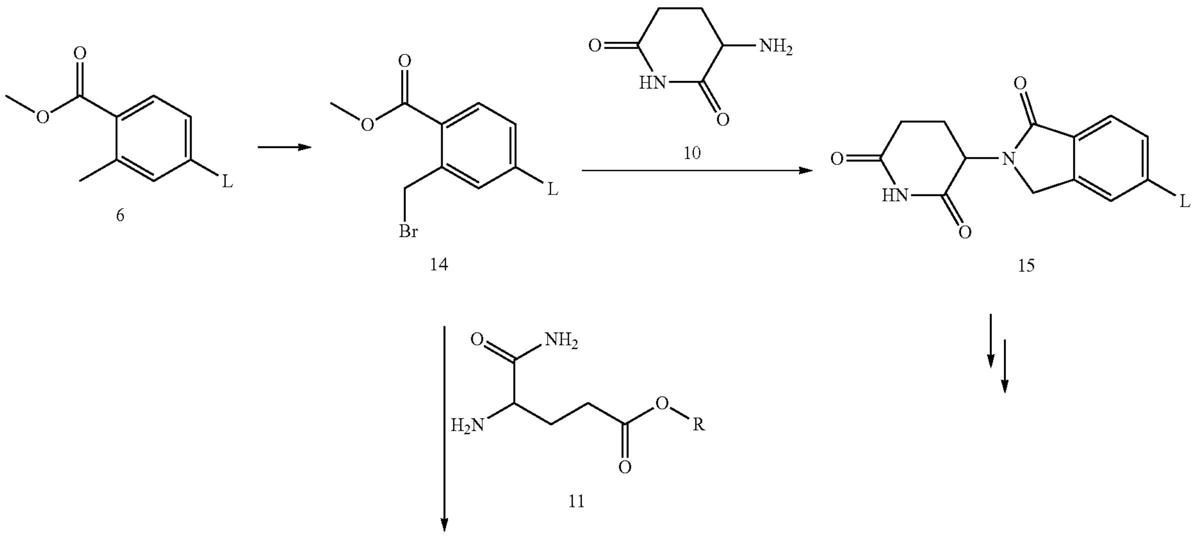

6 14 10 15

11

-continued

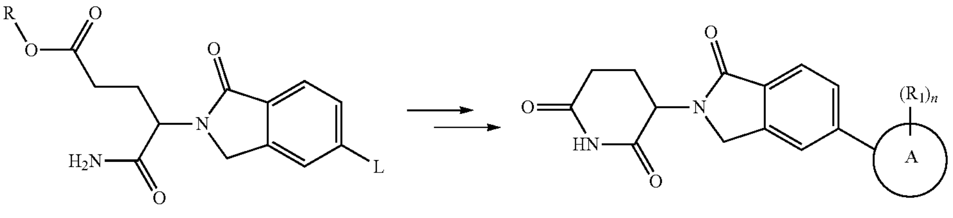

16 5

EXAMPLES

The following examples illustrate the particular embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example. Compounds of the Examples are identified by the example and step in which they were prepared (e.g., “1-A” denotes the Example 1, step A), or by the example only where the compound is the title compound of the example (for example, “1” denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well-known bioisosteric replacements known in the art, for example, replacement of a carboxylic acid group with a tetrazole or a phosphate moiety.

Abbreviations

AcOH acetic acid
ACN acetonitrile
AIBN 2,2-azobisiosbutyronitrile
BuLi n-butyl lithium
DCE dichloroethane
DCM dichloromethane
DIEA N,N-diisopropylethylamine
DMF dimethylformamide
DMPU N,N-dimethylpropyleneurea
DMSO dimethyl sulfoxide
dppf bis(diphenylphosphino)ferrocene
EtOH ethanol
EtOAc ethyl acetate
Hex hexanes
HPLC High Performance Liquid Chromatography
Hunig’s base N,N-diisopropylethylamine
LDA lithium diisopropylamide
LiHMDS lithium bis(trimethylsilyl)amide
m-CPBA 3-chloroperbenzoic acid
MeCN acetonitrile
min minute(s)
mL milliliter(s)
$NaBH(OAc)_3$ sodium triacetoxyborohydride
NBS n-bromosuccinimide
$PdCl_2(dppf)_2$ [1,1'-bis(diphenylphosphino)ferrocene]dichloropalladium(II)
$PdCl_2(dtbpf)$ [1,1'-Bis(di-tert-butylphosphino)ferrocene] dichloropalladium(II)
$Pd_2(dba)_3$ tris-(dibenzylideneacetone)dipalladium
$Pd(PPh_3)_4$ tetrakis(triphenylphosphine)palladium
$PhSO_3H$ benzene sulfonic acid
TEA triethylamine
THE tetrahydrofuran
TPGS D-α-tocopheryl polyethylene glycol succinate
XantPhos 4,5-bis(diphenylphosphino)-9,9 dimethylxanthene
XPhos Pd G2 chloro(2-dicyclohexylphosphino-2',4',6'-triisopropyl-1,1'-biphenyl)[2-(2'-amino-1,1'-biphenyl)] palladium(II)

HPLC Conditions:

Analytical HPLC Method 1: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Analytical HPLC Method 2: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

Preparative HPLC Method 1: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 15% B, 15-50% B over 25 min, then a 6-min hold at 100% B; Flow Rate: 20 mL/min; Column Temperature: 25° C. Fraction collection was triggered by MS signals.

Preparative HPLC Method 2: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 0% B, 0-40% B over 24 min, then a 4-min hold at 100% B; Flow Rate: 20 mL/min; Column Temperature: 25° C. Fraction collection was triggered by MS signals.

Preparative HPLC Method 3: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-min hold at 0% B, 0-25% B over 28 min, then a 4-min hold at 100% B; Flow Rate: 20 mL/min; Column Temperature: 25° C. Fraction collection was triggered by MS signals.

Preparative HPLC Method 4: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 3-min hold at 0% B, 0-35% B over 30 min, then a 6-min hold at 100% B; Flow Rate: 20 mL/min; Column Temperature: 25° C. Fraction collection was triggered by MS signals. Fractions containing the product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 0% B, 0-40% B over 28 min, then a 6-min hold at 100% B; Flow Rate: 20 mL/min; Column Temperature: 25° C. Fraction collection was triggered by MS signals.

Preparative HPLC Method 5: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 4% B, 4-44% B over 23 min, then a 4-min hold at 100% B; Flow Rate: 20 mL/min; Column Temperature: 25° C. Fraction collection was triggered by MS signals. Fractions containing the product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 26% B, 26-66% B over 20 min, then a 4-min hold at 100% B; Flow Rate: 20 mL/min; Column Temperature: 25° C. Fraction collection was triggered by MS signals.

Preparative HPLC Method 6: Phenomenex Luna Axi C18, 100 mm×30 mm, 5-m particles; Mobile Phase A: 5:95 acetonitrile:water with 0.1% trifluoroacetic acid; Mobile Phase B: 95:5 acetonitrile:water with 0.1% trifluoroacetic acid; Gradient: a 2-mi hold at 20% B, 20-100% B over 11 min, then a 2-min hold at 100% B; Flow Rate: 25 mL/min; Fraction collection was triggered by UV signals.

Preparative HPLC Method 7: Phenomenex Luna Axi C18, 100 mm×30 mm, 5-m particles; Mobile Phase A: 5:95 acetonitrile:water with 0.1% trifluoroacetic acid; Mobile Phase B: 95:5 acetonitrile:water with 0.1% trifluoroacetic acid; Gradient: a 2-mi hold at 7% B, 7-100% B over 10 min, then a 3-min hold at 100% B; Flow Rate: 30 mL/min; Fraction collection was triggered by UV signals.

Preparative HPLC Method 8: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 5% B, 5-55% B over 20 min, then a 4-min hold at 100% B; Flow Rate: 20 mL/min; Column Temperature: 25° C. Fraction collection was triggered by MS signals.

Preparative HPLC Method 9: XBridge C18, 200 mm×19 mm, 5-μm particles; Mobile Phase A: 5:95 acetonitrile:water with ammonium acetate; Mobile Phase B: 95:5 acetonitrile: water with ammonium acetate; Gradient: a 0-min hold at 0% B, 0-30% B over 23 min, then a 4-min hold at 100% B; Flow Rate: 20 mL/min; Column Temperature: 25° C. Fraction collection was triggered by MS signals.

Preparative HPLC Method 10: Phenomenex Luna Axi C18, 100 mm×30 mm, 5-m particles; Mobile Phase A: 5:95 acetonitrile:water with 0.1% trifluoroacetic acid; Mobile Phase B: 95:5 acetonitrile:water with 0.1% trifluoroacetic acid; Gradient: a 3 min hold at 40% B, 40-100% B over 4.5 min, then a 3-min hold at 100% B; Flow Rate: 30 mL/min; Fraction collection was triggered by UV signals.

Example 1

3-(1-Oxo-5-(quinolin-2-yl)isoindolin-2-yl)piperidine-2,6-dione (1)

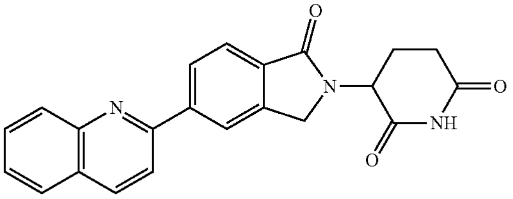

Preparation 1A: tert-Butyl (S)-5-amino-4-(5-bromo-1-oxoisoindolin-2-yl)-5-oxopentanoate To a suspension of tert-butyl (S)-4,5-diamino-5-oxopentanoate hydrochloride (14.46 g, 60.6 mmol) in acetonitrile (231 mL) at 0° C. was added DIEA (20.2 mL, 115 mmol). After stirring for 15 min, the reaction mixture treated with methyl 4-bromo-2-(bromomethyl)benzoate (22 g, 57.7 mmol) as a solid in several portions over 5 min. The reaction mixture stirred at 0° C. for 30 min and then at room temperature overnight. The reaction mixture warmed to 60° C. in an oil bath under a reflux condenser and held at that temperature overnight. The reaction mixture cooled to room temperature with stirring. After cooling to room temperature, a precipitate formed. The flask was placed in a 0° C. bath with stirring. After 30 min, the solid was collected by filtration, rinsed with a minimum of cold acetonitrile, and air dried to give 20.13 g (88% yield) as a white solid. Chiral analytical HPLC analysis indicated that the material was >98% ee. MS (ES): m/z=397.1 $[M+H]^+$. $^1H$ NMR (400 MHz, $CDCl_3$) δ 7.76-7.71 (m, 1H), 7.68-7.62 (m, 2H), 6.22 (br s, 1H), 5.31 (br s, 1H), 4.91 (dd, J=8.7, 6.3 Hz, 1H), 4.62-4.53 (m, 1H), 4.51-4.40 (m, 1H), 2.47-2.10 (m, 4H), 1.44 (s, 9H).

Preparation 1B: tert-Butyl (S)-5-amino-5-oxo-4-(1-oxo-5-(4,4,5,5-tetramethyl-1,3,2-dioxaborolan-2-yl)isoindolin-2-yl)pentanoate A dry flask was charged with Preparation 1A (10.0 g, 25.2 mmol), 4,4,4',4',5,5,5',5'-octamethyl-2,2'-bi(1,3,2-dioxaborolane) (7.67 g, 30.2 mmol), and potassium acetate (7.41 g, 76 mmol) and flushed with nitrogen. The solids were suspended in dioxane (100 mL) and degassed with a stream of nitrogen for 5 min with stirring. The reaction mixture treated with [1,1'-bis(diphenylphosphino)ferrocene]dichloropalladium(II) (0.737 g, 1.007 mmol), degassed for 5 min, sealed, and heated to 60° C. for 18 h. The reaction mixture diluted with EtOAc, filtered through a plug of celite, and rinsed with additional EtOAc. The filtrate was concentrated and purified by 220 gram silica gel column by ISCO (0%→20% B/DCM, where B=15% EtOH/EtOAc+0.1% TEA) to give 9.9 g (89% yield) of Preparation 1B as a white solid. MS (ES): m/z=445.3 $[M+H]^+$. $^1$H NMR (400 MHz, $CDCl_3$) δ 7.99-7.90 (m, 2H), 7.88-7.83 (m, 1H), 6.32 (br s, 1H), 5.36 (br s, 1H), 4.97-4.88 (m, 1H), 4.58-4.41 (m, 2H), 2.48-2.13 (m, 4H), 1.44 (s, 9H), 1.39 (s, 12H).

Example 1: 3-(1-Oxo-5-(quinolin-2-yl)isoindolin-2-yl)piperidine-2,6-dione

A vial was charged with Preparation 1B (30 mg, 0.068 mmol) and 2-chloroquinoline (16.57 mg, 0.101 mmol) and flushed with nitrogen. The solids were suspended in dioxane (540 μL), treated with cesium carbonate (2M in water, 101 μL, 0.203 mmol) and degassed with a stream of nitrogen for 5 min with stirring. The reaction mixture treated with [1,1'-bis(diphenylphosphino)ferrocene]dichloropalladium (II) (4.94 mg, 6.75 μmol), degassed for 5 min, sealed, and heated at 90° C. overnight. The reaction mixture treated with celite, diluted with EtOAc, filtered, and concentrated. The reaction mixture divided into two equal portions in Teflon-lined screw cap vials. To one of these vials was added acetonitrile (0.3 mL) and benzenesulfonic acid (10.7 mg, 0.068 mmol). The reaction vial sealed and placed into pre-heated 90° C. bath and held at that temperature for 1.25 h. The reaction mixture concentrated under a stream of nitrogen, diluted to 2 mL with DMF, and purified by Preparative HPLC Method 1 to give 7.1 mg of Example 1 (28% yield). Optical purity was not determined. MS (ES): m/z=372.0 $[M+H]^+$. $^1$H NMR (400 MHz, DMSO-d6) δ 11.05 (s, 1H), 8.58-8.49 (m, 2H), 8.44 (br d, J=8.0 Hz, 1H), 8.25 (br d, J=8.5 Hz, 1H), 8.13 (d, J=8.5 Hz, 1H), 8.05 (d, J=8.1 Hz, 1H), 7.92 (d, J=8.0 Hz, 1H), 7.83 (t, J=7.5 Hz, 1H), 7.71-7.61 (m, 1H), 5.17 (br dd, J=13.2, 4.5 Hz, 1H), 4.68-4.42 (m, 2H), 3.00-2.89 (m, 1H), 2.64 (br d, J=18.3 Hz, 1H), 2.49-2.39 (m, 1H), 2.12-2.01 (m, 1H).

Example 2

3-(5-(4-Aminoisoquinolin-3-yl)-1-oxoisoindolin-2-yl)piperidine-2,6-dione (2)

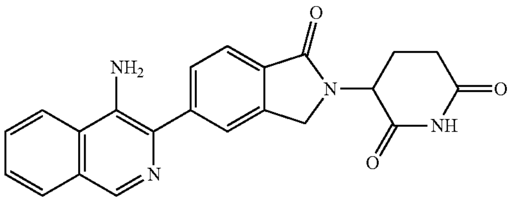

Preparation 1B (20.9 mg, 0.047 mmol), 3-bromoisoquinolin-4-amine (10 mg, 0.045 mmol), and $PdCl_2(dppf)_2$ (3.28 mg, 4.48 μmol) were added to a vial, followed by dioxane (0.5 mL). To this was added cesium carbonate (2M aqueous solution, 67 μL, 0.134 mmol). The vial was sealed and the air was replaced with nitrogen. The reaction mixture heated at 140° C. for 15 min via microwave. After cooling, the reaction mixture diluted with EtOAc, washed with brine, dried over $MgSO_4$, and concentrated. To this was added 1 mL of a solution of benzenesulfonic acid (0.72 gram in 20 mL ACN). The vial was sealed and heated at 140° C. for 8 min via microwave. The reaction mixture diluted with 1 mL of DMSO and purified by Preparative HPLC Method 2 to give 8.8 mg (49% yield) of Example 2. Optical purity was not determined. MS (ES): m/z=387.1 $[M+H]^+$. $^1$H NMR (500 MHz, DMSO-d6) δ 11.04 (s, 1H), 8.82 (s, 1H), 8.43 (br d, J=8.4 Hz, 1H), 8.16 (br d, J=7.8 Hz, 1H), 8.00-7.83 (m, 4H), 7.81-7.74 (m, 1H), 7.17 (s, 2H), 5.17 (br dd, J=13.3, 5.0 Hz, 1H), 4.61-4.41 (m, 2H), 2.93 (br d, J=11.8 Hz, 1H), 2.64 (br d, J=15.7 Hz, 1H), 2.46 (br dd, J=13.6, 4.1 Hz, 1H), 2.06 (br dd, J=10.4, 5.2 Hz, 1H).

Examples 3-45

The compounds in Table 1 were prepared according to the procedures described for Example 2 using the appropriate aryl bromide or aryl chloride:

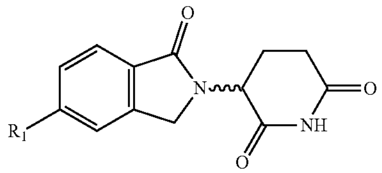

TABLE 1

| Ex. No. | $R_1$ | HPLC[a] $T_{Ret}$ (min) | LC/MS (M + H) | NMR |
|---|---|---|---|---|
| 3 | 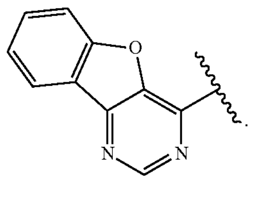 [SMILES: *c1ncnc2c1oc1ccccc12] | 1.38 | 413.1 | $^1$H NMR (500 MHz, DMSO-$d_6$) δ 9.34 (s, 1H), 8.76 (s, 1H), 8.71 (d, J = 7.9 Hz, 1H), 8.33 (d, J = 7.9 Hz, 1H), 8.03 (t, J = 8.2 Hz, 2H), 7.89 (t, J = 7.8 Hz, 1H), 7.64 (t, J = 7.3 Hz, 1H), 5.20 (dd, J = 13.4, 4.9 Hz, 1H), 4.71-4.63 (m, 1H), 4.59-4.50 (m, 1H), 3.03-2.89 (m, 1H), 2.65 (br d, J = 15.9 Hz, 1H), 2.47 (br d, J = 9.2 Hz, 1H), 2.15-2.04 (m, 1H) |

TABLE 1-continued

| Ex. No. | $R_1$ | HPLC[a] $T_{Ret}$ (min) | LC/MS (M + H) | NMR |
|---|---|---|---|---|
| 4 | 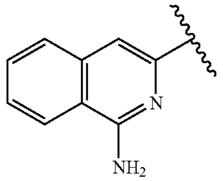 [SMILES: *c1cc2ccccc2c(N)n1] | 0.86 | 387.0 | $^1$H NMR (500 MHz, DMSO-$d_6$) δ 11.03 (s, 1H), 8.88-8.36 (m, 3H), 8.17 (s, 1H), 8.07 (d, J = 8.9 Hz, 1H), 8.01-7.93 (m, 3H), 7.78-7.72 (m, 2H), 5.18 (dd, J = 13.3, 5.1 Hz, 1H), 4.61-4.55 (m, 1H), 4.51-4.44 (m, 1H), 3.00-2.90 (m, 1H), 2.64 (br dd, J = 15.8, 1.9 Hz, 1H), 2.49-2.42 (m, 1H), 2.10-2.02 (m, 1H) |
| 5 | 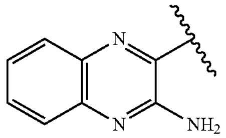 [SMILES: *c1nc2ccccc2nc1N] | 1.06 | 388.2 | $^1$H NMR (500 MHz, DMSO-$d_6$) δ 11.04 (s, 1H), 7.99 (s, 1H), 7.92-7.81 (m, 3H), 7.61 (d, J = 3.3 Hz, 2H), 7.44-7.37 (m, 1H), 6.69 (br s, 2H), 5.18 (br dd, J = 13.3, 5.1 Hz, 1H), 4.60-4.52 (m, 1H), 4.50-4.42 (m, 1H), 2.99-2.88 (m, 1H), 2.64 (br d, J = 16.2 Hz, 1H), 2.49-2.39 (m, 1H), 2.09-2.02 (m, 1H) |
| 6 | 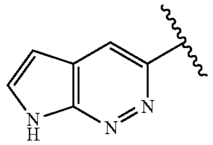 [SMILES: *c1cc2cc[nH]c2nn1] | 0.62 | 362.4 | $^1$H NMR (500 MHz, DMSO-$d_6$) δ 12.59 (br s, 1H), 11.02 (s, 1H), 8.49 (s, 1H), 8.40 (s, 1H), 8.30 (br d, J = 8.5 Hz, 1H), 7.98 (br s, 1H), 7.88 (d, J = 7.9 Hz, 1H), 6.66 (br d, J = 1.2 Hz, 1H), 5.17 (dd, J = 13.4, 4.6 Hz, 1H), 4.63-4.54 (m, 1H), 4.51-4.40 (m, 1H), 3.02-2.87 (m, 1H), 2.68-2.58 (m, 1H), 2.47-2.42 (m, 1H), 2.12-2.01 (m, 1H) |
| 7 | 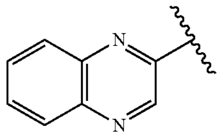 [SMILES: *c1cnc2ccccc2n1] | 1.32 | 373.2 | $^1$H NMR (500 MHz, DMSO-$d_6$) δ 11.05 (s, 1H), 9.65 (s, 1H), 8.56 (s, 1H), 8.48 (br d, J = 8.0 Hz, 1H), 8.18 (dd, J = 15.4, 8.0 Hz, 2H), 7.99-7.86 (m, 3H), 5.16 (br dd, J = 13.3, 4.5 Hz, 1H), 4.67-4.58 (m, 1H), 4.54-4.45 (m, 1H), 2.98-2.87 (m, 1H), 2.65 (br d, J = 17.9 Hz, 1H), 2.50-2.38 (m, 1H), 2.14-2.01 (m, 1H) |
| 8 | 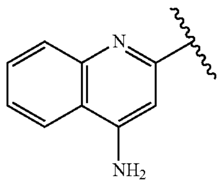 [SMILES: *c1cc(N)c2ccccc2n1] | 0.78 | 387.2 | $^1$H NMR (500 MHz, DMSO-$d_6$) δ 11.03 (s, 1H), 8.30 (br s, 1H), 8.25-8.11 (m, 2H), 7.88 (dd, J = 12.9, 8.2 Hz, 2H), 7.66 (br t, J = 7.7 Hz, 1H), 7.43 (br t, J = 7.5 Hz, 1H), 7.19 (s, 1H), 6.93 (br s, 2H), 5.12 (br dd, J = 13.3, 5.2 Hz, 1H), 4.58 (br d, J = 17.4 Hz, 1H), 4.49-4.39 (m, 1H), 2.96-2.84 (m, 1H), 2.65 (br dd, J = 18.1, 1.4 Hz, 1H), 2.47-2.37 (m, 1H), 2.12-2.01 (m, 1H) |
| 9 | 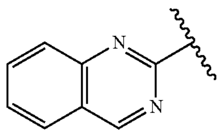 [SMILES: *c1ncc2ccccc2n1] | 1.34 | 373.2 | $^1$H NMR (500 MHz, DMSO-$d_6$) δ 11.01 (s, 1H), 9.71 (s, 1H), 8.74 (s, 1H), 8.69 (br d, J = 8.2 Hz, 1H), 8.19 (d, J = 7.9 Hz, 1H), 8.12-8.03 (m, 2H), 7.92 (d, J = 7.9 Hz, 1H), 7.77 (br t, J = 7.2 Hz, 1H), 5.10 (br dd, J = 13.3, 5.0 Hz, 1H), 4.66-4.56 (m, 1H), 4.53-4.43 (m, 1H), 2.96-2.83 (m, 1H), 2.66 (br d, J = 17.4 Hz, 1H), 2.48-2.37 (m, 1H), 2.14-2.04 (m, 1H) |
| 10 | 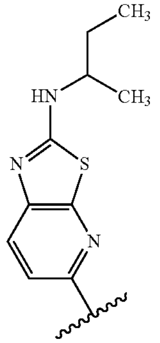 [SMILES: *c1ccc2nc(NC(C)CC)sc2n1] | 1.33 | 450.2 | $^1$H NMR (500 MHz, DMSO-$d_6$) δ 11.02 (s, 1H), 8.39 (d, J = 7.9 Hz, 1H), 8.26 (s, 1H), 8.18 (d, J = 8.0 Hz, 1H), 7.94 (d, J = 8.5 Hz, 1H), 7.81 (d, J = 8.1 Hz, 1H), 7.74 (d, J = 8.4 Hz, 1H), 5.11 (br dd, J = 13.2, 4.9 Hz, 1H), 4.59-4.49 (m, 1H), 4.45-4.36 (m, 1H), 3.79-3.70 (m, 1H), 2.97-2.85 (m, 1H), 2.63 (br d, J = 17.4 Hz, 1H), 2.42 (qd, J = 13.2, 4.3 Hz, 1H), 2.10-2.00 (m, 1H), 1.57 (br dd, J = 12.2, 6.6 Hz, 2H), 1.20 (d, J = 6.6 Hz, 3H), 0.91 (t, J = 7.4 Hz, 3H) |

TABLE 1-continued

| Ex. No. | $R_1$ | HPLC[a] $T_{Ret}$ (min) | LC/MS (M + H) | NMR |
|---|---|---|---|---|
| 11 | 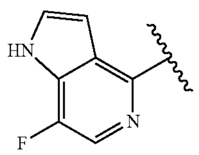 [SMILES: *c1ncc(F)c2[nH]ccc12] | 0.61 | 379.2 | $^1H$ NMR (500 MHz, DMSO-$d_6$) δ 12.14 (br s, 1H), 11.04 (s, 1H), 8.24 (s, 1H), 8.09 (s, 1H), 8.01 (br d, J = 7.9 Hz, 1H), 7.92 (d, J = 7.9 Hz, 1H), 7.75 (br s, 1H), 6.79 (br s, 1H), 5.15 (br dd, J = 12.9, 2.8 Hz, 1H), 4.63-4.54 (m, 1H), 4.51-4.42 (m, 1H), 2.91 (br d, J = 13.4 Hz, 1H), 2.65 (br d, J = 16.7 Hz, 1H), 2.48-2.39 (m, 1H), 2.12-2.03 (m, 1H) |
| 12 | 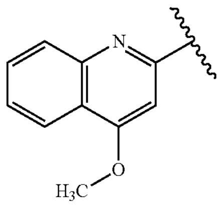 [SMILES: *c1cc(OC)c2ccccc2n1] | 1.05 | 402.2 | $^1H$ NMR (500 MHz, DMSO-$d_6$) δ 11.06 (s, 1H), 8.52-8.45 (m, 1H), 8.43-8.37 (m, 1H), 8.22 (d, J = 8.3 Hz, 1H), 8.11 (d, J = 8.3 Hz, 1H), 7.94 (d, J = 8.0 Hz, 1H), 7.91-7.83 (m, 1H), 7.72-7.62 (m, 2H), 5.20-5.11 (m, 1H), 4.65-4.57 (m, 1H), 4.53-4.45 (m, 1H), 4.24 (s, 3H), 2.98-2.86 (m, 1H), 2.65 (br d, J = 16.8 Hz, 1H), 2.49-2.39 (m, 1H), 2.13-2.02 (m, 1H) |
| 13 | 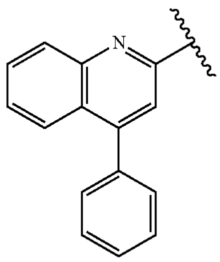 [SMILES: *c1cc(-c2ccccc2)c2ccccc2n1] | 1.68 | 448.3 | $^1H$ NMR (500 MHz, DMSO-$d_6$) δ 11.02 (s, 1H), 8.58 (s, 1H), 8.51 (br d, J = 7.9 Hz, 1H), 8.21 (d, J = 8.2 Hz, 1H), 8.14 (s, 1H), 7.98-7.83 (m, 3H), 7.70-7.56 (m, 6H), 5.16 (br dd, J = 13.4, 5.2 Hz, 1H), 4.63-4.56 (m, 1H), 4.51-4.43 (m, 1H), 2.92 (br d, J = 14.0 Hz, 1H), 2.63 (br d, J = 17.1 Hz, 1H), 2.48-2.40 (m, 1H), 2.11-2.03 (m, 1H) |
| 14 | 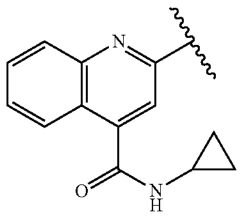 [SMILES: *c1cc(C(=O)NC2CC2)c2ccccc2n1] | 1.17 | 455.1 | $^1H$ NMR (500 MHz, DMSO-$d_6$) δ 11.02 (s, 1H), 8.96 (br d, J = 4.0 Hz, 1H), 8.52 (s, 1H), 8.45 (br d, J = 7.6 Hz, 1H), 8.21-8.12 (m, 3H), 7.96-7.90 (m, 1H), 7.86 (br t, J = 7.5 Hz, 1H), 7.69 (br t, J = 7.6 Hz, 1H), 5.13 (br dd, J = 13.1, 5.2 Hz, 1H), 4.66-4.57 (m, 1H), 4.52-4.44 (m, 1H), 3.04-2.89 (m, 2H), 2.65 (br d, J = 16.8 Hz, 1H), 2.45 (br dd, J = 13.6, 3.8 Hz, 1H), 2.07 (br dd, J = 11.9, 5.8 Hz, 1H), 0.80 (br d, J = 5.5 Hz, 2H), 0.71-0.60 (m, 2H) |
| 15 | 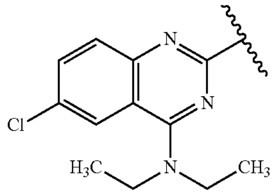 [SMILES: *c1nc(N(CC)CC)c2cc(Cl)ccc2n1] | 1.49 | 478.3 | $^1H$ NMR (500 MHz, DMSO-$d_6$) δ 11.02 (s, 1H), 7.99-7.88 (m, 2H), 7.83 (br d, J = 7.9 Hz, 1H), 7.72 (dd, J = 8.9, 1.8 Hz, 1H), 7.66-7.57 (m, 2H), 5.14 (br dd, J = 13.4, 4.9 Hz, 1H), 4.66-4.57 (m, 1H), 4.53-4.43 (m, 1H), 3.64 (s, 4H), 2.98-2.90 (m, 1H), 2.68-2.61 (m, 1H), 2.46-2.35 (m, 1H), 2.14-2.01 (m, 1H), 1.25-1.13 (m, 6H) |
| 16 | 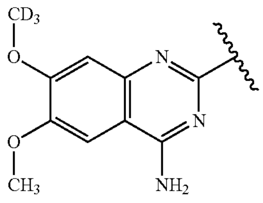 [SMILES: *c1nc(N)c2cc(OC)c(OC([2H])([2H])[2H])cc2n1] | 0.99 | 448.3 | NA |

TABLE 1-continued

| Ex. No. | $R_1$ | HPLC[a] $T_{Ret}$ (min) | LC/MS (M + H) | NMR |
|---|---|---|---|---|
| 17 | 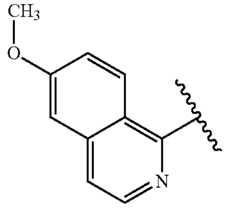 [SMILES: *c1nccc2cc(OC)ccc12] | 0.84 | 402.4 | $^1$H NMR (500 MHz, DMSO-$d_6$) δ 8.53 (d, J = 5.8 Hz, 1H), 7.97-7.85 (m, 3H), 7.79 (dd, J = 14.2, 6.6 Hz, 2H), 7.48 (d, J = 2.1 Hz, 1H), 7.27 (dd, J = 9.2, 2.4 Hz, 1H), 5.18 (dd, J = 13.4, 5.2 Hz, 1H), 4.65-4.53 (m, 1H), 4.51-4.41 (m, 1H), 3.95 (s, 3H), 2.99-2.87 (m, 1H), 2.70-2.60 (m, 1H), 2.45 (br dd, J = 12.8, 4.0 Hz, 1H), 2.13-2.02 (m, 1H) |
| 18 | 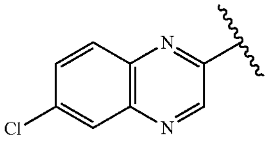 [SMILES: *c1cnc2cc(Cl)ccc2n1] | 1.57 | 407.0 | $^1$H NMR (500 MHz, DMSO-$d_6$) δ 11.03 (s, 1H), 9.68 (s, 1H), 8.57 (s, 1H), 8.49 (br d, J = 7.9 Hz, 1H), 8.27-8.18 (m, 2H), 8.00-7.91 (m, 2H), 5.15 (br dd, J = 13.1, 5.2 Hz, 1H), 4.67-4.57 (m, 1H), 4.54-4.45 (m, 1H), 2.97-2.85 (m, 1H), 2.64 (br d, J = 16.5 Hz, 1H), 2.48-2.38 (m, 1H), 2.12-2.03 (m, 1H) |
| 19 | 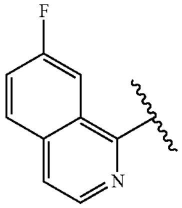 [SMILES: *c1nccc2ccc(F)cc12] | 0.89 | 390.0 | $^1$H NMR (500 MHz, DMSO-$d_6$) δ 11.03 (s, 1H), 8.64 (d, J = 5.5 Hz, 1H), 8.23 (dd, J = 9.0, 5.6 Hz, 1H), 8.01-7.90 (m, 3H), 7.86-7.76 (m, 2H), 7.73-7.65 (m, 1H), 5.19 (br dd, J = 13.1, 4.9 Hz, 1H), 4.65-4.57 (m, 1H), 4.52-4.44 (m, 1H), 3.00-2.91 (m, 1H), 2.64 (br d, J = 16.5 Hz, 1H), 2.48-2.39 (m, 1H), 2.12-2.03 (m, 1H) |
| 20 | 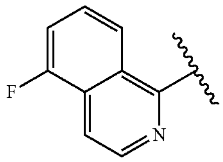 [SMILES: *c1nccc2c(F)cccc12] | 1.16 | 390.0 | $^1$H NMR (500 MHz, DMSO-$d_6$) δ 11.11-10.98 (m, 1H), 8.73 (d, J = 5.7 Hz, 1H), 8.02 (d, J = 5.8 Hz, 1H), 7.96-7.85 (m, 3H), 7.82 (br d, J = 7.9 Hz, 1H), 7.73-7.64 (m, 2H), 5.17 (br dd, J = 13.2, 4.8 Hz, 1H), 4.60 (br d, J = 17.6 Hz, 1H), 4.52-4.44 (m, 1H), 3.01-2.87 (m, 1H), 2.64 (br d, J = 16.7 Hz, 1H), 2.49-2.39 (m, 1H), 2.13-2.04 (m, 1H) |
| 21 | 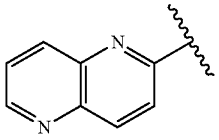 [SMILES: *c1ccc2ncccc2n1] | 1.06 | 373.2 | $^1$H NMR (500 MHz, DMSO-$d_6$) δ 9.02 (br d, J = 3.7 Hz, 1H), 8.61-8.40 (m, 5H), 7.96-7.88 (m, 1H), 7.85 (dd, J = 8.2, 3.7 Hz, 1H), 5.19-5.11 (m, 1H), 4.62 (br d, J = 17.4 Hz, 1H), 4.53-4.44 (m, 1H), 2.97-2.85 (m, 1H), 2.65 (br d, J = 17.7 Hz, 1H), 2.48-2.39 (m, 1H), 2.08 (br dd, J = 13.1, 6.4 Hz, 1H) |
| 22 | 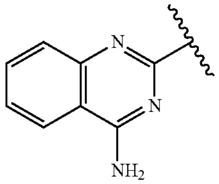 [SMILES: *c1nc(N)c2ccccc2n1] | 0.65 | 388.0 | $^1$H NMR (500 MHz, DMSO-$d_6$) δ 8.68-8.59 (m, 2H), 8.27 (br d, J = 7.9 Hz, 1H), 7.92 (br s, 2H), 7.87-7.76 (m, 3H), 7.56-7.48 (m, 1H), 5.16 (br dd, J = 13.3, 4.7 Hz, 1H), 4.63-4.53 (m, 1H), 4.50-4.41 (m, 1H), 2.99-2.87 (m, 1H), 2.68-2.59 (m, 1H), 2.46-2.35 (m, 1H), 2.12-2.01 (m, 1H) |
| 23 | 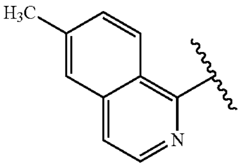 [SMILES: *c1nccc2cc(C)ccc12] | 1.05 | 386.2 | $^1$H NMR (500 MHz, DMSO-$d_6$) δ 11.05 (s, 1H), 8.58 (d, J = 5.7 Hz, 1H), 7.99-7.87 (m, 4H), 7.85 (d, J = 5.6 Hz, 1H), 7.80 (d, J = 7.8 Hz, 1H), 7.53 (br d, J = 8.7 Hz, 1H), 5.19 (br dd, J = 13.2, 4.8 Hz, 1H), 4.60 (d, J = 17.2 Hz, 1H), 4.51-4.42 (m, 1H), 3.00-2.88 (m, 1H), 2.64 (br d, J = 15.9 Hz, 1H), 2.55 (br s, 3H), 2.48-2.38 (m, 1H), 2.14-2.02 (m, 1H) |

TABLE 1-continued

| Ex. No. | $R_1$ | HPLC[a] $T_{Ret}$ (min) | LC/MS (M + H) | NMR |
|---|---|---|---|---|
| 24 | 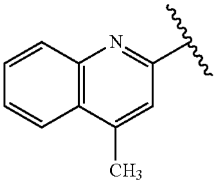 [SMILES: *c1cc(C)c2ccccc2n1] | 1.20 | 386.3 | $^1$H NMR (500 MHz, DMSO-$d_6$) δ 11.05 (br s, 1H), 8.51 (s, 1H), 8.44 (d, J = 8.4 Hz, 1H), 8.17-8.09 (m, 3H), 7.91 (d, J = 8.0 Hz, 1H), 7.82 (t, J = 7.4 Hz, 1H), 7.66 (t, J = 7.5 Hz, 1H), 5.17 (br dd, J = 13.3, 4.9 Hz, 1H), 4.66-4.54 (m, 1H), 4.52-4.43 (m, 1H), 2.99-2.87 (m, 1H), 2.80 (s, 3H), 2.71-2.58 (m, 1H), 2.49-2.40 (m, 1H), 2.11-2.02 (m, 1H) |
| 25 | 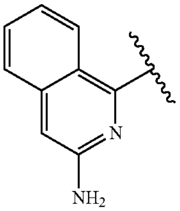 [SMILES: *c1nc(N)cc2ccccc12] | 1.03 | 387.2 | $^1$H NMR (500 MHz, DMSO-$d_6$) δ 11.02 (s, 1H), 7.88 (br d, J = 7.6 Hz, 1H), 7.82 (s, 1H), 7.71 (br dd, J = 15.1, 8.1 Hz, 2H), 7.62 (br d, J = 8.5 Hz, 1H), 7.48 (br t, J = 7.8 Hz, 1H), 7.38-6.95 (m, 3H), 6.72 (s, 1H), 5.16 (br dd, J = 13.1, 5.2 Hz, 1H), 4.63-4.52 (m, 1H), 4.50-4.40 (m, 1H), 3.00-2.86 (m, 1H), 2.63 (br d, J = 17.4 Hz, 1H), 2.47-2.37 (m, 1H), 2.12-2.03 (m, 1H) |
| 26 | 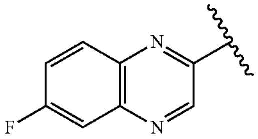 [SMILES: *c1cnc2cc(F)ccc2n1] | 1.45 | 391.2 | $^1$H NMR (500 MHz, DMSO-$d_6$) δ 11.02 (s, 1H), 9.64 (s, 1H), 8.52 (s, 1H), 8.45 (br d, J = 8.5 Hz, 1H), 8.25 (br dd, J = 9.0, 6.0 Hz, 1H), 7.98-7.88 (m, 2H), 7.84 (td, J = 8.7, 2.7 Hz, 1H), 5.13 (br dd, J = 13.1, 4.9 Hz, 1H), 4.66-4.55 (m, 1H), 4.54-4.43 (m, 1H), 2.96-2.84 (m, 1H), 2.64 (br d, J = 16.2 Hz, 1H), 2.47-2.37 (m, 1H), 2.12-2.00 (m, 1H) |
| 27 | 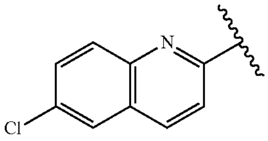 [SMILES: *c1ccc2cc(Cl)ccc2n1] | 1.69 | 406.2 | $^1$H NMR (500 MHz, DMSO-$d_6$) δ 11.00 (s, 1H), 8.53-8.44 (m, 2H), 8.39 (br d, J = 8.5 Hz, 1H), 8.25 (d, J = 8.5 Hz, 1H), 8.18-8.09 (m, 2H), 7.91 (d, J = 7.9 Hz, 1H), 7.81 (dd, J = 9.0, 2.3 Hz, 1H), 5.11 (br dd, J = 13.1, 4.9 Hz, 1H), 4.64-4.55 (m, 1H), 4.47 (br d, J = 17.4 Hz, 1H), 2.95-2.83 (m, 1H), 2.69-2.59 (m, 1H), 2.45-2.38 (m, 1H), 2.13-2.00 (m, 1H) |
| 28 | 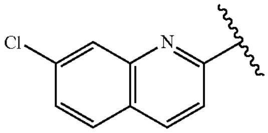 [SMILES: *c1ccc2ccc(Cl)cc2n1] | 1.65 | 406.1 | $^1$H NMR (500 MHz, DMSO-$d_6$) δ 11.01 (s, 1H), 8.56 (br d, J = 8.9 Hz, 1H), 8.48 (s, 1H), 8.41 (br d, J = 8.2 Hz, 1H), 8.25 (d, J = 8.5 Hz, 1H), 8.16 (s, 1H), 8.09 (d, J = 8.8 Hz, 1H), 7.91 (d, J = 7.9 Hz, 1H), 7.66 (dd, J = 8.7, 2.0 Hz, 1H), 5.13 (br dd, J = 13.3, 4.7 Hz, 1H), 4.64-4.56 (m, 1H), 4.51-4.42 (m, 1H), 2.96-2.84 (m, 1H), 2.64 (br d, J = 15.6 Hz, 1H), 2.46-2.38 (m, 1H), 2.12-2.02 (m, 1H) |
| 29 | 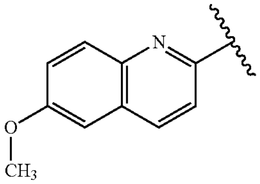 [SMILES: *c1ccc2cc(OC)ccc2n1] | 1.29 | 402.3 | $^1$H NMR (500 MHz, DMSO-$d_6$) δ 11.05 (s, 1H), 8.48 (s, 1H), 8.41 (dd, J = 8.0, 5.3 Hz, 2H), 8.20 (d, J = 8.7 Hz, 1H), 8.03 (d, J = 8.9 Hz, 1H), 7.89 (d, J = 8.0 Hz, 1H), 7.48-7.42 (m, 2H), 5.17 (dd, J = 13.2, 5.1 Hz, 1H), 4.59 (d, J = 17.4 Hz, 1H), 4.50-4.43 (m, 1H), 3.94 (s, 3H), 3.00-2.89 (m, 1H), 2.64 (br dd, J = 16.2, 1.5 Hz, 1H), 2.49-2.40 (m, 1H), 2.12-2.02 (m, 1H) |
| 30 | 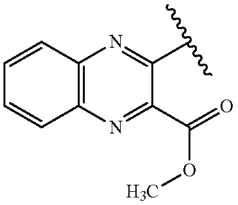 [SMILES: *c1nc2ccccc2nc1C(=O)OC] | 1.35 | 445.2 | $^1$H NMR (500 MHz, DMSO-$d_6$) δ 11.04 (s, 1H), 8.29-8.20 (m, 2H), 8.08-7.98 (m, 2H), 7.98-7.89 (m, 2H), 7.83 (br d, J = 7.8 Hz, 1H), 5.15 (br dd, J = 13.3, 2.3 Hz, 1H), 4.64-4.55 (m, 1H), 4.51-4.41 (m, 1H), 4.35-4.25 (m, 2H), 2.97-2.90 (m, 1H), 2.65 (br d, J = 17.5 Hz, 1H), 2.49-2.36 (m, 1H), 2.12-2.03 (m, 1H), 1.16 (t, J = 7.1 Hz, 3H) |

TABLE 1-continued

| Ex. No. | $R_1$ | HPLC[a] $T_{Ret}$ (min) | LC/MS (M + H) | NMR |
|---|---|---|---|---|
| 31 | 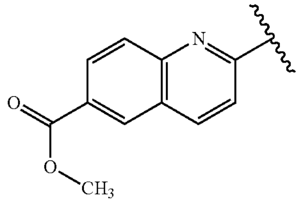 [SMILES: *c1ccc2cc(C(=O)OC)ccc2n1] | 1.52 | 430.3 | $^1$H NMR (500 MHz, DMSO-$d_6$) δ 11.02 (s, 1H), 8.76-8.68 (m, 2H), 8.51 (s, 1H), 8.44 (br d, J = 7.9 Hz, 1H), 8.31 (d, J = 8.9 Hz, 1H), 8.28-8.23 (m, 1H), 8.22-8.16 (m, 1H), 7.92 (d, J = 7.9 Hz, 1H), 5.14 (br dd, J = 13.3, 5.0 Hz, 1H), 4.65-4.56 (m, 1H), 4.52-4.43 (m, 1H), 3.94 (s, 3H), 3.00-2.82 (m, 1H), 2.64 (br d, J = 17.4 Hz, 1H), 2.47-2.34 (m, 1H), 2.14-1.98 (m, 1H) |
| 32 | 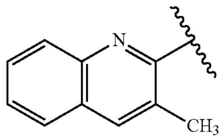 [SMILES: *c1nc2ccccc2cc1C] | 1.07 | 386.3 | $^1$H NMR (500 MHz, DMSO-$d_6$) δ 11.02 (s, 1H), 8.32 (s, 1H), 8.02 (br d, J = 8.2 Hz, 1H), 7.97 (br d, J = 7.9 Hz, 1H), 7.90-7.82 (m, 2H), 7.79-7.70 (m, 2H), 7.62 (br t, J = 7.2 Hz, 1H), 5.17 (br dd, J = 13.4, 4.9 Hz, 1H), 4.63-4.52 (m, 1H), 4.49-4.39 (m, 1H), 2.99-2.86 (m, 1H), 2.63 (br d, J = 17.7 Hz, 1H), 2.47 (s, 3H), 2.45-2.37 (m, 1H), 2.13-2.01 (m, 1H) |
| 33 | 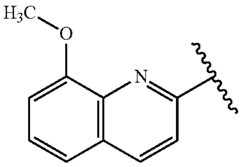 [SMILES: *c1ccc2cccc(OC)c2n1] | 1.35 | 402.2 | $^1$H NMR (500 MHz, DMSO-$d_6$) δ 8.53-8.41 (m, 3H), 8.25 (d, J = 8.7 Hz, 1H), 7.92 (d, J = 8.0 Hz, 1H), 7.59-7.53 (m, 2H), 7.31-7.22 (m, 1H), 5.17 (br dd, J = 13.0, 5.0 Hz, 1H), 4.66-4.56 (m, 1H), 4.53-4.44 (m, 1H), 4.04 (s, 3H), 2.99-2.87 (m, 1H), 2.64 (br d, J = 18.2 Hz, 1H), 2.50-2.39 (m, 1H), 2.13-2.02 (m, 1H) |
| 34 | 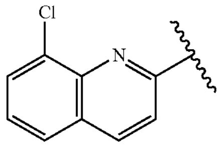 [SMILES: *c1ccc2cccc(Cl)c2n1] | 1.64 | 406.0 | $^1$H NMR (500 MHz, DMSO-$d_6$) δ 11.04 (s, 1H), 8.63-8.46 (m, 3H), 8.34 (br dd, J = 8.7, 2.9 Hz, 1H), 8.01 (br dd, J = 9.5, 8.0 Hz, 2H), 7.94 (d, J = 8.0 Hz, 1H), 7.61 (t, J = 7.9 Hz, 1H), 5.19-5.09 (m, 1H), 4.67-4.58 (m, 1H), 4.54-4.44 (m, 1H), 2.97-2.85 (m, 1H), 2.65 (br d, J = 17.0 Hz, 1H), 2.49-2.37 (m, 1H), 2.12-2.02 (m, 1H) |
| 35 | 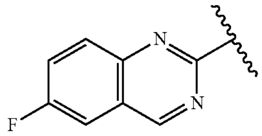 [SMILES: *c1ncc2cc(F)ccc2n1] | 1.52 | 391.2 | $^1$H NMR (500 MHz, DMSO-$d_6$) δ 11.05 (s, 1H), 9.75 (s, 1H), 8.75 (s, 1H), 8.71 (d, J = 8.0 Hz, 1H), 8.20 (dd, J = 9.0, 5.0 Hz, 1H), 8.06-7.97 (m, 2H), 7.93 (d, J = 8.1 Hz, 1H), 5.16 (br dd, J = 13.3, 5.1 Hz, 1H), 4.67-4.58 (m, 1H), 4.53-4.44 (m, 1H), 2.98-2.87 (m, 1H), 2.64 (br d, J = 17.7 Hz, 1H), 2.50-2.39 (m, 1H), 2.12-2.02 (m, 1H) |
| 36 | 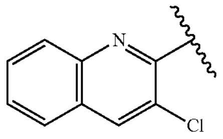 [SMILES: *c1nc2ccccc2cc1Cl] | 1.62 | 406.1 | $^1$H NMR (500 MHz, DMSO-$d_6$) δ 11.00 (s, 1H), 8.70 (s, 1H), 8.07 (br d, J = 8.2 Hz, 1H), 8.03 (br d, J = 8.2 Hz, 1H), 7.94 (s, 1H), 7.92-7.80 (m, 3H), 7.70 (br t, J = 7.3 Hz, 1H), 5.11 (br dd, J = 13.4, 4.9 Hz, 1H), 4.63-4.53 (m, 1H), 4.49-4.39 (m, 1H), 2.95-2.83 (m, 1H), 2.64 (br d, J = 18.3 Hz, 1H), 2.47-2.35 (m, 1H), 2.14-2.02 (m, 1H) |
| 37 | 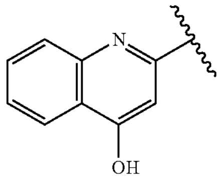 [SMILES: *c1cc(O)c2ccccc2n1] | 1.13 | 388.1 | $^1$H NMR (500 MHz, DMSO-$d_6$) δ 11.98 (br s, 1H), 11.01 (s, 1H), 7.91 (d, J = 7.9 Hz, 1H), 7.73 (s, 1H), 7.61 (d, J = 7.9 Hz, 1H), 7.59-7.53 (m, 1H), 7.44 (d, J = 8.2 Hz, 1H), 7.38 (d, J = 8.2 Hz, 1H), 7.18 (t, J = 7.6 Hz, 1H), 6.49 (s, 1H), 5.12 (dd, J = 13.3, 5.0 Hz, 1H), 4.63-4.52 (m, 1H), 4.49-4.39 (m, 1H), 2.94-2.84 (m, 1H), 2.69-2.60 (m, 1H), 2.48-2.36 (m, 1H), 2.11-2.02 (m, 1H) |

TABLE 1-continued

| Ex. No. | $R_1$ | HPLC[a] $T_{Ret}$ (min) | LC/MS (M + H) | NMR |
| --- | --- | --- | --- | --- |
| 38 | 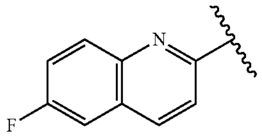 [SMILES: *c1ccc2cc(F)ccc2n1] | 1.42 | 390.0 | $^1$H NMR (500 MHz, DMSO-$d_6$) δ 11.02 (s, 1H), 8.56-8.47 (m, 2H), 8.42 (br d, J = 7.6 Hz, 1H), 8.29 (d, J = 8.5 Hz, 1H), 8.19 (dd, J = 9.5, 5.2 Hz, 1H), 7.91 (d, J = 7.9 Hz, 1H), 7.85 (br dd, J = 9.5, 2.7 Hz, 1H), 7.73 (td, J = 9.0, 2.7 Hz, 1H), 5.16 (br dd, J = 13.3, 5.0 Hz, 1H), 4.65-4.55 (m, 1H), 4.52-4.42 (m, 1H), 3.01-2.87 (m, 1H), 2.67-2.60 (m, 1H), 2.46-2.39 (m, 1H), 2.11-2.01 (m, 1H) |
| 39 | 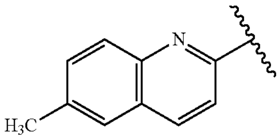 [SMILES: *c1ccc2cc(C)ccc2n1] | 1.12 | 386.2 | $^1$H NMR (500 MHz, DMSO-$d_6$) δ 11.01 (br s, 1H), 8.46 (s, 1H), 8.40 (br t, J = 8.4 Hz, 2H), 8.16 (d, J = 8.5 Hz, 1H), 8.01 (d, J = 8.9 Hz, 1H), 7.90 (d, J = 8.2 Hz, 1H), 7.79 (s, 1H), 7.66 (br d, J = 7.9 Hz, 1H), 5.12 (br dd, J = 13.0, 5.3 Hz, 1H), 4.64-4.55 (m, 1H), 4.51-4.42 (m, 1H), 2.96-2.84 (m, 1H), 2.69-2.59 (m, 1H), 2.53 (s, 3H), 2.46-2.36 (m, 1H), 2.06 (br dd, J = 11.1, 6.3 Hz, 1H) |
| 40 | 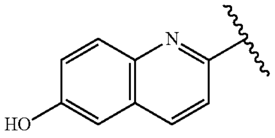 [SMILES: *c1ccc2cc(O)ccc2n1] | 0.72 | 388.2 | 1$^1$H H NMR (500 MHz, DMSO-$d_6$) δ 11.02 (s, 1H), 10.25 (s, 1H), 8.43 (s, 1H), 8.37 (br d, J = 8.2 Hz, 1H), 8.28 (d, J = 8.9 Hz, 1H), 8.10 (d, J = 8.5 Hz, 1H), 7.98 (d, J = 9.2 Hz, 1H), 7.88 (d, J = 7.9 Hz, 1H), 7.37 (dd, J = 9.2, 2.1 Hz, 1H), 7.21 (d, J = 2.1 Hz, 1H), 5.14 (br dd, J = 13.1, 4.9 Hz, 1H), 4.64-4.54 (m, 1H), 4.51-4.40 (m, 1H), 2.97-2.85 (m, 1H), 2.70-2.60 (m, 1H), 2.47-2.38 (m, 1H), 2.12-2.02 (m, 1H) |
| 41 | 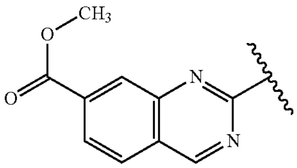 [SMILES: *c1ncc2ccc(C(=O)OC)cc2n1] | 1.43 | 431.3 | $^1$H NMR (500 MHz, DMSO-$d_6$) δ 11.03 (s, 1H), 9.90 (s, 1H), 8.81 (s, 1H), 8.76 (br d, J = 7.6 Hz, 1H), 8.64 (s, 1H), 8.36 (br d, J = 7.9 Hz, 1H), 8.23 (br d, J = 8.9 Hz, 1H), 7.95 (br d, J = 8.5 Hz, 1H), 5.16 (br dd, J = 13.0, 5.3 Hz, 1H), 4.67-4.59 (m, 1H), 4.51 (br d, J = 17.4 Hz, 1H), 3.99 (s, 3H), 2.98-2.88 (m, 1H), 2.68-2.59 (m, 1H), 2.45-2.40 (m, 1H), 2.11-2.02 (m, 1H) |
| 42 | 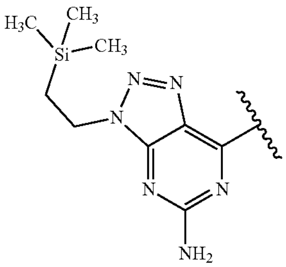 [SMILES: *c1nc(N)nc2c1nnn2CC[Si](C)(C)C] | 1.73 | 479.3 | $^1$H NMR (500 MHz, DMSO-$d_6$) δ 11.01 (s, 1H), 8.91 (s, 1H), 8.87 (br d, J = 7.9 Hz, 1H), 7.97 (d, J = 7.9 Hz, 1H), 7.33 (br s, 2H), 5.14 (br dd, J = 13.4, 4.9 Hz, 1H), 4.67-4.60 (m, 1H), 4.55-4.46 (m, 3H), 2.96-2.85 (m, 1H), 2.63 (br d, J = 16.2 Hz, 1H), 2.46-2.39 (m, 1H), 2.11-2.02 (m, 1H), 1.30-1.23 (m, 2H), 0.00 (s, 9H) |
| 43 | 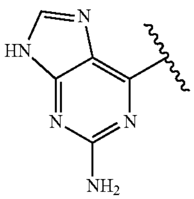 [SMILES: *c1nc(N)nc2[nH]cnc12] | 0.57 | 378.2 | NA |

TABLE 1-continued

| Ex. No. | $R_1$ | HPLC[a] $T_{Ret}$ (min) | LC/MS (M + H) | NMR |
|---|---|---|---|---|
| 44 | 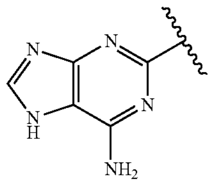 [SMILES: *c1nc(N)c2[nH]cnc2n1] | 0.92 | 378.1 | NA |
| 45 | 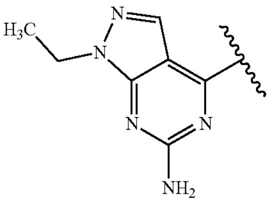 [SMILES: *c1nc(N)nc2c1cnn2CC] | 1.11 | 406.0 | $^1H$ NMR (500 MHz, DMSO-$d_6$) δ 11.02 (br s, 1H), 8.35 (s, 1H), 8.32 (s, 1H), 8.28 (br d, J = 7.9 Hz, 1H), 7.92 (d, J = 8.2 Hz, 1H), 6.93 (br s, 2H), 5.13 (br dd, J = 13.4, 4.9 Hz, 1H), 4.65-4.56 (m, 1H), 4.53-4.44 (m, 1H), 4.26 (q, J = 7.2 Hz, 2H), 2.97-2.83 (m, 1H), 2.64 (br d, J = 18.0 Hz, 1H), 2.46-2.37 (m, 1H), 2.13-2.01 (m, 1H), 1.37 (t, J = 7.2 Hz, 3H) |

[a]HPLC Retention time using Analytical HPLC Method 1. NA = not available.

Example 46

3-{5-[5-Amino-1-(2,2-dimethylpropyl)-4-oxo-1,4-dihydro-1,6-naphthyridin-7-yl]-1-oxo-2,3-dihydro-1H-isoindol-2-yl}piperidine-2,6-dione (46)

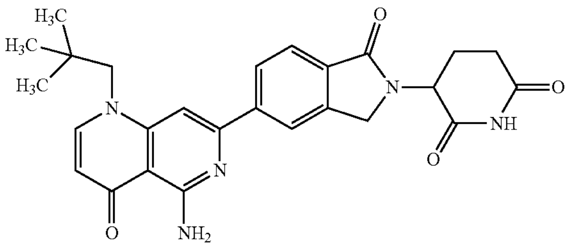

A vial was charged with Preparation 1B (25 mg, 0.056 mmol) and a solution of benzenesulfonic acid (2M solution in acetonitrile, 0.268 mL, 0.536 mmol). The vial was sealed and heated at 125° C. for 7 min via microwave. The reaction mixture concentrated to dryness. To this was added 5-amino-7-chloro-1-neopentyl-1,6-naphthyridin-4(1H)-one (14.24 mg, 0.054 mmol), $Pd(PPh_3)_4$ (6.19 mg, 5.36 μmol), and $K_2CO_3$ (89 mg, 0.643 mmol), followed by DMF (1 mL). The vial was sealed and the air replaced with nitrogen. The reaction mixture heated at 150° C. for 15 min via microwave. The reaction mixture diluted with 0.8 mL DMSO, filtered, and purified by Preparative HPLC Method 2 to give 5.9 mg (22% yield) of Example 46. MS (ES): m/z=474.2 $[M+H]^+$. $^1H$ NMR (500 MHz, DMSO-d6) δ 11.03 (s, 1H), 8.30 (s, 1H), 8.24 (br d, J=7.6 Hz, 1H), 7.84 (dd, J=9.6, 8.1 Hz, 2H), 7.33 (s, 1H), 7.19 (s, 1H), 7.09 (s, 1H), 6.18 (d, J=7.7 Hz, 1H), 5.13 (br dd, J=13.0, 4.5 Hz, 1H), 4.61-4.53 (m, 1H), 4.48-4.39 (m, 1H), 4.15 (br s, 2H), 2.98-2.86 (m, 1H), 2.69-2.59 (m, 1H), 2.48-2.36 (m, 1H), 2.12-2.00 (m, 1H), 0.97 (s, 9H).

Example 47

3-[5-(5-Amino-4-oxo-1,4-dihydro-1,6-naphthyridin-7-yl)-1-oxo-2,3-dihydro-1H-isoindol-2-yl]piperidine-2,6-dione (47)

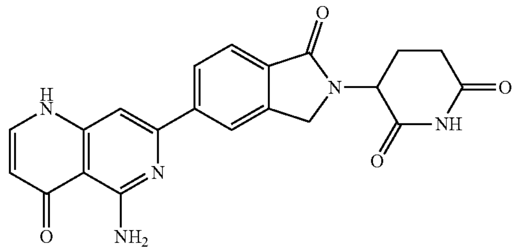

A vial was charged with Preparation 1B (25 mg, 0.056 mmol) and a solution of benzenesulfonic acid (2 M solution in acetonitrile, 0.281 mL, 0.563 mmol). The vial was sealed and heated at 125° C. for 7 min via microwave. The reaction mixture concentrated to dryness. To this was added 5-amino-7-chloro-1,6-naphthyridin-4(1H)-one (11.01 mg, 0.056 mmol), $Pd(PPh_3)_4$ (6.50 mg, 5.63 μmol), and $K_2CO_3$ (93 mg, 0.675 mmol), followed by DMF (1 mL). The vial was sealed and the air replaced with nitrogen. The reaction mixture heated at 150° C. for 15 min via microwave. The reaction mixture diluted with 0.8 mL DMSO, filtered, and purified by Preparative HPLC Method 3 to give 2.5 mg (11% yield) of Example 47. MS (ES): m/z=403.9 $[M+H]^+$. $^1H$ NMR (500 MHz, DMSO-d6) δ 11.04 (s, 1H), 8.19 (s, 1H), 8.10 (br d, J=7.7 Hz, 1H), 7.90-7.79 (m, 2H), 7.27 (s, 1H), 7.16 (s, 1H), 7.06 (s, 2H), 6.15 (br d, J=6.6 Hz, 1H), 5.14 (br dd, J=12.3, 5.1 Hz, 1H), 4.57 (br d, J=17.5 Hz, 1H), 4.48-4.39 (m, 1H), 2.98-2.85 (m, 1H), 2.69-2.59 (m, 1H), 2.48-2.36 (m, 1H), 2.09-2.00 (m, 1H).

Example 48

N-{3-[2-(2,6-Dioxopiperidin-3-yl)-1-oxo-2,3-dihydro-1H-isoindol-5-yl]isoquinolin-1-yl}acetamide (48)

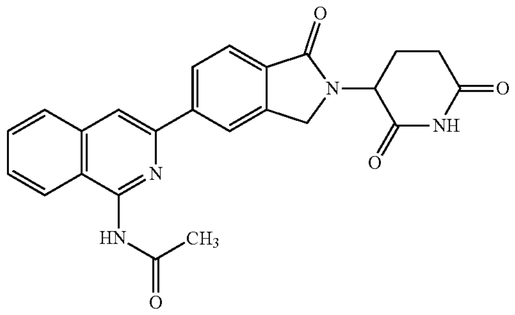

Preparation 48A: N-(3-Chloroisoquinolin-1-yl)acetamide

To a 10 mL vial was added 3-chloroisoquinolin-1-amine (30 mg, 0.168 mmol), 5 mL DCM, and acetyl chloride (65.9 mg, 0.840 mmol), followed by Hunig's base (0.044 mL, 0.252 mmol). The reaction mixture stirred at room temperature for 1 h. The reaction was quenched by addition of methanol (1 mL) and the reaction concentrated. The crude product was used without purification. MS (ES): m/z=221.0 $[M+H]^+$.

Preparation 48B: N-{3-[2-(2,6-Dioxopiperidin-3-yl)-1-oxo-2,3-dihydro-1H-isoindol-5-yl]isoquinolin-1-yl}acetamide A vial was charged with Preparation 48A (21.85 mg, 0.099 mmol), Preparation 1B (44 mg, 0.099 mmol), $Pd(PPh_3)_4$ (11.44 mg, 9.90 μmol), and dioxane (1 mL). To this was added $NaHCO_3$ (0.5M aqueous solution, 0.594 mL, 0.297 mmol). The vial was sealed and the air was replaced with nitrogen. The reaction mixture heated at 150° C. for 15 min via microwave. The reaction mixture concentrated to dryness, and 2 mL of a benzenesulfonic acid solution (0.72 gram in 20 mL ACN) was added. The vial was sealed and heated at 130° C. for 7 min via microwave. The solvents were removed and the residue dissolved in 2 mL DMSO. The resulting mixture was filtered and purified by Preparative HPLC Method 4 to give 4.8 mg (11% yield) of Example 48. MS (ES): m/z=430.3 $[M+H]^+$. $^1H$ NMR (500 MHz, DMSO-d6) δ 10.65 (s, 1H), 8.47 (s, 1H), 8.44 (s, 1H), 8.37 (d, J=7.9 Hz, 1H), 8.10 (d, J=8.3 Hz, 1H), 8.08 (d, J=8.3 Hz, 1H), 7.89 (d, J=8.0 Hz, 1H), 7.82 (t, J=7.4 Hz, 1H), 7.68 (t, J=7.7 Hz, 1H), 5.16 (dd, J=13.2, 5.1 Hz, 1H), 4.59 (d, J=17.4 Hz, 1H), 4.50-4.42 (m, 1H), 2.99-2.88 (m, 1H), 2.64 (br dd, J=16.5, 2.7 Hz, 1H), 2.48-2.41 (m, 1H), 2.29 (s, 3H), 2.10-2.01 (m, 1H).

Example 49

3-{5-[1-(Dimethylamino)isoquinolin-3-yl]-1-oxo-2,3-dihydro-1H-isoindol-2-yl}piperidine-2,6-dione (49)

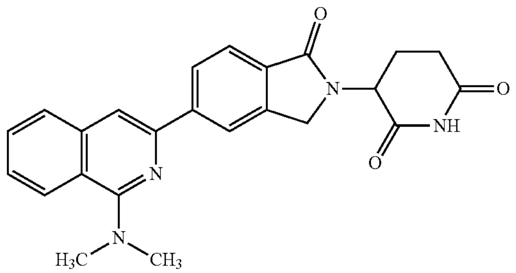

Preparation 49A: 3-Chloro-N,N-dimethylisoquinolin-1-amine

A vial was charged with 3-chloroisoquinolin-1-amine (25 mg, 0.140 mmol), THE (2 mL), and iodomethane (49.7 mg, 0.350 mmol), followed by NaH (56.0 mg, 1.400 mmol). The reaction mixture stirred at room temperature for 1 h. The reaction was quenched by addition of methanol (1 mL) and the reaction mixture concentrated to dryness. The crude Preparation 49A (39 mg, quant.) was used without purification. MS (ES): m/z=207.1 $[M+H]^+$.

Example 49

Preparation 49A (20.5 mg, 0.099 mmol), tert-butyl (S)-5-amino-5-oxo-4-(1-oxo-5-(4,4,5,5-tetramethyl-1,3,2-dioxaborolan-2-yl)isoindolin-2-yl)pentanoate (55.1 mg, 0.124 mmol), $Pd(PPh_3)_4$ (11.46 mg, 9.92 μmol) and dioxane (1 mL) were added to a vial, followed by $NaHCO_3$ (0.5 M aqueous solution, 0.595 mL, 0.298 mmol). The vial was sealed and the air was replaced with nitrogen. The reaction mixture heated at 140° C. for 10 min via microwave. The reaction mixture concentrated to dryness, treated with 2 mL of a benzenesulfonic acid solution (0.72 gram in 20 mL ACN), and heated at 130° C. for 7 min via microwave. The solvents were removed and the residue dissolved in 2 mL DMSO, filtered, and purified by Preparative HPLC Method 5 to give 15.4 mg (38% yield) of Example 49. MS (ES): m/z=415.4 $[M+H]^+$. $^1H$ NMR (500 MHz, DMSO-d6) δ 11.02 (s, 1H), 8.43 (s, 1H), 8.38 (d, J=7.9 Hz, 1H), 8.16 (d, J=8.5 Hz, 1H), 8.00 (s, 1H), 7.95 (d, J=8.2 Hz, 1H), 7.85 (d, J=7.9 Hz, 1H), 7.71 (t, J=7.6 Hz, 1H), 7.58 (t, J=7.6 Hz, 1H), 5.15 (dd, J=13.4, 5.2 Hz, 1H), 4.62-4.53 (m, 1H), 4.49-4.41 (m, 1H), 3.17 (s, 6H), 2.98-2.87 (m, 1H), 2.64 (br d, J=17.7 Hz, 1H), 2.44 (qd, J=13.2, 4.4 Hz, 1H), 2.12-2.00 (m, 1H).

Example 50

3-{5-[1-(Methylamino)isoquinolin-3-yl]-1-oxo-2,3-dihydro-1H-isoindol-2-yl}piperidine-2,6-dione (50)

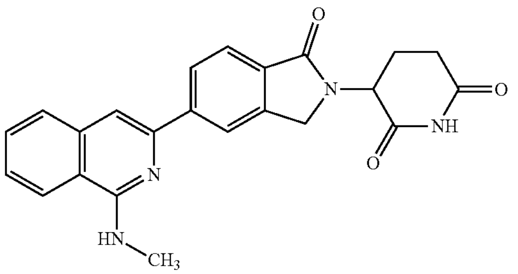

Preparation 50A: 3-Chloro-N-methylisoquinolin-1-amine

A vial was charged 3-chloroisoquinolin-1-amine (60 mg, 0.336 mmol), THE (2 mL), and iodomethane (52.4 mg, 0.370 mmol), followed by NaH (67.2 mg, 1.680 mmol). The reaction mixture stirred at room temperature for 1 h. The reaction was quenched by addition of methanol (1 mL) and the reaction mixture was concentrated to dryness. The material was purified by Preparative HPLC Method 6 to give 23 mg (36% yield) of Preparation 50A. MS (ES): m/z=193.1 $[M+H]^+$.

Example 50

This compound was prepared according to the general method used to prepare 3-{5-[1-(dimethylamino)isoquinolin-3-yl]-1-oxo-2,3-dihydro-1H-isoindol-2-yl}piperidine-2,6-dione using Preparation 50A. MS (ES): m/z=401.3 $[M+H]^+$. $^1$H NMR (500 MHz, DMSO-d6) δ 11.04 (s, 1H), 8.43 (s, 1H), 8.38 (br d, J=7.8 Hz, 1H), 8.22 (br d, J=8.1 Hz, 1H), 7.86-7.79 (m, 2H), 7.70-7.62 (m, 2H), 7.52 (br t, J=7.5 Hz, 1H), 5.16 (br dd, J=13.0, 4.5 Hz, 1H), 4.62-4.53 (m, 1H), 4.48-4.37 (m, 1H), 3.13 (br d, J=2.5 Hz, 3H), 2.93 (br dd, J=12.8, 4.2 Hz, 1H), 2.68-2.60 (m, 1H), 2.48-2.39 (m, 1H), 2.10-2.02 (m, 1H).

Example 51

3-{5-[5-(Methylamino)-1,6-naphthyridin-7-yl]-1-oxo-2,3-dihydro-1H-isoindol-2-yl}piperidine-2,6-dione (51)

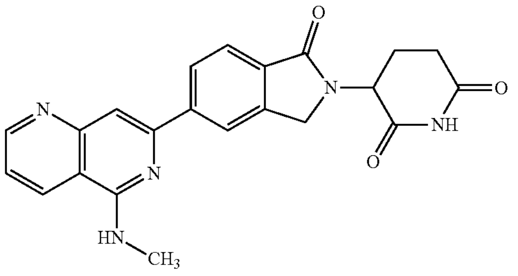

Preparation 51A: 7-Chloro-N-methyl-1,6-naphthyridin-5-amine

A vial was charged with 5,7-dichloro-1,6-naphthyridine (250 mg, 1.256 mmol) and methanamine (40% in water, 2 mL). The vial was sealed and heated at 40° C. overnight. The reaction mixture was concentrated to dryness and purified by Preparative HPLC Method 7 to give 121 mg (50% yield) of Preparation 51A. MS (ES): m/z=194.1 $[M+H]^+$. $^1$H NMR (400 MHz, DMSO-d6) δ 8.90 (dd, J=4.2, 1.3 Hz, 1H), 8.67 (d, J=8.2 Hz, 1H), 8.28 (br d, J=3.5 Hz, 1H), 7.49 (dd, J=8.4, 4.3 Hz, 1H), 6.95 (s, 1H), 2.96 (d, J=4.5 Hz, 3H).

Example 51: 3-{5-[5-(Methylamino)-1,6-naphthyridin-7-yl]-1-oxo-2,3-dihydro-1H-isoindol-2-yl}piperidine-2,6-dione A vial was charged with Preparation 1B (40 mg, 0.090 mmol), Preparation 51A (14.53 mg, 0.075 mmol), $Pd(PPh_3)_4$ (8.67 mg, 7.50 μmol) and dioxane (0.5 mL), followed by $NaHCO_3$ (0.5 M aqueous solution, 0.450 mL, 0.225 mmol). The vial was sealed and the air was replaced with nitrogen. The reaction mixture was heated at 130° C. for 15 min via microwave. The reaction mixture was diluted with EtOAc and brine. The organic phase was separated, dried over $MgSO_4$, and concentrated. The residue was dissolved in 1 mL of a benzenesulfonic acid solution (0.72 gram in 20 mL ACN) and heated at 130° C. for 10 min via microwave. The solvents were removed and the residue dissolved in 2 mL DMSO, filtered, and purified by Preparative HPLC Method 8 to give 9.0 mg (30% yield) of Example 51. MS (ES): m/z=402.3 $[M+H]^+$. $^1$H NMR (500 MHz, DMSO-d6) δ 11.04 (s, 1H), 9.00-8.94 (m, 1H), 8.68 (br d, J=8.3 Hz, 1H), 8.46 (s, 1H), 8.40 (d, J=8.2 Hz, 1H), 7.85 (d, J=8.0 Hz, 1H), 7.67 (s, 1H), 7.55 (dd, J=8.3, 4.4 Hz, 1H), 5.16 (br dd, J=13.3, 4.9 Hz, 1H), 4.58 (d, J=17.3 Hz, 1H), 4.49-4.39 (m, 1H), 3.14 (br s, 3H), 2.99-2.87 (m, 1H), 2.69-2.59 (m, 1H), 2.48-2.38 (m, 1H), 2.12-2.00 (m, 1H).

Example 52

N-{3-[2-(2,6-Dioxopiperidin-3-yl)-1-oxo-2,3-dihydro-1H-isoindol-5-yl]isoquinolin-1-yl}-N-methylacetamide (51)

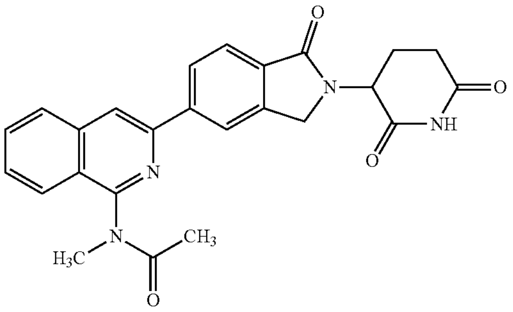

Preparation 52A: N-(3-Chloroisoquinolin-1-yl)-N-methylacetamide

A vial was charged with 3-chloro-N-methylisoquinolin-1-amine (13 mg, 0.067 mmol), DCM (5 mL), and acetic anhydride (344 mg, 3.37 mmol), followed by Hunig's base (0.018 mL, 0.101 mmol). The reaction mixture was heated at 80° C. for 1 h. The reaction mixture concentrated and crude Preparation 52A was used without purification.

Example 52: N-{3-[2-(2,6-Dioxopiperidin-3-yl)-1-oxo-2,3-dihydro-1H-isoindol-5-yl]isoquinolin-1-yl}-N-methylacetamide A vial was charged with Preparation 1B (35 mg, 0.079 mmol), Preparation 52A (12.0 mg, 0.051 mmol), $Pd(PPh_3)_4$ (7.59 mg, 6.56 μmol), and dioxane (0.5 mL), followed by $NaHCO_3$ (0.5 M aqueous solution, 0.394 mL, 0.197 mmol). The vial was sealed and the air was replaced with nitrogen. The reaction mixture heated at 130° C. for 15 min via microwave. The reaction mixture diluted with EtOAc and brine. The organics were separated, dried over $MgSO_4$, filtered, and concentrated. The resulting residue was dissolved in 1 mL of a benzenesulfonic acid solution (0.72 gram in 20 mL ACN). The reaction mixture heated at 130° C. for 10 min via microwave, then at 155° C. for 15 min. The reaction mixture concentrated, dissolved in 2 mL DMSO, filtered, and purified by Preparative HPLC Method 8 to give 6.5 mg (22% yield) of Example 52. MS (ES): m/z=442.9 $[M+H]^+$. $^1H$ NMR (500 MHz, DMSO-d6) δ 11.10-10.99 (m, 1H), 8.68 (br d, J=0.9 Hz, 1H), 8.44 (s, 1H), 8.36 (br d, J=8.1 Hz, 1H), 8.20 (br d, J=6.7 Hz, 1H), 8.03 (br d, J=7.8 Hz, 1H), 7.96-7.86 (m, 2H), 7.85-7.76 (m, 1H), 5.16 (br dd, J=13.3, 5.0 Hz, 1H), 4.63-4.55 (m, 1H), 4.51-4.42 (m, 1H), 3.47 (br s, 3H), 2.93 (br d, J=3.5 Hz, 1H), 2.68-2.60 (m, 1H), 2.47-2.40 (m, 1H), 2.10-2.02 (m, 1H), 1.76 (br s, 3H).

Example 53

3-[5-(6-Amino-1,7-naphthyridin-8-yl)-1-oxo-2,3-dihydro-1H-isoindol-2-yl]piperidine-2,6-dione (53)

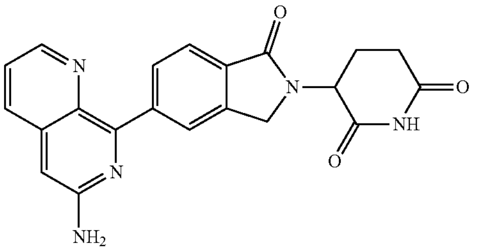

Preparation 53A: 8-Bromo-1,7-naphthyridin-6-amine

A vial was charged with acetic acid (0.1 mL) and hydrogen bromide (30% in acetic acid, 170 mg, 0.629 mmol) and cooled to 0° C. To this was added 3-(cyanomethyl)picolinonitrile (30 mg, 0.210 mmol). The reaction mixture stirred at 0° C. for 10 min, warmed to room temperature, and stirred 1 h longer. The reaction mixture diluted with EtOAc (10 mL) and quenched by addition of saturated aqueous $NaHCO_3$. The layers were separated and the organic layer concentrated to give 33 mg (70% yield) of Preparation 53A. MS (ES): m/z=224.0 $[M+H]^+$. $^1H$ NMR (400 MHz, DMSO-d6) δ 8.60 (dd, J=4.0, 1.5 Hz, 1H), 8.03 (dd, J=8.5, 1.3 Hz, 1H), 7.49 (dd, J=8.5, 4.0 Hz, 1H), 7.26-6.83 (br, 2H), 6.61 (s, 1H).

Example 53: 3-[5-(6-Amino-1,7-naphthyridin-8-yl)-1-oxo-2,3-dihydro-1H-isoindol-2-yl]piperidine-2,6-dione A vial was charged with Preparation 1B (44.1 mg, 0.099 mmol), Preparation 53A (18.5 mg, 0.083 mmol), $Pd(PPh_3)_4$ (9.56 mg, 8.27 μmol), and dioxane (0.5 mL), followed by $NaHCO_3$ (0.5 M aqueous solution, 0.496 mL, 0.248 mmol). The vial was sealed and the air was replaced with nitrogen. The reaction mixture heated at 130° C. for 15 min via microwave. The reaction mixture diluted with EtOAc and brine. The organics were separated, dried over $MgSO_4$, filtered, and concentrated. The resulting residue was dissolved in 1 mL of a benzenesulfonic acid solution (0.72 gram in 20 mL ACN), and heated at 130° C. for 15 min via microwave. The reaction mixture concentrated, dissolved in 2 mL DMSO, filtered, and purified by Preparative HPLC Method 9 to give 12.2 mg (38% yield) of Example 53. MS (ES): m/z=388.2 $[M+H]^+$. $^1H$ NMR (500 MHz, DMSO-d6) δ 11.04 (s, 1H), 8.57 (dd, J=3.9, 1.6 Hz, 1H), 8.19 (s, 1H), 8.11 (d, J=8.3 Hz, 1H), 8.06 (dd, J=8.6, 1.4 Hz, 1H), 7.84 (d, J=7.9 Hz, 1H), 7.46 (dd, J=8.5, 3.9 Hz, 1H), 6.71 (s, 1H), 5.17 (dd, J=13.4, 5.0 Hz, 1H), 4.57 (d, J=17.3 Hz, 1H), 4.47-4.38 (m, 1H), 2.99-2.88 (m, 1H), 2.68-2.59 (m, 1H), 2.49-2.39 (m, 1H), 2.11-2.01 (m, 1H).

Example 54

3-[5-(3-Amino-5-methoxyisoquinolin-1-yl)-1-oxo-2,3-dihydro-1H-isoindol-2-yl]piperidine-2,6-dione (54)

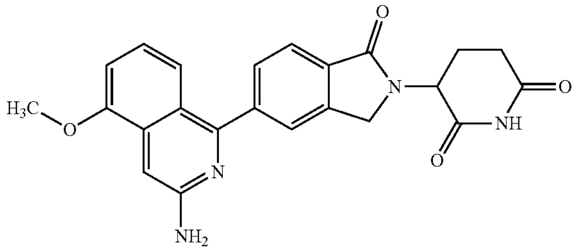

Preparation 54A: 1-Bromo-2-(bromomethyl)-3-methoxybenzene

A vial was charged with 1-bromo-3-methoxy-2-methylbenzene (800 mg, 3.98 mmol), N-bromosuccinimide (744 mg, 4.18 mmol), and $CCl_4$ (10 mL), followed by AIBN (16.33 mg, 0.099 mmol). The vial was sealed and heated at 75° C. overnight. The reaction mixture cooled to room temperature. The precipitate was isolated by removing the liquid with a pipette and removing traces of solvent under vacuum to give the product which was contaminated by succinimide. The crude Preparation 54A was used without purification. $^1H$ NMR (400 MHz, $CDCl_3$) δ 7.22-7.14 (m, 2H), 6.85 (d, J=8.1 Hz, 1H), 4.76 (s, 2H), 3.92 (s, 3H), 0.04-0.03 (m, 1H).

Preparation 54B: 2-(2-Bromo-6-methoxyphenyl)acetonitrile

A vial was charged with Preparation 54A (1150 mg, 4.11 mmol), potassium cyanide (401 mg, 6.16 mmol), and EtOH (10 mL), followed by water (3 mL). The reaction mixture stirred for 1 h at 75° C. The reaction was quenched with saturated aqueous $NaHCO_3$ and the reaction mixture was diluted with EtOAc. The organic layer was separated, concentrated, and purified by ISCO using a 40 gram column and eluting with 1-35% EtOAc/Hex to obtain 799 mg (86% yield) of Preparation 54B. $^1H$ NMR (400 MHz, $CDCl_3$) δ 7.25-7.18 (m, 2H), 6.89 (dd, J=7.2, 2.0 Hz, 1H), 3.92 (s, 3H), 3.91 (s, 2H).

Preparation 54C: 2-(Cyanomethyl)-3-methoxybenzonitrile

A vial was charged with Preparation 54B (250 mg, 1.106 mmol), dicyanozinc (78 mg, 0.664 mmol), Xantphos (19.20 mg, 0.033 mmol), and $Pd_2(dba)_3$ (30.4 mg, 0.033 mmol), followed by DMF (5 mL). The air was replaced by nitrogen and the reaction mixture was heated at 130° C. for 1 h. After cooling, the reaction was quenched with aqueous LiCl. The reaction mixture was diluted with EtOAc. The organic layer was separated, concentrated, and purified by Preparative HPLC Method 10 to obtain 115 mg (60% yield) of Preparation 54C. $^1H$ NMR (400 MHz, $CDCl_3$) δ 7.47 (t, J=8.1 Hz, 1H), 7.32 (dd, J=7.8, 1.0 Hz, 1H), 7.20 (d, J=8.5 Hz, 1H), 3.99 (s, 3H), 3.91 (s, 2H).

Preparation 54D: 1-Bromo-5-methoxyisoquinolin-3-amine

A vial was charged with acetic acid (0.2 mL) and hydrogen bromide (30% in acetic acid, 329 mg, 1.22 mmol) and cooled to 0° C. To this was added Preparation 54C (35 mg, 0.203 mmol). The vial was sealed and stirred at 0° C. for 10 min. The ice bath was removed and the reaction mixture was stirred 1 h longer. The reaction mixture diluted with EtOAc (20 mL). The reaction was quenched by addition of saturated aqueous $NaHCO_3$. The organic layer was separated and concentrated to give 48 mg (84% yield) Preparation 54D. $^1H$ NMR (400 MHz, $CDCl_3$) δ 7.67 (d, J=8.7 Hz, 1H), 7.23 (t, J=8.1 Hz, 1H), 7.10 (d, J=0.8 Hz, 1H), 6.87 (d, J=7.5 Hz, 1H), 4.51 (br s, 2H), 3.99 (s, 3H).

Example 54: 3-[5-(3-Amino-5-methoxyisoquinolin-1-yl)-1-oxo-2,3-dihydro-1H-isoindol-2-yl]piperidine-2,6-dione A vial was charged with Preparation 1B (39.5 mg, 0.089 mmol), Preparation 54D (18 mg, 0.071 mmol), $Pd(PPh_3)_4$ (8.22 mg, 7.11 μmol) and dioxane (0.5 mL), followed by $NaHCO_3$ (0.5M aqueous solution, 0.427 mL, 0.213 mmol). The vial was sealed and the air was replaced with nitrogen. The reaction mixture heated at 130° C. for 15 min via microwave. The reaction mixture diluted with EtOAc and brine and the layers separated. The organics were dried over $MgSO_4$, filtered, and concentrated. The resulting residue was dissolved in 2 mL of a benzenesulfonic acid solution (0.72 gram in 20 mL ACN), and heated at 130° C. for 15 min via microwave. The solvents were removed and the residue dissolved in 2 mL DMSO, filtered, and purified by Preparative HPLC Method 8 to give 5.1 mg (17% yield) of Example 54. MS (ES): m/z=417.1 $[M+H]^+$. $^1H$ NMR (500 MHz, DMSO-d6) δ 11.03 (s, 1H), 7.96 (s, 1H), 7.89 (d, J=7.6 Hz, 1H), 7.81 (s, 1H), 7.72 (d, J=7.0 Hz, 1H), 7.27 (d, J=8.5 Hz, 1H), 7.05 (t, J=7.9 Hz, 1H), 7.01 (s, 1H), 6.94 (d, J=7.3 Hz, 1H), 5.17 (br dd, J=13.1, 4.9 Hz, 1H), 4.63-4.54 (m, 1H), 4.49-4.41 (m, 1H), 3.96 (s, 3H), 2.98-2.93 (m, 1H), 2.65 (br dd, J=16.3, 2.0 Hz, 1H), 2.47-2.39 (m, 1H), 2.12-2.04 (m, 1H).

Examples 55-67

The compounds in Table 2 were prepared according to the procedures described for Example 54 (Step 5) using the appropriate aryl bromide or aryl chloride:

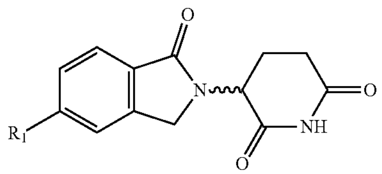

TABLE 3

| Ex. No. | $R_1$ | HPLC[a] $T_{Ret}$ (min) | LC/ MS (M + H) | NMR |
|---|---|---|---|---|
| 55 | 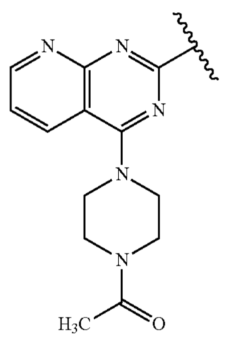 [SMILES: *c1nc(N2CCN(C(C)=O)CC2)c2cccnc2n1] | 0.92 | 499.8 | NA |

TABLE 3-continued

| Ex. No. | $R_1$ | HPLC[a] $T_{Ret}$ (min) | LC/MS (M + H) | NMR |
|---|---|---|---|---|
| 56 | 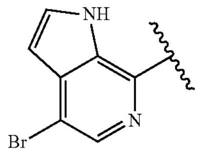 [SMILES: *c1ncc(Br)c2cc[nH]c12] | 1.03 | 439.8 | $^1$H NMR (500 MHz, DMSO-$d_6$) δ 8.39 (s, 1H), 8.14 (s, 1H), 8.06 (d, J = 7.9 Hz, 1H), 7.90 (d, J = 8.0 Hz, 1H), 7.80 (d, J = 3.0 Hz, 1H), 6.64 (d, J = 3.0 Hz, 1H), 5.19 (br dd, J = 13.1, 4.9 Hz, 1H), 4.62-4.53 (m, 1H), 4.51-4.43 (m, 1H), 3.01-2.90 (m, 1H), 2.64 (br dd, J = 15.6, 2.4 Hz, 1H), 2.50-2.41 (m, 1H), 2.10-2.01 (m, 1H) |
| 57 | 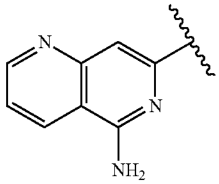 [SMILES: *c1cc2ncccc2c(N)n1] | 0.91 | 387.9 | $^1$H NMR (500 MHz, DMSO-$d_6$) δ 11.04 (s, 1H), 8.96 (dd, J = 4.2, 1.6 Hz, 1H), 8.66 (d, J = 8.1 Hz, 1H), 8.38 (s, 1H), 8.35-8.28 (m, 1H), 7.84 (d, J = 8.1 Hz, 1H), 7.67 (s, 1H), 7.51 (dd, J = 8.3, 4.3 Hz, 1H), 7.31 (s, 2H), 5.16 (dd, J = 13.1, 5.1 Hz, 1H), 4.61-4.52 (m, 1H), 4.48-4.39 (m, 1H), 2.98-2.88 (m, 1H), 2.66-2.59 (m, 1H), 2.49-2.39 (m, 1H), 2.10-2.03 (m, 1H) |
| 58 | 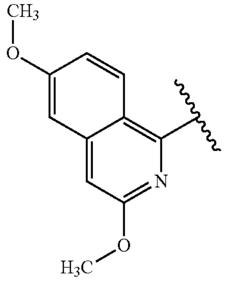 [SMILES: *c1nc(OC)cc2cc(OC)ccc12] | 1.48 | 432.2 | $^1$H NMR (500 MHz, DMSO-$d_6$) δ 11.03 (s, 1H), 7.93-7.88 (m, 2H), 7.83 (d, J = 9.5 Hz, 1H), 7.79 (d, J = 7.6 Hz, 1H), 7.30 (d, J = 2.4 Hz, 1H), 7.15 (s, 1H), 7.03 (dd, J = 9.2, 2.4 Hz, 1H), 5.18 (dd, J = 13.4, 5.2 Hz, 1H), 4.64-4.55 (m, 1H), 4.51-4.42 (m, 1H), 3.96 (s, 3H), 3.92 (s, 3H), 3.00-2.91 (m, 1H), 2.68-2.61 (m, 1H), 2.45 (br dd, J = 13.1, 4.6 Hz, 1H), 2.12-2.04 (m, 1H) |
| 59 | 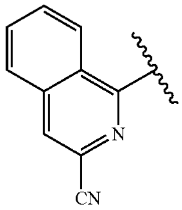 [SMILES: *c1nc(C#N)cc2ccccc12] | 1.44 | 397.2 | $^1$H NMR (500 MHz, DMSO-$d_6$) δ 11.03 (s, 1H), 8.69 (s, 1H), 8.24 (d, J = 8.2 Hz, 1H), 8.10 (d, J = 8.8 Hz, 1H), 8.00 (t, J = 7.2 Hz, 1H), 7.96 (d, J = 7.9 Hz, 1H), 7.93 (s, 1H), 7.92-7.86 (m, 1H), 7.82 (d, J = 8.9 Hz, 1H), 5.15 (dd, J = 13.4, 5.2 Hz, 1H), 4.66-4.57 (m, 1H), 4.54-4.45 (m, 1H), 2.98-2.86 (m, 1H), 2.65 (br d, J = 15.9 Hz, 1H), 2.50-2.37 (m, 1H), 2.14-2.04 (m, 1H) |
| 60 | 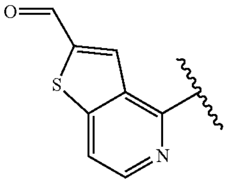 [SMILES: *c1nccc2sc(C=O)cc12] | 1.08 | 406.1 | $^1$H NMR (500 MHz, DMSO-$d_6$) δ 11.04 (s, 1H), 10.19 (s, 1H), 8.73 (d, J = 5.5 Hz, 1H), 8.70 (s, 1H), 8.24 (d, J = 5.8 Hz, 1H), 8.12 (s, 1H), 8.03 (d, J = 8.5 Hz, 1H), 7.95 (d, J = 7.6 Hz, 1H), 5.19 (dd, J = 13.3, 5.0 Hz, 1H), 4.67-4.56 (m, 1H), 4.55-4.44 (m, 1H), 2.99-2.89 (m, 1H), 2.65 (br d, J = 15.9 Hz, 1H), 2.50-2.40 (m, 1H), 2.15-2.02 (m, 1H) |
| 61 | 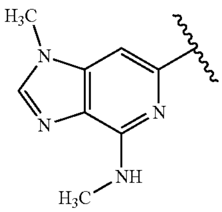 [SMILES: *c1cc2c(ncn2C)c(NC)n1] | 0.91 | 405.2 | $^1$H NMR (500 MHz, DMSO-$d_6$) δ 11.01 (s, 1H), 8.37 (s, 1H), 8.33 (d, J = 8.2 Hz, 1H), 8.07 (s, 1H), 7.79 (d, J = 7.9 Hz, 1H), 7.56 (s, 1H), 6.81-6.73 (m, 1H), 5.13 (br dd, J = 13.1, 5.2 Hz, 1H), 4.56 (br d, J = 17.4 Hz, 1H), 4.46-4.37 (m, 1H), 3.85 (s, 3H), 3.08 (d, J = 4.9 Hz, 3H), 2.97-2.87 (m, 1H), 2.68-2.60 (m, 1H), 2.46-2.39 (m, 1H), 2.09-2.01 (m, 1H) |
| 62 | 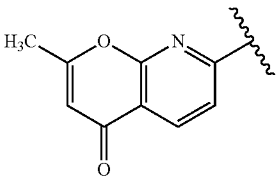 [SMILES: *c1ccc2c(=O)cc(C)oc2n1] | 1.16 | 403.9 | $^1$H NMR (500 MHz, DMSO-$d_6$) δ 11.05 (s, 1H), 8.54 (d, J = 8.1 Hz, 1H), 8.42 (s, 1H), 8.33 (br d, J = 8.2 Hz, 1H), 8.25 (br d, J = 8.1 Hz, 1H), 7.90 (d, J = 8.0 Hz, 1H), 6.34 (s, 1H), 5.15 (br dd, J = 13.3, 4.8 Hz, 1H), 4.63-4.53 (m, 1H), 4.50-4.40 (m, 1H), 2.98-2.87 (m, 1H), 2.64 (br d, J = 16.1 Hz, 1H), 2.46 (s, 3H), 2.43 (br d, J = 4.5 Hz, 1H), 2.12-1.99 (m, 1H) |

TABLE 3-continued

| Ex. No. | $R_1$ | HPLC[a] $T_{Ret}$ (min) | LC/MS (M + H) | NMR |
|---|---|---|---|---|
| 63 | 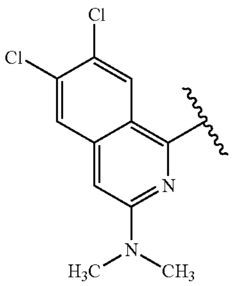 [SMILES: *c1nc(N(C)C)cc2cc(Cl)c(Cl)cc12] | 2.25 | 484.2 | $^1$H NMR (500 MHz, DMSO-$d_6$) δ 11.03 (s, 1H), 7.93 (d, J = 7.6 Hz, 1H), 7.89 (s, 1H), 7.87 (d, J = 1.8 Hz, 1H), 7.78 (d, J = 7.9 Hz, 1H), 7.67 (s, 1H), 6.87 (s, 1H), 5.19 (br dd, J = 13.1, 4.9 Hz, 1H), 4.62 (br d, J = 17.7 Hz, 1H), 4.53-4.42 (m, 1H), 3.20 (s, 6H), 3.01-2.93 (m, 1H), 2.68-2.61 (m, 1H), 2.48-2.40 (m, 1H), 2.12-2.02 (m, 1H) |
| 64 | 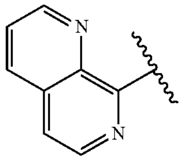 [SMILES: *c1nccc2cccnc12] | 0.91 | 373.2 | $^1$H NMR (500 MHz, DMSO-$d_6$) δ 11.04 (s, 1H), 9.09 (dd, J = 4.0, 1.6 Hz, 1H), 8.75 (d, J = 5.5 Hz, 1H), 8.54 (dd, J = 8.4, 1.5 Hz, 1H), 8.25 (s, 1H), 8.18 (d, J = 7.8 Hz, 1H), 7.99 (d, J = 5.5 Hz, 1H), 7.88 (d, J = 7.9 Hz, 1H), 7.84 (dd, J = 8.4, 4.0 Hz, 1H), 5.18 (dd, J = 13.5, 5.0 Hz, 1H), 4.59 (d, J = 17.3 Hz, 1H), 4.49-4.40 (m, 1H), 3.00-2.91 (m, 1H), 2.68-2.61 (m, 1H), 2.49-2.40 (m, 1H), 2.07 (td, J = 5.2, 2.9 Hz, 1H) |
| 65 | 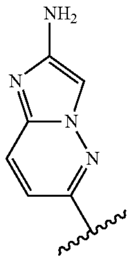 [SMILES: *c1ccc2nc(N)cn2n1] | 0.92 | 377.3 | $^1$H NMR (500 MHz, DMSO-$d_6$) δ 11.07-10.99 (m, 1H), 8.23 (s, 1H), 8.15 (d, J = 8.8 Hz, 1H), 7.95 (s, 1H), 7.86 (d, J = 7.9 Hz, 1H), 7.77 (d, J = 9.2 Hz, 1H), 7.62 (d, J = 9.2 Hz, 1H), 7.43 (s, 1H), 5.59 (s, 1H), 5.14 (dd, J = 13.3, 5.3 Hz, 1H), 4.61-4.53 (m, 1H), 4.49-4.39 (m, 1H), 2.98-2.91 (m, 1H), 2.64 (br d, J = 17.1 Hz, 1H), 2.44 (td, J = 13.0, 8.7 Hz, 1H), 2.08-2.03 (m, 1H) |
| 66 | 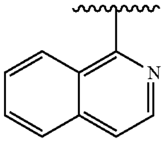 [SMILES: *c1nccc2ccccc12] | 1.02 | 372.2 | $^1$H NMR (500 MHz, DMSO-$d_6$) δ 8.63 (d, J = 5.5 Hz, 1H), 8.10 (d, J = 8.2 Hz, 1H), 8.04 (d, J = 8.2 Hz, 1H), 7.95-7.88 (m, 3H), 7.86-7.78 (m, 2H), 7.68 (t, J = 7.6 Hz, 1H), 5.18 (dd, J = 13.3, 5.0 Hz, 1H), 4.65-4.57 (m, 1H), 4.51-4.44 (m, 1H), 2.98-2.89 (m, 1H), 2.65 (dt, J = 15.3, 1.9 Hz, 1H), 2.49-2.39 (m, 1H), 2.12-2.05 (m, 1H) |
| 67 | 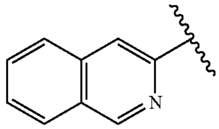 [SMILES: *c1cc2ccccc2cn1] | 1.15 | 372.1 | $^1$H NMR (500 MHz, DMSO-$d_6$) δ 11.02 (s, 1H), 9.47 (s, 1H), 8.58 (s, 1H), 8.48 (s, 1H), 8.40 (d, J = 7.9 Hz, 1H), 8.20 (d, J = 8.2 Hz, 1H), 8.08 (d, J = 8.2 Hz, 1H), 7.88 (d, J = 8.2 Hz, 1H), 7.85 (t, J = 7.6 Hz, 1H), 7.76-7.70 (m, 1H), 5.17 (dd, J = 13.3, 5.0 Hz, 1H), 4.63-4.56 (m, 1H), 4.51-4.44 (m, 1H), 2.99-2.90 (m, 1H), 2.69-2.60 (m, 1H), 2.49-2.40 (m, 1H), 2.11-2.02 (m, 1H) |
| 68 | 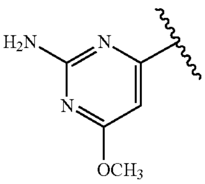 [SMILES: *c1cc(OC)nc(N)n1] | 0.93 | 368.3 | $^1$H NMR (500 MHz, DMSO-$d_6$) δ 11.03 (s, 1H), 8.25 (s, 1H), 8.18 (br d, J = 8.2 Hz, 1H), 7.82 (d, J = 8.1 Hz, 1H), 6.67 (s, 1H), 5.18-5.08 (m, 1H), 4.59-4.50 (m, 1H), 4.46-4.36 (m, 1H), 3.88 (s, 3H), 2.96-2.85 (m, 1H), 2.67-2.59 (m, 1H), 2.45-2.39 (m, 1H), 2.05 (br dd, J = 11.5, 6.1 Hz, 1H) |

TABLE 3-continued

| Ex. No. | $R_1$ | HPLC[a] $T_{Ret}$ (min) | LC/MS (M + H) | NMR |
|---|---|---|---|---|
| 69 | 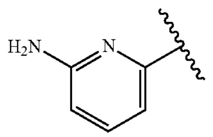 [SMILES: *c1cccc(N)n1] | 0.57 | 337.2 | $^1$H NMR (500 MHz, DMSO-$d_6$) δ 11.02 (s, 1H), 8.20 (s, 1H), 8.13 (br d, J = 7.8 Hz, 1H), 7.79 (d, J = 7.9 Hz, 1H), 7.51 (t, J = 7.8 Hz, 1H), 7.17 (d, J = 7.4 Hz, 1H), 6.49 (d, J = 8.2 Hz, 1H), 6.07 (br s, 2H), 5.19-5.08 (m, 1H), 4.57-4.49 (m, 1H), 4.43-4.34 (m, 1H), 2.97-2.86 (m, 1H), 2.63 (br d, J = 16.4 Hz, 1H), 2.46-2.35 (m, 1H), 2.10-1.98 (m, 1H) |

[a]HPLC Retention time using Analytical HPLC Method 1.
NA = not available.

Examples 70-76

The compounds in Table 3 were prepared according to the procedures described for Example 2 using the appropriate aryl bromide or aryl chloride:

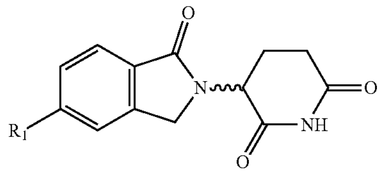

TABLE 4

| Ex. No. | $R_1$ | HPLC[a] $T_{Ret}$ (min) | LC/MS (M + H) | NMR |
|---|---|---|---|---|
| 70 | 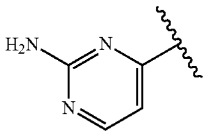 | 0.56 | 338.1 | $^1$H NMR (500 MHz, DMSO-$d_6$) δ 11.01 (s, 1H), 8.37 (d, J = 5.2 Hz, 1H), 8.28 (s, 1H), 8.21 (br d, J = 7.9 Hz, 1H), 7.85 (d, J = 7.9 Hz, 1H), 7.22 (d, J = 5.2 Hz, 1H), 5.11 (br dd, J = 13.1, 4.9 Hz, 1H), 4.61-4.49 (m, 1H), 4.47-4.37 (m, 1H), 2.96-2.82 (m, 1H), 2.63 (br d, J = 16.8 Hz, 1H), 2.45-2.34 (m, 1H), 2.11-1.97 (m, 1H) |
| 71 | 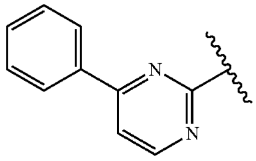 [SMILES: *c1nccc(-c2ccccc2)n1] | 1.58 | 399.2 | $^1$H NMR (500 MHz, DMSO-$d_6$) δ 11.04 (s, 1H), 9.00 (br d, J = 5.4 Hz, 1H), 8.74 (s, 1H), 8.69 (br d, J = 8.1 Hz, 1H), 8.41-8.31 (m, 2H), 8.06 (br d, J = 5.3 Hz, 1H), 7.92 (d, J = 8.0 Hz, 1H), 7.62 (br d, J = 2.9 Hz, 3H), 5.20-5.10 (m, 1H), 4.67-4.56 (m, 1H), 4.53-4.44 (m, 1H), 2.97-2.86 (m, 1H), 2.65 (br d, J = 17.6 Hz, 1H), 2.44 (qd, J = 13.2, 4.2 Hz, 1H), 2.13-2.02 (m, 1H) |
| 72 | 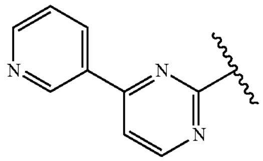 [SMILES: *c1nccc(-c2cccnc2)n1] | 0.75 | 400.0 | $^1$H NMR (500 MHz, DMSO-$d_6$) δ 11.02 (s, 1H), 9.52 (s, 1H), 9.07 (d, J = 5.2 Hz, 1H), 8.82-8.75 (m, 2H), 8.72 (br dd, J = 11.7, 8.4 Hz, 2H), 8.16 (d, J = 5.2 Hz, 1H), 7.92 (d, J = 7.9 Hz, 1H), 7.65 (dd, J = 7.6, 4.9 Hz, 1H), 5.15 (dd, J = 13.4, 5.2 Hz, 1H), 4.69-4.56 (m, 1H), 4.54-4.44 (m, 1H), 2.98-2.86 (m, 1H), 2.65 (br d, J = 17.4 Hz, 1H), 2.47-2.35 (m, 1H), 2.12-2.03 (m, 1H) |

TABLE 4-continued

| Ex. No. | $R_1$ | HPLC[a] $T_{Ret}$ (min) | LC/MS (M + H) | NMR |
|---|---|---|---|---|
| 73 | 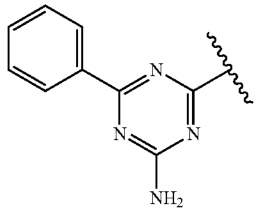 [SMILES: *c1nc(N)nc(-c2ccccc2)n1] | 1.39 | 415.2 | $^1$H NMR (500 MHz, DMSO-$d_6$) δ 11.03 (s, 1H), 8.69 (s, 1H), 8.64 (br d, J = 8.2 Hz, 1H), 8.51 (br d, J = 7.0 Hz, 2H), 7.92 (d, J = 7.9 Hz, 1H), 7.75 (br s, 2H), 7.66-7.53 (m, 3H), 5.16 (br dd, J = 13.1, 5.2 Hz, 1H), 4.67-4.57 (m, 1H), 4.54-4.43 (m, 1H), 2.99-2.86 (m, 1H), 2.64 (br d, J = 17.7 Hz, 1H), 2.48-2.38 (m, 1H), 2.16-1.99 (m, 1H) |
| 74 | 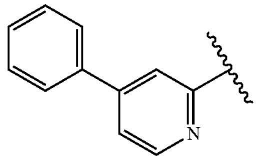 [SMILES: *c1cc(-c2ccccc2)ccn1] | 1.07 | 398.2 | $^1$H NMR (500 MHz, DMSO-$d_6$) δ 11.02 (s, 1H), 8.76 (br d, J = 5.0 Hz, 1H), 8.41 (s, 1H), 8.36-8.26 (m, 2H), 7.96-7.90 (m, 2H), 7.88 (d, J = 8.0 Hz, 1H), 7.74 (br d, J = 5.0 Hz, 1H), 7.59-7.54 (m, 2H), 7.54-7.49 (m, 1H), 5.19-5.02 (m, 1H), 4.64-4.52 (m, 1H), 4.49-4.38 (m, 1H), 2.97-2.83 (m, 1H), 2.69-2.61 (m, 1H), 2.44 (br dd, J = 12.7, 4.0 Hz, 1H), 2.11-2.02 (m, 1H) |
| 75 | 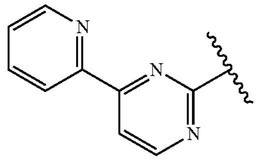 [SMILES: *c1nccc(-c2ccccn2)n1] | 1.20 | 400.2 | $^1$H NMR (500 MHz, DMSO-$d_6$) δ 11.00 (s, 1H), 9.07 (d, J = 5.2 Hz, 1H), 8.77 (br d, J = 4.3 Hz, 1H), 8.75 (s, 1H), 8.69 (br d, J = 7.9 Hz, 2H), 8.30 (d, J = 5.2 Hz, 1H), 8.08 (br t, J = 7.3 Hz, 1H), 7.92 (d, J = 8.2 Hz, 1H), 7.61 (dd, J = 7.2, 4.7 Hz, 1H), 5.09 (br dd, J = 13.0, 5.0 Hz, 1H), 4.64-4.57 (m, 1H), 4.53-4.44 (m, 1H), 2.93-2.82 (m, 1H), 2.66 (br d, J = 16.5 Hz, 1H), 2.43 (br dd, J = 13.3, 4.4 Hz, 1H), 2.13-2.04 (m, 1H) |
| 76 | 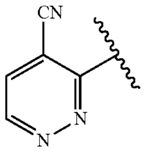 [SMILES: *c1nnccc1C#N] | 0.66 | 348.1 | $^1$H NMR (500 MHz, DMSO-$d_6$) δ 11.05 (s, 1H), 9.66-9.51 (m, 1H), 8.44-8.32 (m, 1H), 8.15 (s, 1H), 8.08-8.02 (m, 1H), 8.01-7.95 (m, 1H), 5.21-5.10 (m, 1H), 4.66-4.58 (m, 1H), 4.54-4.45 (m, 1H), 2.90 (br d, J = 12.4 Hz, 1H), 2.65 (br d, J = 17.3 Hz, 1H), 2.49-2.39 (m, 1H), 2.14-2.04 (m, 1H) |

[a]HPLC Retention time using Analytical HPLC Method 1.

Example 77 and Example 78

6-[2-(2,6-Dioxopiperidin-3-yl)-1-oxo-2,3-dihydro-1H-isoindol-5-yl]pyridazine-3-carbonitrile (77) and 6-[2-(2,6-dioxopiperidin-3-yl)-1-oxo-2,3-dihydro-1H-isoindol-5-yl]pyridazine-3-carboxamide (78)

(77)

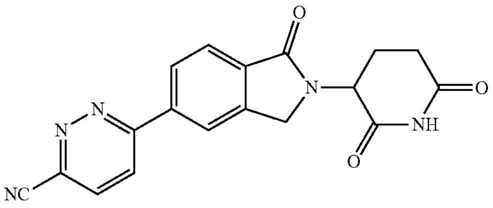

-continued (78)

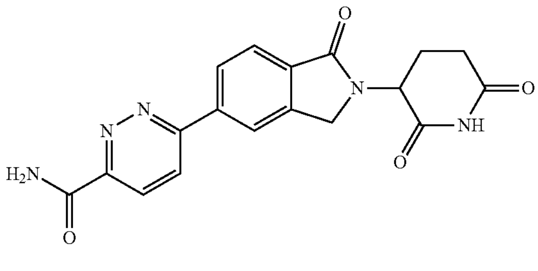

The title compounds were prepared according to the general procedure described for Example 2 using 6-chloropyridazine-3-carbonitrile. Both products were isolated from the reaction mixture by preparative HPLC.

Example 77: MS (ES): m/z=348.1 [M+H]$^+$. $^1$H NMR (500 MHz, DMSO-d6) δ 11.00 (s, 1H), 8.51 (d, J=8.9 Hz, 1H), 8.43 (s, 1H), 8.38 (d, J=8.9 Hz, 1H), 8.32 (br d, J=8.2 Hz, 1H), 7.95 (d, J=7.9 Hz, 1H), 5.10 (br dd, J=13.1, 4.6 Hz, 1H), 4.66-4.56 (m, 1H), 4.53-4.42 (m, 1H), 2.94-2.82 (m, 1H), 2.65 (br d, J=16.2 Hz, 1H), 2.43 (br dd, J=12.7, 4.4 Hz, 1H), 2.14-2.01 (m, 1H).

Example 78: MS (ES): m/z=366.0 $[M+H]^+$. $^1H$ NMR (500 MHz, DMSO-d6) δ 11.04 (s, 1H), 8.62 (br s, 1H), 8.48 (dt, J=8.8, 1.8 Hz, 1H), 8.43 (s, 1H), 8.38-8.27 (m, 2H), 7.95 (d, J=8.1 Hz, 1H), 5.18-5.07 (m, 1H), 4.66-4.56 (m, 1H), 4.53-4.44 (m, 1H), 2.95-2.85 (m, 1H), 2.65 (br d, J=16.3 Hz, 1H), 2.44 (br dd, J=13.9, 4.1 Hz, 1H), 2.14-2.01 (m, 1H).

Example 79

3-[5-(6-Amino-3-nitropyridin-2-yl)-1-oxo-2,3-dihydro-1H-isoindol-2-yl]piperidine-2,6-dione (79)

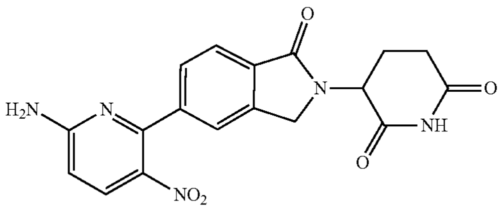

A vial was charged with Preparation 1B (25 mg, 0.056 mmol), 6-chloro-5-nitropyridin-2-amine (9.30 mg, 0.054 mmol), and $PdCl_2(dppf)_2$ (3.92 mg, 5.36 μmol). The vial was flushed with nitrogen. To this was added dioxane (1 mL) and $NaHCO_3$ (0.5 M aqueous solution, 0.214 mL, 0.107 mmol). The vial was sealed, flushed with nitrogen, and heated via microwave at 125° C. for 11 min. The reaction mixture was cooled, diluted with EtOAc, washed with brine, dried over $MgSO_4$, and concentrated. The residue was dissolved in 1 mL of a benzenesulfonic acid solution in acetonitrile (0.72 gram in 20 mL ACN), and microwaved at 120° C. for 7 min. The resulting residue was purified by preparative HPLC to afford 4.3 mg (21% yield) of Example 79. MS (ES): m/z=382.1 $[M+H]^+$. $^1H$ NMR (500 MHz, DMSO-d6) δ 11.00 (s, 1H), 8.18 (d, J=9.2 Hz, 1H), 7.78 (d, J=7.9 Hz, 1H), 7.62 (s, 1H), 7.51 (d, J=7.6 Hz, 1H), 7.43 (br s, 2H), 6.57 (d, J=9.2 Hz, 1H), 5.11 (dd, J=13.3, 5.0 Hz, 1H), 4.55-4.46 (m, 1H), 4.42-4.32 (m, 1H), 2.97-2.83 (m, 1H), 2.67-2.59 (m, 1H), 2.41 (td, J=13.1, 8.5 Hz, 1H), 2.10-2.01 (m, 1H).

Examples 80 and 81

4-Amino-2-[2-(2,6-dioxopiperidin-3-yl)-1-oxo-2,3-dihydro-1H-isoindol-5-yl]pyrimidine-5-carbonitrile (80) and 4-amino-2-[2-(2,6-dioxopiperidin-3-yl)-1-oxo-2,3-dihydro-1H-isoindol-5-yl]pyrimidine-5-carboxamide (81)

(80)

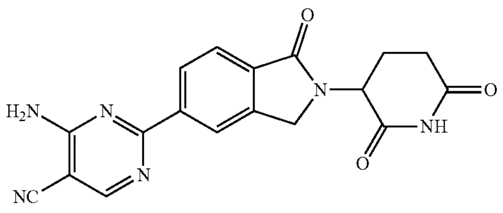

-continued (81)

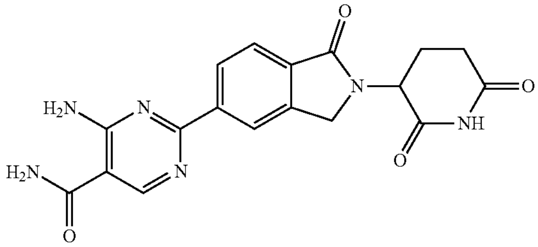

The title compounds were prepared according to the general procedure described for Example 79 using 4-amino-2-chloropyrimidine-5-carbonitrile. Both products were isolated from the reaction mixture by preparative HPLC.

Example 80: MS (ES): m/z=363.0 $[M+H]^+$. $^1H$ NMR (500 MHz, DMSO-d6) δ 10.99 (s, 1H), 8.73 (s, 1H), 8.51 (s, 1H), 8.46 (br d, J=7.9 Hz, 1H), 8.14-7.90 (m, 2H), 7.86 (br d, J=7.9 Hz, 1H), 5.08 (br dd, J=13.1, 5.2 Hz, 1H), 4.63-4.51 (m, 1H), 4.46-4.38 (m, 1H), 2.93-2.82 (m, 1H), 2.63 (br dd, J=14.8, 2.3 Hz, 1H), 2.46-2.32 (m, 1H), 2.04 (br dd, J=12.1, 5.6 Hz, 1H).

Example 81: MS (ES): m/z=381.0 $[M+H]^+$. $^1H$ NMR (500 MHz, DMSO-d6) δ 11.04 (s, 1H), 8.85 (s, 1H), 8.54 (s, 1H), 8.50 (d, J=8.1 Hz, 1H), 8.18 (br s, 1H), 7.86 (d, J=8.1 Hz, 1H), 7.56 (br s, 1H), 5.20-5.12 (m, 1H), 4.57 (br d, J=17.3 Hz, 1H), 4.50-4.38 (m, 1H), 2.98-2.88 (m, 1H), 2.69-2.59 (m, 1H), 2.47-2.36 (m, 1H), 2.12-2.00 (m, 1H).

Example 82

(3S)-3-[5-(1-aminoisoquinolin-3-yl)-1-oxo-2,3-dihydro-1H-isoindol-2-yl]piperidine-2,6-dione (82)

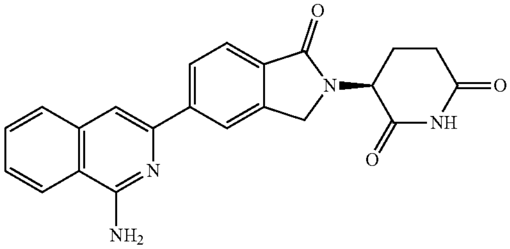

Preparation 82A: tert-butyl (S)-5-amino-4-(5-bromo-1-oxoisoindolin-2-yl)-5-oxopentanoate To a suspension of tert-butyl (S)-4,5-diamino-5-oxopentanoate hydrochloride (4.16 g, 17.43 mmol) in acetonitrile (54.1 mL) was added DIEA (6.09 mL, 34.9 mmol). After stirring for 5 min, the reaction mixture was treated with methyl 4-bromo-2-(bromomethyl)benzoate (5.78 g, 15.16 mmol) as a solid in small portions. After stirring for 1 h at room temperature, the reaction mixture was warmed to 70° C. in an oil bath under a reflux condenser overnight. LCMS indicated clean, complete conversion to product. The mixture was cooled to room temperature, diluted with EtOAc and washed with 1 M HCl (2×) then 1.5M $K_2HPO_4$ (2×), then brine, dried over $MgSO_4$, filtered, and concentrated. The resulting residue was purified by column chromatography (50-100% EtOAc/Hex to give Preparation 82A (82% yield). $^1$H NMR (400 MHz, CHLOROFORM-d) δ 7.76-7.71 (m, 1H), 7.68-7.62 (m, 2H), 6.22 (br s, 1H), 5.31 (br s, 1H), 4.91 (dd, J=8.7, 6.3 Hz, 1H), 4.62-4.53 (m, 1H), 4.51-4.40 (m, 1H), 2.47-2.10 (m, 4H), 1.44 (s, 9H).

Preparation 82B: tert-butyl (S)-5-amino-5-oxo-4-(1-oxo-5-(4,4,5,5-tetramethyl-1,3,2-dioxaborolan-2-yl)isoindolin-2-yl)pentanoate A dry 250 mL round bottom flask was charged with tert-butyl (S)-5-amino-4-(5-bromo-1-oxoisoindolin-2-yl)-5-oxopentanoate (9.07 g, 22.83 mmol), 4,4,4',4',5,5,5',5'-octamethyl-2,2'-bi(1,3,2-dioxaborolane) (6.96 g, 27.4 mmol), and potassium acetate (6.72 g, 68.5 mmol) and flushed with nitrogen. The solids were suspended in dioxane (90 mL) and degassed with a stream of nitrogen for 5 min with stirring. The reaction mixture was treated with $Pd(dppf)Cl_2$ (0.668 g, 0.913 mmol), degassed for 5 min, sealed, and heated to 60° C. for 18 hours under nitrogen. LCMS showed clean, complete conversion (LCMS showed both ester and acid). The reaction mixture was diluted with EtOAc, washed with brine, and dried over $MgSO_4$. The filtrate was concentrated and purified by 220 gram silica gel column by ISCO (0-20% B/DCM, where B=15% EtOH/EtOAc+0.1% TEA) to give Preparation 82B (7.7 g, 17.33 mmol, 76% yield) as an off-white solid. $^1$H NMR was consistent with the product.

Preparation 82C: tert-butyl (S)-5-amino-4-(5-(1-aminoisoquinolin-3-yl)-1-oxoisoindolin-2-yl)-5-oxopentanoate Preparation 82B (7.47 g, 16.81 mmol), 3-bromoisoquinolin-1-amine (3 g, 13.45 mmol), $PdCl_2(dtbpf)$ (0.263 g, 0.403 mmol) and TEA (9.37 mL, 67.2 mmol) were added to a 100 mL round bottom flask, followed by 2% TPGS in water (40 mL). The flask was sealed and the air was replaced with nitrogen. The reaction mixture was heated at 40° C. overnight. LCMS showed the uncyclized product as the major peak. The reaction mixture was diluted with 5% EtOH/EtOAc, and filtered through a pad of Celite. The slimy cake was washed thoroughly with 5% EtOH/EtOAc, and then the organic layer was separated and washed with brine, dried over $MgSO_4$ and filtered. The filtrate was concentrated and purified using a 220 gram silica gel column (equilibrated with 10% DCM/hexanes), eluting with 0-80% B/DCM (B=15% EtOH/EtOAc+0.1% TEA) to afford Preparation 82C. $^1$H NMR (400 MHz, METHANOL-d4) δ 8.21 (s, 1H), 8.14 (dd, J=13.4, 8.2 Hz, 2H), 7.86 (d, J=7.7 Hz, 1H), 7.81 (d, J=7.7 Hz, 1H), 7.67 (t, J=7.2 Hz, 1H), 7.57-7.49 (m, 2H), 5.05-4.96 (m, 1H), 4.75 (d, J=17.4 Hz, 1H), 4.63 (d, J=17.5 Hz, 1H), 4.12 (q, J=7.2 Hz, 1H), 2.38-2.19 (m, 4H), 1.41 (s, 9H), 0.92 (d, J=6.7 Hz, 1H).

Example 82

Preparation 82C (2.71 g, 5.88 mmol), and benzenesulfonic acid (1.862 g, 11.77 mmol) and acetic acid (75 mL) were added to a round bottom flask. The flask was sealed and the reaction mixture was heated at 100° C. After 6.5 hours, the flask was placed in water at room temperature. After about 5 minutes, the precipitates were filtered, washed with 80 mL room temperature acetic acid, followed by a 40 mL room temperature MeCN wash, and then another 40 mL MeCN. The solids were air dried to obtain 1.9 grams of Example 82 (79% yield). Enantiopurity testing showed that the chiral purity was >99% e.e. MS (ES): m/z=387.1 $[M+H]^+$. $^1$H NMR (500 MHz, DMSO-d6) δ 11.05 (s, 1H), 8.50 (br d, J=8.4 Hz, 1H), 8.17 (s, 1H), 8.08 (d, J=8.0 Hz, 1H), 8.01-7.96 (m, 1H), 7.96-7.91 (m, 2H), 7.78-7.70 (m, 2H), 5.16 (br dd, J=13.0, 4.1 Hz, 1H), 4.62-4.54 (m, 1H), 4.51-4.42 (m, 1H), 3.00-2.87 (m, 1H), 2.69-2.60 (m, 1H), 2.49-2.36 (m, 1H), 2.10-2.03 (m, 1H).

Example 83

(3R)-3-[5-(1-aminoisoquinolin-3-yl)-1-oxo-2,3-dihydro-1H-isoindol-2-yl]piperidine-2,6-dione (83)

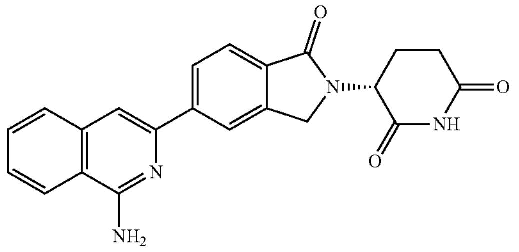

Example 83 was prepared according to the general procedure outlined for the synthesis of Example 82 using tert-butyl (R)-4,5-diamino-5-oxopentanoate. MS (ES): m/z=387.1 $[M+H]^+$. $^1$H NMR (500 MHz, DMSO-d6) δ 11.05 (s, 1H), 8.50 (br d, J=8.4 Hz, 1H), 8.17 (s, 1H), 8.08 (d, J=8.0 Hz, 1H), 8.01-7.96 (m, 1H), 7.96-7.90 (m, 2H), 7.76-7.70 (m, 2H), 5.16 (br dd, J=13.0, 4.1 Hz, 1H), 4.62-4.55 (m, 1H), 4.49-4.43 (m, 1H), 3.00-2.88 (m, 1H), 2.70-2.60 (m, 1H), 2.50-2.36 (m, 1H), 2.11-2.03 (m, 1H).

Example 84

(3S)-3-[5-(1-amino-4-ethoxyisoquinolin-3-yl)-1-oxo-2,3-dihydro-1H-isoindol-2-yl]piperidine-2,6-dione (84)

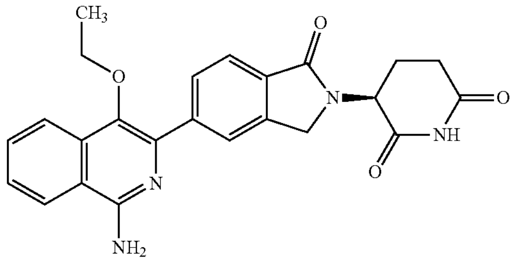

Preparation 84A: 4-ethoxyisoquinoline

To a solution of 4-bromoisoquinoline (2.3 g, 11.05 mmol) in DMPU (30 mL) was added potassium ethanolate (1.023 g, 12.16 mmol). The reaction flask was placed on a hot plate at 105° C. (pre-heated) for 20 min. The reaction mixture was cooled to room temperature and was diluted with water. The product was extracted by ether (multiple extractions) and filtered through Celite. The organic layer was concentrated, and purified by ISCO, using an 80 gram silica gel column, and eluting with 0-100% ether/hexanes to afford Preparation 84A. $^1$H NMR (400 MHz, CHLOROFORM-d) δ 8.91 (s, 1H), 8.26 (d, J=8.5 Hz, 1H), 8.09 (s, 1H), 7.95 (d, J=8.1 Hz, 1H), 7.71 (ddd, J=8.3, 7.0, 1.3 Hz, 1H), 7.67-7.60 (m, 1H), 4.32 (q, J=7.0 Hz, 2H), 1.59 (t, J=7.0 Hz, 3H).

Preparation 84B: 3-bromo-4-ethoxyisoquinoline

To a mixture of Preparation 84A (385 mg, 2.223 mmol) and 1-bromopyrrolidine-2,5-dione (475 mg, 2.67 mmol) in a round bottom flask was added DCE (30 mL). The reaction mixture was heated to 60° C. After 16 h, only a trace of starting material remained. An extra 47.5 mg of NBS was added, and the reaction was allowed to proceed for an additional hour. The reaction mixture was concentrated to dryness, and purified by ISCO, using a 24 gram silica gel column, and eluting with 0-100% ether/hexanes to obtain 560 mg (77%) of Preparation 84B. $^1$H NMR (400 MHz, CHLOROFORM-d) δ 8.86 (s, 1H), 8.13 (dd, J=8.5, 0.8 Hz, 1H), 8.01 (d, J=8.2 Hz, 1H), 7.77 (ddd, J=8.3, 7.0, 1.2 Hz, 1H), 7.70-7.63 (m, 1H), 4.27 (q, J=7.1 Hz, 2H), 1.60 (t, J=7.1 Hz, 3H).

Preparation 84C: 3-bromo-4-ethoxyisoquinoline 2-oxide

To a mixture of Preparation 84B (400 mg, 1.587 mmol) dissolved in DCM (20 mL) at room temperature was added 3-chlorobenzoperoxoic acid (412 mg, 1.840 mmol). The reaction mixture was stirred at room temperature for 5 hours. The reaction mixture was concentrated to dryness, diluted with EtOAc, washed with brine, dried over $MgSO_4$, filtered and then concentrated to dryness to afford preparation 84C (437 mg). MS (ES): m/z=268.1 [M+H]+ and 270.1 [M+H]$^+$.

Preparation 84D: 3-bromo-1-chloro-4-ethoxyisoquinoline

To Preparation 84C (200 mg, 0.746 mmol) was added phosphoryl trichloride (3.49 mL, 37.3 mmol) and the resulting mixture stirred at room temperature. After 3 days, LCMS showed the product as the major peak. The reaction mixture was concentrated, and purified using a 24 gram silica gel column by ISCO, and eluting with 2-100% DCM/hexanes to afford Preparation 84D. $^1$H NMR (400 MHz, CHLOROFORM-d) δ 8.31 (dt, J=8.4, 0.9 Hz, 1H), 8.18-8.12 (m, 1H), 7.83 (t, J=7.6 Hz, 1H), 7.74 (t, J=7.6 Hz, 1H), 4.31-4.23 (m, 2H), 1.65-1.58 (m, 3H).

Preparation 84E: 3-bromo-4-ethoxyisoquinolin-1-amine

Preparation 84D (40 mg, 0.140 mmol) and 28% aqueous $NH_3$ (1.942 mL, 13.96 mmol) were added to a sealed tube, followed by MeOH (0.5 mL). The tube was sealed and heated to 140° C. for 2 h. LCMS showed the product, but the reaction was not complete. The reaction mixture was purified by Preparative HPLC Method 1 to obtain 13 mg of Preparation 84E.

Example 84

Preparation 84E (23.95 mg, 0.054 mmol), 3-bromo-4-ethoxyisoquinolin-1-amine (12 mg, 0.045 mmol), $PdCl_2$(dtbpf) (1.464 mg, 2.246 μmol) and 1,4-dioxane (1 mL) were added to a vial, followed by $Cs_2CO_3$ (1 M aqueous solution) (0.135 mL, 0.135 mmol). The reaction mixture was sealed and the air was replaced with nitrogen. The reaction mixture was heated at 40° C. for 16 h. LCMS showed the uncyclized product as the major peak. The reaction mixture was diluted with EtOAc, washed with brine, and the organic layer separated and concentrated. The crude material was dissolved in 0.5 mL AcOH, and 2 equivalents of $PhSO_3H$ was added. The reaction mixture was microwaved for 10 minutes at 120° C. The reaction mixture was concentrated to dryness, the residue dissolved in 1.8 mL of DMSO, and purified by Preparative HPLC Method 1 to give 1.9 mg of Example 84 (10% yield). MS (ES): m/z=431.3 [M+H]$^+$. $^1$H NMR (500 MHz, DMSO-d6) δ 8.29-8.20 (m, 3H), 8.05-7.98 (m, J=8.2 Hz, 1H), 7.85-7.79 (m, J=8.1 Hz, 1H), 7.76 (t, J=7.6 Hz, 1H), 7.57 (t, J=7.6 Hz, 1H), 6.75 (br s, 2H), 5.14 (br dd, J=13.5, 4.4 Hz, 1H), 4.56 (d, J=17.3 Hz, 1H), 4.45-4.39 (m, 1H), 3.73-3.58 (m, 2H), 3.00-2.90 (m, 1H), 2.69-2.61 (m, 1H), 2.49-2.36 (m, 1H), 2.10-2.02 (m, 1H), 1.24 (t, J=6.9 Hz, 3H).

The compounds in Table 5, were prepared by following the general procedure below. The aryl halides used were obtained from commercial sources, or by following precedent literature procedures. Optical rotations were not determined.

General procedure 1: To a 2 mL microwave vial was added 1.0 equivalent of aryl halide, 1.25 equivalents Preparation 1B, 3 mol % $PdCl_2$(dtbpf), 1 mL dioxane, and 5 equivalents of 3 M aqueous $K_3PO_4$. The vial was sealed and the air was replaced with nitrogen. The reaction mixture was microwaved for 10 min at 120° C. The reaction mixture was diluted with EtOAc and brine. The organic layer was separated, dried over $MgSO_4$, and concentrated. The crude material was transferred to another 2 mL microwave vial, and 2 equivalents of $PhSO_3H$ and 1 mL of MeCN were added and the mixture was microwaved at 120° C. for 10 min. The mixture was concentrated and the residue dissolved in 1.8 mL of DMSO and purified by Preparative HPLC Method 1.

TABLE 5

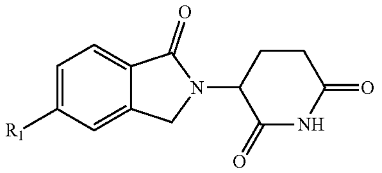

| Ex. No. | $R_1$ | HPLC[a] $T_{Ret}$ (min) | LC/MS (M + H) | $^1$H NMR |
|---|---|---|---|---|
| 85 | 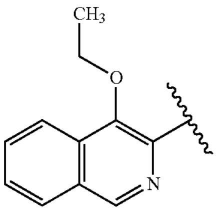 [SMILES: *c1ncc2ccccc2c1OCC] | 1.35 | 416.1 | $^1$H NMR (500 MHz, DMSO-$d_6$) δ 9.27 (s, 1H), 8.30 (s, 1H), 8.27-8.21 (m, 3H), 7.93-7.87 (m, 2H), 7.78 (t, J = 7.5 Hz, 1H), 5.17 (t, J = 1.0 Hz, 1H), 4.60 (d, J = 1.0 Hz, 1H), 4.47 (d, J = 1.0 Hz, 1H), 3.83 (q, J = 6.9 Hz, 2H), 3.01-2.89 (m, 1H), 2.65 (br dd, J = 15.4, 2.3 Hz, 1H), 2.59-2.55 (m, 7H), 2.50-2.40 (m, 1H), 2.13-2.04 (m, 1H), 1.29 (t, J = 7.0 Hz, 3H) |
| 86 | 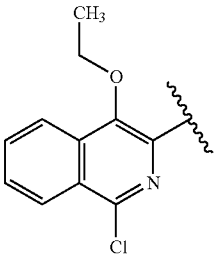 [SMILES: *c1nc(Cl)c2ccccc2c1OCC] | 1.86 | 450.2 | $^1$H NMR (500 MHz, DMSO-$d_6$) δ 11.05 (s, 1H), 8.25 (d, J = 8.3 Hz, 1H), 8.06 (d, J = 8.6 Hz, 1H), 7.97-7.89 (m, 3H), 7.80 (d, J = 8.0 Hz, 1H), 7.73 (t, J = 7.4 Hz, 1H), 5.19 (br dd, J = 13.2, 5.0 Hz, 1H), 4.64-4.57 (m, 1H), 4.51-4.44 (m, 1H), 4.31-4.24 (m, 2H), 2.99-2.89 (m, 1H), 2.69-2.60 (m, 1H), 2.49-2.36 (m, 1H), 2.122.04 (m, 1H), 1.52 (t, J = 7.0 Hz, 3H) |
| 87 | 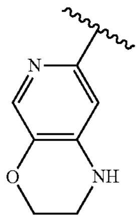 [SMILES: *c1cc2c(cn1)OCCN2] | 0.98 | 379.2 | $^1$H NMR (500 MHz, DMSO-$d_6$) δ 11.00 (s, 1H), 8.12 (s, 1H), 8.07 (d, J = 7.9 Hz, 1H), 7.76 (d, J = 7.9 Hz, 1H), 7.17 (d, J = 7.9 Hz, 1H), 7.05 (d, J = 8.2 Hz, 1H), 6.83 (br s, 1H), 5.14-5.07 (m, 1H), 4.55-4.48 (m, J = 1.0 Hz, 1H), 4.41-4.35 (m, 1H), 4.19-4.14 (m, 2H), 3.72-3.29 (m, 2H), 2.96-2.85 (m, 1H), 2.63 (br d, J = 16.8 Hz, 1H), 2.46-2.36 (m, 1H), 2.07-2.00 (m, 1H) |
| 88 | 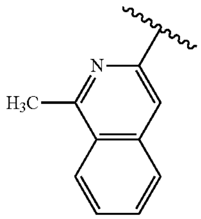 [SMILES: *c1cc2ccccc2c(C)n1] | 1.10 | 386.3 | $^1$H NMR (500 MHz, DMSO-$d_6$) δ 11.03 (s, 1H), 8.46 (s, 1H), 8.43-8.37 (m, 2H), 8.26 (d, J = 1.0 Hz, 1H), 8.06 (d, J = 8.0 Hz, 1H), 7.87 (d, J = 8.1 Hz, 1H), 7.82 (t, J = 7.7 Hz, 1H), 7.75-7.69 (m, 1H), 5.15 (br dd, J = 13.3, 5.3 Hz, 1H), 4.63-4.55 (m, 1H), 4.50-4.43 (m, 1H), 3.00 (s, 3H), 2.98-2.89 (m, 1H), 2.68-2.61 (m, 1H), 2.49-2.39 (m, 1H), 2.11-2.02 (m, 1H) |
| 89 | 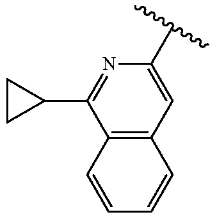 [SMILES: *c1cc2ccccc2c(C2CC2)n1] | 1.76 | 412.3 | 1H NMR (500 MHz, DMSO-d6) δ 11.03 (s, 1H), 8.57 (d, J = 8.3 Hz, 1H), 8.42 (s, 1H), 8.36 (d, J = 7.9 Hz, 1H), 8.33 (s, 1H), 8.05 (d, J = 8.2 Hz, 1H), 7.86 (d, J = 7.9 Hz, 1H), 7.81 (t, J = 7.6 Hz, 1H), 7.73 (t, J = 7.7 Hz, 1H), 5.16 (br dd, J = 13.2, 5.1 Hz, 1H), 4.58 (d, J = 17.3 Hz, 1H), 4.45 (d, J = 17.2 Hz, 1H), 3.08-3.00 (m, 1H), 2.99-2.89 (m, 1H), 2.67-2.60 (m, 1H), 2.49-2.39 (m, 1H), 2.20-2.00 (m, 1H), 1.34-1.28 (m, 2H), 1.17 (dd, J = 7.9, 3.3 Hz, 2H) |
| 90 | 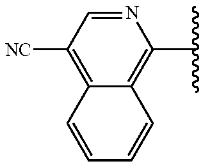 [SMILES: *c1ncc(C#N)c2ccccc12] | 1.29 | 397.2 | $^1$H NMR (500 MHz, DMSO-$d_6$) δ 11.13-10.97 (m, 1H), 9.19 (s, 1H), 8.27-8.18 (m, 2H), 8.12 (t, J = 7.6 Hz, 1H), 8.00-7.94 (m, 2H), 7.91-7.84 (m, 2H), 5.18 (dd, J = 13.5, 5.1 Hz, 1H), 4.65-4.58 (m, 1H), 4.53-4.46 (m, 1H), 2.99-2.87 (m, 1H), 2.69-2.61 (m, 1H), 2.49-2.40 (m, 1H), 2.12-2.04 (m, 1H) |

TABLE 5-continued

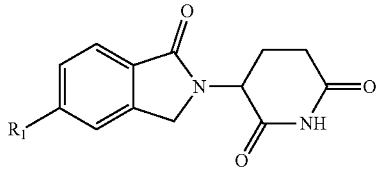

| Ex. No. | $R_1$ | HPLC[a] $T_{Ret}$ (min) | LC/MS (M + H) | $^1$H NMR |
|---|---|---|---|---|
| 91 | 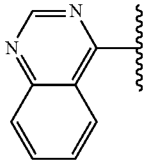 [SMILES: *c1ncnc2ccccc12] | 1.14 | 373.2 | $^1$H NMR (500 MHz, DMSO-$d_6$) δ 11.05 (s, 1H), 9.40 (s, 1H), 8.17-8.07 (m, 3H), 8.04 (s, 1H), 8.00-7.91 (m, 2H), 7.83-7.74 (m, 1H), 5.19 (dd, J = 13.4, 5.1 Hz, 1H), 4.63 (d, J = 1.0 Hz, 1H), 4.51 (d, J = 1.0 Hz, 1H), 3.04-2.89 (m, 1H), 2.64 (d, J = 1.0 Hz, 1H), 2.50-2.40 (m, 1H), 2.13-2.04 (m, 1H) |
| 92 | 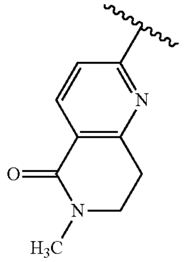 [SMILES: *c1ccc2c(n1)CCN(C)C2=O] | 0.88 | 405.1 | $^1$H NMR (500 MHz, DMSO-$d_6$) δ 11.02 (s, 1H), 8.40-8.35 (m, 1H), 8.29 (d, J = 8.1 Hz, 2H), 8.11-8.06 (m, 1H), 7.87 (d, J = 7.9 Hz, 1H), 5.14 (t, J = 1.0 Hz, 1H), 4.57 (d, J = 1.0 Hz, 1H), 4.45 (d, J = 1.0 Hz, 1H), 3.73-3.68 (m, 2H), 3.26-3.19 (m, 2H), 3.07 (s, 3H), 2.98-2.87 (m, 1H), 2.67-2.60 (m, 1H), 2.49-2.36 (m, 1H), 2.09-2.02 (m, 1H) |
| 93 | 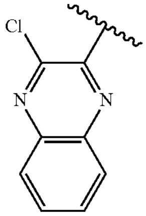 [SMILES: *c1nc2ccccc2nc1Cl] | 1.51 | 407.1 | $^1$H NMR (500 MHz, DMSO-$d_6$) δ 8.24-8.19 (m, 1H), 8.18-8.13 (m, 1H), 8.08 (s, 1H), 8.03-7.96 (m, 3H), 7.95-7.91 (m, 1H), 5.20 (dd, J = 13.1, 5.2 Hz, 1H), 4.62 (d, J = 1.0 Hz, 1H), 4.49 (d, J = 1.0 Hz, 1H), 3.01-2.90 (m, 1H), 2.70-2.60 (m, 1H), 2.50-2.39 (m, 1H), 2.13-2.04 (m, 1H) |
| 94 | 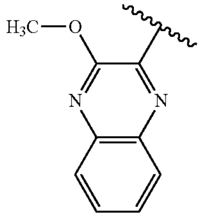 [SMILES: *c1nc2ccccc2nc1OC] | 1.50 | 403.1 | $^1$H NMR (500 MHz, DMSO-$d_6$) δ 8.28 (s, 1H), 8.20 (d, J = 8.2 Hz, 1H), 8.10 (d, J = 7.6 Hz, 1H), 7.93 (br d, J = 8.5 Hz, 1H), 7.90 (br d, J = 7.9 Hz, 1H), 7.81 (t, J = 7.7 Hz, 1H), 7.71 (t, J = 7.8 Hz, 1H), 5.18 (dd, J = 13.1, 5.2 Hz, 1H), 4.60 (d, J = 1.0 Hz, 1H), 4.47 (d, J = 1.0 Hz, 1H), 4.13 (s, 3H), 2.99-2.90 (m, 1H), 2.64 (br dd, J = 15.6, 2.1 Hz, 1H), 2.56 (s, 7H), 2.49-2.40 (m, 1H), 2.11-2.05 (m, 1H) |
| 95 | 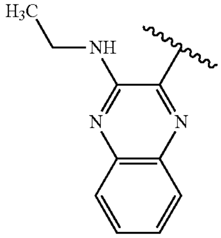 [SMILES: *c1nc2ccccc2nc1NCC] | 1.26 | 416.2 | $^1$H NMR (500 MHz, DMSO-$d_6$) δ 11.03 (s, 1H), 7.94 (s, 1H), 7.91 (d, J = 7.9 Hz, 1H), 7.82 (dd, J = 7.8, 4.4 Hz, 2H), 7.67-7.63 (m, 1H), 7.62-7.57 (m, 1H), 7.38 (t, J = 7.0 Hz, 1H), 6.76 (t, J = 6.0 Hz, 1H), 5.19 (dd, J = 13.6, 5.0 Hz, 1H), 4.57 (d, J = 1.0 Hz, 1H), 4.47 (d, J = 1.0 Hz, 1H), 3.56-3.43 (m, 1H), 3.00-2.91 (m, 1H), 2.65 (br d, J = 1.0 Hz, 1H), 2.50-2.41 (m, 1H), 2.09-2.02 (m, 1H), 1.19 (t, J = 7.0 Hz, 3H) |
| 96 | 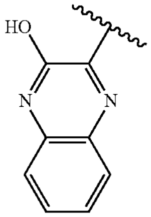 [SMILES: *c1nc2ccccc2nc1O] | 1.19 | 389.1 | $^1$H NMR (500 MHz, DMSO-$d_6$) δ 12.77-12.58 (m, 1H), 11.03 (s, 1H), 8.54 (s, 1H), 8.44 (br d, J = 7.7 Hz, 1H), 7.89 (d, J = 7.9 Hz, 1H), 7.88-7.85 (m, 1H), 7.60 (t, J = 7.7 Hz, 1H), 7.43-7.32 (m, 2H), 5.16 (br dd, J = 13.4, 4.6 Hz, 1H), 4.58 (d, J = 1.0 Hz, 1H), 4.45 (d, J = 1.0 Hz, 1H), 2.99-2.88 (m, 1H), 2.68-2.61 (m, 1H), 2.49-2.37 (m, 1H), 2.11-2.02 (m, 1H) |

TABLE 5-continued

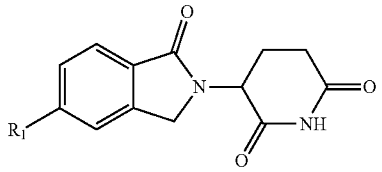

| Ex. No. | $R_1$ | HPLC[a] $T_{Ret}$ (min) | LC/MS (M + H) | $^1H$ NMR |
|---|---|---|---|---|
| 97 | 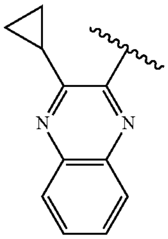 [SMILES: *c1nc2ccccc2nc1C1CC1] | 1.75 | 413.2 | $^1H$ NMR (500 MHz, DMSO-$d_6$) δ 8.08 (d, J = 7.7 Hz, 1H), 8.03 (s, 1H), 7.99 (d, J = 8.1 Hz, 1H), 7.96-7.91 (m, 2H), 7.86-7.75 (m, 2H), 5.17 (br dd, J = 13.3, 5.0 Hz, 1H), 4.61 (d, J = 1.0 Hz, 1H), 4.49 (d, J = 1.0 Hz, 1H), 2.99-2.89 (m, 1H), 2.64 (br d, J = 16.1 Hz, 1H), 2.49-2.39 (m, 1H), 2.30-2.23 (m, 1H), 2.11-2.03 (m, 1H), 1.31-1.24 (m, 2H), 1.11 (br dd, J = 7.7, 3.2 Hz, 2H) |
| 98 | 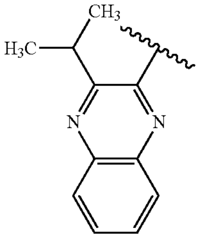 [SMILES: *c1nc2ccccc2nc1C(C)C] | 1.73 | 415.2 | $^1H$ NMR (500 MHz, DMSO-$d_6$) δ 11.04 (s, 1H), 8.17-8.06 (m, 2H), 7.96-7.83 (m, 4H), 7.78 (br d, J = 7.9 Hz, 1H), 5.19 (t, J = 1.0 Hz, 1H), 4.60 (d, J = 1.0 Hz, 1H), 4.48 (d, J = 1.0 Hz, 1H), 3.46-3.37 (m, 1H), 3.00-2.90 (m, 1H), 2.64 (br d, J = 17.3 Hz, 1H), 2.49-2.38 (m, 1H), 2.13-2.04 (m, 1H), 1.31-1.23 (m, 6H) |
| 99 | 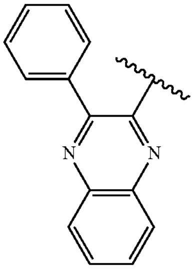 [SMILES: *c1nc2ccccc2nc1-c1ccccc1] | 1.68 | 449.3 | $^1H$ NMR (500 MHz, DMSO-$d_6$) δ 8.20 (d, J = 6.7 Hz, 2H), 7.96-7.90 (m, 2H), 7.85 (s, 1H), 7.66 (d, J = 7.8 Hz, 1H), 7.54-7.48 (m, 3H), 7.44-7.37 (m, 3H), 5.12 (dd, J = 13.5, 5.0 Hz, 1H), 4.48 (d, J = 1.0 Hz, 1H), 4.36 (d, J = 1.0 Hz, 1H), 2.96-2.85 (m, 1H), 2.62 (d, J = 1.0 Hz, 1H), 2.41 (qd, J = 13.2, 3.9 Hz, 1H), 2.09-2.00 (m, 1H) |
| 100 | 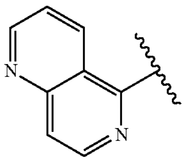 [SMILES: *c1nccc2ncccc12] | 0.85 | 373.1 | $^1H$ NMR (500 MHz, DMSO-$d_6$) δ 9.18 (dd, J = 4.3, 1.2 Hz, 1H), 8.86 (d, J = 5.8 Hz, 1H), 8.46 (d, J = 8.9 Hz, 1H), 8.00 (d, J = 6.1 Hz, 1H), 7.97-7.92 (m, 2H), 7.84 (d, J = 7.9 Hz, 1H), 7.70 (dd, J = 8.5, 4.3 Hz, 1H), 5.18 (dd, J = 13.4, 5.2 Hz, 1H), 4.61 (d, J = 1.0 Hz, 1H), 4.49 (d, J = 1.0 Hz, 1H), 3.02-2.89 (m, 1H), 2.65 (br d, J = 17.7 Hz, 1H), 2.50-2.41 (m, 1H), 2.12-2.04 (m, 1H) |
| 101 | 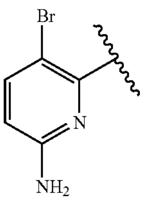 | 0.75 | 415.2 | $^1H$ NMR (500 MHz, DMSO-$d_6$) δ 11.01 (s, 1H), 7.82-7.66 (m, 4H), 6.50 (d, J = 8.9 Hz, 1H), 5.15 (dd, J = 13.3, 5.3 Hz, 1H), 4.53 (d, J = 1.0 Hz, 1H), 4.40 (d, J = 1.0 Hz, 1H), 2.99-2.86 (m, 1H), 2.63 (br d, J = 18.6 Hz, 1H), 2.48-2.37 (m, 1H), 2.09-2.01 (m, 1H) |

TABLE 5-continued

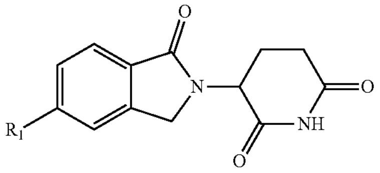

| Ex. No. | $R_1$ | HPLC[a] $T_{Ret}$ (min) | LC/MS (M + H) | $^1H$ NMR |
|---|---|---|---|---|
| 102 | 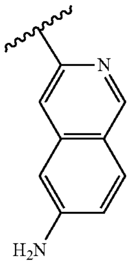 [SMILES: *c1cc2cc(N)ccc2cn1] | 0.99 | 387.3 | $^1H$ NMR (500 MHz, DMSO-$d_6$) δ 8.99 (s, 1H), 8.41 (s, 1H), 8.35-8.30 (m, 1H), 8.09 (s, 1H), 7.85-7.79 (m, 2H), 7.05 (dd, J = 8.7, 2.0 Hz, 1H), 6.87-6.84 (m, 1H), 6.07 (s, 2H), 5.16 (dd, J = 13.1, 4.9 Hz, 1H), 4.56 (d, J = 1.0 Hz, 1H), 4.44 (d, J = 1.0 Hz, 1H), 2.99-2.89 (m, 1H), 2.64 (d, J = 1.0 Hz, 1H), 2.49-2.40 (m, 1H), 2.10-2.02 (m, 1H) |
| 103 | 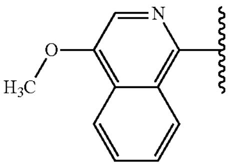 [SMILES: *c1ncc(OC)c2ccccc12] | 1.16 | 402.3 | $^1H$ NMR (500 MHz, DMSO-$d_6$) δ 11.03 (s, 1H), 8.32 (s, 1H), 8.26 (d, J = 8.3 Hz, 1H), 8.01 (d, J = 8.2 Hz, 1H), 7.91 (d, J = 7.9 Hz, 1H), 7.88-7.82 (m, 2H), 7.77 (d, J = 7.6 Hz, 1H), 7.70 (t, J = 7.5 Hz, 1H), 5.18 (dd, J = 13.3, 5.0 Hz, 1H), 4.59 (d, J = 1.0 Hz, 1H), 4.47 (d, J = 1.0 Hz, 1H), 4.13 (s, 3H), 3.01-2.89 (m, 1H), 2.65 (d, J = 1.0 Hz, 1H), 2.50-2.37 (m, 1H), 2.12-2.04 (m, 1H) |
| 104 | 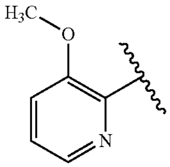 [SMILES: *c1ncccc1OC] | 0.97 | 352.0 | $^1H$ NMR (500 MHz, DMSO-$d_6$) δ 11.01 (s, 1H), 8.32 (d, J = 5.0 Hz, 1H), 8.09 (s, 1H), 8.02 (d, J = 8.2 Hz, 1H), 7.81 (d, J = 7.9 Hz, 1H), 7.66 (d, J = 8.5 Hz, 1H), 7.46 (dd, J = 8.5, 4.6 Hz, 1H), 5.16 (t, J = 1.0 Hz, 1H), 4.54 (d, J = 1.0 Hz, 1H), 4.41 (d, J = 1.0 Hz, 1H), 3.90 (s, 3H), 2.99-2.89 (m, 1H), 2.63 (d, J = 1.0 Hz, 1H), 2.49-2.36 (m, 1H), 2.09-2.02 (m, 1H) |
| 105 | 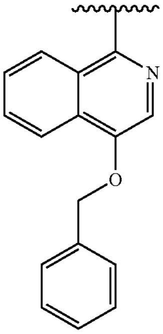 [SMILES: *c1ncc(OCc2ccccc2)c2ccccc12] | 1.52 | 478.2 | $^1H$ NMR (500 MHz, DMSO-$d_6$) δ 11.03 (s, 1H), 8.42 (s, 1H), 8.33 (d, J = 8.2 Hz, 1H), 8.03 (d, J = 8.2 Hz, 1H), 7.91 (d, J = 7.6 Hz, 1H), 7.89-7.84 (m, 2H), 7.77 (d, J = 7.6 Hz, 1H), 7.72 (br t, J = 7.6 Hz, 1H), 7.62 (br d, J = 7.3 Hz, 2H), 7.47 (t, J = 7.5 Hz, 2H), 7.40 (t, J = 1.0 Hz, 1H), 5.50 (s, 2H), 5.18 (dd, J = 13.4, 5.2 Hz, 1H), 4.59 (d, J = 1.0 Hz, 1H), 4.47 (d, J = 1.0 Hz, 1H), 3.01-2.89 (m, 1H), 2.65 (d, J = 1.0 Hz, 1H), 2.49-2.38 (m, 1H), 2.12-2.03 (m, 1H) |
| 106 | 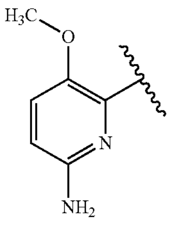 [SMILES: *c1nc(N)ccc1OC] | 0.94 | 367.3 | $^1H$ NMR (500 MHz, DMSO-$d_6$) δ 11.01 (s, 1H), 7.97 (s, 1H), 7.91-7.79 (m, 3H), 6.86 (br d, J = 9.2 Hz, 1H), 5.13 (t, J = 1.0 Hz, 1H), 4.54 (d, J = 1.0 Hz, 1H), 4.41 (d, J = 1.0 Hz, 1H), 3.77 (s, 3H), 2.97-2.86 (m, 1H), 2.64 (br d, J = 16.5 Hz, 1H), 2.55 (s, 7H), 2.49-2.36 (m, 1H), 2.09-2.02 (m, 1H) |

TABLE 5-continued

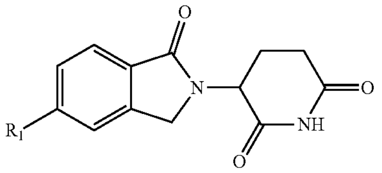

| Ex. No. | $R_1$ | HPLC[a] $T_{Ret}$ (min) | LC/MS (M + H) | $^1$H NMR |
|---|---|---|---|---|
| 107 | 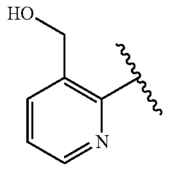 [SMILES: *c1ncccc1CO] | 0.96 | 352.1 | $^1$H NMR (500 MHz, DMSO-$d_6$) δ 8.60 (d, J = 5.1 Hz, 1H), 8.01 (br d, J = 7.6 Hz, 1H), 7.87-7.78 (m, 2H), 7.73 (d, J = 7.6 Hz, 1H), 7.48 (dd, J = 7.6, 4.9 Hz, 1H), 5.15 (dd, J = 13.3, 5.0 Hz, 1H), 4.59-4.49 (m, 3H), 4.43 (d, J = 1.0 Hz, 1H), 2.98-2.88 (m, 1H), 2.64 (br dd, J = 15.0, 2.1 Hz, 1H), 2.50-2.37 (m, 1H), 2.10-2.03 (m, 1H) |
| 108 | 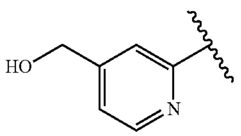 [SMILES: *c1cc(CO)ccn1] | 0.86 | 352.1 | $^1$H NMR (500 MHz, DMSO-$d_6$) δ 11.01 (s, 1H), 8.64 (d, J = 5.0 Hz, 1H), 8.30 (br s, 1H), 8.22 (br d, J = 8.1 Hz, 1H), 7.97 (s, 1H), 7.84 (d, J = 8.0 Hz, 1H), 7.37 (d, J = 4.9 Hz, 1H), 5.25-5.06 (m, 1H), 4.64 (d, J = 5.6 Hz, 2H), 4.55 (d, J = 1.0 Hz, 1H), 4.43 (d, J = 1.0 Hz, 1H), 2.97-2.85 (m, 1H), 2.63 (d, J = 1.0 Hz, 1H), 2.49-2.37 (m, 1H), 2.09-2.01 (m, 1H) |
| 109 | 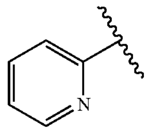 [SMILES: *c1ccccn1] | 0.92 | 322.0 | $^1$H NMR (500 MHz, DMSO-$d_6$) δ 11.04 (s, 1H), 8.75 (br d, J = 4.0 Hz, 1H), 8.35 (s, 1H), 8.25 (d, J = 7.7 Hz, 1H), 8.14-8.07 (m, 1H), 8.00 (t, J = 7.8 Hz, 1H), 7.87 (d, J = 1.0 Hz, 1H), 7.47 (dd, J = 6.9, 5.0 Hz, 1H), 5.16 (t, J = 1.0 Hz, 1H), 4.58 (br d, J = 17.4 Hz, 1H), 4.46 (d, J = 1.0 Hz, 1H), 3.00-2.88 (m, 1H), 2.65 (d, J = 1.0 Hz, 1H), 2.50-2.38 (m, 1H), 2.12-2.03 (m, 1H) |
| 110 | 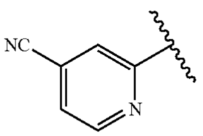 [SMILES: *c1cc(C#N)ccn1] | 1.19 | 347.1 | $^1$H NMR (500 MHz, DMSO-$d_6$) δ 11.01 (s, 1H), 8.94 (d, J = 5.0 Hz, 1H), 8.53 (s, 1H), 8.36 (s, 1H), 8.28 (d, J = 8.0 Hz, 1H), 7.88 (d, J = 7.9 Hz, 1H), 7.85 (d, J = 5.1 Hz, 1H), 5.12 (dd, J = 13.3, 5.1 Hz, 1H), 4.56 (d, J = 1.0 Hz, 1H), 4.44 (d, J = 1.0 Hz, 1H), 2.96-2.84 (m, 1H), 2.63 (d, J = 1.0 Hz, 1H), 2.49-2.36 (m, 1H), 2.12-1.99 (m, 1H) |
| 111 | 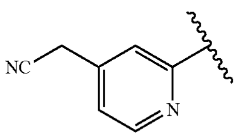 [SMILES: *c1cc(CC#N)ccn1] | 1.04 | 361.0 | $^1$H NMR (500 MHz, DMSO-$d_6$) δ 11.03 (s, 1H), 8.75 (d, J = 4.9 Hz, 1H), 8.33 (s, 1H), 8.26-8.22 (m, J = 7.9 Hz, 1H), 8.06 (s, 1H), 7.93-7.84 (m, J = 7.9 Hz, 1H), 7.45 (br d, J = 4.9 Hz, 1H), 5.15 (br dd, J = 13.1, 4.9 Hz, 1H), 4.58 (d, J = 1.0 Hz, 1H), 4.46 (d, J = 1.0 Hz, 1H), 4.23 (s, 2H), 2.99-2.85 (m, 1H), 2.64 (d, J = 1.0 Hz, 1H), 2.50-2.38 (m, 1H), 2.11-2.02 (m, 1H) |
| 112 | 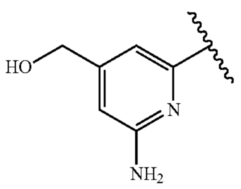 [SMILES: *c1cc(CO)cc(N)n1] | 1.03 | 367.2 | $^1$H NMR (500 MHz, DMSO-$d_6$) δ 11.02 (s, 1H), 8.19 (s, 1H), 8.13 (br d, J = 7.9 Hz, 1H), 7.80 (d, J = 7.9 Hz, 1H), 7.11 (s, 1H), 6.53 (s, 1H), 5.15 (br dd, J = 13.3, 5.0 Hz, 1H), 4.58-4.39 (m, 4H), 2.99-2.89 (m, 1H), 2.64 (br d, J = 18.0 Hz, 1H), 2.50-2.36 (m, 1H), 2.09-2.01 (m, 1H) |
| 113 | 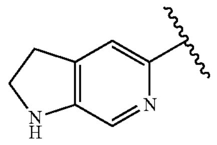 [SMILES: *c1cc2c(cn1)NCC2] | 0.96 | 363.1 | $^1$H NMR (500 MHz, DMSO-$d_6$) δ 11.02 (s, 1H), 8.12 (s, 1H), 8.04 (d, J = 1.0 Hz, 1H), 7.92 (s, 1H), 7.87 (s, 1H), 7.84 (d, J = 7.9 Hz, 1H), 5.14 (br dd, J = 13.1, 5.2 Hz, 1H), 4.54 (d, J = 1.0 Hz, 1H), 4.42 (d, J = 1.0 Hz, 1H), 3.69-3.61 (m, 1H), 3.18 (t, J = 1.0 Hz, 2H), 2.99-2.88 (m, 1H), 2.64 (br d, J = 16.8 Hz, 1H), 2.50-2.39 (m, 1H), 2.10-2.02 (m, 1H) |

TABLE 5-continued

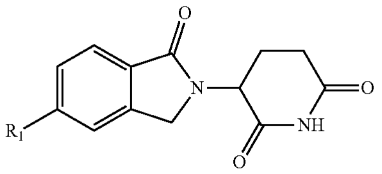

| Ex. No. | $R_1$ | HPLC[a] $T_{Ret}$ (min) | LC/MS (M + H) | $^1H$ NMR |
|---|---|---|---|---|
| 114 | 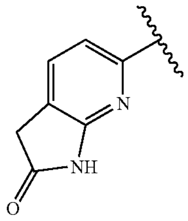 [SMILES: *c1ccc2c(n1)NC(=O)C2] | 1.06 | 377.1 | $^1H$ NMR (500 MHz, DMSO-$d_6$) δ 11.14 (s, 1H), 11.02 (br s, 1H), 8.23 (s, 1H), 8.17 (br d, J = 8.2 Hz, 1H), 7.83 (br d, J = 7.9 Hz, 1H), 7.70 (br d, J = 7.6 Hz, 1H), 7.64 (br d, J = 7.3 Hz, 1H), 5.15 (br dd, J = 13.1, 4.9 Hz, 1H), 4.56 (br d, J = 16.8 Hz, 1H), 4.43 (br d, J = 17.4 Hz, 1H), 3.63 (s, 2H), 3.02-2.89 (m, 1H), 2.64 (br d, J = 1.0 Hz, 1H), 2.50-2.37 (m, 1H), 2.10-2.01 (m, 1H) |
| 115 | 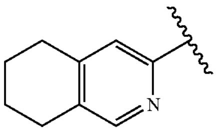 [SMILES: *c1cc2c(cn1)CCCC2] | 1.03 | 376.0 | $^1H$ NMR (500 MHz, DMSO-$d_6$) δ 8.40 (s, 1H), 8.31-8.24 (m, 1H), 8.22-8.14 (m, 1H), 7.88-7.72 (m, 2H), 5.20-5.09 (m, 1H), 4.59-4.49 (m, 1H), 4.47-4.39 (m, 1H), 3.02-2.87 (m, 1H), 2.83 (br s, 2H), 2.77 (br s, 2H), 2.64 (d, J = 1.0 Hz, 1H), 2.50-2.37 (m, 1H), 2.15-2.02 (m, 1H), 1.79 (br s, 4H) |
| 116 | 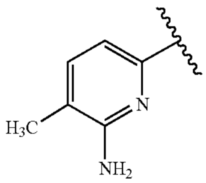 [SMILES: *c1ccc(C)c(N)n1] | 0.91 | 351.2 | $^1H$ NMR (500 MHz, DMSO-$d_6$) δ 11.01 (s, 1H), 7.78 (d, J = 7.6 Hz, 1H), 7.69 (s, 1H), 7.61 (br d, J = 7.9 Hz, 1H), 7.37 (d, J = 8.2 Hz, 1H), 6.47 (d, J = 8.2 Hz, 1H), 5.14 (br dd, J = 13.3, 5.0 Hz, 1H), 4.52 (br d, J = 17.1 Hz, 1H), 4.39 (br d, J = 17.4 Hz, 1H), 2.98-2.87 (m, 1H), 2.64 (br d, J = 16.8 Hz, 1H), 2.49-2.37 (m, 1H), 2.15 (s, 3H), 2.09-2.01 (m, 1H) |
| 117 | 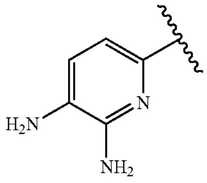 [SMILES: *c1ccc(N)c(N)n1] | 0.87 | 352.1 | $^1H$ NMR (500 MHz, DMSO-$d_6$) δ 8.10 (s, 1H), 8.05 (br d, J = 8.2 Hz, 1H), 7.70 (d, J = 1.0 Hz, 1H), 7.14 (d, J = 7.9 Hz, 1H), 6.81 (d, J = 7.9 Hz, 1H), 5.58 (s, 2H), 5.12 (br dd, J = 13.3, 5.0 Hz, 1H), 5.02 (s, 1H), 4.49 (br d, J = 17.1 Hz, 1H), 4.36 (d, J = 1.0 Hz, 1H), 3.01 (s, 2H), 2.97-2.87 (m, 1H), 2.67-2.59 (m, 1H), 2.49-2.37 (m, 1H), 2.07-1.99 (m, 1H) |
| 118 | 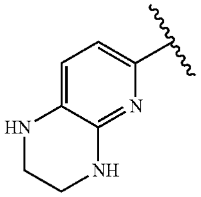 [SMILES: *c1ccc2c(n1)NCCN2] | 1.07 | 378.1 | $^1H$ NMR (500 MHz, DMSO-$d_6$) δ 11.00 (s, 1H), 8.03 (br s, 1H), 7.96 (br d, J = 7.3 Hz, 1H), 7.76 (br d, J = 7.9 Hz, 1H), 7.33-7.19 (m, 1H), 7.18-7.09 (m, 1H), 7.04 (s, 1H), 6.83-6.75 (m, 1H), 5.14 (br dd, J = 13.4, 5.2 Hz, 1H), 4.50 (br d, J = 17.1 Hz, 1H), 4.38 (d, J = 1.0 Hz, 1H), 2.99-2.89 (m, 1H), 2.63 (br d, J = 16.5 Hz, 1H), 2.48-2.36 (m, 1H), 2.08-1.99 (m, 1H) |
| 119 | 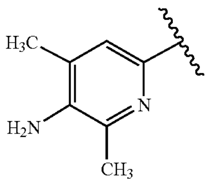 | 0.66 | 365.2 | $^1H$ NMR (500 MHz, DMSO-$d_6$) δ 10.99 (s, 1H), 8.16 (s, 1H), 8.10 (d, J = 8.3 Hz, 1H), 7.72 (d, J = 8.0 Hz, 1H), 7.59 (s, 1H), 5.11 (br dd, J = 13.1, 4.7 Hz, 1H), 4.49 (d, J = 1.0 Hz, 1H), 4.37 (d, J = 1.0 Hz, 1H), 2.96-2.86 (m, 1H), 2.63 (d, J = 1.0 Hz, 1H), 2.49-2.42 (m, 1H), 2.40 (s, 3H), 2.19 (s, 3H) |

TABLE 5-continued

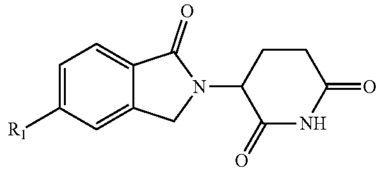

| Ex. No. | $R_1$ | HPLC[a] $T_{Ret}$ (min) | LC/MS (M + H) | $^1H$ NMR |
|---|---|---|---|---|
| 120 | 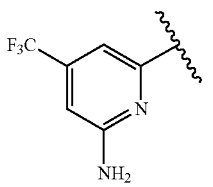 [SMILES: *c1cc(C(F)(F)F)cc(N)n1] | 1.40 | 405.1 | $^1H$ NMR (500 MHz, DMSO-$d_6$) δ 11.03 (s, 1H), 8.28 (s, 1H), 8.22 (br d, J = 8.2 Hz, 1H), 7.91 (d, J = 7.7 Hz, 1H), 7.86 (d, J = 7.8 Hz, 1H), 7.35 (d, J = 7.9 Hz, 1H), 5.15 (br dd, J = 13.1, 4.9 Hz, 1H), 4.56 (d, J = 1.0 Hz, 1H), 4.44 (d, J = 1.0 Hz, 1H), 2.99-2.88 (m, 1H), 2.64 (d, J = 1.0 Hz, 1H), 2.49-2.39 (m, 1H), 2.11-2.02 (m, 1H) |
| 121 | 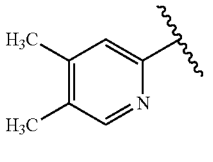 | 0.95 | 350.1 | $^1H$ NMR (500 MHz, DMSO-$d_6$) δ 11.01 (s, 1H), 8.43 (s, 1H), 8.27 (s, 1H), 8.19 (br d, J = 8.2 Hz, 1H), 7.89 (s, 1H), 7.82 (d, J = 8.0 Hz, 1H), 5.15-5.09 (m, 1H), 4.54 (d, J = 17.3 Hz, 1H), 4.41 (d, J = 17.2 Hz, 1H), 2.97-2.86 (m, 1H), 2.62 (d, J = 1.0 Hz, 1H), 2.48-2.40 (m, 1H), 2.35 (s, 3H), 2.28 (s, 3H), 2.09-2.01 (m, 1H) |

[a]HPLC Retention time using Analytical HPLC Method 1.

General Procedure 2: Same as general procedure 1, except acetic acid was used instead of acetonitrile for the cyclization reaction.

General Procedure 3: Same as general procedure 1, except $PdCl_2(dppf)_2$ was used as catalyst instead of $PdCl_2(dtbpf)$.

Example 122

(3S)-3-[5-(1,8-naphthyridin-2-yl)-1-oxo-2,3-dihydro-1H-isoindol-2-yl]piperidine-2,6-dione (122)

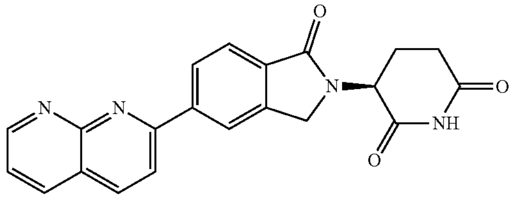

Example 122 was prepared according to General Procedure 2. MS (ES): m/z=373.3 $[M+H]^+$. HPLC[a] $T_{Ret}$=0.99 min. $^1H$ NMR (500 MHz, DMSO-d6) δ 11.05 (br s, 1H), 9.15 (br d, J=2.3 Hz, 1H), 8.64 (d, J=8.5 Hz, 1H), 8.58 (s, 1H), 8.54 (br d, J=8.0 Hz, 1H), 8.49 (br d, J=7.7 Hz, 1H), 8.39 (d, J=8.5 Hz, 1H), 7.94 (d, J=8.0 Hz, 1H), 7.68 (dd, J=8.1, 4.2 Hz, 1H), 5.18 (br dd, J=13.3, 5.1 Hz, 1H), 4.66-4.60 (m, 1H), 4.54-4.47 (m, 1H), 3.01-2.90 (m, 1H), 2.68-2.61 (m, 1H), 2.50-2.40 (m, 1H), 2.12-2.04 (m, 1H).

Example 123

(S)-3-(5-(3-aminoisoquinolin-1-yl)-1-oxoisoindolin-2-yl)piperidine-2,6-dione (123)

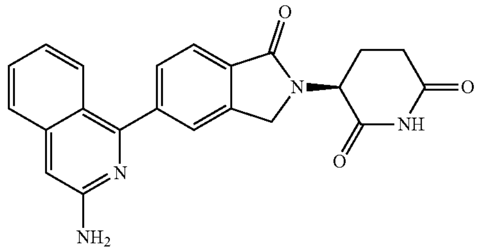

Example 123 was prepared according to General Procedure 2. MS (ES): m/z=387.2 $[M+H]^+$. HPLC[a] $T_{Ret}$=0.87 min. $^1H$ NMR (500 MHz, DMSO-d6) δ 7.89 (d, J=7.6 Hz, 1H), 7.83 (s, 1H), 7.75-7.67 (m, 2H), 7.62 (d, J=8.3 Hz, 1H), 7.51-7.45 (m, 1H), 7.12 (t, J=7.6 Hz, 1H), 6.72 (s, 1H), 6.10-5.97 (m, 2H), 5.17 (br dd, J=13.3, 4.8 Hz, 1H), 4.61-4.55 (m, 1H), 4.49-4.42 (m, 1H), 3.00-2.88 (m, 1H), 2.68-2.60 (m, 1H), 2.49-2.36 (m, 1H), 2.11-2.03 (m, 1H).

Example 124

(S)—N-(1-(2-(2,6-dioxopiperidin-3-yl)-1-oxoisoindolin-5-yl)isoquinolin-3-yl)acetamide (124)

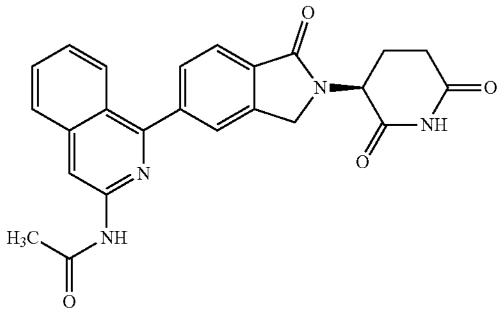

Example 124 was a side product obtained during the final synthetic step (cyclization using AcOH as solvent) in the preparation of Example 123. MS (ES): m/z=429.2 $[M+H]^+$. HPLC[a] $T_{Ret}$=1.21 min. $^1$H NMR (500 MHz, DMSO-d6) δ 11.03 (s, 1H), 10.66 (s, 1H), 8.50 (s, 1H), 7.99 (d, J=8.2 Hz, 1H), 7.96-7.89 (m, 3H), 7.81 (d, J=7.8 Hz, 1H), 7.73 (t, J=7.5 Hz, 1H), 7.50 (t, J=7.5 Hz, 1H), 5.20-5.13 (m, 1H), 4.63-4.56 (m, 1H), 4.50-4.43 (m, 1H), 2.98-2.89 (m, 1H), 2.68-2.61 (m, 1H), 2.48-2.40 (m, 1H), 2.16 (s, 3H), 2.08 (br dd, J=10.1, 5.5 Hz, 1H).

Example 125

3-{2-[(3 S)-2,6-dioxopiperidin-3-yl]-1-oxo-2,3-dihydro-1H-isoindol-5-yl}isoquinoline-1-carbonitrile (125)

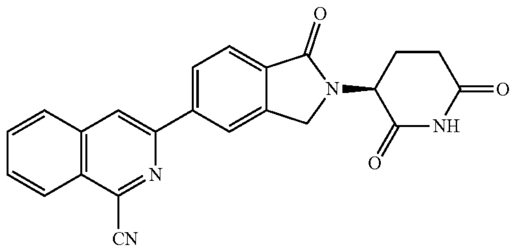

Example 125 was prepared according to General Procedure 2. MS (ES): m/z=397.2 $[M+H]^+$. HPLC[a] $T_{Ret}$=1.40 min. $^1$H NMR (500 MHz, DMSO-d6) δ 11.06 (s, 1H), 8.82-8.74 (m, 1H), 8.31-8.24 (m, 1H), 8.19-8.12 (m, 1H), 8.05 (br t, J=7.0 Hz, 1H), 8.01-7.89 (m, 3H), 7.89-7.83 (m, 1H), 5.27-5.18 (m, 1H), 4.68-4.60 (m, 1H), 4.57-4.48 (m, 1H), 3.04-2.91 (m, 1H), 2.71-2.63 (m, 1H), 2.51-2.42 (m, 1H), 2.15-2.06 (m, 1H).

Example 126

3-{2-[(3S)-2,6-dioxopiperidin-3-yl]-1-oxo-2,3-dihydro-1H-isoindol-5-yl}isoquinoline-1-carboxamide (126)

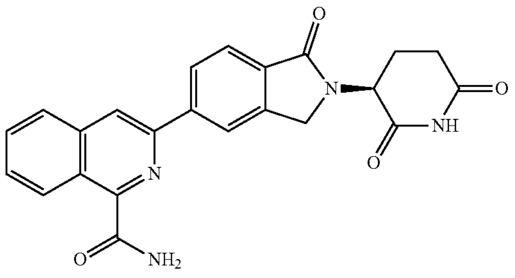

Example 126 was a side product obtained during the final synthetic step (cyclization using AcOH as solvent) in the preparation of Example 125. MS (ES): m/z=415.2 $[M+H]^+$. HPLC[a] $T_{Ret}$=1.29 min. $^1$H NMR (500 MHz, DMSO-d6) δ 8.74 (s, 1H), 8.26 (br d, J=7.9 Hz, 1H), 8.14 (br d, J=8.5 Hz, 1H), 8.03 (br t, J=7.5 Hz, 1H), 7.97-7.88 (m, 3H), 7.84-7.79 (m, 1H), 7.66-7.62 (m, 1H), 7.24 (br s, 1H), 4.86-4.81 (m, 1H), 4.80-4.74 (m, 1H), 4.66-4.60 (m, 1H), 2.57-2.55 (m, 1H), 2.50-2.30 (m, 2H), 2.24 (s, 3H), 2.10-2.01 (m, 1H).

Example 127

(4S)-7-{2-[(3S)-2,6-dioxopiperidin-3-yl]-1-oxo-2,3-dihydro-1H-isoindol-5-yl}-2H,3H,4H-pyrano[2,3-b]pyridin-4-yl acetate (127)

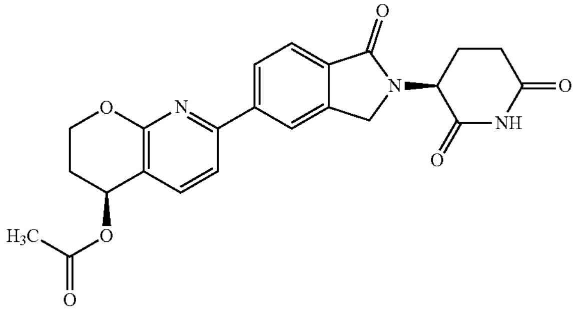

Example 127 was prepared according to General Procedure 2 using (S)-7-chloro-3,4-dihydro-2H-pyrano[2,3-b]pyridin-4-ol as the aryl halide. The alcohol was acetylated during the final synthetic step (cyclization using AcOH as solvent). MS (ES): m/z=436.2 $[M+H]^+$. HPLC[a] $T_{Ret}$=1.29 min. $^1$H NMR (500 MHz, DMSO-d6) δ 11.01 (s, 1H), 8.26 (s, 1H), 8.17 (d, J=7.6 Hz, 1H), 7.87 (d, J=7.9 Hz, 1H), 7.83 (d, J=7.9 Hz, 1H), 7.70 (d, J=7.9 Hz, 1H), 5.94 (t, J=4.0 Hz, 1H), 5.13 (br dd, J=13.3, 5.0 Hz, 1H), 4.58-4.52 (m, 1H), 4.51-4.40 (m, 2H), 4.38-4.32 (m, 1H), 2.96-2.87 (m, 1H), 2.63 (br d, J=17.7 Hz, 1H), 2.49-2.37 (m, 1H), 2.27-2.18 (m, 1H), 2.08 (s, 3H).

Example 128

(4R)-7-{2-[(3S)-2,6-dioxopiperidin-3-yl]-1-oxo-2,3-dihydro-1H-isoindol-5-yl}-2H,3H,4H-pyrano[2,3-b]pyridin-4-yl acetate (128)

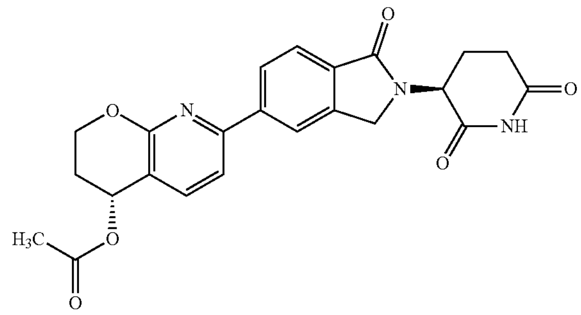

Example 128 was prepared according to General Procedure 2 using (R)-7-chloro-3,4-dihydro-2H-pyrano[2,3-b]pyridin-4-ol as the aryl halide. The alcohol was acetylated during the final synthetic step (cyclization using AcOH as solvent). MS (ES): m/z=436.2 $[M+H]^+$. HPLC[a] $T_{Ret}$=1.30 min. $^1$H NMR (500 MHz, DMSO-d6) δ 8.25 (s, 1H), 8.17 (br d, J=8.2 Hz, 1H), 7.87 (d, J=7.6 Hz, 1H), 7.83 (d, J=7.9 Hz, 1H), 7.70 (d, J=7.6 Hz, 1H), 5.93 (br t, J=4.0 Hz, 1H), 5.13 (br dd, J=13.1, 5.2 Hz, 1H), 4.58-4.52 (m, 1H), 4.50-4.40 (m, 2H), 4.38-4.31 (m, 1H), 2.96-2.87 (m, 1H), 2.67-2.59 (m, 1H), 2.48-2.36 (m, 1H), 2.28-2.15 (m, 1H), 2.08 (s, 3H).

Example 129

3-{5-[7-chloro-4-(dimethylamino)isoquinolin-1-yl]-1-oxo-2,3-dihydro-1H-isoindol-2-yl}piperidine-2,6-dione (129)

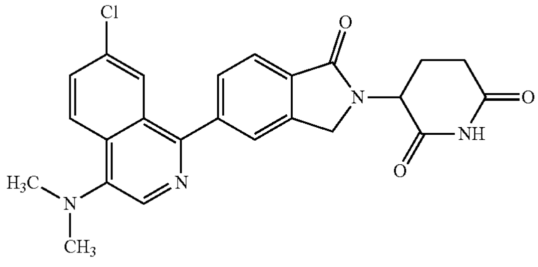

Preparation 129A: 1,7-dichloroisoquinolin-4-amine

To a slurry of 4-bromo-1,7-dichloroisoquinoline (2.15 g, 7.76 mmol) in THE (40 mL) at −78° C. was added BuLi (12.13 mL, 19.41 mmol) dropwise. A dark brown solution was formed. After 30 min, diphenyl phosphoryl azide (1.678 mL, 7.76 mmol) was added. After 1 h, Vitride™ (9.47 mL, 31.1 mmol) was added to the reaction mixture. Then the reaction bottle was warmed up to 0° C. After 30 min, the reaction mixture was quenched with ice-water (10 mL) and filtered. The cake was washed with water and then with ethyl acetate. The organic layers were combined and washed with aqueous saturated NaCl, and dried with $Na_2SO_4$, filtered and concentrated to afford Preparation 129A as a red solid (210 mg).

Preparation 129B: 1,7-dichloro-N,N-dimethylisoquinolin-4-amine

Preparation 128A (450 mg, 2.1 mmol) was dissolved in DMF (10 mL) at 0° C. Sodium hydride (152 mg, 6.34 mmol) was added in one portion. The reaction mixture was stirred for 20 min, then iodomethane (0.224 mL, 3.59 mmol) was added dropwise. The reaction mixture was stirred for 1 h. The reaction was quenched with water. The reaction mixture was extracted with ethyl acetate, washed with aqueous saturated NaCl, and dried over sodium sulfate. The product was purified by ISCO using a silica gel column and eluting with 1-2% EtOAc/hexanes to afford Preparation 129B in 79% yield. $^1$H NMR (400 MHz, CHLOROFORM-d) δ 8.20 (d, J=2.3 Hz, 1H), 8.05 (d, J=9.1 Hz, 1H), 7.85 (s, 1H), 7.61 (dd, J=9.1, 2.0 Hz, 1H), 2.87 (s, 6H).

Example 129

The Suzuki coupling and cyclization were accomplished by following General Procedure 1 using Preparation 129B and Preparation 1B. MS (ES): m/z=449.2 $[M+H]^+$. HPLC[a] $T_{Ret}$=1.31 min. $^1$H NMR (500 MHz, DMSO-d6) δ 11.04 (s, 1H), 8.32 (s, 1H), 8.25 (d, J=8.7 Hz, 1H), 7.96-7.89 (m, 2H), 7.87 (s, 1H), 7.83 (dd, J=9.0, 2.1 Hz, 1H), 7.77 (d, J=7.8 Hz, 1H), 5.19 (t, J=1.0 Hz, 1H), 4.60 (d, J=1.0 Hz, 1H), 4.47 (d, J=1.0 Hz, 1H), 3.02-2.91 (m, 7H), 2.67-2.61 (m, 1H), 2.50-2.39 (m, 1H), 2.14-2.03 (m, 1H).

Example 130

1-amino-3-[2-(2,6-dioxopiperidin-3-yl)-1-oxo-2,3-dihydro-1H-isoindol-5-yl]-N,N-dimethylisoquinoline-4-carboxamide (130)

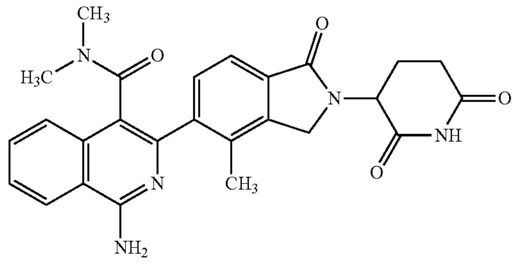

Preparation 130A: Methyl 1,3-dichloroisoquinoline-4-carboxylate

To a solution of 1,3-dichloroisoquinoline (2 g, 10.10 mmol) in THE (40 mL) at −78° C. was added LDA (5.55 mL, 11.11 mmol) dropwise. After stirring for 30 minutes at this temperature, methyl carbonochloridate (1.017 mL, 13.13 mmol) was added. The mixture was stirred for an additional hour and then slowly warmed to room temperature. The reaction was quenched with ice-water. The reaction mixture was diluted with EtOAc. The organic layer was separated, washed with brine and dried with sodium sulfate. The solvents were removed under reduced pressure and the residue was purified using an 80 gram silica gel column by ISCO eluting with 5-100% DCM/hexanes to afford Preparation 130A (2.34 g, 9.14 mmol, 90% yield). $^1$H NMR (400 MHz, CHLOROFORM-d) δ 8.41 (d, J=8.2 Hz, 1H), 7.90-7.82 (m, 2H), 7.79-7.74 (m, 1H), 4.11 (s, 3H).

Preparation 130B: 1-Amino-3-chloroisoquinoline-4-carboxylic acid

Preparation 130A (1.00 g, 3.90 mmol) and 28% aqueous $NH_3$ (10.86 mL, 78 mmol) were added to a sealed tube, followed by the addition of MeOH (0.5 mL). The reaction mixture was heated to 140° C. for 4 hours and cooled. The mixture was rotovapped to remove the majority of the methanol, and diluted with iced-water. The precipitate (product) was filtered and air dried. The solid residue was purified by using Preparative HPLC Method 2 to obtain 50% yield of Preparation 130B.

Preparation 130C: 1-amino-3-chloro-N,N-dimethylisoquinoline-4-carboxamide

Preparation 130B (30 mg, 0.135 mmol), HATU (64.0 mg, 0.168 mmol) and DMF (1 mL) were added to a sealed tube, followed by triethylamine (0.038 mL, 0.270 mmol). After 10 minutes, dimethylamine (6.68 mg, 0.148 mmol) was added. The tube was sealed and heated to 50° C. for 2 h. The reaction mixture was diluted with 15% EtOH/EtOAc and washed with 10% aqueous LiCl. The organic layer was concentrated and purified using Preparative HPLC Method 2 to obtain 14 mg (42% yield) Preparation 130C.

Example 130

The Suzuki coupling and cyclization were accomplished by following General Procedure 1 with Preparation 130C and Preparation 1B. MS (ES): m/z=458.1 [M+H]$^+$. HPLC$^a$ $T_{Ret}$=0.92 min. $^1$H NMR (500 MHz, DMSO-d6) δ 11.03 (s, 1H), 8.58 (br d, J=7.9 Hz, 1H), 7.98-7.93 (m, 1H), 7.90 (d, J=7.9 Hz, 1H), 7.87 (s, 1H), 7.83-7.77 (m, 2H), 7.66 (d, J=8.5 Hz, 1H), 5.20-5.14 (m, 1H), 4.62-4.52 (m, 1H), 4.48-4.39 (m, 1H), 3.00-2.93 (m, 1H), 2.92 (d, J=5.5 Hz, 3H), 2.69-2.61 (m, 1H), 2.59 (d, J=1.8 Hz, 3H), 2.48-2.40 (m, 1H), 2.12-2.03 (m, 1H).

Example 131

3-[5-(1-amino-4-methylisoquinolin-3-yl)-1-oxo-2,3-dihydro-1H-isoindol-2-yl]piperidine-2,6-dione (131)

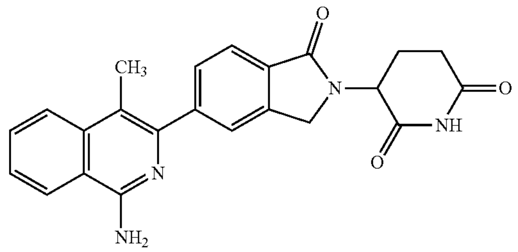

Preparation 131A: 3-chloro-4-methylisoquinolin-1-amine

A solution of 1-amino-3-chloroisoquinoline-4-carboxylic acid (40 mg, 0.180 mmol) in THE (10 mL) was placed in an ice-water bath and borane-THF (0.359 mL, 0.359 mmol) was added dropwise. After 90 min, it was observed that there was significant byproduct (loss of the hydroxy group). The reaction was quenched by the addition of several drops of formaldehyde. The reaction mixture was concentrated and the crude material was purified using Preparative HPLC Method 2 to afford Preparation 131A as a mixture of 1-amino-3-chloroisoquinolin-4-yl)methanol and 3-chloro-4-methylisoquinolin-1-amine in a 2:1 ratio.

Example 131

The Suzuki coupling and cyclization were accomplished by following General Procedure 1 using Preparation 131A and Preparation 1B to afford Example 131. MS (ES): m/z=401.3 [M+H]$^+$. HPLC$^a$ $T_{Ret}$=1.24 min. $^1$H NMR (500 MHz, DMSO-d6) δ 8.27 (d, J=8.2 Hz, 1H), 7.94 (d, J=8.2 Hz, 1H), 7.80 (d, J=7.8 Hz, 1H), 7.77-7.71 (m, 2H), 7.65 (d, J=7.9 Hz, 1H), 7.55 (t, J=7.4 Hz, 1H), 6.74 (s, 2H), 5.17 (dd, J=13.5, 5.2 Hz, 1H), 4.54 (d, J=17.5 Hz, 1H), 4.41 (d, J=17.1 Hz, 1H), 2.99-2.90 (m, 1H), 2.67-2.60 (m, 1H), 2.48-2.41 (m, 1H), 2.40 (s, 3H), 2.10-2.02 (m, 1H).

Example 132

3-[5-(6-amino-3-cyclopropylpyridin-2-yl)-1-oxo-2,3-dihydro-1H-isoindol-2-yl]piperidine-2,6-dione (132)

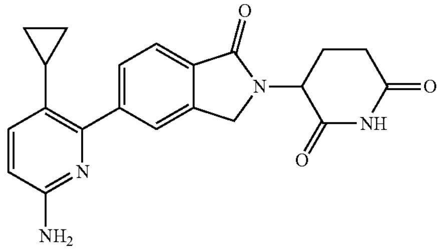

Preparation 132A: tert-butyl 5-amino-4-(5-(6-amino-3-bromopyridin-2-yl)-1-oxoisoindolin-2-yl)-5-oxopentanoate To a stirred solution of 5,6-dibromopyridin-2-amine (135 mg, 0.536 mmol) in a mixture of methanol (1 mL) and toluene (10 mL) was added Preparation 1B (250 mg, 0.563 mmol) followed by the addition of aqueous $Na_2CO_3$ (2.143 mL, 1.072 mmol). The mixture was purged with nitrogen for 5 min and then $Pd(PPh_3)_4$ (18.58 mg, 0.016 mmol) was added. The reaction mixture was heated to 110° C. for two days. The reaction mixture was cooled to room temperature and diluted with water (20 mL). The mixture was extracted with EtOAc (3×10 mL). The combined organic layers were washed with water (2×10 mL) and dried over anhydrous $Na_2SO_4$. The mixture was concentrated under reduced pressure and the crude product was purified by flash silica gel column chromatography using 2-80% B/DCM [where B=15% EtOH/EtOAc with 0.1% TEA] to afford 69 mg of Preparation 132A. MS (ES): m/z=489.1 $[M+H]^+$.

Example 132

A 2 mL microwave vial was charged with cyclopropylboronic acid (3.95 mg, 0.046 mmol), Preparation 132A (15 mg, 0.031 mmol), $PdCl_2$(dtbpf) (0.599 mg, 0.920 μmol), 1,4-dioxane (1 mL) and aqueous $K_2CO_3$ (0.092 mL, 0.092 mmol). The vial was sealed and the air was replaced with nitrogen. The reaction mixture was microwaved for 10 min at 130° C. The reaction mixture was diluted with EtOAc, washed with brine, and the organic layer separated and concentrated. The crude product was dissolved in 0.5 mL of $PhSO_3H$ solution in MeCN (0.228 M) was added and microwaved for 10 minutes at 120° C. The mixture was concentrated to dryness, and purified using Preparative HPLC Method 1 to afford Example 132. MS (ES): m/z=377.0 $[M+H]^+$. HPLC[a] $T_{Ret}$=1.05 min. $^1H$ NMR (500 MHz, DMSO-d6) δ 7.78 (d, J=8.5 Hz, 2H), 7.75-7.70 (m, 1H), 7.15 (d, J=8.5 Hz, 1H), 6.45 (d, J=8.5 Hz, 1H), 5.89-5.78 (m, 2H), 5.16 (br dd, J=13.3, 5.0 Hz, 1H), 4.53 (d, J=1.0 Hz, 1H), 4.41 (d, J=1.0 Hz, 1H), 2.99-2.89 (m, 1H), 2.67-2.60 (m, 1H), 2.47-2.37 (m, 1H), 2.10-2.00 (m, 1H), 1.84-1.77 (m, 1H), 0.79-0.72 (m, 2H), 0.56-0.47 (m, 2H).

Example 133

3-[5-(6-aminoisoquinolin-1-yl)-1-oxo-2,3-dihydro-1H-isoindol-2-yl]piperidine-2,6-dione (133)

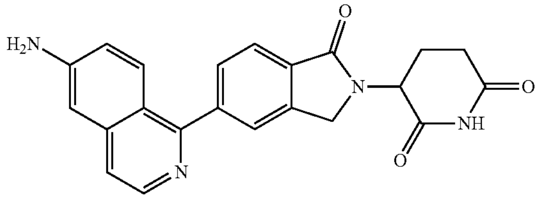

Preparation 1B (44.4 mg, 0.100 mmol), 1-chloroisoquinolin-6-amine (17 mg, 0.095 mmol), $PdCl_2$(dtbpf) (6.96 mg, 9.52 μmol) and dioxane (1 mL) were added to a vial, followed by the addition of aqueous $K_2CO_3$ (0.190 mL, 0.190 mmol). The vial was sealed and the air was replaced with nitrogen. The reaction mixture was microwaved at 125° C. for 11 min. The reaction mixture was diluted with EtOAc, washed with brine, and the organic layer separated and concentrated. The crude material was divided into two equal samples. One sample of the crude intermediate was suspended in 1 mL solution of $PhSO_3H$ in MeCN (0.228 M), microwaved for 10 min at 130° C., and concentrated to dryness, and the residue dissolved in 1.8 mL of DMSO, and purified using Preparative HPLC Method 1 to afford Example 133. MS (ES): m/z=387.1 $[M+H]^+$. HPLC[a] $T_{Ret}$=0.62 min. $^1H$ NMR (500 MHz, DMSO-d6) δ 11.05 (s, 1H), 8.23 (d, J=6.4 Hz, 1H), 8.03-7.95 (m, 2H), 7.86 (br d, J=7.6 Hz, 1H), 7.78 (br d, J=8.5 Hz, 2H), 7.25-7.18 (m, 1H), 7.00-6.97 (m, 1H), 5.21 (dd, J=13.3, 5.0 Hz, 1H), 4.62 (d, J=1.0 Hz, 1H), 4.51 (d, J=1.0 Hz, 1H), 3.00-2.90 (m, 1H), 2.65 (d, J=1.0 Hz, 1H), 2.50-2.37 (m, 1H), 2.13-2.04 (m, 1H).

The second sample of the crude intermediate was suspended in 1 mL solution of $PhSO_3H$ in AcOH (0.228 M) and microwaved for 10 min at 120° C. The sample was concentrated to dryness, and the residue dissolved in 1.8 mL of DMSO, and purified using Preparative HPLC Method 1 to afford Example 134.

Example 134

N-{1-[2-(2,6-dioxopiperidin-3-yl)-1-oxo-2,3-dihydro-1H-isoindol-5-yl]isoquinolin-6-yl}acetamide (134)

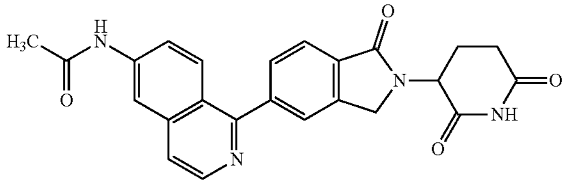

This was prepared as described in Example 133, see preparation above. MS (ES): m/z=429.2 $[M+H]^+$. HPLC[a] $T_{Ret}$=0.98 min. $^1H$ NMR (500 MHz, DMSO-d6) δ 10.44 (s, 1H), 8.52 (d, J=5.8 Hz, 1H), 8.46 (s, 1H), 7.98 (d, J=8.9 Hz, 1H), 7.92 (d, J=7.8 Hz, 1H), 7.89 (s, 1H), 7.80 (s, 1H), 7.79 (s, 1H), 7.65 (dd, J=9.3, 1.7 Hz, 1H), 5.18 (dd, J=13.1, 5.2 Hz, 1H), 4.60 (d, J=1.0 Hz, 1H), 4.48 (d, J=1.0 Hz, 1H), 3.01-2.90 (m, 1H), 2.65 (br d, J=17.1 Hz, 1H), 2.50-2.38 (m, 1H), 2.15 (s, 3H), 2.12-2.05 (m, 1H).

Example 135

3-{5-[6-amino-4-(chloromethyl)pyridin-2-yl]-1-oxo-2,3-dihydro-1H-isoindol-2-yl}piperidine-2,6-dione (135)

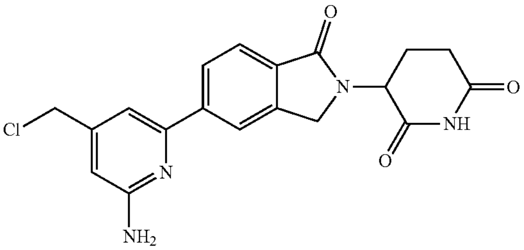

Preparation 135A: tert-butyl (S)-5-amino-4-(5-(6-amino-4-(hydroxymethyl)pyridin-2-yl)-1-oxoisoindolin-2-yl)-5-oxopentanoate A 20 mL microwave vial was charged with (2-amino-6-chloropyridin-4-yl) methanol (211 mg, 1.331 mmol), Preparation 1B (739 mg, 1.663 mmol), $PdCl_2$(dtbpf) (43.4 mg, 0.067 mmol), dioxane (10 mL) and aqueous $K_3PO_4$ (2.218 mL, 6.65 mmol). The vial was sealed and the air was replaced with nitrogen. The reaction mixture was heated at 130° C. for 30 min in the microwave. The reaction mixture was diluted with EtOAc, washed with brine, and the organic layer separated and concentrated. The crude material was purified using 40 gram column by ISCO eluting with 0-100% B/DCM; [where B=15% EtOH/EtOAc with 0.1% TEA] to obtain 267 mg of Preparation 135A.

Preparation 135B: tert-butyl (S)-5-amino-4-(5-(6-amino-4-(chloromethyl)pyridin-2-yl)-1-oxoisoindolin-2-yl)-5-oxopentanoate Preparation 135A (140 mg, 0.318 mmol) was dissolved in DCM (15 mL) and cooled in an ice-water bath followed by dropwise addition of thionyl chloride (0.461 mL, 6.36 mmol). After 5 minutes, the ice bath was removed, and the reaction mixture was allowed to warm to room temperature. After 1 hour, the reaction mixture was concentrated to dryness to afford Preparation 135B (100% yield).

Example 135

A 2 mL microwave vial was charged with 30 mg of Preparation 136B and 1 mL of $PhSO_3H$ solution in acetonitrile (0.228 M). The reaction mixture was heated in the microwave for 30 min at 120° C. The reaction mixture was concentrated to dryness and the residue purified using Preparative HPLC Method 1 to afford Example 135. MS (ES): m/z=385.0 $[M+H]^+$. HPLC $T_{Ret}$=1.02 min. $^1H$ NMR (500 MHz, DMSO-d6) δ 11.02 (s, 1H), 8.20-8.15 (m, 1H), 8.09 (br d, J=8.5 Hz, 1H), 7.85 (br d, J=7.9 Hz, 1H), 7.27-7.21 (m, 1H), 6.73-6.68 (m, 1H), 5.15-5.09 (m, 1H), 4.72 (s, 2H), 4.59-4.53 (m, 1H), 4.47-4.40 (m, 1H), 2.95-2.87 (m, 1H), 2.68-2.63 (m, 1H), 2.49-2.37 (m, 1H), 2.09-2.02 (m, 1H).

Example 136

3-(1-oxo-5-{5H,6H,7H,8H,9H-pyrido[2,3-b]azepin-2-yl}-2,3-dihydro-1H-isoindol-2-yl) piperidine-2,6-dione (136)

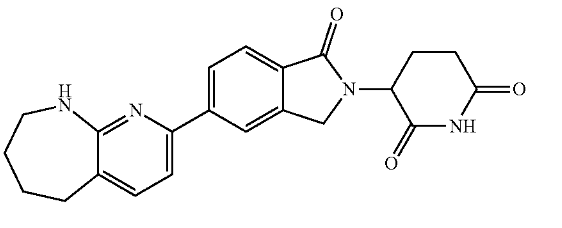

Example 136 was prepared according to General Procedure 1 using commercially available tert-butyl 2-chloro-5,6,7,8-tetrahydro-9H-pyrido[2,3-b]azepine-9-carboxylate as the aryl halide and Preparation 1B. The Boc-protecting group was removed during the cyclization step. MS (ES): m/z=391.0 $[M+H]^+$. HPLC[a] $T_{Ret}$=1.10 min. $^1H$ NMR (500 MHz, DMSO-d6) δ 11.01 (s, 1H), 8.23 (s, 1H), 8.17 (br d, J=7.9 Hz, 1H), 7.80 (d, J=7.9 Hz, 1H), 7.50 (br d, J=7.6 Hz, 1H), 7.33 (d, J=7.1 Hz, 1H), 6.02 (br s, 1H), 5.15 (br dd, J=13.1, 4.9 Hz, 1H), 4.53 (d, J=1.0 Hz, 1H), 4.41 (d, J=1.0 Hz, 1H), 3.20-3.08 (m, 2H), 2.99-2.89 (m, 1H), 2.75-2.69 (m, 2H), 2.64 (d, J=1.0 Hz, 1H), 2.50-2.38 (m, 1H), 2.08-2.02 (m, 1H), 1.80-1.68 (m, 4H).

Example 137

3-[1-oxo-5-(5,6,7,8-tetrahydro-1,8-naphthyridin-2-yl)-2,3-dihydro-1H-isoindol-2-yl]piperidine-2,6-dione (137)

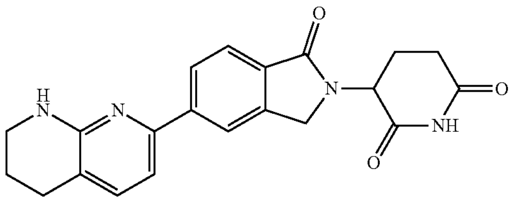

Example 137 was prepared according to General Procedure 1 using commercially available tert-butyl 7-chloro-3,4-dihydro-1,8-naphthyridine-1(2H)-carboxylate as the aryl halide and Preparation 1B. The Boc-protecting group was removed during the cyclization step. MS (ES): m/z=377.2 $[M+H]^+$. HPLC[a] $T_{Ret}$=0.97 min. $^1H$ NMR (500 MHz, DMSO-d6) δ 11.01 (s, 1H), 8.03 (s, 1H), 7.94 (d, J=1.0 Hz, 1H), 7.88 (d, J=1.0 Hz, 1H), 7.63 (d, J=7.5 Hz, 1H), 7.12 (d, J=7.5 Hz, 1H), 5.14-5.06 (m, 1H), 4.55 (d, J=17.6 Hz, 1H), 4.43 (d, J=17.6 Hz, 1H), 3.43 (br t, J=5.3 Hz, 2H), 2.95-2.85 (m, J=5007.1 Hz, 1H), 2.79 (br t, J=6.1 Hz, 2H), 2.64 (br dd, J=15.7, 1.7 Hz, 1H), 2.50-2.35 (m, 1H), 2.09-2.01 (m, 1H), 1.90-1.82 (m, 2H).

Example 138

3-{5-[6-(2,2-dimethylhydrazin-1-yl)pyridin-2-yl]-1-oxo-2,3-dihydro-1H-isoindol-2-yl}piperidine-2,6-dione (138)

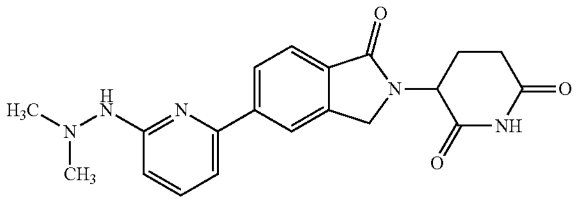

Preparation 138A: 2-chloro-6-(2,2-dimethylhydrazineyl)pyridine

To a stirred solution of paraformaldehyde (50.0 mg, 1.666 mmol) and 2-chloro-6-hydrazineylpyridine-HCl salt (50 mg, 0.278 mmol) in DCE (10 mL) was added 0.3 mL of AcOH. The reaction mixture was heated with stirring to 60° C. for 10 minutes. Next, $NaBH(OAc)_3$ (177 mg, 0.833 mmol) was added and the reaction mixture was stirred at room temperature for 1 hour. The reaction mixture was diluted with EtOAc, washed with 1 N aqueous KOH solution, dried over $MgSO_4$ and concentrated. The crude material was purified by Preparative HPLC Method 2 to afford 16 mg (34% yield) of Preparation 138A. $^1H$ NMR (400 MHz, CHLORO- FORM-d) δ 7.61 (t, J=8.1 Hz, 1H), 7.29 (s, 1H), 6.95 (d, J=8.5 Hz, 1H), 6.84 (d, J=7.6 Hz, 1H), 3.12-3.07 (m, 6H)

Example 138

Example 138 was prepared according to the General Procedure 1 using 2-chloro-6-(2,2-dimethylhydrazineyl) pyridine as the aryl halide. MS (ES): m/z=380.3 $[M+H]^+$. HPLC[a] $T_{Ret}$=1.05 min. $^1H$ NMR (500 MHz, DMSO-d6) δ 11.01 (s, 1H), 8.29 (s, 1H), 8.24 (br d, J=8.0 Hz, 1H), 7.86-7.78 (m, 2H), 7.49 (br d, J=7.2 Hz, 1H), 6.87 (d, J=8.3 Hz, 1H), 5.15 (br dd, J=13.4, 5.1 Hz, 1H), 4.54 (d, J=17.2 Hz, 1H), 4.42 (d, J=17.1 Hz, 1H), 3.00-2.92 (m, 1H), 2.68-2.59 (m, 1H), 2.57-2.53 (m, 6H), 2.49-2.39 (m, 1H), 2.09-2.01 (m, J=10.9, 5.2 Hz, 1H).

Example 139

3-(5-(1H-imidazo[4,5-b]pyridin-5-yl)-1-oxoisoindolin-2-yl)piperidine-2,6-dione (139)

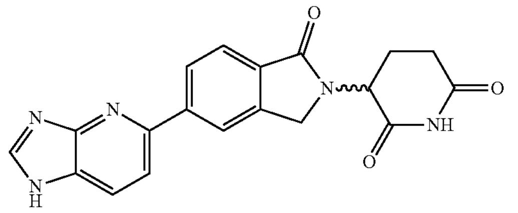

A vial was charged with Preparation 1B (53.9 mg, 0.121 mmol), 5-bromo-1H-imidazo[4,5-b]pyridine (16 mg, 0.081 mmol), $Pd(PPh_3)_4$ (9.34 mg, 8.08 μmol) and $NaHCO_3$ (0.5 M aqueous solution) (0.485 mL, 0.242 mmol) followed by dioxane (0.5 mL). The vial was sealed, evacuated, and back-filled with $N_2$. The reaction mixture was microwaved at 130° C. for 15 minutes. The reaction mixture was concentrated, then 1 mL of benzenesulfonic acid solution in acetonitrile (1.44 gram in 40 mL ACN) was added and the reaction mixture was heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 5-minute hold at 0% B, 0-22% B over 28 minutes, then a 0-minute hold at 100% B; Flow Rate: 20 mL/min; Column Temperature: 25° C. Fractions containing the product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 0% B, 0-20% B over 28 minutes, then a 0-minute hold at 100% B; Flow Rate: 20 mL/min; Column Temperature: 25° C. Fractions containing the product were combined and dried via centrifugal evaporation to afford Example 139 (0.6 mg, 2%). ESI MS $(M+H)^+$=362.2. HPLC Peak $t_r$=0.68 min (Analytical HPLC Method 2). Purity=100%.

Example 140

3-(5-(6-amino-4-methylpyridin-2-yl)-1-oxoisoindolin-2-yl)piperidine-2,6-dione (140)

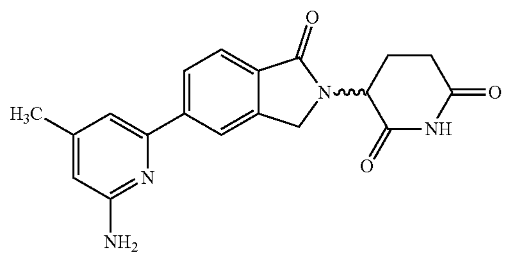

A vial was charged with Preparation 1B (74.8 mg, 0.168 mmol), 6-chloro-4-methylpyridin-2-amine (16 mg, 0.112 mmol), $Pd(PPh_3)_4$ (12.97 mg, 0.011 mmol) and $NaHCO_3$ (0.5 M aqueous solution) (0.673 mL, 0.337 mmol) followed by dioxane (0.5 mL). The vial was sealed, evacuated, and back-filled with $N_2$. The reaction mixture was microwaved at 130° C. for 15 minutes. The reaction mixture was concentrated, then 1 mL of benzenesulfonic acid solution in acetonitrile (1.44 gram in 40 mL ACN) was added and the reaction mixture was heated in the microwave for 10 minutes at 155° C. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-minute hold at 0% B, 0-18% B over 28 minutes, then a 0-minute hold at 100% B; Flow Rate: 20 mL/min; Column Temperature: 25° C. Fractions containing the product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-30% B over 25 minutes, then a 0-minute hold at 100% B; Flow Rate: 20 mL/min; Column Temperature: 25° C. Fractions containing the product were combined and dried via centrifugal evaporation to afford Example 140 (0.9 mg, 2%). ESI MS $(M+H)^+$=351.3. HPLC Peak $t_r$=1.04 min (Analytical HPLC Method 2). Purity=100%.

Example 141

3-(5-(3,4-dihydro-2H-pyrido[3,2-b][1,4]oxazin-6-yl)-1-oxoisoindolin-2-yl)piperidine-2,6-dione (141)

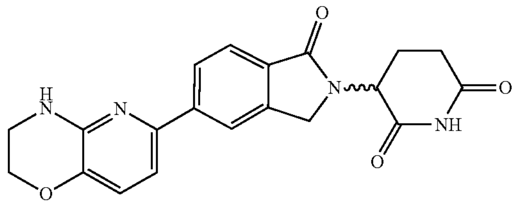

A vial was charged with Preparation 1B (62.5 mg, 0.141 mmol), 6-chloro-3,4-dihydro-2H-pyrido[3,2-b][1,4]oxazine (16 mg, 0.094 mmol), $Pd(PPh_3)_4$ (10.84 mg, 9.38 μmol) and $NaHCO_3$ (0.5 M aqueous solution) (0.563 mL, 0.281 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated, then dissolved in AcOH (0.5 mL) and benzenesulfonic acid (14.83 mg, 0.094 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 6% B, 6-46% B over 20 minutes, then a 0-minute hold at 100% B; Flow Rate: 20 mL/min; Column Temperature: 25° C. Fractions containing the product were combined and dried via centrifugal evaporation to afford Example 141 (2.1 mg, 6%). ESI MS $(M+H)^+$ =379.3. HPLC Peak $t_r$=1.28 min (Analytical HPLC Method 2). Purity=99%.

Example 142

3-(5-(6-aminopyrazin-2-yl)-1-oxoisoindolin-2-yl) piperidine-2,6-dione (142)

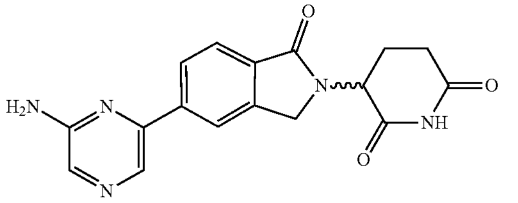

A vial was charged with Preparation 1B (53.1 mg, 0.120 mmol), 6-bromopyrazin-2-amine (16 mg, 0.092 mmol), $Pd(PPh_3)_4$ (10.63 mg, 9.20 μmol) and $NaHCO_3$ (0.5 M aqueous solution) (0.552 mL, 0.276 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (14.54 mg, 0.092 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile: water with ammonium acetate; Gradient: a 0-minute hold at 0% B, 0-55% B over 23 minutes, then a 0-minute hold at 100% B; Flow Rate: 20 mL/min; Column Temperature: 25° C. Fraction collection was triggered by MS signals. Fractions containing the product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-30% B over 25 minutes, then a 0-minute hold at 100% B; Flow Rate: 20 mL/min; Column Temperature: 25° C. Fractions containing the product were combined and dried via centrifugal evaporation to afford Example 142 (1.7 mg, 5%). ESI MS $(M+H)^+$=338.2. HPLC Peak $t_r$=0.98 min (Analytical HPLC Method 2). Purity=97%.

Example 143

3-(5-(2-amino-6-methylpyrimidin-4-yl)-1-oxoisoindolin-2-yl)piperidine-2,6-dione (143)

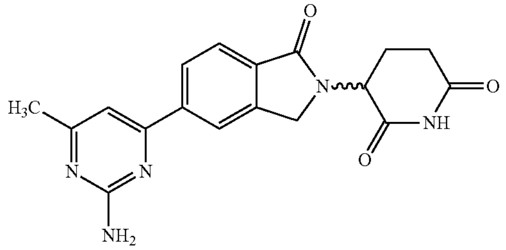

A vial was charged with Preparation 1B (61.4 mg, 0.138 mmol), 4-bromo-6-methylpyrimidin-2-amine (20 mg, 0.106 mmol), $Pd(PPh_3)_4$ (12.29 mg, 10.64 μmol) and $NaHCO_3$ (0.5 M aqueous solution) (0.638 mL, 0.319 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (16.82 mg, 0.106 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile: water with ammonium acetate; Gradient: a 0-minute hold at 0% B, 0-40% B over 20 minutes, then a 0-minute hold at 100% B; Flow Rate: 20 mL/min; Column Temperature: 25° C. Fraction collection was triggered by MS signals. Fractions containing the product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 5-minute hold at 0% B, 0-28% B over 28 minutes, then a 0-minute hold at 100% B; Flow Rate: 20 mL/min; Column Temperature: 25° C. Fractions containing the product were combined and dried via centrifugal evaporation to afford Example 143 (4.5 mg, 12%). ESI MS $(M+H)^+$=352.1. HPLC Peak $t_r$=1.06 min (Analytical HPLC Method 2). Purity=100%.

Example 144

3-(5-(4,6-dimethylpyridin-2-yl)-1-oxoisoindolin-2-yl)piperidine-2,6-dione (144)

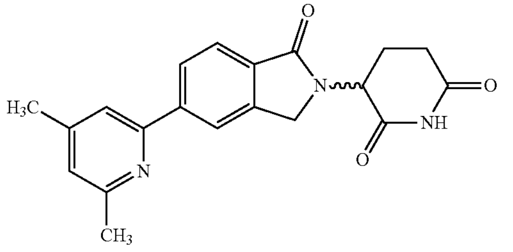

A vial was charged with Preparation 1B (75 mg, 0.169 mmol), 2-bromo-4,6-dimethylpyridine (0.021 mL, 0.161 mmol), $Pd(PPh_3)_4$ (18.63 mg, 0.016 mmol) and $NaHCO_3$ (0.5 M aqueous solution) (0.967 mL, 0.484 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (25.5 mg, 0.161 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 11% B, 11-51% B over 20 minutes, then a 0-minute hold at 100% B; Flow Rate: 20 mL/min; Column Temperature: 25° C. Fractions containing the product were combined and dried via centrifugal evaporation to afford Example 144 (4.8 mg, 9%). ESI MS $(M+H)^+$=350.2. HPLC Peak $t_r$=1.43 min (Analytical HPLC Method 2). Purity=100%.

Example 145

3-(5-(5-chloro-3-hydroxyisoquinolin-1-yl)-1-oxoisoindolin-2-yl)piperidine-2,6-dione (145)

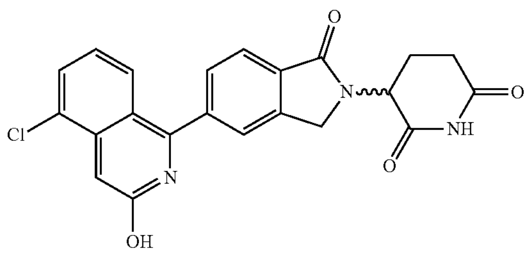

A vial was charged with Preparation 1B (45.7 mg, 0.103 mmol), 1,5-dichloroisoquinolin-3-ol (20 mg, 0.093 mmol), $Pd(PPh_3)_4$ (10.80 mg, 9.34 μmol) and $NaHCO_3$ (0.5 M aqueous solution) (0.561 mL, 0.280 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (16.26 mg, 0.103 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 10% B, 10-55% B over 27 minutes, then a 0-minute hold at 100% B; Flow Rate: 20 mL/min; Column Temperature: 25° C. Fraction collection was triggered by MS signals. Fractions containing the product were combined and dried via centrifugal evaporation to afford Example 145 (5.6 mg, 14%). ESI MS $(M+H)^+$=422.2. HPLC Peak $t_r$=1.43 min. Purity=98%. (Analytical HPLC Method 2)

Example 146

3-(5-(6-methoxy-4-methylpyridin-2-yl)-1-oxoisoindolin-2-yl)piperidine-2,6-dione (146)

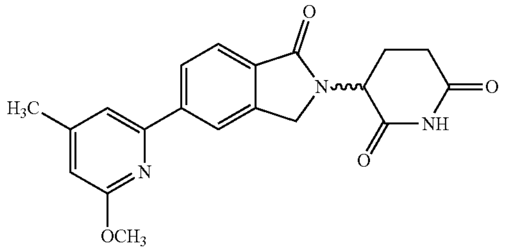

A vial was charged with Preparation 1B (62.0 mg, 0.140 mmol), 2-chloro-6-methoxy-4-methylpyridine (0.017 mL, 0.127 mmol), $Pd(PPh_3)_4$ (14.67 mg, 0.013 mmol) and $NaHCO_3$ (0.5 M aqueous solution) (0.761 mL, 0.381 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (22.08 mg, 0.140 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 18% B, 18-58% B over 25 minutes, then a 0-minute hold at 100% B; Flow Rate: 20 mL/min; Column Temperature: 25° C. Fraction collection was triggered by MS and UV signals. Fractions containing the product were combined and dried via centrifugal evaporation. The material was further purified via preparative LC/MS with the following conditions: Column: XBridge C18, 200 mm×19 mm, 5-μm particles;

Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 16% B, 16-56% B over 25 minutes, then a 0-minute hold at 100% B; Flow Rate: 20 mL/min; Column Temperature: 25° C. Fractions containing the product were combined and dried via centrifugal evaporation to afford Example 146 (4.9 mg, 10%). ESI MS $(M+H)^+$=366.2. HPLC Peak $t_r$=1.61 min. Purity=99%. (Analytical HPLC Method 2).

Example 147

3-(5-(6-hydroxy-4-methylpyridin-2-yl)-1-oxoisoindolin-2-yl)piperidine-2,6-dione (147)

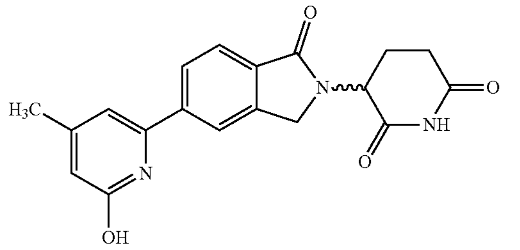

To a suspension of Example 145 and sodium iodide (37.2 mg, 0.248 mmol) in MeCN (827 μL) was added trimethylchlorosilane (31.7 μL, 0.248 mmol) under a nitrogen atmosphere. The resulting mixture was heated at 80° C. overnight. The solvent was evaporated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 0% B, 0-40% B over 20 minutes, then a 0-minute hold at 100% B; Flow Rate: 20 mL/min; Column Temperature: 25° C. Fraction collection was triggered by MS signals. Fractions containing the product were combined and dried via centrifugal evaporation to afford Example 147 (3.6 mg, 24%). ESI MS $(M+H)^+$=352.2. HPLC Peak $t_r$=1.05 min. Purity=95%. (Analytical HPLC Method 2)

Example 148

2-amino-6-(2-(2,6-dioxopiperidin-3-yl)-1-oxoisoindolin-5-yl)-4-methylnicotinonitrile (148)

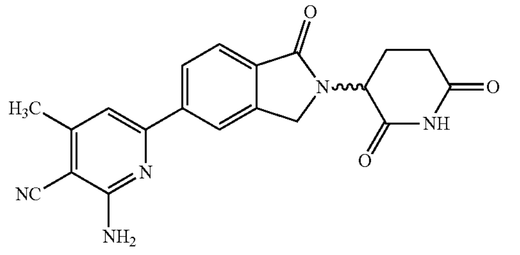

A vial was charged with Preparation 1B (58.3 mg, 0.131 mmol), 2-amino-6-chloro-4-methylnicotinonitrile (20 mg, 0.119 mmol), $Pd(PPh_3)_4$ (13.79 mg, 0.012 mmol) and $NaHCO_3$ (0.5 M aqueous solution) (0.716 mL, 0.358 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL), and benzenesulfonic acid (20.76 mg, 0.131 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile: water with ammonium acetate; Gradient: a 0-minute hold at 5% B, 5-45% B over 25 minutes, then a 0-minute hold at 100% B; Flow Rate: 20 mL/min; Column Temperature: 25° C. Fraction collection was triggered by MS signals. Fractions containing the product were combined and dried via centrifugal evaporation to afford Example 148 (3.7 mg, 8%). ESI MS $(M+H)^+$=376.2. HPLC Peak $t_r$=1.25 min. Purity=97%. (Analytical HPLC Method 2).

Example 149

2-amino-6-(2-(2,6-dioxopiperidin-3-yl)-1-oxoisoindolin-5-yl)isonicotinonitrile (149)

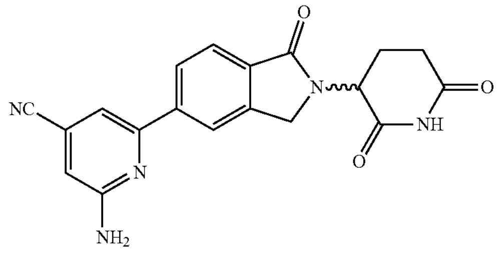

A vial was charged with Preparation 1B (37.0 mg, 0.083 mmol), 2-amino-6-bromoisonicotinonitrile (15 mg, 0.076 mmol), $Pd(PPh_3)_4$ (8.75 mg, 7.57 μmol) and $NaHCO_3$ (0.5 M aqueous solution) (0.454 mL, 0.227 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (13.18 mg, 0.083 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile: water with ammonium acetate; Gradient: a 3-minute hold at 0% B, 0-37% B over 20 minutes, then a 0-minute hold at 100% B; Flow Rate: 20 mL/min; Column Temperature: 25° C. Fraction collection was triggered by MS signals. Fractions containing the product were combined and dried via centrifugal evaporation to afford Example 149 (0.3 mg, 1%). ESI MS $(M+H)^+$=362.3. HPLC Peak $t_r$=1.20 min. Purity=98%. (Analytical HPLC Method 2).

Example 150

3-(5-(1-amino-5,6,7,8-tetrahydroisoquinolin-3-yl)-1-oxoisoindolin-2-yl)piperidine-2,6-dione (150)

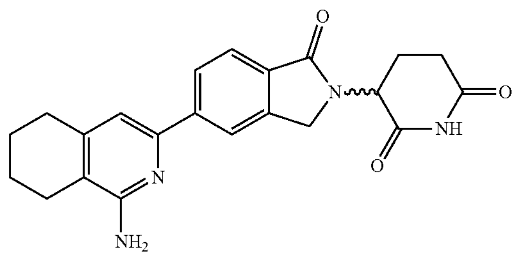

Preparation 150A. 2-(5,6,7,8-tetrahydroisoquinolin-1-yl)isoindoline-1,3-dione

A solution of 5,6,7,8-tetrahydroisoquinolin-1-amine (150 mg, 1.012 mmol) and isobenzofuran-1,3-dione (150 mg, 1.012 mmol) in AcOH (5060 μL) was heated at 90° C. overnight. The reaction was quenched with saturated aqueous. The reaction mixture was diluted with EtOAc. Layers were separated. The aqueous phase was extracted with EtOAc (3×). The organic phases were combined, dried over $Na_2SO_4$, filtered, and concentrated to afford a yellow residue. The crude material was dissolved in a minimal amount of $CH_2Cl_2$ and chromatographed. Purification by silica gel chromatography using an ISCO machine (40 g column, 40 mL/min, 0-100% EtOAc in hexanes over 14 min, $t_r$=11 min) gave Preparation 150A (23.4 mg, 0.084 mmol, 8.31% yield) as a white solid. ESI MS $(M+H)^+$=279.3.

Preparation 150B. 1-(1,3-dioxoisoindolin-2-yl)-5,6,7,8-tetrahydroisoquinoline 2-oxide To a solution of Preparation 150A (23.4 mg, 0.084 mmol) in $CH_2Cl_2$ (420 μL) was added m-CPBA (29.0 mg, 0.168 mmol). The reaction mixture was allowed to stir at room temperature overnight. Additional m-CPBA (29.0 mg, 0.168 mmol) and DCM (1 mL) were added. The reaction mixture was allowed to stir at room temperature overnight. The reaction was quenched with saturated aqueous $Na_2S_2O_3$. The reaction mixture was diluted with $CH_2Cl_2$. The layers were separated. The aqueous phase was extracted with $CH_2Cl_2$ (3×). The combined organic phases were dried over $Na_2SO_4$, filtered, and concentrated to afford Preparation 150B (25 mg, 100%) as an off-white solid. ESI MS $(M+H)^+$=295.1.

Preparation 150C. 2-(3-chloro-5,6,7,8-tetrahydroisoquinolin-1-yl)isoindoline-1,3-dione To a solution of Preparation 150B (37.3 mg, 0.134 mmol) in $POCl_3$ (1722 μL, 18.47 mmol) was added $Et_3N$ (18.66 μL, 0.134 mmol). The reaction mixture was heated at 80° C. for 2 h, then allowed to cool to room temperature. The reaction mixture was carefully poured into an ice cold solution of saturated aqueous $NaHCO_3$, then extracted with EtOAc (3×). The organic phases were combined, dried over $Na_2SO_4$, and filtered. The crude material was dissolved in a minimal amount of $CH_2Cl_2$ and chromatographed. Purification by silica gel chromatography using an ISCO machine (12 g column, 30 mL/min, 0-100% EtOAc in hexanes over 14 min, $t_r$=9 min) gave Preparation 150C (3.8 mg, 10.94 μmol, 8.17% yield) as a white film. ESI MS $(M+H)^+$=313.2.

Preparation 150D. 3-chloro-5,6,7,8-tetrahydroisoquinolin-1-amine

To a solution of Preparation 150C (33.5 mg, 0.107 mmol) in EtOH (536 μL) was added triethylamine (16.42 μL, 0.118 mmol) followed by hydrazine (3.70 μL, 0.118 mmol). The reaction mixture was stirred at room temperature. The reaction mixture was diluted with water and extracted with EtOAc (3×). The organic phases were combined, dried over $Na_2SO_4$, and filtered. The crude material was dissolved in a minimal amount of $CH_2Cl_2$ and chromatographed. Purification by silica gel chromatography using an ISCO machine (12 g column, 30 mL/min, 0-100% EtOAc in hexanes over 15 min, $t_r$=9 min) gave Preparation 150D (9.7 mg, 0.050 mmol, 47.1% yield) as a white solid. ESI MS $(M+H)^+$=183.1.

Example 152

A vial was charged with Preparation 150D (26.0 mg, 0.058 mmol), 3-chloro-5,6,7,8-tetrahydroisoquinolin-1-amine (9.7 mg, 0.053 mmol), $Pd(PPh_3)_4$ (6.14 mg, 5.31 μmol) and $NaHCO_3$ (0.5 M aqueous solution) (0.319 mL, 0.159 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (9.24 mg, 0.058 mmol) was added. The reaction vial was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 0% B, 0-50% B over 20 minutes, then a 0-minute hold at 100% B; Flow Rate: 20 mL/min; Column Temperature: 25° C. Fractions containing the product were combined and dried via centrifugal evaporation to afford Example 150 (1.3 mg, 6%). ESI MS $(M+H)^+$=391.3. HPLC Peak $t_r$=1.50 min. Purity=100%. (Analytical HPLC Method 2).

Example 151

3-(5-(6-amino-4,5-dimethylpyridin-2-yl)-1-oxoisoindolin-2-yl)piperidine-2,6-dione (151)

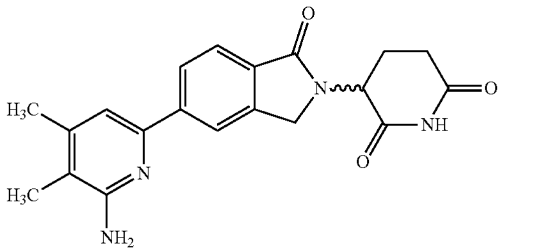

Preparation 151A. 2-(3,4-dimethylpyridin-2-yl)isoindoline-1,3-dione

A solution of 3,4-dimethylpyridin-2-amine (150 mg, 1.228 mmol) and isobenzofuran-1,3-dione (182 mg, 1.228 mmol) in AcOH (6139 μL) was heated at 90° C. overnight. The reaction was quenched with saturated aqueous $NaHCO_3$. The reaction mixture was diluted with EtOAc. The layers were separated. The aqueous phase was extracted with EtOAc (3×). The organic phases were combined, dried over $Na_2SO_4$, filtered, and concentrated to afford a yellow residue. The crude material was dissolved in a minimal amount of $CH_2Cl_2$ and chromatographed. Purification by silica gel chromatography using an ISCO machine (40 g column, 40 mL/min, 0-100% EtOAc in hexanes over 21 min, $t_r$=11 min) afforded Preparation 153A (63.8 mg, 0.253 mmol, 20.60% yield) as a white solid. ESI MS $(M+H)^+$=253.2.

Preparation 151B. 2-(1,3-dioxoisoindolin-2-yl)-3,4-dimethylpyridine 1-oxide

To a solution of Preparation 151A (63.8 mg, 0.253 mmol) in $CH_2Cl_2$ (1265 μL) was added m-CPBA (87 mg, 0.506 mmol). The reaction mixture was allowed to stir at room temperature overnight. The reaction was quenched with saturated aqueous $Na_2S_2O_3$. The reaction mixture was diluted with $CH_2Cl_2$. The layers were separated. The aqueous phase was extracted with $CH_2Cl_2$ (3×). The combined organic phases were dried over $Na_2SO_4$, filtered, and concentrated to afford Preparation 151B (68 mg, 100%) an off-white solid. ESI MS $(M+H)^+$=269.3.

Preparation 151C. 2-(6-chloro-3,4-dimethylpyridin-2-yl)isoindoline-1,3-dione

To a solution of Preparation 151B (67.8 mg, 0.253 mmol) in $POCl_3$ (3251 μL, 34.9 mmol) was added TEA (35.2 μL, 0.253 mmol). The reaction mixture was heated at 80° C. for 2 h, then allowed to cool to room temperature. The reaction mixture was carefully poured into an ice cold solution of saturated aqueous $NaHCO_3$, then extracted with EtOAc (3×). The organic phases were combined, dried over $Na_2SO_4$, and filtered. The crude material was dissolved in a minimal amount of $CH_2Cl_2$ and chromatographed. Purification by silica gel chromatography using an ISCO machine (24 g column, 35 mL/min, 0-100% EtOAc in hexanes over 15 min, $t_r$=9 min) gave Preparation 151C (31 mg, 0.108 mmol, 42.8% yield) as a white solid. ESI MS $(M+H)^+$=287.1.

Preparation 151D. 6-chloro-3,4-dimethylpyridin-2-amine

To a solution of Preparation 151C (31 mg, 0.108 mmol) in EtOH (541 μL) was added triethylamine (16.58 μL, 0.119 mmol) followed by hydrazine (3.73 μL, 0.119 mmol). The reaction mixture was stirred at room temperature for 2 h. The reaction mixture was diluted with water and extracted with EtOAc (3×). The organic phases were combined, dried over $Na_2SO_4$, and filtered. The crude material was dissolved in a minimal amount of $CH_2Cl_2$ and chromatographed. Purification by silica gel chromatography using an ISCO machine (12 g column, 30 mL/min, 0-100% EtOAc in hexanes over 14 min, $t_r$=9.5 min) gave Preparation 151D (5.8 mg, 0.035 mmol, 32.5% yield) as a white solid. ESI MS $(M+H)^+$=156.9.

Example 151

A vial was charged with tert-butyl 5-amino-5-oxo-4-(1-oxo-5-(4,4,5,5-tetramethyl-1,3,2-dioxaborolan-2-yl)isoindolin-2-yl)pentanoate (61.8 mg, 0.139 mmol), Preparation 151D (21.8 mg, 0.139 mmol), $Pd(PPh_3)_4$ (161 mg, 0.139 mmol) and $NaHCO_3$ (0.5 M aqueous solution) (0.835 mL, 0.418 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (22.02 mg, 0.139 mmol) was added. The reaction vial was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 2-minute hold at 8% B, 8-48% B over 20 minutes, then a 0-minute hold at 100% B; Flow Rate: 20 mL/min; Column Temperature: 25° C. Fractions containing the product were combined and dried via centrifugal evaporation to afford Example 151 (2.2 mg, 4%). ESI MS $(M+H)^+$=365.2. HPLC Peak $t_r$=1.35 min. Purity=100%. (Analytical HPLC Method 2)

Example 152

6-(2-(2,6-dioxopiperidin-3-yl)-1-oxoisoindolin-5-yl)-4-methylnicotinonitrile (152)

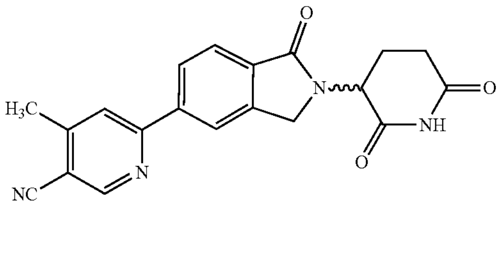

A vial was charged with Preparation 1B (96 mg, 0.216 mmol), 6-chloro-4-methylnicotinonitrile (30 mg, 0.197 mmol), $Pd(PPh_3)_4$ (22.72 mg, 0.020 mmol) and $NaHCO_3$ (0.5 M aqueous solution) (1.180 mL, 0.590 mmol) followed by dioxane (0.5 mL). The vial was sealed, evacuated, and back-filled with $N_2$. The reaction mixture was microwaved at 130° C. for 15 minutes. The reaction mixture was extracted with EtOAc (2×). The organic phases were combined, concentrated and dried under high vacuum, then dissolved in AcOH (0.5 mL) and benzenesulfonic acid (34.2 mg, 0.216 mmol) was added. The reaction vial was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 8% B, 8-48% B over 20 minutes, then a 0-minute hold at 100% B; Flow Rate: 20 mL/min; Column Temperature: 25° C. Fractions containing the product were combined and dried via centrifugal evaporation to afford Example 154 (7.3 mg, 10%). ESI MS $(M+H)^+$=361.2. HPLC Peak $t_r$=1.28 min. Purity=96%. (Analytical HPLC Method 2)

Example 153

3-(5-(6-amino-5-methoxy-4-methylpyridin-2-yl)-1-oxoisoindolin-2-yl)piperidine-2,6-dione (153)

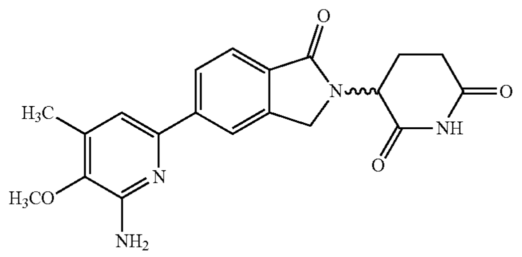

Preparation 153A. 2-(3-methoxy-4-methylpyridin-2-yl)isoindoline-1,3-dione

A solution of 3-methoxy-4-methylpyridin-2-amine (350 mg, 2.53 mmol) and isobenzofuran-1,3-dione (375 mg, 2.53 mmol) in AcOH (5.730 mL) was heated at 90° C. overnight. The reaction was quenched with saturated aqueous $NaHCO_3$. The reaction mixture was diluted with EtOAc. The layers were separated. The aqueous phase was extracted with EtOAc (3×). The organic phases were combined, dried over $Na_2SO_4$, filtered, and concentrated to afford a yellow residue. The crude material was dissolved in a minimal amount of $CH_2Cl_2$ and chromatographed. Purification by silica gel chromatography using an ISCO machine (40 g column, 40 mL/min, 0-100% EtOAc in hexanes over 22 min, $t_r$=12 min) gave Preparation 153A (243 mg, 0.861 mmol, 34.0% yield) as a white solid. ESI MS $(M+H)^+$=269.4.

Preparation 153B. 2-(1,3-dioxoisoindolin-2-yl)-3-methoxy-4-methylpyridine 1-oxide To a solution of Preparation 153A (243 mg, 0.906 mmol) in $CH_2Cl_2$ (4529 μL) was added m-CPBA (313 mg, 1.812 mmol). The reaction mixture was allowed to stir at room temperature overnight. The reaction was quenched with saturated aqueous $Na_2S_2O_3$. The reaction mixture was diluted with $CH_2Cl_2$. The layers were separated. The aqueous phase was extracted with $CH_2Cl_2$ (3×). The combined organic phases were dried over $Na_2SO_4$, filtered, and concentrated to afford Preparation 153B (257 mg, 100%) as an off-white solid. ESI MS $(M+H)^+$=285.3.

Preparation 153C. 2-(6-chloro-3-methoxy-4-methylpyridin-2-yl)isoindoline-1,3-dione To a solution of Preparation 153B (243 mg, 0.904 mmol) in $POCl_3$ (11.628 mL, 125 mmol) was added TEA (0.126 mL, 0.904 mmol). The reaction mixture was heated at 80° C. for 2 h, then allowed to cool to room temperature. The reaction mixture was carefully poured into an ice cold solution of saturated aqueous $NaHCO_3$, then extracted with EtOAc (3×). The organic phases were combined, dried over $Na_2SO_4$, and filtered. The crude material was dissolved in a minimal amount of $CH_2Cl_2$ and chromatographed. Purification by silica gel chromatography using an ISCO machine (40 g column, 40 mL/min, 0-100% EtOAc in hexanes over 15 min, $t_r$=9 min) gave Preparation 153C (217 mg, 0.717 mmol, 79% yield) as a white solid. ESI MS $(M+H)^+$=303.1.

Preparation 153D. 6-chloro-3-methoxy-4-methylpyridin-2-amine

To a solution of Preparation 153C (217 mg, 0.717 mmol) in EtOH (3584 μL) was added triethylamine (110 μL, 0.789 mmol) followed by hydrazine (24.75 μL, 0.789 mmol). The reaction mixture was stirred at room temperature for 2 h. The reaction mixture was diluted with water and extracted with EtOAc (3×). The organic phases were combined, dried over $Na_2SO_4$, and filtered. The crude material was dissolved in a minimal amount of $CH_2Cl_2$ and chromatographed. Purification by silica gel chromatography using an ISCO machine (40 g column, 40 mL/min, 0-100% EtOAc in hexanes over 15 min, $t_r$=9.5 min) gave Preparation 153D (85.1 mg, 0.493 mmol, 68.8% yield) as a white solid. ESI MS $(M+H)^+$=173.0.

Example 153

A vial was charged with Preparation 1B (122 mg, 0.274 mmol), Preparation 153D (43 mg, 0.249 mmol), $Pd(PPh_3)_4$ (28.8 mg, 0.025 mmol) and $NaHCO_3$ (0.5 M aqueous solution) (1495 μL, 0.747 mmol) followed by dioxane (1246 μL). The vial was sealed, evacuated, and back-filled with $N_2$. The reaction mixture was microwaved at 130° C. for 15 minutes. The reaction mixture was extracted with EtOAc (3×). The organic phases were combined, dried over $Na_2SO_4$, filtered, and concentrated to afford an orange residue which was further dried under high vacuum. The crude material was dissolved in 1.6 mL AcOH and benzenesulfonic acid (43.3 mg, 0.274 mmol) was added. The reaction vial was sealed and heated in the microwave for 10 minutes at 155° C. The solvent was evaporated and the crude material was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 7% B, 7-43% B over 30 minutes, then a 0-minute hold at 100% B; Flow Rate: 20 mL/min; Column Temperature: 25° C. Fractions containing the product were combined and dried via centrifugal evaporation to afford Example 153 (4.9 mg, 5%). ESI MS $(M+H)^+$=381.2. HPLC Peak $t_r$=1.22 min. Purity=100%. (Analytical HPLC Method 2).

Example 154

3-(5-(6-amino-5-methoxy-4-methylpyridin-2-yl)-1-oxoisoindolin-2-yl)piperidine-2,6-dione (154)

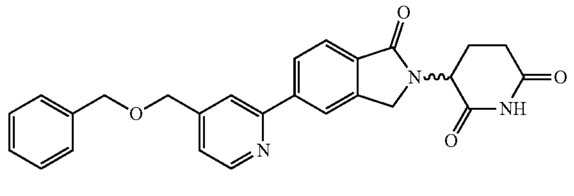

Preparation 154A. 2-chloro-4-(chloromethyl)pyridine

A solution of (2-chloropyridin-4-yl)methanol (0.100 g, 0.697 mmol), methanesulfonyl chloride (0.109 mL, 1.393 mmol), and triethylamine (0.204 mL, 1.463 mmol) in DMF (1.393 mL) was stirred at room temperature for 1.5 h. The solution became cloudy and a solid precipitated out. The reaction was quenched with water. The reaction mixture was diluted with EtOAc. Layers were separated. The aqueous phase was extracted with EtOAc (2×). The organic phases were combined, dried over $Na_2SO_4$, filtered, and concentrated to afford a residue. The crude material was dissolved in a minimal amount of $CH_2Cl_2$ and chromatographed. Purification by silica gel chromatography using an ISCO machine (24 g column, 35 mL/min, 0-100% EtOAc in hexanes over 15 min, $t_r$=8 min) gave Preparation 154A (65.6 mg, 0.405 mmol, 58.1% yield) as a colorless liquid. ESI MS $(M+H)^+$=161.9.

Preparation 154B. 4-((benzyloxy)methyl)-2-chloropyridine

To a solution of phenylmethanol (100 μL, 0.966 mmol) in DMF (966 μL) was added NaH (39.4 mg, 0.985 mmol). The reaction mixture was allowed to stir at room temperature for 15 min, then Preparation 156A (31.3 mg, 0.193 mmol) was added. After 2 h, the reaction was quenched with water. The reaction mixture was diluted with EtOAc. Layers were separated. The aqueous phase was extracted with EtOAc (2×). The organic phases were combined, dried over $Na_2SO_4$, filtered, and concentrated to afford a residue. The crude material was dissolved in a minimal amount of $CH_2Cl_2$ and chromatographed. Purification by silica gel chromatography using an ISCO machine (12 g column, 30 mL/min, 0-100% EtOAc in hexanes over 19 min, $t_r$=8.5 min) gave Preparation 154B (26.3 mg, 0.113 mmol, 58.3% yield). ESI MS $(M+H)^+$=234.4.

Example 154

A vial was charged with tert-butyl 5-amino-5-oxo-4-(1-oxo-5-(4,4,5,5-tetramethyl-1,3,2-dioxaborolan-2-yl)isoindolin-2-yl)pentanoate (54.4 mg, 0.122 mmol), Preparation 154B (26 mg, 0.111 mmol), $Pd(PPh_3)_4$ (12.86 mg, 0.011 mmol) and $NaHCO_3$ (0.5 M aqueous solution) (668 μL, 0.334 mmol) followed by dioxane (556 μL). The vial was sealed, evacuated, and back-filled with $N_2$. The reaction mixture was microwaved at 130° C. for 15 minutes. The reaction mixture was extracted with EtOAc (3×). The organic phases were combined, dried over $Na_2SO_4$, filtered, and concentrated to afford an orange residue which was further dried under high vacuum. The crude material was dissolved in 1.6 mL AcOH and benzenesulfonic acid (19.36 mg, 0.122 mmol) was added. The reaction mixture was sealed and heated in the microwave for 10 minutes at 155° C. The reaction mixture was concentrated and the crude material was purified via preparative LC/MS with the following conditions: Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 8% B, 8-48% B over 20 minutes, then a 0-minute hold at 100% B; Flow Rate: 20 mL/min; Column Temperature: 25° C. Fractions containing the product were combined and dried via centrifugal evaporation to afford Example 154 (1.2 mg, 2%). ESI MS $(M+H)^+$=442.2. HPLC Peak $t_r$=1.76 min. Purity=99%. (Analytical HPLC Method 2).

Example 155

3-[5-(6-Methoxypyridin-2-yl)-1-oxo-2,3-dihydro-1H-isoindol-2-yl]piperidine-2,6-dione (155)

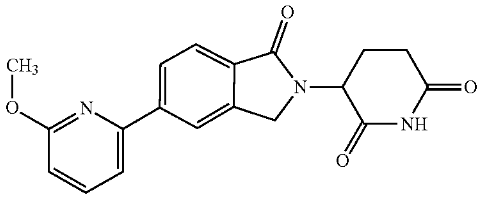

Preparation 155A: Methyl 4-iodo-2-methylbenzoate

To a solution of methyl 4-amino-2-methylbenzoate (4.5 g, 27.2 mmol) in DMSO (75 mL) at room temperature was added solid sodium nitrite (3.76 g, 54.5 mmol). The reaction mixture was warmed to 40° C. in an oil bath. To this was added a solution of hydrogen iodide (55% in water, 25.3 g, 109 mmol) in DMSO (38 mL) dropwise. The reaction mixture was allowed to stir at 40° C. for 15 min after addition was complete. The reaction mixture was cooled to room temperature, poured into water/ether (300 mL/300 mL). To this was slowly added sodium thiosulfate with stirring until the mixture decolorized and the layers separated. The aqueous layer was again extracted with ether. The combined organics were washed again with a dilute solution of sodium thiosulfate in water (~2 g in 100 mL water), then with water (100 mL), then brine. The organics were dried over $MgSO_4$, filtered, and concentrated. The reaction was repeated on the same scale and worked up under an identical protocol. The crude product from both runs was combined and purified by ISCO (330 g column, 5% EtOAc/Hex; isocratic) to give Preparation 155A, 13.44 g (89% yield) as an oil. $^1H$ NMR (400 MHz, $CDCl_3$) δ 7.69-7.66 (m, 1H), 7.64-7.61 (m, 2H), 3.91 (s, 3H), 2.57 (s, 3H).

Preparation 155B: Methyl 2-(bromomethyl)-4-iodobenzoate

To a solution of Preparation 155A (17.85 g, 64.7 mmol) in isopropyl acetate (211 mL) was added N-bromosuccinimide (14.96 g, 84 mmol) and AIBN (0.265 g, 1.616 mmol). The resulting suspension was placed in a preheated 70° C. bath. A very slow flow of nitrogen was maintained over the reaction mixture (in through syringe, out through another syringe into a bubbler) to aid in removal of bromine. The reaction mixture was heated at 70° C. for 5 h, cooled to room temperature, and concentrated. The resulting solid was stirred under ether and filtered to remove the solids, rinsing with ether. The solids were discarded. The ethereal was washed with a solution of sodium sulfite (5 g) in water (400 mL), split between two washes, then water, then brine. The organics were dried over $MgSO_4$, filtered, and concentrated. The material was purified by Isco (2% EtOAc/Hex, 5 min hold, then ramp to 7% isocratic) to give impure product as a gummy solid. The material was suspended in a minimum of hexanes. The resulting solid was collected in a Buchner funnel to give 13.3 g (58% yield) of Preparation 155B. $^1H$ NMR (400 MHz, $CDCl_3$) δ 7.86 (d, J=1.8 Hz, 1H), 7.78-7.73 (m, 1H), 7.72-7.67 (m, 1H), 4.89 (s, 2H), 3.96 (s, 3H).

Preparation 155C: 3-(5-Iodo-1-oxoisoindolin-2-yl) piperidine-2,6-dione

To a suspension of 3-aminopiperidine-2,6-dione hydrochloride (5.15 g, 31.3 mmol) in acetonitrile (95 mL) was added Hunig's base (10.9 mL, 62.5 mmol). After stirring for 5 min, the reaction mixture was treated with Preparation 157B (10.09 g, 28.4 mmol) as a solid in small portions over 5 min. After stirring for 1 h at room temperature, the reaction vessel was fitted with a reflux condenser, slowly warmed to 70° C. in an oil bath, and held at that temperature for 2 days. The reaction mixture was cooled to room temperature and stirred overnight. The resulting precipitate was collected in a Buchner funnel, rinsing with additional acetonitrile. The solid was air dried to give 8.9 g (85% yield) of Preparation 155C as a white powder. $^1H$ NMR (400 MHz, DMSO-d6) δ 10.99 (s, 1H), 8.06 (s, 1H), 7.89 (d, J=6.8 Hz, 1H), 7.52 (d, J=8.0 Hz, 1H), 5.11 (dd, J=13.4, 5.2 Hz, 1H), 4.49-4.41 (m, 1H), 4.36-4.28 (m, 1H), 2.98-2.84 (m, 1H), 2.70-2.56 (m, 1H), 2.43-2.29 (m, 1H), 2.06-1.96 (m, 1H).

Example 155

To a nitrogen-flushed vial containing a suspension of Preparation 155C (18.5 mg, 50 μmol), 2-methoxy-6-(4,4,5,5-tetramethyl-1,3,2-dioxaborolan-2-yl)pyridine (23.5 mg, 100 μmol), and XPhos Pd G2 (2.0 mg, 2.5 μmol) in DMF (500 μL) (degassed) was added tripotassium phosphate (21.2 mg, 100 μmol). The reaction mixture was stirred at 90° C. in a microwave reactor. After 3 hours, the reaction mixture was filtered, diluted with EtOAc (5 mL), and washed with saturated aqueous ammonium chloride (2 mL). The aqueous phase was back-extracted with EtOAc (5 mL), and the combined organic layers were concentrated in vacuo. The crude material was purified via preparative HPLC (Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 13% B, 13-53% B over 20 minutes, then a 0-minute hold at 100% B; Flow Rate: 20 mL/min; Column Temperature: 25° C.) to give 4.9 mg (28% yield) of Example 155. LCMS (Analytical HPLC Method 1): $T_{Ret}$=1.44 min; m/z=352.1 $[M+H]^+$. $^1H$ NMR (500 MHz, DMSO-d6) δ 11.01 (s, 1H), 8.32 (s, 1H), 8.26 (d, J=7.9 Hz, 1H), 7.89-7.78 (m, 2H), 7.67 (d, J=7.5 Hz, 1H), 6.85 (d, J=8.2 Hz, 1H), 5.14 (br dd, J=13.2, 4.9 Hz, 1H), 4.55 (d, J=17.4 Hz, 1H), 4.42 (d, J=17.1 Hz, 1H), 3.98 (s, 3H), 2.98-2.86 (m, 1H), 2.67-2.58 (m, 1H), 2.48-2.37 (m, 1H), 2.10-1.98 (m, 1H).

Examples 156 and 157

3-[5-(1-Methoxyisoquinolin-3-yl)-1-oxo-2,3-dihydro-1H-isoindol-2-yl]piperidine-2,6-dione (156) and 3-[1-Oxo-5-(1-oxo-1,2-dihydroisoquinolin-3-yl)-2,3-dihydro-1H-isoindol-2-yl]piperidine-2,6-dione (156)

(156)

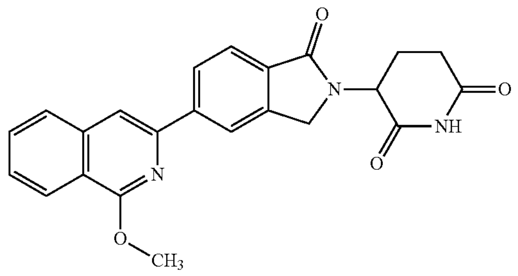

(157)

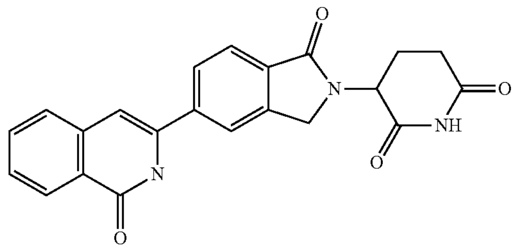

Preparation 156A: 3-Bromo-1-methoxyisoquinoline

A suspension of 1,3-dibromoisoquinoline (215 mg, 750 μmol) and sodium methoxide (40.5 mg, 750 μmol) in toluene (3.0 mL) was stirred in a 110° C. heating block. Additional portions of sodium methoxide (203 mg, 3750 μmol) were added at 1.5 hours and 5 hours. After a total time of 20.5 hours, the reaction mixture was allowed to cool to room temperature, quenched with water (0.1 mL), and concentrated in vacuo. The crude product was dissolved in a small amount of DCM, adsorbed onto a plug of $SiO_2$, and purified by flash chromatography ($SiO_2$, 40 g column, 1% EtOAc/hexanes, isocratic, 40 mL/min) to afford 160 mg (90% yield) Preparation 156A as a white solid. MS (ES): m/z=238.1, 240.1 $[M+H]^+$. $^1H$ NMR (500 MHz, CHLOROFORM-d) δ 8.19 (dd, J=8.3, 1.0 Hz, 1H), 7.69-7.62 (m, 2H), 7.53 (ddd, J=8.3, 5.9, 2.3 Hz, 1H), 7.44 (d, J=0.8 Hz, 1H), 4.14 (s, 3H).

Examples 156 and 157

To a solution of Preparation 156A (40.0 mg, 0.168 mmol) and Preparation 1B (149 mg, 0.336 mmol) in 1,4-dioxane (0.50 mL) was added a solution of potassium carbonate (46.4 mg, 0.336 mmol) in water (336 μL). The reaction vessel was evacuated and backfilled with nitrogen 3×, then $PdCl_2$(dppf) (6.2 mg, 8.4 μmol) was added. The resulting mixture was stirred at 100° C. After 45 min, the reaction mixture was filtered, diluted with EtOAc (5 mL), and washed with saturated aqueous ammonium chloride (2 mL). The aqueous phase was back-extracted with EtOAc (5 mL), and the combined organic layers were concentrated in vacuo. The crude intermediate was suspended in acetonitrile (840 μL), then benzenesulfonic acid (26.6 mg, 168 μmol) was added. The resulting mixture was stirred at 90° C. After 3 hours, a second portion of benzenesulfonic acid (26.6 mg, 168 μmol) was added and stirring was resumed at 90° C. After a total time of 4.5 hours, the reaction mixture was allowed to cool to room temperature and concentrated in vacuo. The crude material was purified via preparative HPLC (Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 7% B, 7-69% B over 30 minutes, then a 0-minute hold at 100% B; Flow Rate: 20 mL/min; Column Temperature: 25° C.) to give Example 156 (14.8 mg, 22% yield). LCMS (Analytical HPLC Method 1): $T_{Ret}$=1.9 min; m/z=402.2 $[M+H]^+$. $^1H$ NMR (500 MHz, DMSO-d6) δ 11.03 (s, 1H), 8.45 (s, 1H), 8.40 (br d, J=8.4 Hz, 1H), 8.20 (br d, J=8.2 Hz, 1H), 8.17 (s, 1H), 8.00 (d, J=8.4 Hz, 1H), 7.86 (d, J=7.9 Hz, 1H), 7.80 (t, J=7.6 Hz, 1H), 7.65 (t, J=7.9 Hz, 1H), 5.15 (br dd, J=13.5, 4.7 Hz, 1H), 4.58 (d, J=17.1 Hz, 1H), 4.44 (d, J=16.9 Hz, 1H), 4.21 (s, 3H), 2.98-2.88 (m, 1H), 2.67-2.59 (m, 1H), 2.47-2.39 (m, 1H), 2.10-1.99 (m, 1H).

A second product was isolated from the same preparation: Example 157 (14.3 mg, 22% yield). LCMS (Analytical HPLC Method 1): $T_{Ret}$=1.26 min; m/z=388.2 $[M+H]^+$. $^1H$ NMR (500 MHz, DMSO-d6) δ 11.65 (br s, 1H), 11.03 (s, 1H), 8.23 (d, J=8.1 Hz, 1H), 8.01 (s, 1H), 7.91 (d, J=7.6 Hz, 1H), 7.84 (d, J=8.0 Hz, 1H), 7.80-7.72 (m, 2H), 7.54 (ddd, J=8.1, 5.1, 3.1 Hz, 1H), 7.04 (s, 1H), 5.13 (br dd, J=13.4, 4.7 Hz, 1H), 4.54 (d, J=17.5 Hz, 1H), 4.42 (d, J=17.6 Hz, 1H), 2.97-2.85 (m, 1H), 2.68-2.60 (m, 1H), 2.49-2.39 (m, 1H), 2.11-2.00 (m, 1H).

Example 158

3-(5-{1-Benzyl-1H-pyrrolo[3,2-c]pyridin-6-yl}-1-oxo-2,3-dihydro-1H-isoindol-2-yl) piperidine-2,6-dione (158)

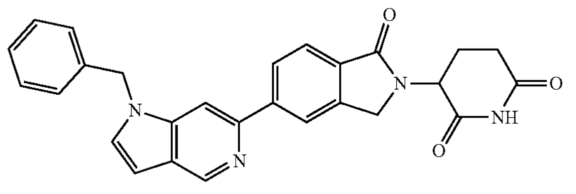

Preparation 158A: 1-Benzyl-6-chloro-1H-pyrrolo[3,2-c]pyridine

To a suspension of 6-chloro-1H-pyrrolo[3,2-c]pyridine (76 mg, 500 μmol) and potassium carbonate (138 mg, 1.00 mmol) in acetonitrile (5.0 mL) was added benzyl bromide (65 μL, 550 μmol). The resulting mixture was stirred at 80° C. After 20 hours, a second portion of benzyl bromide (24 μL, 200 μmol) was added, then stirring was resumed at 80° C. After a total time of 24 hours, the reaction mixture was allowed to cool to room temperature, filtered, and concentrated in vacuo. The crude material was purified via preparative HPLC (Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 13% B, 13-53% B over 20 minutes, then a 0-minute hold at 100% B; Flow Rate: 20 mL/min; Column Temperature: 25° C.). Fractions containing the product were combined and dried via centrifugal evaporation. The material was further purified via preparative HPLC (Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 28% B, 28-68% B over 20 minutes, then a 0-minute hold at 100% B; Flow Rate: 20 mL/min; Column Temperature: 25° C.) to give 20.1 mg (17% yield) of Preparation 158A. MS (ES): m/z=243.3 $[M+H]^+$. $^1H$ NMR (500 MHz, CHLOROFORM-d) δ 8.68 (d, J=0.8 Hz, 1H), 7.37-7.29 (m, 3H), 7.22 (t, J=0.9 Hz, 1H), 7.14 (d, J=3.3 Hz, 1H), 7.12-7.07 (m, 2H), 6.63 (dd, J=3.3, 0.9 Hz, 1H), 5.27 (s, 2H).

Example 158

To a solution of Preparation 158A (20.1 mg, 0.083 mmol) and Preparation 1B (55.2 mg, 0.124 mmol) in 1,4-dioxane (0.50 mL) was added a solution of potassium carbonate (22.9 mg, 0.166 mmol) in water (0.33 mL). The reaction vessel was evacuated and backfilled with nitrogen 3×, then XPhos Pd G2 (3.3 mg, 4.14 μmol) was added. The resulting mixture was stirred at 100° C. After 4.5 hours, the reaction mixture was filtered, diluted with EtOAc (5 mL), and washed with saturated aqueous ammonium chloride (2 mL). The aqueous phase was back-extracted with EtOAc (5 mL), and the combined organic layers were concentrated in vacuo. The crude residue was suspended in acetonitrile (1.0 mL), then benzenesulfonic acid (26.2 mg, 0.166 mmol) was added. The resulting mixture was stirred at 90° C. After 15 hours, the reaction mixture was allowed to cool to room temperature and concentrated in vacuo. The crude material was purified via preparative HPLC (Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 4% B, 4-44% B over 20 minutes, then a 0-minute hold at 100% B; Flow Rate: 20 mL/min; Column Temperature: 25° C.) to give 15.9 mg (40% yield) of Example 158. LCMS (Analytical HPLC Method 1): $T_{Ret}$=1.25 min; m/z=451.2 $[M+H]^+$. $^1H$ NMR (500 MHz, DMSO-d6) δ 11.02 (s, 1H), 9.20 (s, 1H), 8.57 (s, 1H), 8.24 (s, 1H), 8.14 (br d, J=8.3 Hz, 1H), 7.99-7.91 (m, 2H), 7.40-7.23 (m, 5H), 7.02 (d, J=2.8 Hz, 1H), 5.68 (s, 2H), 5.15 (dd, J=13.1, 5.1 Hz, 1H), 4.59 (d, J=17.9 Hz, 1H), 4.47 (d, J=17.3 Hz, 1H), 2.98-2.86 (m, 1H), 2.69-2.58 (m, 1H), 2.48-2.38 (m, 1H), 2.10-2.01 (m, 1H).

Examples 159-161

The compounds in Table 6 were prepared according to the procedures described for Example 157 using the appropriate aryl chloride:

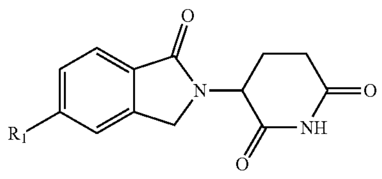

TABLE 6

| Ex. No. | $R_1$ | HPLC[a] $T_{Ret}$ (min) | LC/MS (M + H) | $^1H$ NMR |
|---|---|---|---|---|
| 159 | 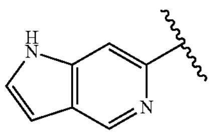 [SMILES: *c1cc2[nH]ccc2cn1] | 0.99 | 361.3 | $^1H$ NMR (500 MHz, DMSO-$d_6$) δ 12.04 (br s, 1H), 11.02 (s, 1H), 9.05 (s, 1H), 8.29 (s, 1H), 8.20 (d, J = 7.9 Hz, 1H), 8.09 (s, 1H), 7.85 (d, J = 7.9 Hz, 1H), 7.65 (br s, 1H), 6.76 (br s, 1H), 5.14 (dd, J = 13.0, 5.2 Hz, 1H), 4.56 (d, J = 17.5 Hz, 1H), 4.43 (d, J = 17.2 Hz, 1H), 2.97-2.88 (m, 1H), 2.66-2.59 (m, 1H), 2.48-2.41 (m, 1H), 2.10-2.01 (m, 1H) |
| 160 | 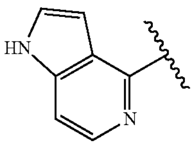 | 0.92 | 361.0 | $^1H$ NMR (500 MHz, DMSO-$d_6$) δ 11.76 (br s, 1H), 11.04 (br s, 1H), 8.32 (d, J = 5.6 Hz, 1H), 8.23 (s, 1H), 8.16 (d, J = 7.9 Hz, 1H), 7.88 (d, J = 8.0 Hz, 1H), 7.61-7.56 (m, 1H), 7.46 (d, J = 5.6 Hz, 1H), 6.88 (br s, 1H), 5.18 (br dd, J = 13.4, 5.3 Hz, 1H), 4.59 (d, J = 17.2 Hz, 1H), 4.47 (d, J = 17.5 Hz, 1H), 3.01-2.87 (m, 1H), 2.68-2.61 (m, 1H), 2.49-2.39 (m, 1H), 2.13-2.01 (m, 1H) |
| 161 | 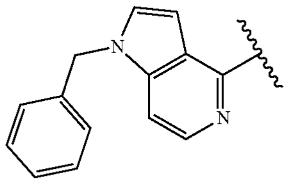 [SMILES: *c1nccc2c1ccn2Cc1ccccc1] | 1.24 | 451.1 | $^1H$ NMR (500 MHz, DMSO-$d_6$) δ 11.02 (br s, 1H), 8.32 (br d, J = 5.1 Hz, 1H), 8.18 (s, 1H), 8.11 (br d, J = 8.0 Hz, 1H), 7.87 (d, J = 7.9 Hz, 1H), 7.72 (d, J = 2.9 Hz, 1H), 7.57 (d, J = 5.8 Hz, 1H), 7.36-7.30 (m, 2H), 7.29-7.22 (m, 3H), 6.91 (d, J = 3.1 Hz, 1H), 5.50 (s, 2H), 5.13 (br dd, J = 12.5, 5.0 Hz, 1H), 4.57 (d, J = 17.4 Hz, 1H), 4.45 (d, J = 17.2 Hz, 1H), 2.97-2.85 (m, 1H), 2.67-2.59 (m, 1H), 2.46-2.38 (m, 1H), 2.12-2.00 (m, 1H) |

[a]HPLC Retention time using Analytical HPLC Method 1.

Examples 162-166

The compounds in Table 7 were prepared according to the procedures described for Example 144 using the appropriate aryl bromide:

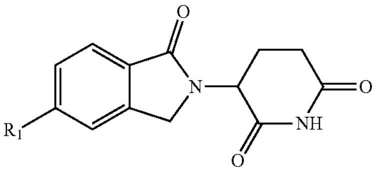

TABLE 7

| Ex. No. | $R_1$ | HPLC[a] $T_{Ret}$ (min) | LC/MS (M + H) | $^1H$ NMR |
|---|---|---|---|---|
| 162 | 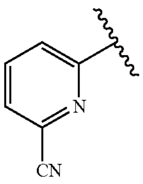 [SMILES: *c1cccc(C#N)n1] | 1.25 | 347.0 | $^1H$ NMR (500 MHz, DMSO-$d_6$) d 11.02 (s, 1H), 8.42 (d, J = 8.2 Hz, 1H), 8.36 (s, 1H), 8.26 (d, J = 7.7 Hz, 1H), 8.21 (t, J = 7.9 Hz, 1H), 8.07 (d, J = 7.6 Hz, 1H), 7.90 (d, J = 7.9 Hz, 1H), 5.16 (dd, J = 13.3, 5.0 Hz, 1H), 4.58 (br d, J = 17.7 Hz, 1H), 4.46 (br d, J = 17.1 Hz, 1H), 3.01-2.88 (m, 1H), 2.76-2.59 (m, 1H), 2.50-2.38 (m, 1H), 2.13-1.98 (m, 1H) |

TABLE 7-continued

| Ex. No. | $R_1$ | HPLC[a] $T_{Ret}$ (min) | LC/MS (M + H) | $^1H$ NMR |
|---|---|---|---|---|
| 163 | 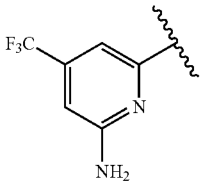 [SMILES: *c1cc(C(F)(F)F)cc(N)n1] | 1.54 | 404.9 | $^1H$ NMR (500 MHz, DMSO-$d_6$) d 11.01 (s, 1H), 8.29 (s, 1H), 8.23 (d, J = 7.6 Hz, 1H), 7.82 (d, J = 7.9 Hz, 1H), 7.40 (s, 1H), 6.77 (s, 1H), 6.71 (s, 1H), 5.15 (br dd, J = 13.1, 4.9 Hz, 1H), 4.54 (br d, J = 17.1 Hz, 1H), 4.42 (d, J = 17.4 Hz, 1H), 3.04-2.85 (m, 1H), 2.63 (br d, J = 17.4 Hz, 1H), 2.49-2.35 (m, 1H), 2.11-2.00 (m, 1H) |
| 164 | 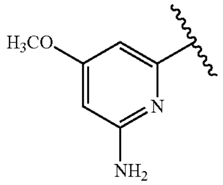 [SMILES: *c1cc(OC)cc(N)n1] | 1.15 | 367.3 | $^1H$ NMR (500 MHz, DMSO-$d_6$) d 11.01 (s, 1H), 8.29 (s, 1H), 8.23 (d, J = 7.6 Hz, 1H), 7.82 (d, J = 7.9 Hz, 1H), 7.40 (s, 1H), 6.77 (s, 1H), 6.71 (s, 1H), 5.15 (br dd, J = 13.1, 4.9 Hz, 1H), 4.54 (br d, J = 17.1 Hz, 1H), 4.42 (d, J = 17.4 Hz, 1H), 3.04-2.85 (m, 1H), 2.63 (br d, J = 17.4 Hz, 1H), 2.49-2.35 (m, 1H), 2.11-2.00 (m, 1H) |
| 165 | 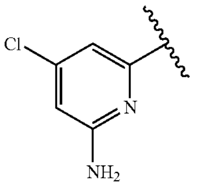 [SMILES: *c1cc(Cl)cc(N)n1] | 1.05 | 372.3 | $^1H$ NMR (500 MHz, DMSO-$d_6$) Shift 11.01 (s, 1H), 8.23 (s, 1H), 8.17 (d, J = 7.9 Hz, 1H), 7.80 (d, J = 7.9 Hz, 1H), 7.25 (s, 1H), 6.55 (s, 1H), 5.14 (dd, J = 13.3, 5.0 Hz, 1H), 4.53 (d, J = 17.4 Hz, 1H), 4.41 (d, J = 17.1 Hz, 1H), 3.01 (s, 1H), 2.98-2.78 (m, 1H), 2.63 (br d, J = 17.7 Hz, 1H), 2.50-2.37 (m, 1H), 2.16-1.99 (m, 1H) |
| 166 | 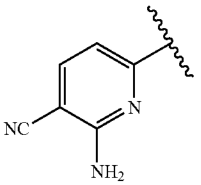 [SMILES: *c1ccc(C#N)c(N)n1] | 1.15 | 361.9 | $^1H$ NMR (500 MHz, DMSO-$d_6$) d 11.02 (s, 1H), 8.28 (s, 1H), 8.21 (d, J = 8.2 Hz, 1H), 8.02 (d, J = 8.1 Hz, 1H), 7.85 (d, J = 8.0 Hz, 1H), 7.35 (d, J = 8.1 Hz, 1H), 7.04 (br s, 2H), 5.15 (br dd, J = 13.2, 5.2 Hz, 1H), 4.55 (d, J = 17.3 Hz, 1H), 4.42 (d, J = 17.4 Hz, 1H), 3.03-2.86 (m, 1H), 2.73-2.58 (m, 1H), 2.50-2.37 (m, 1H), 2.16-2.01 (m, 1H) |

[a]HPLC Retention time using Analytical HPLC Method 1.

Example 167

N-(6-(2-(2,6-dioxopiperidin-3-yl)-1-oxoisoindolin-5-yl)-3,4-dimethylpyridin-2-yl) acetamide (167)

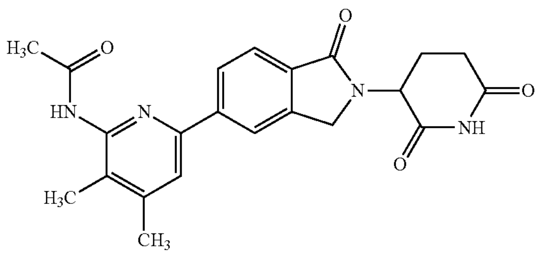

To a solution of Example 151 (20 mg, 0.046 mmol) dissolved in DCM (3 mL) was added acetyl chloride (5.37 mg, 0.068 mmol) followed by Hunig's base (0.016 mL, 0.091 mmol). The reaction mixture was stirred at room temperature for 4 h, and then concentrated to dryness. The residue obtained was dissolved in 1.5 mL of 2 M solution of $PhSO_3H$ in AcOH, and microwaved for 0.5 h at 130° C., and then purified by Preparative HPLC Method 1 to obtain the titled product in 49% yield.

Preparative HPLC method: XBridge C18, 200 mm×19 mm, 5-μm particles; Mobile Phase A: 5:95 acetonitrile:water with 10-mM ammonium acetate; Mobile Phase B: 95:5 acetonitrile:water with 10 mM ammonium acetate; Gradient: a 0 min hold at 15% B, 15-50% B over 25 min, then a 6-min hold at 100% B; Flow Rate: 20 mL/min; Column Temperature: 25° C.

MS (ES): m/z=407.1 $[M+H]^+$. $^1H$ NMR (500 MHz, DMSO-d6) δ 10.01-10.09 (m, 1H) 8.27 (s, 1H) 8.21 (br d, J=7.96 Hz, 1H) 7.79-7.85 (m, 2H) 5.10-5.17 (m, 1H) 4.51-4.58 (m, 1H) 4.38-4.46 (m, 1H) 2.88-2.99 (m, 1H) 2.63 (br d, J=18.66 Hz, 1H) 2.41-2.46 (m, 1H) 2.39 (s, 3H) 2.10-2.10 (m, 1H) 2.10 (br s, 2H) 2.09 (s, 3H) 2.00-2.07 (m, 1H).

Example 168

2-amino-6-(2-(2,6-dioxopiperidin-3-yl)-1-oxoisoindolin-5-yl)pyridine-3,5-dicarbonitrile (168)

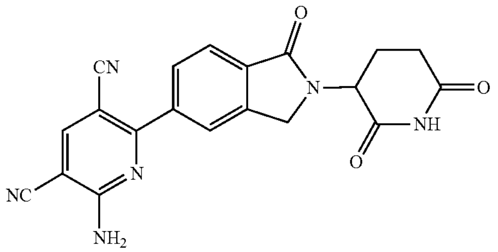

Preparation 168A. tert-butyl (S)-5-amino-4-(5-(6-amino-3,5-dicyanopyridin-2-yl)-1-oxoisoindolin-2-yl)-5-oxopentanoate To a stirred solution of tert-butyl (S)-5-amino-5-oxo-4-(1-oxo-5-(4,4,5,5-tetramethyl-1,3,2-dioxaborolan-2-yl) isoindolin-2-yl)pentanoate (750 mg, 1.688 mmol) in 1,4-dioxane (5 mL) in a sealed tube at room temperature was added 2-amino-6-chloropyridine-3,5-dicarbonitrile (271 mg, 1.519 mmol) followed by potassium carbonate (583 mg, 4.22 mmol)) in water (1 mL). The reaction mixture was degassed for 15 min at atmospheric pressure (under nitrogen). To this reaction mixture, $PdCl_2(dppf)-CH_2Cl_2$ adduct (68.9 mg, 0.084 mmol) was added at room temperature under nitrogen and degassed again for 5 min. The tube was sealed, heated to 100° C. and allowed to stir for 2 h. Progress of the reaction was monitored by TLC. The reaction mixture was allowed to cool to room temperature. The reaction mixture was filtered through a Celite pad in a Buchner funnel. The filtrate was concentrated under reduced pressure to afford 950 mg of crude mass, which was purified by silica gel column chromatography (Isolera) using 50-80% EtOAc-hexane as eluent to afford tert-butyl (S)-5-amino-4-(5-(6-amino-3,5-dicyanopyridin-2-yl)-1-oxoisoindolin-2-yl)-5-oxopentanoate (500 mg, 1.003 mmol, 59.4%) as a light yellow solid.

Example 168

To a stirred solution of tert-butyl (S)-5-amino-4-(5-(6-amino-3,5-dicyanopyridin-2-yl)-1-oxoisoindolin-2-yl)-5-oxopentanoate (500 mg, 1.086 mmol) in acetonitrile (5 mL) in a microwave via, benzenesulfonic acid (172 mg, 1.086 mmol) was added. The reaction mixture was sealed and irradiated in the microwave reactor for 30 minutes at 120° C. After completion of the reaction (monitored by LCMS), solid precipitated on cooling to room temperature. The solid was filtered through a Buchner funnel and dried under vacuum to afford 2-amino-6-(2-(2,6-dioxopiperidin-3-yl)-1-oxoisoindolin-5-yl)pyridine-3,5-dicarbonitrile (195 mg, 0.484 mmol, 44.6%) as a light yellow solid.

LCMS: Column: Kinetex XB—C18 (75×30) mm, 2.6 μm; Mobile Phase A: 5 mM ammonium formate. Mobile Phase B: ACN. Flow Rate: 1.0 mL/min; Purity=96.95% (RT=1.07 min).

HPLC: Column: Kinetex Biphenyl (100×4.6) mm, 2.6 μm, Mobile phase A: 0.05% TFA in water. Mobile phase B: ACN, Flow rate: 1.0 mL/min; Purity=95.9% (RT=5.95 min).

$^1$H-NMR (400 MHz, DMSO-d6) δ 11.04 (s, 1H), 8.62 (s, 1H), 8.10 (m, 2H), 8.00 (s, 1H), 7.90 (d, J=1.20 Hz, 2H), 5.17 (dd, J=5.20, 13.20 Hz, 1H), 4.56 (d, J=17.60 Hz, 1H), 4.43 (d, J=17.60 Hz, 1H), 2.89-2.98 (m, 1H), 2.53-2.68 (m, 1H), 2.41-2.50 (m, 1H), 2.03-2.08 (m, 1H).

Example 169

2-amino-6-(2-(2,6-dioxopiperidin-3-yl)-1-oxoisoindolin-5-yl)-5-fluoronicotinonitrile (169)

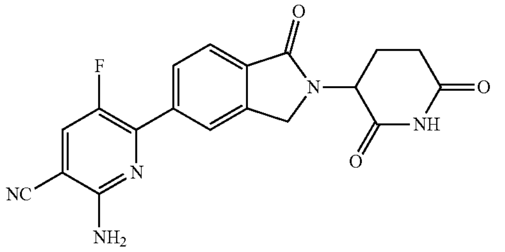

Preparation 169A: tert-butyl(S)-5-amino-5-oxo-4-(1-oxo-5-(4,4,5,5-tetramethyl-1,3,2-dioxaborolan-2-yl)isoindolin-2-yl)pentanoate To a stirred solution of tert-butyl (S)-5-amino-4-(5-bromo-1-oxoisoindolin-2-yl)-5-oxopentanoate (5 g, 12.59 mmol) in 1,4-dioxane (80 mL) were added potassium acetate (3.71 g, 37.8 mmol) and bis(pinacolato)diboron (4.79 g, 18.88 mmol) under a nitrogen atmosphere. The reaction mixture was degassed with $N_2$ gas for 10 minutes followed by the addition of $PdCl_2(dppf)-CH_2Cl_2$ adduct (1.028 g, 1.259 mmol. The resulting reaction mixture was heated at 80° C. for 4 hours. The reaction mixture was allowed to cool to room temperature and filtered through celite pad, the filtrate was diluted with EtOAc (450 mL) and water (200 mL) and the layers were separated. The organic layer was washed with brine (50 mL), dried over $Na_2SO_4$ and concentrated under reduced pressure to get crude mass (15 g), which was purified by silica gel column chromatography (Isolera) using 50-60% EtOAc-hexane as eluent to afford tert-butyl (S)-5-amino-5-oxo-4-(1-oxo-5-(4,4,5,5-tetramethyl-1,3,2-dioxaborolan-2-yl)isoindolin-2-yl)pentanoate (4.6 g, 8.38 mmol, 66.6%) as a reddish solid.

Preparation 169B. tert-butyl (S)-5-amino-4-(5-(6-amino-5-cyano-3-fluoropyridin-2-yl)-1-oxoisoindolin-2-yl)-5-oxopentanoate To a stirred solution of tert-butyl (S)-5-amino-5-oxo-4-(1-oxo-5-(4,4,5,5-tetramethyl-1,3,2-dioxaborolan-2-yl) isoindolin-2-yl)pentanoate (500 mg, 1.125 mmol) in 1,4-dioxane (4 mL) in a sealed tube at room temperature was added 2-amino-6-chloro-5-fluoronicotinonitrile (174 mg, 1.013 mmol) followed by potassium carbonate (389 mg, 2.81 mmol)) in water (0.8 mL). The reaction mixture was degassed for 15 min using nitrogen. To this reaction mixture, $PdCl_2(dppf)-CH_2Cl_2$ adduct (45.9 mg, 0.056 mmol) was added at room temperature under nitrogen and degassed again for 5 min. The tube was sealed, heated to 100° C. and allowed to stir for 2 h. The progress of the reaction was monitored by TLC and LCMS. The reaction mixture was allowed to cool to room temperature and filtered through a celite bed. The filtrate was concentrated under reduced pressure to afford 650 mg of crude mass, which was purified by silica gel column chromatography (Isolera) using 50-80% EtOAc in petroleum ether as eluent to afford tert-buty (S)-5-amino-4-(5-(6-amino-5-cyano-3-fluoropyridin-2-yl)-

1-oxoisoindolin-2-yl)-5-oxopentanoate (300 mg, 0.604 mmol, 53.6%) as a yellowish solid.

Example 169

To a stirred solution of tert-butyl (S)-5-amino-4-(5-(6-amino-5-cyano-3-fluoropyridin-2-yl)-1-oxoisoindolin-2-yl)-5-oxopentanoate (300 mg, 0.662 mmol) in acetonitrile (3 mL) in a microwave vial was added benzenesulfonic acid (105 mg, 0.662 mmol). The reaction vial was sealed and irradiated in the microwave reactor for 30 minutes at 120° C. The progress of the reaction was monitored by LCMS. After completion of the reaction, the mixture was concentrated under reduced pressure to afford 400 mg of crude mass, which was purified by preparative HPLC to afford 2-amino-6-(2-(2,6-dioxopiperidin-3-yl)-1-oxoisoindolin-5-yl)-5-fluoronicotinonitrile, formic acid salt (56 mg, 0.127 mmol, 19.20% yield) as an off-white solid.

Preparative HPLC Method Details: Column: YMC C18 (250×20) mm, 5 μm, Mobile Phase A: 0.1% formic acid in water, Mobile Phase B: Acetonitrile, Flow rate: 15 mL/min.

Analytical data: HPLC: Column: Kinetex Biphenyl (100×4.6) mm, 2.6 μm, Mobile phase A: 0.05% TFA in water, Mobile phase B: ACN, Flow: 1.0 mL/min. RT=7.243 min. Purity=96.46%. LCMS: Column: Kinetex XB—C18 (75×30) mm, 2.6 μm; Mobile Phase A: 5 mM Ammonium formate, Mobile Phase B: ACN, Flow Rate: 1.0 mL/min; RT=1.11 min, Purity=98.01%. $^1$HNMR (400 MHz, DMSO-d6) δ 11.03 (s, 1H), 8.01 (d, J=10.80 Hz, 1H), 7.94 (s, 1H), 7.85 (t, J=9.60 Hz, 2H), 5.16 (dd, J=5.20, 13.20 Hz, 1H), 4.55 (d, J=17.60 Hz, 1H), 4.41 (d, J=17.60 Hz, 1H), 2.89-2.98 (m, 1H), 2.60-2.68 (m, 1H), 2.41-2.50 (m, 1H), 2.03-2.08 (m, 1H).

Example 170

3-(5-(6-amino-4-phenylpyridin-2-yl)-1-oxoisoindolin-2-yl)piperidine-2,6-dione (170)

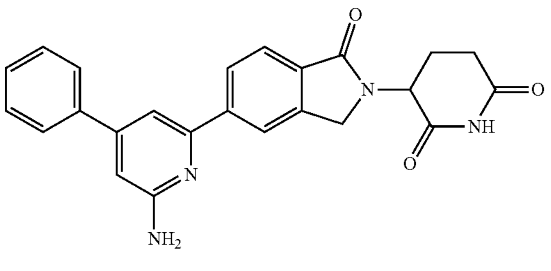

Preparation 170A. tert-butyl (S)-5-amino-4-(5-(6-amino-4-phenylpyridin-2-yl)-1-oxoisoindolin-2-yl)-5-oxopentanoate A mixture of tert-butyl (S)-5-amino-5-oxo-4-(1-oxo-5-(4,4,5,5-tetramethyl-1,3,2-dioxaborolan-2-yl)isoindolin-2-yl) pentanoate (0.5 g, 1.125 mmol), 6-chloro-4-phenylpyridin-2-amine (0.184 g, 0.900 mmol) and potassium carbonate (0.389 g, 2.81 mmol) was treated with previously degassed 1,4-dioxane (16 mL) and water (4 mL) (4:1) in a seal tube. The reaction mixture was purged with $N_2$ for 10 min, followed by the addition of $PdCl_2(dppf)$-$CH_2Cl_2$ adduct (0.046 g, 0.056 mmol). The tube was sealed immediately and was stirred at 100° C. for 3 h. After completion of the reaction, the reaction vessel was allowed to cool to ambient temperature. The reaction mixture was diluted with ethyl acetate (50 mL), filtered through a bed of Celite, and concentrated in vacuo to afford the crude product. The crude product obtained was purified by column chromatography (Grace, 25 g snap, dry pack) over silica gel (230-400 mesh) by eluting with 0-20% ethyl acetate in petroleum ether. The desired fractions pooled and concentrated under reduced pressure to afford tert-butyl (S)-5-amino-4-(5-(6-amino-4-phenylpyridin-2-yl)-1-oxoisoindolin-2-yl)-5-oxopentanoate (0.291 g, 0.549 mmol, 48.8%) as a pale brown solid.

Example 170

To a stirred solution of tert-butyl (S)-5-amino-4-(5-(6-amino-4-phenylpyridin-2-yl)-1-oxoisoindolin-2-yl)-5-oxopentanoate 1 (125 mg, 0.257 mmol) in acetonitrile (1.6 mL) in microwave vial was added benzenesulfonic acid (40.6 mg, 0.257 mmol). The reaction vial was sealed and irradiated in the microwave reactor for 30 minutes at 120° C. After completion of the reaction, the mixture was concentrated under reduced pressure to get 350 mg of crude mass, which was purified by preparative HPLC to afford 3-(5-(6-amino-4-phenylpyridin-2-yl)-1-oxoisoindolin-2-yl)piperidine-2,6-dione (13 mg, 0.030 mmol, 11.8%) as an off-white solid.

Preparative Purification Method Details: Column: YMC C18 (250×20) mm, 5 μm, Mobile Phase A: 0.1% formic acid in water, Mobile Phase B: Acetonitrile, Flow rate: 15 mL/min.

Analytical data: HPLC: Column: Kinetex Biphenyl (100×4.6) mm, 2.6 μm, Mobile phase A: 0.05% TFA in water, Mobile phase B: ACN, Flow rate: 1.0 mL/min. RT=5.248 min. Purity=96.4%. LCMS: Column: Kinetex XB—C18 (75×30) mm, 2.6 μm; Mobile Phase A: 5 mM Ammonium formate, Mobile Phase B: ACN, Flow Rate: 1.0 mL/min; RT=1.10 min, Purity=92.45%. $^1$HNMR (400 MHz, DMSO-d6) δ 11.03 (s, 1H), 8.30 (s, 1H), 8.23 (d, J=8.00 Hz, 1H), 7.79-7.84 (m, 3H), 7.51-7.56 (m, 4H), 6.84 (s, 1H), 6.45 (bs, 2H), 5.15 (dd, J=5.20, 13.20 Hz, 1H), 4.55 (d, J=17.60 Hz, 1H), 4.42 (d, J=17.60 Hz, 1H), 2.88-2.96 (m, 1H), 2.65-2.69 (m, 1H), 2.39-2.43 (m, 1H), 2.02-2.05 (m, 1H).

Example 171

6-amino-2-(2-(2,6-dioxopiperidin-3-yl)-1-oxoisoindolin-5-yl)-4-(trifluoromethyl)nicotine-nitrile (171)

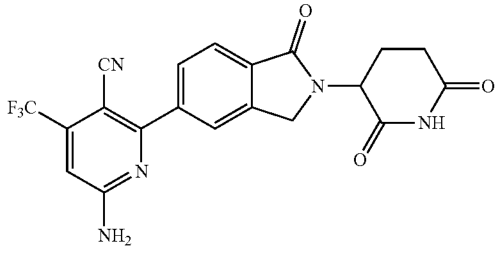

Preparation 171A and 171B: 2-amino-6-chloro-4-(trifluoromethyl)nicotinonitrile and 6-amino-2-chloro-4-(trifluoromethyl)nicotinonitrile (171A)

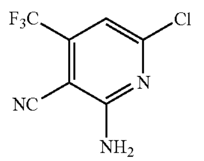

(171B)

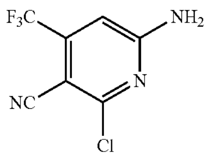

A well stirred solution of 2,6-dichloro-4-(trifluoromethyl) nicotinonitrile (650 mg, 2.70 mmol) and ammonium hydroxide (1.050 mL, 27.0 mmol) in ethanol (10 mL) in a 50 mL Tinyclave was heated at 50° C. for 12 h. After completion of the reaction, the solvent was concentrated under reduced pressure to afford crude material. This was purified by flash silica-gel (230-400 mesh) column chromatography using 10-30% EtOAc in petroleum ether to afford 2-amino-6-chloro-4-(trifluoromethyl)nicotinonitrile—171A (30 mg, 0.126 mmol, 4.67%) as a white solid. The second compound eluted at 40% of EtOAc in petroleum ether yielding 6-amino-2-chloro-4-(trifluoromethyl)nicotinonitrile—171B (301 mg, 1.267 mmol, 47.0%) as a white solid.

Preparation 171C. tert-butyl (S)-5-amino-4-(5-(6-amino-3-cyano-4-(trifluoromethyl) pyridin-2-yl)-1-oxoisoindolin-2-yl)-5-oxopentanoate Into a 30 mL microwave vial containing a well-stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (600 mg, 1.350 mmol) and 6-amino-2-chloro-4-(trifluoromethyl) nicotinonitrile—171B (299 mg, 1.350 mmol) was added aqueous sodium bicarbonate (284 mg, 3.38 mmol, 2 M, 1 mL) at ambient temperature. The resulting reaction mixture was degassed by bubbling nitrogen gas into the reaction mixture for 10 minutes. Then tetrakis(triphenylphosphine)palladium(0) (46.8 mg, 0.041 mmol) was added to the reaction mixture, and the resulting reaction mixture was heated at 120° C. in a microwave reactor for 1 h. After cooling to room temperature, the reaction mixture was poured into water (30 mL) and was extracted with EtOAc (2×50 mL). Organic phases were combined, washed with brine (30 mL), dried over anhydrous $Na_2SO_4$, and concentrated under reduced pressure to get a crude residue. The residue was purified by silica gel column chromatography (Biotage, eluted with 50% ethyl acetate in petroleum ether) to yield tert-butyl(S)-5-amino-4-(5-(6-amino-3-cyano-4-(trifluoromethyl)pyridin-2-yl)-1-oxoisoindolin-2-yl)-5-oxopentanoate (401 mg, 0.755 mmol, 55.9%) as a brown solid.

Example 171

Into a 30 mL microwave vial containing a well-stirred solution of tert-butyl (S)-5-amino-4-(5-(6-amino-3-cyano-4-(trifluoromethyl)pyridin-2-yl)-1-oxoisoindolin-2-yl)-5-oxopentanoate (400 mg, 0.794 mmol) in anhydrous acetonitrile (4.0 mL) was added benzenesulfonic acid (126 mg, 0.794 mmol) at ambient temperature under nitrogen atmosphere. The contents were heated in a microwave reactor at 120° C. for 2 h. After completion of the reaction, excess solvents were removed from the reaction mixture under reduced pressure to get the crude compound. Purification was done by using preparative HPLC to get 6-amino-2-(2-(2,6-dioxopiperidin-3-yl)-1-oxoisoindolin-5-yl)-4-(trifluoromethyl)nicotinonitrile (177.94 mg, 0.413 mmol, 52.0%) as a white solid.

Preparative HPLC Method Details: Column: XBridge C18 (150×19) mm, 5 μm, Mobile Phase A: 0.1% TFA in water, Mobile Phase B: Acetonitrile, Flow rate: 15 mL/min.

Analytical data: LCMS: Column-XBridge C8 (50×4.6 mm) 5 μm, wavelength: 220 nm; Mobile Phase—0.1% TFA in water and Acetonitrile. RT=1.96 min. MS (ES): m/z=430.0 $(M+H)^+$. Purity 99.42%. HPLC: Kinetex EVO C18 (100×4.6) mm, 2.6 μm. Mobile phase A: 0.05% TFA in water; Mobile phase B: ACN; Flow rate: 1.0 mL/min. RT=7.14 min, Purity: 99.69%. $^1$H NMR (400 MHz, DMSO-d6) δ 11.02 (s, 1H), 7.97-7.84 (m, 5H), 6.96 (s, 1H), 5.17 (dd, J=4.80, 13.40 Hz, 1H), 4.58-4.41 (m, 2H), 2.97-2.89 (m, 1H), 2.52-2.61 (m, 1H), 2.43-2.42 (m, 1H), 2.08-2.05 (m, 1H).

Example 172

2-amino-6-(2-(2,6-dioxopiperidin-3-yl)-1-oxoisoindolin-5-yl)-4-propylnicotinonitrile (172)

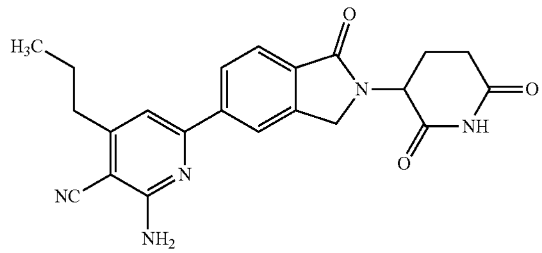

Preparation 172A. 6-hydroxy-2-oxo-4-propyl-1,2-dihydropyridine-3-carbonitrile

In a sealed tube, KOH (3.55 g, 63.2 mmol) was slowly added to a stirred solution of ethyl 3-oxohexanoate (10 g, 63.2 mmol) and 2-cyanoacetamide (5.31 g, 63.2 mmol) in ethanol (100 mL). The mixture was stirred at 85° C. for 18 h. After completion of the reaction, the reaction mixture was cooled to room temperature. The solid precipitated was filtered off and made soluble in warm water (100 mL). The solution was acidified using 40 mL of 4 N HCl, giving an off-white residue, which was filtered off and washed with water and cold diethyl ether. The solid residue was dried in vacuum to yield the 6-hydroxy-2-oxo-4-propyl-1,2-dihydropyridine-3-carbonitrile (7.5 g, 41.8 mmol, 66.2%) as an off-white powder.

Preparation 172B. 2,6-dichloro-4-propylnicotinonitrile

Phosphoryl chloride (10 mL) was added to a mixture of 6-hydroxy-2-oxo-4-propyl-1,2-dihydropyridine-3-carbonitrile (3 g, 16.84 mmol) and tetramethylammonium chloride (3.69 g, 33.7 mmol) dropwise at room temperature under nitrogen atmosphere in a sealed tube. The mixture was then heated at 145° C. for 20 h. After 20 h, TLC analysis indicated complete consumption of starting material. The reaction mixture was then cooled to room temperature, poured over crushed ice, and stirred for 2 h. The solution was extracted with ethyl acetate (150 mL), dried with sodium sulfate, and concentrated to yield 2,6-dichloro-4-propylnicotinonitrile (2.6 g, 12.07 mmol, 71.7%) as a thick syrup.

Preparation 172C and 172D. 2-amino-6-chloro-4-propylnicotinonitrile and 6-amino-2-chloro-4-propylnicotinonitrile Into a 50 mL Tinyclave flask containing a well-stirred solution of 2,6-dichloro-4-propylnicotinonitrile (2.0 g, 9.30 mmol) in ethanol (25 mL) was added aqueous $NH_3$ (15 mL) at ambient temperature. The reaction mixture was then heated at 50° C. for 16 h. After completing the reaction, the solvent was concentrated under reduced pressure to afford the product as a regio-isomeric mixture. The crude material was purified by flash silica-gel (230-400 mesh) column with 10-15% EtOAc in petroleum ether to yield 2-amino-6-chloro-4-propylnicotinonitrile—171C (170 mg, 0.864 mmol, 9.29% yield) as white solid. The second isomer eluted at 30% of EtOAc concentration to yield 6-amino-2-chloro-4-propylnicotinonitrile—171D (340 mg, 1.732 mmol, 18.62% yield) as a white solid.

Preparation 172E. tert-butyl (S)-5-amino-4-(5-(6-amino-5-cyano-4-propylpyridin-2-yl)-1-oxoisoindolin-2-yl)-5-oxopentanoate Into a 10 mL microwave vial containing a well-stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (250 mg, 0.562 mmol) and 2-amino-6-chloro-4-propylnicotinonitrile (100 mg, 0.511 mmol) in 1,4-dioxane (5 mL) was added sodium hydrogen carbonate (129 mg, 1.533 mmol) in water (1 mL) at ambient temperature under nitrogen atmosphere. The resulting reaction mixture was degassed by bubbling with nitrogen gas into reaction mixture for 10 minutes. Then tetrakis(triphenylphosphine)palladium(0) (59.1 mg, 0.051 mmol) was added to the reaction mixture, and the resulting reaction mixture was heated at 120° C. under microwave irradiation in a MW reactor for 1 h. The reaction mixture was then poured in water (20 mL) and extracted with EtOAc (2×50 mL). Organic phases were combined and washed with brine (20 mL). Combined organic phases were dried over anhydrous $Na_2SO_4$, filtered, and concentrated under reduced pressure to get a crude residue. The crude material was purified by flash silica-gel (230-400 mesh) column with 50-60% EtOAc in petroleum ether to yield tert-butyl (S)-5-amino-4-(5-(6-amino-5-cyano-4-propylpyridin-2-yl)-1-oxoisoindolin-2-yl)-5-oxopentanoate (130 mg, 0.152 mmol, 29.8%) as an off-white solid.

Example 172

To a stirred solution of tert-butyl (S)-5-amino-4-(5-(6-amino-5-cyano-4-propylpyridin-2-yl)-1-oxoisoindolin-2-yl)-5-oxopentanoate (75 mg, 0.157 mmol) in anhydrous acetonitrile (4.0 mL) in microwave vial under $N_2$ atmosphere was added benzenesulfonic acid (24.84 mg, 0.157 mmol). The reaction vial was sealed and irradiated in microwave reactor for 1 h at 130° C. After completing the reaction, the reaction mass was concentrated to provide the crude product as an off-white solid. Purification using preparative HPLC yielded 2-amino-6-(2-(2,6-dioxopiperidin-3-yl)-1-oxoisoindolin-5-yl)-4-propylnicotinonitrile, TFA (55 mg, 0.106 mmol, 67.5% yield) as a white solid.

Preparative HPLC Method Details: Column: XSelect C18 (150×19) mm, 5 μm; Mobile phase A: 0.1% TFA in water, Mobile phase B: Acetonitrile, Flow rate: 15 mL/min.

Analytical data: LCMS: Column: Kinetex XB—C18 (75×3.0) mm, 2.6 μm; Mobile Phase A: 5 mM Ammonium formate. Mobile Phase B: ACN, Flow Rate: 1.0 mL/min; RT=1.826, MS (ES): m/z=404.2 $[M+H]^+$. HPLC Purity: Column: Kinetex EVO C18 (100×4.6) mm, 2.6 μm; Mobile phase A: 0.05% TFA in water; Mobile phase B: ACN. Flow rate: 1.0 mL/min; RT=6.927 min; HPLC purity: 99.68%. $^1$HNMR: 400 MHZ (DMSO): δ 11.01 (s, 1H), 8.28-8.21 (m, 2H), 7.93 (d, J=8.0 Hz, 1H), 7.31 (s, 1H), 6.93 (br s, 1H), 5.15 (dd, J=5.20, 13.20 Hz, 1H), 5.15 (dd, J=5.20, 13.20 Hz, 1H), 2.90 (m, 1H), 2.70-2.50 (m, 3H), 2.46-2.33 (m, 3H), 2.08-2.01 (m, 1H), 1.74-1.68 (m, 2H), 0.97 (t, J=7.60 Hz, 3H). $^{19}$FNMR: 400 MHZ (DMSO): δ −74.52.

Example 173

6-amino-2-(2-(2,6-dioxopiperidin-3-yl)-1-oxoisoindolin-5-yl)-4-propylnicotinonitrile (173)

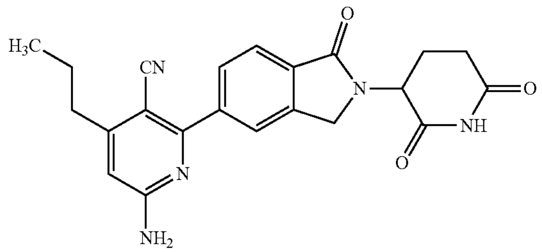

Preparation 173A. tert-butyl (S)-5-amino-4-(5-(6-amino-3-cyano-4-propylpyridin-2-yl)-1-oxoisoindolin-2-yl)-5-oxopentanoate Into a 30 mL microwave vial containing a well stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (250 mg, 0.562 mmol) and 6-amino-2-chloro-4-propylnicotinonitrile—172D (100 mg, 0.511 mmol) in 1,4-dioxane (5 mL) was added sodium hydrogen carbonate (129 mg, 1.533 mmol) in water (1 mL) at ambient temperature under nitrogen atmosphere. The resulting reaction mixture was degassed by bubbling with nitrogen gas into reaction mixture for 10 minutes. Then tetrakis(triphenylphosphine) palladium(0) (59.1 mg, 0.051 mmol) was added to the reaction mixture, and the resulting reaction mixture was heated to 120° C. under microwave irradiation in MW reactor for 1 h. The reaction mixture was then poured in water (30 mL) and extracted with EtOAc (2×50 mL). Organic phases were combined and washed with brine (20 mL). Combined organic phases were dried over anhydrous $Na_2SO_4$, filtered, and concentrated under reduced pressure to get a crude residue. The crude material was purified by flash silica-gel (230-400 mesh) column with 50-60% EtOAc in petroleum ether to yield tert-butyl (S)-5-amino-4-(5-(6-amino-3-cyano-4-propylpyridin-2-yl)-1-oxoisoindolin-2-yl)-5-oxopentanoate (205 mg, 0.388 mmol, 76%) as an off-white solid.

Example 173

To a stirred solution of tert-butyl (S)-5-amino-4-(5-(6-amino-3-cyano-4-propylpyridin-2-yl)-1-oxoisoindolin-2-yl)-5-oxopentanoate (200 mg, 0.419 mmol) in anhydrous acetonitrile (4.0 mL) in microwave vial under $N_2$ atmosphere was added benzenesulfonic acid (66.2 mg, 0.419 mmol). The reaction vial was sealed and irradiated in the microwave for 1 h at 130° C. After completion of the reaction, the reaction mass was concentrated to provide crude product as an off-white solid. Purification using preparative HPLC yielded 6-amino-2-(2-(2,6-dioxopiperidin-3-yl)-1-oxoisoindolin-5-yl)-4-propylnicotinonitrile·TFA (49 mg, 0.093 mmol, 22.3%) as a white solid.

Preparative HPLC Method Details: Column: XSelect C18 (150×19) mm, 5 μm; Mobile phase A: 0.1% TFA in water; Mobile phase B: Acetonitrile; Flow rate: 15 mL/min.

Analytical data: LCMS: Column: Kinetex XB—C18 (75×3.0) mm, 2.6 μm; Mobile Phase A: 5 mM Ammonium formate; Mobile Phase B: ACN; Flow Rate: 1.0 mL/min; RT=1.340, MS (ES): m/z=404.2 $[M+H]^+$. HPLC Purity: Column: XBridge C8(50×4.6) mm, 3.5 μm; Mobile phase: A: 0.1% TFA in water; Mobile phase B: Acetonitrile; Flow rate: 2.0 mL/min; RT=2.788 min. Purity: 99.83%. $^1$HNMR: 400 MHz (DMSO): δ 11.03 (s, 1H), 7.93 (s, 1H), 7.84 (s, 2H), 7.12 (br s, 2H), 6.44 (s, 1H), 5.16 (dd, J=4.80, 13.40 Hz, 1H), 4.48 (dd, J=17.20, 52.80 Hz, 2H), 2.94 (m, 1H), 2.60-2.66 (m, 3H), 2.50 (m, 1H), 2.05 (m, 1H), 1.66 (q, J=7.20 Hz, 2H), 0.97 (t, J=7.20 Hz, 3H). $^{19}$FNMR: 400 MHZ (DMSO): δ −74.73.

Example 174

6-amino-4-(difluoromethyl)-2-(2-(2,6-dioxopiperidin-3-yl)-1-oxoisoindolin-5-yl) nicotinonitrile (174)

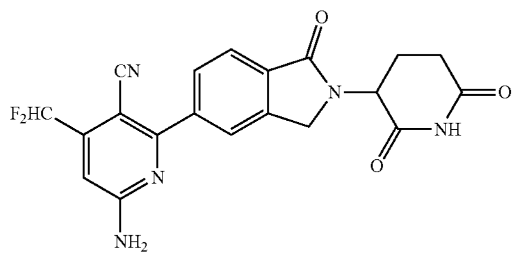

Preparation 174A. tert-butyl (S)-5-amino-4-(5-(6-amino-3-cyano-4-(difluoromethyl) pyridin-2-yl)-1-oxoisoindolin-2-yl)-5-oxopentanoate Into a 30 mL microwave vial containing a well stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (300 mg, 0.614 mmol) and 6-amino-2-chloro-4-(difluoromethyl) nicotinonitrile (125 mg, 0.675 mmol) in 1,4-dioxane (5 mL) was added sodium hydrogen carbonate (155 mg, 1.842 mmol) in water (1 mL) at ambient temperature. The resulting reaction mixture was degassed by bubbling with nitrogen gas into reaction mixture for 10 minutes. Then tetrakis(triphenylphosphine)palladium(0) (71.0 mg, 0.061 mmol) was added to the reaction mixture and resulting reaction mixture was heated at 120° C. under microwave irradiation in MW reactor for 1 h. The reaction mixture was then poured in water (30 mL) and extracted with EtOAc (2×50 mL). Organic phases were combined and washed with brine (20 mL). Combined organic phases were dried over anhydrous $Na_2SO_4$, filtered, and concentrated under reduced pressure to get a crude residue. The crude was purified by flash silica-gel (230-400 mesh) column with 40-50% EtOAc in petroleum ether to yield tert-butyl (S)-5-amino-4-(5-(6-amino-3-cyano-4-(difluoromethyl) pyridin-2-yl)-1-oxoisoindolin-2-yl)-5-oxopentanoate (195 mg, 0.367 mmol, 59.7%) as a thick brown syrup.

Example 174

To a stirred solution of tert-butyl (S)-5-amino-4-(5-(6-amino-5-cyano-4-(difluoromethyl)pyridin-2-yl)-1-oxoisoindolin-2-yl)-5-oxopentanoate (200 mg, 0.412 mmol) in anhydrous acetonitrile (4.0 mL) in microwave vial under $N_2$ atmosphere was added benzenesulfonic acid (65.2 mg, 0.412 mmol). The reaction vial was sealed and irradiated in the microwave for 1 h at 130° C. After completion of the reaction, the reaction mass was concentrated to provide the crude product as an off-white solid. Purification using preparative HPLC yielded 6-amino-4-(difluoromethyl)-2-(2-(2,6-dioxopiperidin-3-yl)-1-oxoisoindolin-5-yl)nicotinonitrile (55 mg, 0.133 mmol, 32.4%) as a white solid.

Preparative HPLC Method Details: Column: XBridge C18 (250×19) mm, 5 μm; Mobile phase A: 0.1% Formic acid in water; Mobile phase B: Acetonitrile; Flow rate: 15 mL/min.

Analytical data: LCMS: Column: Kinetex XB—C18 (75×3.0) mm, 2.6 μm; Mobile Phase A: 5 mm Ammonium formate; Mobile Phase B: ACN: Flow Rate: 1.0 mL/min; RT=1.153, MS (ES): m/z=412.2 $[M+H]^+$. HPLC Purity: Column: Kinetex EVO C18 (100×4.6) mm, 2.6 μm; Mobile phase A: 0.05% TFA in water; Mobile phase B: ACN; Flow rate: 1.0 mL/min; RT=5.230 min. Purity: 99.85%. $^1$HNMR: 400 MHz (DMSO): δ 11.02 (s, 1H), 7.95 (s, 1H), 7.90-7.83 (m, 2H), 7.64 (s, 2H), 7.15 (t, J=53.60 Hz, 1H), 6.80 (s, 1H), 5.17 (dd, J=5.20, 13.20 Hz, 1H), 4.49 (dd, J=17.60, 52.00 Hz, 2H), 2.98-2.88 (m, 1H), 2.70-2.62 (m, 1H), 2.50-2.42 (m, 1H), 2.09-2.03 (m, 1H).

Example 175

2-amino-6-(2-(2,6-dioxopiperidin-3-yl)-1-oxoisoindolin-5-yl)-5-(trifluoromethyl)nicotine-nitrile (175)

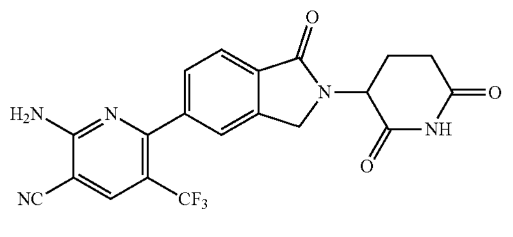

Preparation 175A and 175B. 2-amino-6-chloro-5-(trifluoromethyl)nicotinonitrile and 6-amino-2-chloro-5-(trifluoromethyl)nicotinonitrile To a stirred solution of 2,6-dichloro-5-(trifluoromethyl) nicotinonitrile (800 mg, 3.32 mmol) in ethanol (15 mL) was added ammonium hydroxide (10 mL, 257 mmol). The reaction mixture was heated at 50° C. in a pressure vessel. After 48 h, the mixture was cooled in an ice bath and the resultant mixture was concentrated under reduced pressure to get 1 g of crude mass, which was purified silica gel column chromatography (Isolera) using 10-20% EtOAc-Hexane as eluent to afford a regioisomeric mixture of 2-amino-6-chloro-5-(trifluoromethyl) nicotinonitrile and 6-amino-2-chloro-5-(trifluoromethyl)nicotine-nitrile (250 mg, 71.0%) as a white solid.

Preparation 175C and 175C. tert-Butyl (S)-5-amino-4-(5-(6-amino-5-cyano-3-(trifluoromethyl) pyridin-2-yl)-1-oxoisoindolin-2-yl)-5-oxopentanoate and tert-butyl (S)-5-amino-4-(5-(6-amino-3-cyano-5-(trifluoromethyl)pyridin-2-yl)-1-oxoisoindolin-2-yl)-5-oxopentanoate To a stirred solution of tert-butyl (S)-5-amino-5-oxo-4-(1-oxo-5-(4,4,5,5-tetramethyl-1,3,2-dioxaborolan-2-yl) isoindolin-2-yl)pentanoate (400 mg, 0.900 mmol) in 1,4-dioxane (2 mL) at room temperature was added 2-amino-6-chloro-5-(trifluoromethyl) nicotinonitrile (180 mg, 0.810 mmol) followed by potassium carbonate (311 mg, 2.251 mmol)) in water (0.5 mL). The reaction mixture was degassed for 15 min using nitrogen. To this reaction mixture, $PdCl_2(dppf)-CH_2Cl_2$ adduct (36.8 mg, 0.045 mmol) was added under nitrogen and degassed again for 5 min. The tube was sealed, heated to 100° C., and allowed to stir for 2 h. The progress of the reaction was monitored by TLC. The reaction mixture was allowed to cool to room temperature and filtered through celite pad. The filtrate was concentrated under reduced pressure to get 850 mg of crude mass, which was purified silica gel column chromatography (Isolera) using 60-70% EtOAc-petroleum ether as eluent to afford mixture of tert-butyl (S)-5-amino-4-(5-(6-amino-5-cyano-3-(trifluoromethyl)pyridin-2-yl)-1-oxoisoindolin-2-yl)-5-oxopentanoate (150 mg, 0.281 mmol, 31.2%) as a brown solid.

Example 175

To a stirred solution of tert-butyl (S)-5-amino-4-(5-(6-amino-5-cyano-3-(trifluoromethyl)pyridin-2-yl)-1-oxoisoindolin-2-yl)-5-oxopentanoate and tert-butyl (S)-5-amino-4-(5-(6-amino-3-cyano-5-(trifluoromethyl)pyridin-2-yl)-1-oxoisoindolin-2-yl)-5-oxopentanoate (150 mg, 0.397 mmol) in acetonitrile (3 mL) in microwave vial, was added benzenesulfonic acid (62.8 mg, 0.397 mmol). The reaction vial was sealed and irradiated in the microwave reactor for 1 h at 120° C. The mixture was concentrated under reduced pressure to afford 250 mg of crude mass, which was purified by preparative HPLC yielding both regioisomers.

Preparative HPLC Method Details: Column: Sunfire C18 (150×19) mm, 5 μm, Mobile Phase A: 0.1% TFA in water, Mobile Phase B: Acetonitrile, Flow rate: 15 mL/min.

Analytical data for Regio Isomer 1: 2-amino-6-(2-(2,6-dioxopiperidin-3-yl)-1-oxoisoindolin-5-yl)-5-(trifluoromethyl)nicotinonitrile (7 mg, 0.016 mmol, 4.0%) as a light yellow solid. HPLC: Column: Kinetex Biphenyl (100×4.6) mm, 2.6 μm, Mobile phase A: 0.05% TFA in water, Mobile phase B: ACN, Flow rate: 1.0 mL/min. RT=6.891 min. Purity=97.63%. LCMS: Column: Kinetex XB—C18 (75×30) mm, 2.6 μm; Mobile Phase A: 5 mM Ammonium formate, Mobile Phase B: ACN, Flow Rate: 1.0 mL/min; RT=1.51 min, Purity=99.47%. $^1$H-NMR (400 MHz, DMSO-d6) δ 11.01 (s, 1H), 8.41 (s, 1H), 7.82 (d, J=8.00 Hz, 1H), 7.74 (bs, 2H), 7.65 (s, 1H), 7.54 (d, J=8.00 Hz, 1H), 5.11 (dd, J=4.80, 13.40 Hz, 1H), 4.53 (d, J=17.60 Hz, 1H), 4.39 (d, J=17.60 Hz, 1H), 2.85-2.93 (m, 1H), 2.61-2.65 (m, 1H), 2.40-2.43 (m, 1H), 2.06-2.07 (m, 1H).

Example 176

2-amino-4-(difluoromethyl)-6-(2-(2,6-dioxopiperidin-3-yl)-1-oxoisoindolin-5-yl) nicotinonitrile (176)

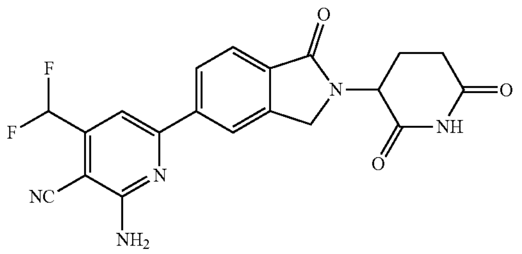

Preparation 176A. tert-butyl (S)-5-amino-4-(5-(6-amino-5-cyano-4-(difluoromethyl) pyridin-2-yl)-1-oxoisoindolin-2-yl)-5-oxopentanoate Into a 30 mL microwave vial containing a well stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (475 mg, 1.069 mmol) and 2-amino-6-chloro-4-(difluoromethyl)nicotinonitrile (218 mg, 1.069 mmol) in anhydrous 1,4-dioxane (9.0 mL) was added 2.0 M sodium bicarbonate (225 mg, 2.67 mmol) in water (1.0 mL) under nitrogen atmosphere. The resulting reaction mixture was degassed by bubbling nitrogen gas into reaction mixture for 10 minutes. Then tetrakis(triphenylphosphine)palladium(0) (37.1 mg, 0.032 mmol) was added to the reaction mixture and resulting reaction mixture was heated at 120° C. in a microwave reactor for 1 h. After completion of the reaction, the reaction mixture was poured in water (20 mL) and extracted with EtOAc (2×50 mL). Organic phases were combined, washed with brine (30 mL), dried over anhydrous $Na_2SO_4$ and concentrated under reduced pressure to get a crude residue. This was mixed with the previous batch crude (102 mg) and purified by silica gel column chromatography (Biotage), using 0-100% ethyl acetate in petroleum ether to yield tert-butyl (S)-5-amino-4-(5-(6-amino-5-cyano-4-(difluoromethyl)pyridin-2-yl)-1-oxoisoindolin-2-yl)-5-oxopentanoate (301 mg, 0.447 mmol, 41.8%) as a brown solid.

Example 176

Into a 30 mL microwave vial containing a well-stirred solution of tert-butyl (S)-5-amino-4-(5-(6-amino-5-cyano-4-(difluoromethyl)pyridin-2-yl)-1-oxoisoindolin-2-yl)-5-oxopentanoate (300 mg, 0.618 mmol) in anhydrous acetonitrile (3.0 mL) were added benzenesulfonic acid (98 mg, 0.618 mmol) at ambient temperature under nitrogen atmosphere.

The contents were heated in microwave reactor at 120° C. for 2 h. After completion of the reaction, excess solvents were removed from the reaction mixture under reduced pressure to get the crude compound. Purification using preparative HPLC yielded 2-amino-4-(difluoromethyl)-6-(2-(2,6-dioxopiperidin-3-yl)-1-oxoisoindolin-5-yl) nicotinonitrile (101.20 mg, 0.244 mmol, 39.5%) as an off white solid.

Preparative Purification Method Details: Column: XBridge C18 (250×19) mm, 5 μm, Mobile Phase A: 0.1% TFA in water, Mobile Phase B: Acetonitrile, Flow rate: 15 mL/min.

Analytical data: LCMS: Column: Kinetex XB—C18 (75×30) mm, 2.6 μm; Mobile Phase A: 5 mM Ammonium formate, Mobile Phase B: ACN, Flow Rate: 1.0 mL/min; RT=1.49 min, Purity=92.25%. MS (ES): m/z=412.2 $(M+H)^+$. HPLC: Kinetex EVO C18 (100×4.6) mm, 2.6 μm. Mobile phase A: 0.05% TFA in water; Mobile phase B: ACN; Flow rate: 1.0 mL/min. RT=7.14 min, Purity: 99.29%. $^1$H-NMR (400 MHz, DMSO-d6) δ 11.03 (s, 1H), 8.33 (s, 1H), 8.26 (dd, J=1.20, 8.00 Hz, 1H), 7.88 (d, J=8.40 Hz, 1H), 7.55 (s, 1H), 7.43 (s, 2H), 7.17 (t, J=54.00 Hz, 1H), 5.18-5.14 (m, 1H), 4.56 (d, J=17.60 Hz, 1H), 4.43 (d, J=17.20 Hz, 1H), 2.98-2.89 (m, 1H), 2.68-2.64 (m, 1H), 2.40-2.33 (m, 1H), 2.08-2.05 (m, 1H).

Example 177

2-amino-6-(2-(2,6-dioxopiperidin-3-yl)-1-oxoisoindolin-5-yl)-4-(trifluoromethyl)nicotine-nitrile (177)

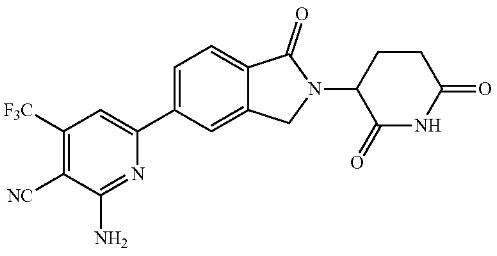

Preparation 177A. 2-amino-6-chloro-4-(trifluoromethyl)nicotinonitrile

A well-stirred solution of 2,6-dichloro-4-(trifluoromethyl) nicotinonitrile (2.0 g, 8.30 mmol) and ammonium hydroxide (1.616 mL, 41.5 mmol) in ethanol (20 mL) in a 50 mL Tinyclave was heated at 50° C. for 12 h. After completion of the reaction, solvent was concentrated under reduced pressure to afford crude material. This was purified by flash silica-gel (230-400 mesh) column chromatography using 10-30% EtOAc in petroleum ether to afford 2-amino-6-chloro-4-(trifluoromethyl)nicotinonitrile—177A (61 mg, 0.265 mmol, 3.20%) as a white solid.

Preparation 177B. tert-butyl (S)-5-amino-4-(5-(6-amino-5-cyano-4-(trifluoromethyl) pyridin-2-yl)-1-oxoisoindolin-2-yl)-5-oxopentanoate Into a 30 mL microwave vial containing a well stirred solution of 2-amino-6-chloro-4-(trifluoromethyl)nicotinonitrile (90 mg, 0.406 mmol) and tert-butyl (S)-5-amino-5-oxo-4-(1-oxo-5-(4,4,5,5-tetramethyl-1,3,2-dioxaborolan-2-yl) isoindolin-2-yl) pentanoate (180 mg, 0.406 mmol) was added 2.0 M sodium bicarbonate (85 mg, 1.015 mmol) in water (0.2 mL) at ambient temperature under nitrogen atmosphere. The resulting reaction mixture was degassed by bubbling nitrogen gas into reaction mixture for 10 minutes. Then tetrakis(triphenylphosphine)palladium(0) (14.08 mg, 0.012 mmol) was added to the reaction mixture and resulting reaction mixture was heated in microwave reactor at 120° C. for 1 h. After cooling to room temperature, the reaction mixture was poured into water (30 mL) and was extracted with EtOAc (2×50 mL). Organic phases were combined, washed with brine (30 mL), dried over anhydrous $Na_2SO_4$, and concentrated under reduced pressure to get a crude residue. The residue was purified by silica gel column chromatography (Biotage, eluted with 90% ethyl acetate in petroleum ether) to yield tert-butyl (S)-5-amino-4-(5-(6-amino-5-cyano-4-(trifluoromethyl)pyridin-2-yl)-1-oxoisoindolin-2-yl)-5-oxopentanoate (130 mg, 0.167 mmol, 41.1%) as a pale brown solid.

Example 177

Into a 30 mL microwave vial containing a well-stirred solution of tert-butyl (S)-5-amino-4-(5-(6-amino-5-cyano-4-(trifluoromethyl)pyridin-2-yl)-1-oxoisoindolin-2-yl)-5-oxopentanoate (130 mg, 0.258 mmol) in anhydrous acetonitrile (2.0 mL) was added benzenesulfonic acid (40.8 mg, 0.258 mmol) at ambient temperature under nitrogen atmosphere. The contents were heated in microwave reactor at 120° C. for 2 h. After completion of the reaction as indicated by LCMS, excess solvents were removed from the reaction mixture under reduced pressure to get the crude compound. The crude compound was purified using preparative HPLC to yield 2-amino-6-(2-(2,6-dioxopiperidin-3-yl)-1-oxoisoindolin-5-yl)-4-(trifluoromethyl)nicotinonitrile (45 mg, 0.101 mmol, 39.0%) as an off-white solid.

Preparative HPLC Method Details: Column: Sunfire C18 (150×19) mm, 5 μm, Mobile Phase A: 0.1% TFA in water, Mobile Phase B: Acetonitrile, Flow rate: 15 mL/min.

Analytical data: LCMS: Column—Kinetex XB—C18 (75×3.0) mm, 2.6 μm, Mobile Phase A: 5 mM Ammonium formate and Mobile Phase B: ACN. RT=1.96 min. MS (ES): m/z=428.2 $(M-H)^+$. LCMS purity 99.91%. HPLC: Kinetex EVO C18 (100×4.6) mm, 2.6 μm. Mobile phase A: 0.05% TFA in water; Mobile phase B: ACN; Flow rate: 1.0 mL/min. RT=7.14 min, Purity: 96.11%. $^1$H-NMR (400 MHz, DMSO-d6): δ 11.02 (s, 1H), 8.33-8.30 (m, 2H), 7.88 (d, J=8.00 Hz, 1H), 7.66 (d, J=10.40 Hz, 3H), 5.18-5.14 (m, 1H), 4.58-4.42 (m, 2H), 2.97-2.89 (m, 1H), 2.65-2.53 (m, 1H), 2.48-2.41 (m, 1H), 2.07-2.02 (m, 1H).

Example 178

2-amino-6-(2-(2,6-dioxopiperidin-3-yl)-1-oxoisoindolin-5-yl)-4-isopropylnicotinonitrile (178)

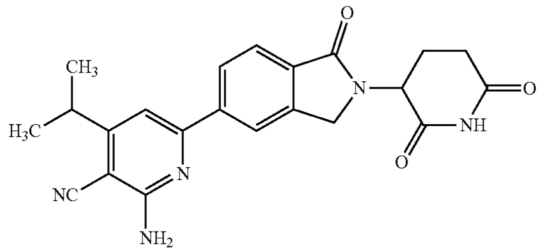

Preparation 178A and 178B. 2-amino-6-chloro-4-isopropylnicotinonitrile and 6-amino-2-chloro-4-isopropylnicotinonitrile Into a 50 mL Tinyclave flask containing a well stirred solution of 2,6-dichloro-4-isopropylnicotinonitrile (1.0 g, 4.65 mmol) in ethanol (10 mL), was added aqueous ammonium hydroxide (40 mL, 1027 mmol) at ambient temperature. The reaction mixture was heated at 50° C. for 16 h. After completion of reaction, the solvent was concentrated under reduced pressure to afford crude as regio-isomeric mixture. The residue was purified by silica gel column chromatography (Biotage, eluted with 20% ethyl acetate in petroleum ether) to yield 2-amino-6-chloro-4-isopropylnicotinonitrile—178A (0.1 g, 0.504 mmol, 10.8%) and 6-amino-2-chloro-4-isopropylnicotinonitrile—178B (0.24 g, 1.173 mmol, 25.2%) as a white solid.

Preparation 178C. tert-butyl (S)-5-amino-4-(5-(6-amino-5-cyano-4-isopropylpyridin-2-yl)-1-oxoisoindolin-2-yl)-5-oxopentanoate Into a 10 mL microwave vial containing a well stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (0.2 g, 0.45 mmol), 2-amino-6-chloro-4-isopropylnicotinonitrile (0.088 g, 0.45 mmol) and 2-amino-6-chloro-4-propylnicotinonitrile (100 mg, 0.511 mmol) in 1,4-dioxane (5 mL) was added sodium bicarbonate (0.095 g, 1.13 mmol) in water (1 mL) at ambient temperature under nitrogen atmosphere. The resulting reaction mixture was degassed by bubbling with nitrogen gas into the reaction mixture for 10 minutes. Tetrakis(triphenylphosphine)palladium(0) (0.052 g, 0.045 mmol) was added and the resulting reaction mixture was heated at 120° C. under MW for 1 h. After cooling, the reaction mixture was poured into water (20 mL) and extracted with EtOAc (2×50 mL). The combined organic layer was washed with brine (20 mL), dried over anhydrous $Na_2SO_4$, filtered and concentrated under reduced pressure to get a crude residue. The crude was purified by flash silica-gel (230-400 mesh) column chromatography (Biotage, eluted with 50-60% ethyl acetate in petroleum ether) to yield tert-butyl (S)-5-amino-4-(5-(6-amino-5-cyano-4-isopropylpyridin-2-yl)-1-oxoisoindolin-2-yl)-5-oxopentanoate (0.12 g, 0.174 mmol, 38.7%) as a pale brown liquid.

Example 178

To a stirred solution of tert-butyl (S)-5-amino-4-(5-(6-amino-5-cyano-4-isopropylpyridin-2-yl)-1-oxoisoindolin-2-yl)-5-oxopentanoate (0.12 g, 0.251 mmol) in anhydrous acetonitrile (4.0 mL) in microwave vial under $N_2$ atmosphere was added benzenesulfonic acid (0.040 g, 0.251 mmol). The reaction vial was sealed and irradiated in the microwave for 1 h at 130° C. After completion of the reaction, the reaction mass was concentrated to provide crude product as an off-white solid. The product was purified by preparative HPLC. The fraction was lyophilized to yield 2-amino-6-(2-(2,6-dioxopiperidin-3-yl)-1-oxoisoindolin-5-yl)-4-isopropylnicotinonitrile·TFA (35 mg, 0.062 mmol, 24.87% yield).

Preparative HPLC Method details: Column: XBridge C-18(150×19) mm 5 μm; Mobile Phase A: 0.1% TFA in water, Mobile Phase B: Acetonitrile, Flow rate: 15 mL/min.

Analytical data: LCMS: RT=1.78 min. ACN/$H_2O$ with ammonium formate, Kinetex XB—C18 (75×3.0) mm, 2.6 μm, (wavelength=220 nm); MS (ES): m/z=404.2 $[M+1]^+$. HPLC: Mobile phase A: 0.05% TFA in water; Mobile phase B: ACN; Flow: 1.0 mL/min. Kinetex EVO C18 (100×4.6) mm, 2.6 μm, RT=6.75 min, Purity: 95.55%. Kinetex Biphenyl (100×4.6) mm, 2.6 μm, RT=7.20 min, Purity: 92.39%. $^1$HNMR (400 MHz, DMSO-d6) δ 11.02 (s, 1H), 8.32 (s, 1H), 8.25 (d, J=7.60 Hz, 1H), 7.84 (d, J=8.00 Hz, 1H), 7.32 (s, 1H), 6.94 (bs, 2H), 5.14-5.18 (m, 1H), 4.53-4.57 (m, 1H), 4.40-4.44 (m, 1H), 3.10-3.17 (m, 1H), 2.89-2.97 (m, 1H), 2.60-2.68 (m, 1H), 2.34-2.43 (m, 1H), 2.03-2.10 (m, 1H), 1.30 (d, J=1.60 Hz, 6H).

Example 179

6-amino-2-(2-(2,6-dioxopiperidin-3-yl)-1-oxoisoindolin-5-yl)-4-isopropylnicotinonitrile (179)

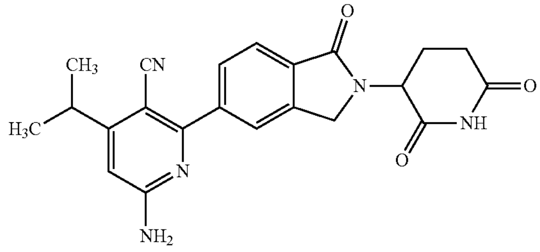

Preparation 179A. tert-butyl (S)-5-amino-4-(5-(6-amino-3-cyano-4-isopropylpyridin-2-yl)-1-oxoisoindolin-2-yl)-5-oxopentanoate Into a 30 mL microwave vial containing a well-stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (0.2 g, 0.450 mmol) and 6-amino-2-chloro-4-isopropylnicotinonitrile (0.088 g, 0.450 mmol) in 1,4-dioxane (5 mL) was added sodium bicarbonate (0.095 g, 1.125 mmol) in degassed water (2 mL) at ambient temperature under nitrogen atmosphere. The resulting reaction mixture was further degassed by bubbling with nitrogen gas into the reaction mixture for 10 minutes. Then tetrakis(triphenylphosphine)palladium(0) (0.052 g, 0.045 mmol) was added to the reaction mixture. The reaction mixture was heated at 120° C. under MW irradiation for 1 h. After cooling to room temperature, the reaction mixture was poured in water (30 mL) and extracted with EtOAc (2×50 mL). The combined organic layer was washed with brine (20 mL), dried over anhydrous $Na_2SO_4$, filtered, and concentrated under reduced pressure to get a crude residue. The crude was purified by flash silica-gel (230-400 mesh) column chromatography (Biotage, eluted with 50-60% ethyl acetate in petroleum ether) to yield tert-butyl (S)-5-amino-4-(5-(6-amino-3-cyano-4-isopropylpyridin-2-yl)-1-oxoisoindolin-2-yl)-5-oxopentano-ate (0.13 g, 0.220 mmol, 48.9%) as a pale brown liquid.

Example 179

To a stirred solution of tert-butyl (S)-5-amino-4-(5-(6-amino-3-cyano-4-isopropylpyridin-2-yl)-1-oxoisoindolin-2-yl)-5-oxopentanoate (0.13 g, 0.272 mmol) in anhydrous acetonitrile (4.0 mL) in microwave vial under $N_2$ atmosphere was added benzenesulfonic acid (0.043 g, 0.272 mmol). The reaction vial was sealed and was heated at 130° C. under MW irradiation for 1 h. After completion of the reaction, the reaction mass was concentrated to provide the crude product as an off-white solid. Purification was done by using preparative HPLC, and the pure fraction was lyophilized to yield 6-amino-2-(2-(2,6-dioxopiperidin-3-yl)-1-oxoisoindolin-5-yl)-4-isopropylnicotinonitrile (23 mg, 0.056 mmol, 20.43% yield) as a white solid.

Preparative HPLC Method Details: Column: XBridge C-18 (150×19) mm 5 μm. Mobile Phase A: 0.1% Formic acid in water, Mobile Phase B: Acetonitrile, Flow: 15 mL/min.

Analytical data: LCMS: Column—Kinetex XB—C18 (75×3.0) mm, 2.6 μm, wavelength=220 nm; Mobile Phase: 5 mM Ammonium formate in water and Acetonitrile. RT=1.43 min. MS (ES): m/z=404.2 $[M+1]^+$. HPLC: Mobile phase A: 0.05% TFA in water; Mobile phase B: ACN: 0.05% TFA in water; Flow rate: 1.0 mL/min. Kinetex EVO C18 (100×4.6) mm, 2.6 μm, RT=5.14 min, Purity: 95.55%. Kinetex Biphenyl (100×4.6) mm, 2.6 μm, RT=5.78 min, Purity: 92.39%. $^1$HNMR 400 MHZ (DMSO) δ 11.02 (s, 1H), 7.93 (s, 1H), 7.84 (s, 2H), 7.12 (s, 2H), 6.50 (s, 1H), 5.15-5.17 (m, 1H), 4.52-4.56 (m, 1H), 4.39-4.43 (m, 1H), 3.07-3.12 (m, 1H), 2.97-2.98 (m, 1H), 2.64-2.68 (m, 1H), 2.51-2.60 (m, 1H), 2.04-2.07 (m, 1H), 1.27 (d, J=6.40 Hz, 6H).

Example 180

6-amino-2-(2-(2,6-dioxopiperidin-3-yl)-1-oxoisoindolin-5-yl)-5-methylnicotinonitrile (180)

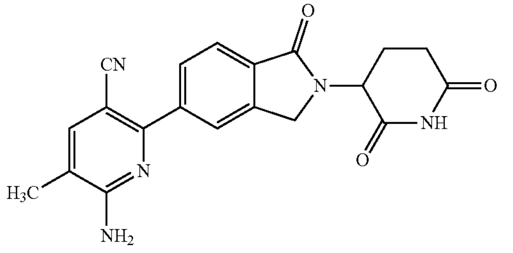

Preparation 180A. 2-chloro-5-cyano-3-methylpyridine 1-oxide

Into a 100 mL single-necked round-bottomed flask containing a well-stirred solution of 6-chloro-5-methylnicotinonitrile (2.0 g, 13.11 mmol) in dry dichloromethane (20 mL) were added trifluoroacetic anhydride (1.851 mL, 13.11 mmol) and urea hydrogen peroxide (1.233 g, 13.11 mmol) at 0° C. and under nitrogen atmosphere. The resulting reaction mixture was stirred at ambient temperature for 12 h. The progress of the reaction was monitored by TLC. After completion of the reaction, the reaction was quenched with 10% saturated bicarbonate solution (50 mL). The aqueous layer was extracted with dichloromethane (2×100 mL). Organic layers were combined, dried over anhydrous $Na_2SO_4$, filtered, and concentrated under reduced pressure to get the crude compound. The residue was purified by silica gel column chromatography (Biotage, eluted with 60% EtOAc in petroleum ether to yield 2-chloro-5-cyano-3-methylpyridine 1-oxide (1.01 g, 5.32 mmol, 40.6%) as a yellow solid.

Preparation 180B. 2,6-dichloro-5-methylnicotinonitrile

A solution of 2-chloro-5-cyano-3-methylpyridine 1-oxide (1.0 g, 5.93 mmol) in $POCl_3$ (5.53 mL, 59.3 mmol) was heated at 90° C. for 3 h. The progress of the reaction was monitored by TLC. After completing the reaction, the reaction mixture was cooled to room temperature and concentrated under reduced pressure to remove excess $POCl_3$. The residue was poured into crushed ice (50 mL) and extracted with EtOAc (2×50 mL). The combined organic layer was washed with saturated sodium bicarbonate solution (50 mL), brine (50 mL), dried over anhydrous $Na_2SO_4$ and concentrated to get a crude residue. The residue was purified by silica gel column chromatography (Biotage, eluted with 20% EtOAc in petroleum ether to yield 2,6-dichloro-5-methylnicotinonitrile (0.890 g, 4.03 mmol, 67.9%) as a brown solid.

Preparation 180B. 6-amino-2-chloro-5-methylnicotinonitrile

A well-stirred solution of 2,6-dichloro-4-(trifluoromethyl) nicotinonitrile (2.0 g, 8.30 mmol) and ammonium hydroxide (1.616 mL, 41.5 mmol) in ethanol (20 mL) in a 50 mL Tinyclave was heated at 50° C. for 12 h. After completion of the reaction, the solvent was removed under reduced pressure to afford crude material. This was purified by flash silica-gel (230-400 mesh) column chromatography using 10-30% EtOAc in petroleum ether to yield 6-amino-2-chloro-5-methylnicotinonitrile (135 mg, 0.746 mmol, 15.5%) and 2-amino-6-chloro-5-methylnicotinonitrile—181B (25 mg, 0.115 mmol, 2.4%) as a white solid.

Preparation 180C. tert-butyl (S)-5-amino-4-(5-(6-amino-3-cyano-5-methylpyridin-2-yl)-1-oxoisoindolin-2-yl)-5-oxopentanoate Into a 30 mL microwave vial containing a well-stirred solution of 6-amino-2-chloro-5-methylnicotinonitrile—180B (130 mg, 0.776 mmol) and tert-butyl (S)-5-amino-5-oxo-4-(1-oxo-5-(4,4,5,5-tetramethyl-1,3,2-dioxaborolan-2-yl)isoindolin-2-yl) pentanoate (345 mg, 0.776 mmol) was added 2.0 M sodium bicarbonate (163 mg, 1.939 mmol) in water (0.3 mL) under nitrogen atmosphere and the resulting reaction mixture was degassed by bubbling nitrogen gas into reaction mixture for 10 minutes. Then tetrakis(triphenylphosphine)palladium(0) (26.9 mg, 0.023 mmol) was added to the reaction mixture and the resulting reaction mixture was heated in microwave reactor at 120° C. for 1 h. Progress of reaction was monitored by TLC and LCMS. The reaction mixture was then poured in water (20 mL) and extracted with EtOAc (2×30 mL). Organic phases were combined, washed with brine (30 mL), dried over anhydrous $Na_2SO_4$ and concentrated under reduced pressure to get a crude residue. The residue was purified by silica gel column chromatography (Biotage, eluted with 90% ethyl acetate in petroleum ether) to yield tert-butyl (S)-5-amino-4-(5-(6-amino-3-cyano-5-methylpyridin-2-yl)-1-oxoisoindolin-2-yl)-5-oxopentanoate (302 mg, 0.629 mmol, 81%) as a brown solid.

Example 180

Into a 30 mL microwave vial containing a well-stirred solution of tert-butyl (S)-5-amino-4-(5-(6-amino-3-cyano-5-methylpyridin-2-yl)-1-oxoisoindolin-2-yl)-5-oxopentanoate (300 mg, 0.667 mmol) in anhydrous acetonitrile (3.0 mL) was added benzenesulfonic acid (106 mg, 0.667 mmol) at ambient temperature under nitrogen atmosphere. The contents were heated in microwave reactor at 120° C. for 2 h. After completing the reaction as indicated by LCMS, excess solvents were removed from the reaction mixture under reduced pressure to get the crude compound. The crude material was purified by preparative HPLC to get 6-amino-2-(2-(2,6-dioxopiperidin-3-yl)-1-oxoisoindolin-5-yl)-5-methylnicotinonitrile·TFA (121 mg, 0.244 mmol, 36.5%) as an off-white solid.

Preparative HPLC Method Details: Column: XSelect C18 (150×19) mm, 5 μm, Mobile Phase A: 0.1% TFA in water, Mobile Phase B: Acetonitrile, Flow rate: 15 mL/min.

Analytical data: LCMS: Column—XBridge C8 (50×4.6 mm) 3.5 μm, Mobile phase A: 0.1% TFA in water Mobile Phase B: 0.1% TFA in ACN. RT=1.38 min. MS (ES): m/z=376.1 $(M+H)^+$. LCMS purity 93.53%. HPLC: Kinetex Biphenyl (100×4.6) mm, 2.6 μm. Mobile phase A: 0.05% TFA in water; Mobile phase B: 0.05% TFA in ACN; Flow rate: 1.0 mL/min. RT—4.88 min, Purity—98.65%. $^1$H-NMR (400 MHz, DMSO-d6) δ 11.03 (bs, 1H), 7.96 (s, 1H), 7.89-7.84 (m, 2H), 7.74 (d, J=0.80 Hz, 1H), 7.03 (s, 2H), 5.16 (dd, J=5.20, 13.20 Hz, 1H), 4.55 (d, J=17.60 Hz, 1H), 4.41 (d, J=17.60 Hz, 1H), 2.98-2.89 (m, 1H), 2.68-2.67 (m, 1H), 2.51-2.34 (m, 1H), 2.12 (s, 3H), 2.08-2.03 (m, 1H).

Example 181

2-amino-6-(2-(2,6-dioxopiperidin-3-yl)-1-oxoisoindolin-5-yl)-5-methoxynicotinonitrile (181)

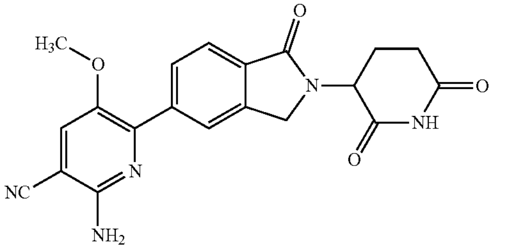

Preparation 181A. 2-amino-6-chloro-5-methoxynicotinonitrile

To a stirred solution of 2,6-dichloro-5-methoxynicotinonitrile (500 mg, 2.463 mmol) in ethanol (10 mL) was added ammonium hydroxide (5 mL, 128 mmol). The reaction mixture was heated at 50° C. in a pressure vessel. After 48 h, the mixture was cooled in an ice bath and the resultant mixture was concentrated under reduced pressure to yield 620 mg of crude mass. The residue was purified by silica gel column chromatography (Isolera) using 5-10% EtOAc in hexane as eluent yielding 2-amino-6-chloro-5-methoxynicotinonitrile (100 mg, 0.426 mmol, 17.3%) and 6-amino-2-chloro-5-methoxynicotinonitrile (80 mg, 0.42 mmol, 17.2%) as white solids.

Preparation 181B. tert-butyl (S)-5-amino-4-(5-(6-amino-5-cyano-3-methoxypyridin-2-yl)-1-oxoisoindolin-2-yl)-5-oxopentanoate To a stirred solution of tert-butyl (S)-5-amino-5-oxo-4-(1-oxo-5-(4,4,5,5-tetramethyl-1,3,2-dioxaborolan-2-yl)isoindolin-2-yl)pentanoate (250 mg, 0.563 mmol) in 1,4-dioxane (2 mL) at room temperature was added 2-amino-6-chloro-5-methoxynicotinonitrile (93 mg, 0.506 mmol) followed by potassium carbonate (194 mg, 1.407 mmol)) in water (0.5 mL). The reaction mixture was degassed for 15 min using nitrogen. To this reaction mixture $PdCl_2$(dppf)-$CH_2Cl_2$ adduct (22.97 mg, 0.028 mmol) was added under nitrogen atmosphere. The tube was sealed, heated to 100° C. and allowed to stir for 2 h. The reaction mixture was allowed to cool to room temperature and filtered through celite pad. The filtrate was concentrated under reduced pressure to afford crude mass, which was purified by silica gel column chromatography (Isolera) using 60-70% EtOAc-hexane as eluent to afford tert-butyl (S)-5-amino-4-(5-(6-amino-5-cyano-3-methoxypyridin-2-yl)-1-oxoisoindolin-2-yl)-5-oxopentanoate (80 mg, 0.079 mmol, 14.0%) as a brown solid.

Example 181

To a stirred solution of tert-butyl (S)-5-amino-4-(5-(6-amino-5-cyano-3-methoxypyridin-2-yl)-1-oxoisoindolin-2-yl)-5-oxopentanoate (80 mg, 0.172 mmol) in anhydrous acetonitrile (3 mL) in microwave vial was added benzenesulfonic acid (27.2 mg, 0.172 mmol). The reaction vial was sealed and irradiated in the microwave reactor for 1 h at 120° C. After completion of reaction, the mixture was concentrated under reduced pressure to get 150 mg of crude mass. The residue was purified by preparative HPLC to afford 2-amino-6-(2-(2,6-dioxopiperidin-3-yl)-1-oxoisoindolin-5-yl)-5-methoxynicotinonitrile·TFA (14 mg, 0.027 mmol, 15.9%) as a white solid.

Preparative HPLC Method Details: Column: Sunfire C18 (150×19) mm, 5 μm, Mobile Phase A: 0.1% TFA in water, Mobile Phase B: Acetonitrile, Flow rate: 15 mL/min.

Analytical data: HPLC: Column: Kinetex Biphenyl (100×4.6) mm, 2.6 μm, Mobile phase A: 0.05% TFA in water, Mobile phase B: ACN, Flow rate: 1.0 mL/min. RT=4.98 min. Purity=98.58%. LCMS: Column: Kinetex XB—C18 (75×30) mm, 2.6 μm; Mobile Phase A: 5 mM Ammonium formate, Mobile Phase B: ACN, Flow Rate: 1.0 mL/min; RT=2.597 min, MS (ES): m/z=392.0 $[M+1]^+$. Purity=98.98%. $^1$H NMR (400 MHz, DMSO-d6) δ 11.04 (s, 1H), 8.46 (s, 1H), 8.06 (s, 1H), 7.99 (d, J=8.00 Hz, 1H), 7.85 (d, J=7.60 Hz, 1H), 7.51 (bs, 2H), 5.16 (dd, J=5.20, 13.40

Hz, 1H), 4.55 (d, J=17.60 Hz, 1H), 4.42 (d, J=17.60 Hz, 1H), 3.41 (s, 3H), 2.90-2.94 (m, 1H), 2.60-2.68 (m, 1H), 2.41-2.45 (m, 1H), 2.03-2.06 (m, 1H).

Example 182

6-amino-5-cyclopropyl-2-(2-(2,6-dioxopiperidin-3-yl)-1-oxoisoindolin-5-yl) nicotinonitrile (182)

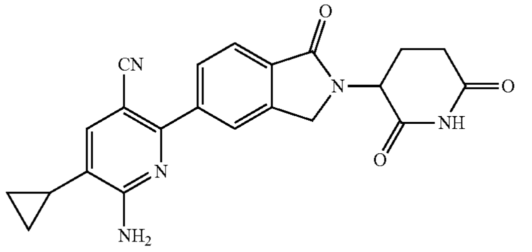

Preparation 182A and 182B. 2-amino-6-chloro-5-cyclopropylnicotinonitrile and 6-amino-2-chloro-5-cyclopropylnicotinonitrile To a 100 mL Tinyclave flask containing a well stirred solution of 2,6-dichloro-5-cyclopropylnicotinonitrile (500 mg, 2.347 mmol) in ethanol (12 mL)), was added aqueous $NH_3$ (8 mL) at ambient temperature. The reaction mixture was heated at 50° C. for 48 h. After completion of starting material, solvent was concentrated under reduced pressure to afford crude product as regio isomeric mixture. The crude material was purified by silica-gel (230-400 mesh) column chromatography with 5-30% EtOAc in petroleum ether to yield 2-amino-6-chloro-5-cyclopropylnicotinonitrile—182A (35 mg, 0.175 mmol, 7.47%) and 6-amino-2-chloro-5-cyclopropylnicotinonitrile—182B (195 mg, 1.003 mmol, 42.7%) as off-white solids.

Preparation 182C. tert-butyl (S)-5-amino-4-(5-(6-amino-3-cyano-5-cyclopropylpyridin-2-yl)-1-oxoisoindolin-2-yl)-5-oxopentanoate Into a 30 mL microwave vial containing a well stirred solution of tert-butyl (S)-5-amino-5-oxo-4-(1-oxo-5-(4,4,5,5-tetramethyl-1,3,2-dioxaborolan-2-yl)isoindolin-2-yl)pentanoate (252 mg, 0.568 mmol) and 6-amino-2-chloro-5-cyclopropylnicotinonitrile—182B (100 mg, 0.516 mmol) in 1,4-dioxane (8 mL) was added sodium hydrogen carbonate (130 mg, 1.549 mmol) in water (2 mL) at ambient temperature. The resulting reaction mixture was degassed by bubbling with nitrogen gas into reaction mixture for 10 minutes. Then tetrakis(triphenylphosphine)palladium(0) (59.7 mg, 0.052 mmol) was added to the reaction mixture and resulting reaction mixture was heated to 120° C. under microwave irradiation in MW reactor for 90 min. The reaction mixture was diluted with EtOAc (25 mL) and filtered through a bed of Celite. The filtrate was concentrated in vacuo to afford the crude compound. The crude material was purified by flash silica-gel (230-400 mesh) column with 80-90% EtOAc in petroleum ether to yield tert-butyl (S)-5-amino-4-(5-(6-amino-3-cyano-5-cyclopropylpyridin-2-yl)-1-oxoisoindolin-2-yl)-5-oxopentanoate (195 mg, 0.373 mmol, 72.3% yield) as light brownish solid.

Example 182

To a stirred solution of tert-butyl (S)-5-amino-4-(5-(6-amino-3-cyano-5-cyclopropylpyridin-2-yl)-1-oxoisoindolin-2-yl)-5-oxopentanoate (190 mg, 0.400 mmol) in anhydrous acetonitrile (7.0 mL) in microwave vial under $N_2$ atmosphere was added benzenesulfonic acid (63.2 mg, 0.400 mmol). The reaction vial was sealed and irradiated in the microwave for 90 min at 130° C. After completion of the reaction, the reaction mass was concentrated to provide crude product as an off-white solid. Purification using preparative HPLC yielded 6-amino-5-cyclopropyl-2-(2-(2,6-dioxopiperidin-3-yl)-1-oxoisoindolin-5-yl) nicotinonitrile·TFA (107 mg, 0.207 mmol, 51.7%) as a white solid.

Analytical data: LCMS: Column: Kinetex XB—C18 (75×3.0) mm, 2.6 μm; Mobile Phase A: 5 mM Ammonium formate in water; Mobile Phase B: ACN; Flow Rate: 1.0 mL/min; RT=1.595, MS (ES): m/z=402.0 $[M+H]^+$. HPLC: Column: Kinetex EVO C18 (100×4.6) mm, 2.6 μm; Mobile phase A: 0.05% TFA in water; Mobile phase B: ACN; Flow rate: 1.0 mL/min; RT=5.598 min; Purity: 99.51%. $^1$HNMR: 400 MHZ (DMSO) S 11.02 (s, 1H), 7.95 (s, 1H), 7.90-7.83 (m, 2H), 7.54 (s, 1H), 7.15 (br s, 2H), 5.16 (dd, J=4.80, 13.40 Hz, 1H), 4.55 (d, J=17.60 Hz, 1H), 4.41 (d, J=17.60 Hz, 1H), 2.90 (m, 1H), 2.63 (m, 1H), 2.45 (m, 1H), 2.05 (m, 1H), 1.70 (m, 1H), 0.92 (m, 2H), 0.67 (m, 2H). $^{19}$FNMR: 400 MHZ (DMSO): δ −74.49.

Example 183

2-amino-5-cyclopropyl-6-(2-(2,6-dioxopiperidin-3-yl)-1-oxoisoindolin-5-yl) nicotinonitrile (183)

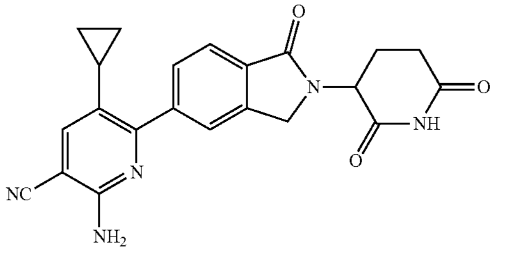

Preparation 183A. tert-butyl (S)-5-amino-4-(5-(6-amino-5-cyano-3-cyclopropylpyridin-2-yl)-1-oxoisoindolin-2-yl)-5-oxopentanoate Into a 10 mL microwave vial containing a well stirred solution of tert-butyl (S)-5-amino-5-oxo-4-(1-oxo-5-(4,4,5,5-tetramethyl-1,3,2-dioxaborolan-2-yl)isoindolin-2-yl) pentanoate (126 mg, 0.284 mmol) and 2-amino-6-chloro-5-cyclopropylnicotinonitrile—182A (50 mg, 0.258 mmol) in 1,4-dioxane (4 mL) was added sodium hydrogen carbonate (65.1 mg, 0.775 mmol) in water (1 mL) at ambient temperature under nitrogen atmosphere. The resulting reaction mixture was degassed by bubbling with nitrogen gas into reaction mixture for 10 minutes. Then tetrakis(triphenylphosphine)palladium(0) (29.8 mg, 0.026 mmol) was added to the reaction mixture and resulting reaction mixture was heated at 120° C. under microwave irradiation in MW reactor for 90 min. Then the reaction mixture was diluted with EtOAc (20 mL) and filtered through a bed of Celite. The filtrate was concentrated in vacuo to afford the crude compound. The crude material was purified by flash silica-gel (230-400 mesh) column with 80-90% EtOAc in petroleum ether to yield tert-butyl (S)-5-amino-4-(5-(6-amino-5-cyano-3-cyclopropylpyridin-2-yl)-1-oxoisoindolin-2-yl)-5-oxopentanoate (65 mg, 0.112 mmol, 43.2%) as a light brown solid.

Example 183

To a stirred solution of tert-butyl (S)-5-amino-4-(5-(6-amino-5-cyano-3-cyclopropylpyridin-2-yl)-1-oxoisoindolin-2-yl)-5-oxopentanoate (60 mg, 0.126 mmol) in anhydrous acetonitrile (3.0 mL) in microwave vial under $N_2$ atmosphere was added benzenesulfonic acid (19.96 mg, 0.126 mmol). The reaction vial was sealed and irradiated in the microwave for 90 min at 130° C. After completion of the reaction, the reaction mass was concentrated to give crude product as an off-white solid. Purification using preparative HPLC yielded 2-amino-5-cyclopropyl-6-(2-(2,6-dioxopiperidin-3-yl)-1-oxoisoindolin-5-yl)nicotinonitrile·TFA (31 mg, 0.060 mmol, 47.5%) as an off-white solid.

Preparative HPLC Method Details: Column: XSelect C18 (150×19) mm, 5 μm; Mobile phase A: 0.1% TFA in water; Mobile phase B: Acetonitrile; Flow rate: 15 mL/min.

Analytical data: (LCMS: Column: Kinetex XB—C18 (75×3.0) mm, 2.6 μm; Mobile Phase A: 5 mM Ammonium formate in water; Mobile Phase B: ACN; Flow Rate: 1.0 mL/min; RT=1.420, MS (ES): m/z=404.2 $[M+H]^+$. HPLC Purity: Column: Kinetex EVO C18 (100×4.6) mm, 2.6 μm; Mobile phase A: 0.05% TFA in water; Mobile phase B: ACN; Flow: 1.0 mL/min; RT=6.09 min; Purity: 99.63%. $^1$HNMR: 400 MHZ (DMSO): δ 11.02 (s, 1H), 7.83-7.80 (m, 2H), 7.74 (d, J=9.20 Hz, 1H), 7.63 (s, 1H), 6.82 (br s, 2H), 5.16 (dd, J=4.80, 13.40 Hz, 1H), 4.53 (d, J=17.60 Hz, 1H), 4.41 (d, J=17.60 Hz, 1H), 2.91 (m, 1H), 2.63 (m, 1H), 2.45 (m, 1H), 2.05 (m, 1H), 1.73 (m, 1H), 0.78 (m, 2H), 0.62 (m, 2H). $^{19}$FNMR: 400 MHZ (DMSO): δ −74.48.

Example 184

3-(5-(6-amino-4-(4-benzylpiperazin-1-yl) pyridin-2-yl)-1-oxoisoindolin-2-yl) piperidine-2,6-dione (184)

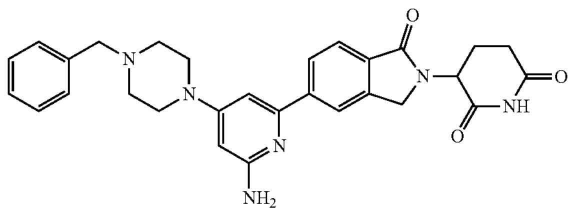

Preparation 184A. 6-chloro-4-iodo-N-(4methoxybenzyl) pyridin-2-amine

To a solution of 2,6-dichloro-4-iodopyridine (5.0 g, 18.26 mmol) in NMP (10 mL) in a Biotage microwave vial were successively added DIPEA (9.57 mL, 54.8 mmol) and 4-methoxybenzylamine (2.62 mL, 20.08 mmol). The resulting mixture was heated under microwave irradiation at 120° C. for 2 h. The reaction mixture was diluted with ice-cold water (50 mL) and extracted with ethyl acetate (50 mL×3). The combined organic layer was washed with water (50 mL), saturated brine solution (50 mL), dried over anhydrous $Na_2SO_4$, filtered, and concentrated under reduced pressure to afford crude product. The crude product obtained was purified by column chromatography (Grace, 100 g snap, dry pack) over silica gel (230-400 mesh) by eluting with 5-30% ethyl acetate in petroleum ether. The desired fractions pooled and concentrated under reduced pressure to afford 6-chloro-4-iodo-N-(4methoxybenzyl) pyridin-2-amine (3.0 g, 7.86 mmol, 43.1%) as an off-white solid.

Preparation 184B. 4-(4-benzylpiperazin-1-yl)-6-chloro-N-(4-methoxybenzyl) pyridin-2-amine 6-Chloro-4-iodo-N-(4-methoxybenzyl)pyridin-2-amine (0.5 g, 1.335 mmol), cesium carbonate (1.305 g, 4.00 mmol) and 1-benzylpiperazine (0.235 g, 1.335 mmol) was mixed with degassed 1,4-dioxane (15.0 mL). The reaction mixture was purged with $N_2$ for 10 min. followed by the addition of XPhos Pd G4 (0.053 g, 0.067 mmol). The reaction mixture was stirred at 70° C. for 16 h. The reaction vessel was allowed to cool to ambient temperature, diluted with ethyl acetate (150 mL), filtered through a bed of Celite, and concentrated in vacuo to afford the crude product. The crude product was purified by column chromatography (Grace, 25 g snap, dry pack) over silica gel (230-400 mesh) by eluting with 50-100% ethyl acetate in petroleum ether. The desired fractions pooled and concentrated under reduced pressure to afford 4-(4-benzylpiperazin-1-yl)-6-chloro-N-(4-methoxybenzyl) pyridin-2-amine (0.4 g, 0.801 mmol, 60.0%) as a pale brown solid.

Preparation 184C. 4-(4-benzylpiperazin-1-yl)-6-chloropyridin2-amine

To a stirred solution of 4-(4-benzylpiperazin-1-yl)-6-chloro-N-(4-methoxybenzyl) pyridin-2-amine (0.4 g, 0.946 mmol) in dichloromethane (10.0 mL) was added TFA (3.0 mL, 38.9 mmol) at 0° C. The reaction mixture was stirred at ambient temperature for 5 h. Solvents were concentrated under reduced pressure to afford crude product. The crude product obtained was purified by column chromatography (Grace, 25 g snap, dry pack) over silica gel (230-400 mesh) by eluting with 5-20% methanol in dichloromethane. The desired fractions pooled and concentrated under reduced pressure to afford 4-(4-benzylpiperazin-1-yl)-6-chloropyridin2-amine·TFA (0.350 g, 1.089 mmol, 11%) as a pale brown solid.

Preparation 184C. tert-butyl (S)-5-amino-4-(5-(6-amino-4-(4-benzylpiperazin-1-yl) pyridin-2-yl)-1-oxoisoindolin-2-yl)-5-oxopentanoate tert-Butyl(S)-5-amino-5-oxo-4-(1-oxo-5-(4,4,5,5-tetramethyl-1,3,2-dioxaborolan-2-yl)isoindolin-2-yl)pentanoate (0.323 g, 0.727 mmol), 4-(4-benzylpiperazin-1-yl)-6-chloropyridin-2-amine (0.2 g, 0.660 mmol), potassium phosphate, tribasic (1.761 mL, 5.28 mmol) was mixed with previously degassed 1,4-dioxane (10.0 mL) and water (0.5 mL). The reaction mixture was purged with $N_2$ for 10 min. followed by the addition of XPhos Pd G4 (0.026 g, 0.033 mmol). The reaction mixture was stirred at 70° C. for 16 h. The reaction vessel was allowed to cool to ambient temperature, diluted with ethyl acetate (150 mL), filtered through a bed of Celite, and concentrated in vacuo to afford the crude product. The crude product obtained was purified by column chromatography (Grace, 25 g snap, dry pack) over silica gel (230-400 mesh) by eluting with 5-20% methanol in dichloromethane. The desired fractions were pooled and concentrated under reduced pressure to afford tert-butyl (S)-5-amino-4-(5-(6-amino-4-(4-benzylpiperazin-1-yl) pyridin-2-yl)-1-oxoisoindolin-2-yl)-5-oxopentanoate (0.13 g, 0.155 mmol, 23.5%) as a pale brown solid.

Example 184

To a stirred solution of tert-butyl (S)-5-amino-4-(5-(6-amino-4-(4-benzylpiperazin-1-yl)pyridin-2-yl)-1-oxoisoindolin-2-yl)-5-oxopentanoate (0.12 g, 0.205 mmol) in acetonitrile (2.0 mL) was added TFA (1.0 mL) at room temperature. The reaction mixture was heated at 130° C. for 30 min. in a microwave reactor. After completion of the reaction, the reaction mass was concentrated to provide the crude product as an off-white solid. Purification using preparative HPLC followed by lyophilization of pure fraction yielded 3-(5-(6-amino-4-(4-benzylpiperazin-1-yl)pyridin-2-yl)-1-oxoisoindolin-2-yl) piperidine-2,6-dione·TFA (35 mg, 0.062 mmol, 24.9%) as a white solid.

Preparative HPLC Condition: Column-X bridge C-18 (150×19) mm, 5 μm, Mobile Phase A: 0.1% TFA in water, Mobile Phase B: Acetonitrile, Flow: 15 mL/min.

Analytical data: LCMS: Column—XBridge C8 (50×4.6 mm) 5 μm, wavelength=220 nm; Mobile Phase—0.1% TFA in water and Acetonitrile. RT=1.30 min. MS (ES): m/z=511.2 $[M+1]^+$. HPLC: Kinetex EVO C18 (100×4.6) mm, 2.6 μm. Mobile phase A: 10 mM Ammonium acetate in water; Mobile Phase B: Acetonitrile. RT=4.59 min, Purity: 99.70% (300 nm). $^1$HNMR (400 MHz, DMSO-d6): δ 11.03 (s, 1H), 8.38 (s, 1H), 8.20 (s, 1H), 8.13 (d, J=1.20 Hz, 1H), 7.74 (d, J=8.00 Hz, 1H), 7.34-7.36 (m, 4H), 7.26-7.30 (m, 1H), 6.82-6.83 (m, 1H), 5.88 (s, 1H), 5.69 (s, 1H), 5.13-5.15 (m, 1H), 4.48-4.52 (m, 2H), 4.35-4.39 (m, 1H), 2.67-2.68 (m, 2H), 2.52-2.53 (m, 1H), 2.40-2.45 (m, 1H), 2.33-2.34 (m, 2H), 1.98-2.02 (m, 2H), 1.68-1.70 (m, 1H), 1.49-1.50 (m, 1H), 1.38-1.25 (m, 3H), 0.84-0.86 (m, 1H).

Example 185

3-(5-(6-amino-4-(4-(methylsulfonyl)piperazin-1-yl) pyridin-2-yl)-1-oxoisoindolin-2-yl) piperidine-2,6-dione (185)

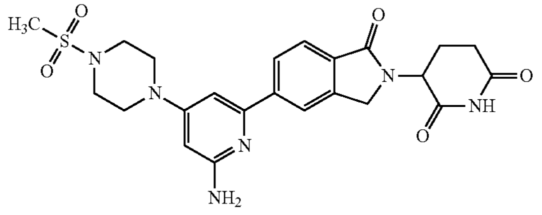

Preparation 185A. 6-chloro-N-(4-methoxybenzyl)-4-(4-(methyl sulfonyl) piperazin-1-yl) pyridin-2-amine 6-chloro-4-iodo-N-(4-methoxybenzyl)pyridin-2-amine (0.5 g, 1.335 mmol), 6-chloro-4-iodo-N-(4-methoxybenzyl) pyridin-2-amine (0.5 g, 1.335 mmol), cesium carbonate (1.31 g, 4.00 mmol) and 1-(methyl sulfonyl)piperazine (0.263 g, 1.602 mmol) was mixed with degassed 1,4-dioxane (10.0 mL). The reaction mixture was purged with $N_2$ for 10 min. followed by the addition of XPhos Pd G4 (0.053 g, 0.067 mmol). The reaction mixture was stirred at 70° C. for 16 h. The reaction vessel was allowed to cool to ambient temperature, diluted with ethyl acetate (20 mL), filtered through a bed of Celite, and concentrated in vacuo to afford the crude product. The crude product obtained was purified by column chromatography (Grace, 25 g snap, dry pack) over silica gel (230-400 mesh) by eluting with 50-100% ethyl acetate petroleum ether. The desired fractions pooled and concentrated under reduced pressure to afford 6-chloro-N-(4-methoxybenzyl)-4-(4-(methylsulfonyl)piperazin-1-yl)pyridin-2-amine (0.23 g, 0.514 mmol, 38.5%) as a pale brown solid.

Preparation 185B. tert-butyl (S)-5-amino-4-(5-(6-((4-methoxybenzyl)amino)-4-(4-(methylsulfonyl) pipe-razin-1-yl)pyridin-2-yl)oxoisoindolin-2-yl)-5-oxopentanoate Into a 10 mL microwave vial containing a well stirred solution of tert-butyl (S)-5-amino-5-oxo-4-(1-oxo-5-(4,4,5,5-tetramethyl-1,3,2-dioxaborolan-2-yl)isoindolin-2-yl)pentanoate (0.274 g, 0.616 mmol), and 6-chloro-N-(4-methoxybenzyl)-4-(4-(methylsulfonyl)piperazin-1-yl)pyridin-2-amine (0.23 g, 0.560 mmol), in 1,4-dioxane (5 mL) was added potassium phosphate, tribasic (1.493 mL, 4.48 mmol) in water (1 mL) at ambient temperature under nitrogen atmosphere. The resulting reaction mixture was degassed by bubbling with nitrogen gas into reaction mixture for 10 minutes. Then XPhos Pd G4 (0.022 g, 0.028 mmol) was added to the reaction mixture and was heated at 70° C. for 16 h. After cooling to room temperature, the reaction mixture was concentrated under reduced pressure to get a crude residue. The residue was purified by silica gel column chromatography (Biotage, eluted with 50% ethyl acetate in petroleum ether) to yield tert-butyl (S)-5-amino-4-(5-(6-((4-methoxybenzyl)amino)-4-(4-(methylsulfonyl)piperazin-1-yl)pyridin-2-yl)oxoiso-indolin-2-yl)-5-oxopentanoate (0.320 g, 0.288 mmol, 51.4%) as pale brown solid.

Example 185

To a stirred solution of tert-butyl (S)-5-amino-4-(5-(6-((4-methoxybenzyl) amino)-4-(4-(methylsulfonyl)piperazin-1-yl)pyridin-2-yl)-1-oxoisoindolin-2-yl)-5-oxopentanoate (0.30 g, 0.433 mmol) in anhydrous acetonitrile (4.0 mL) in microwave vial under $N_2$ atmosphere was added benzenesulfonic acid (0.068 g, 0.433 mmol). The reaction vial was sealed and irradiated in the microwave reactor for 1 h at 130° C. After completion of the reaction, the reaction mass was concentrated to afford an off-white solid. Purification was done by using preparative HPLC and the fraction was lyophilized to yield 3-(5-(6-amino-4-(4-(methylsulfonyl) piperazin-1-yl)pyridin-2-yl)-1-oxoisoindolin-2-yl)piperidine-2,6-dione (23.0 mg, 0.046 mmol, 10.6%) as a white solid.

Preparative HPLC Method Details: Column: XBridge C18 (250×19)mm, 5 μm, Mobile Phase A: 5 mM Ammonium formate in water, Mobile Phase B: Acetonitrile, Flow rate: 15 mL/min.

LCMS: Column—XBridge C8 (50×4.6 mm) 5 μm, wavelength=220 nm; Mobile Phase—0.1% TFA in water and Acetonitrile. RT=1.33 min. MS (ES): m/z=499.1$[M+1]^+$.

HPLC: Kinetex Biphenyl C18 (100×4.6) mm, 2.6 μm. Mobile phase A: 0.05% TFA in water; Mobile phase B: ACN; Flow: 1.0 mL/min. RT=4.59 min, Purity: 99.50% (300 nm). $^1$HNMR: 400 MHZ (DMSO): δ 11.03 (s, 1H), 8.21 (s, 1H), 8.14 (t, J=4.00 Hz, 1H), 7.78 (d, J=8.00 Hz, 1H), 6.90-6.90 (m, 1H), 5.90-5.95 (m, 3H), 5.13-5.17 (m, 1H), 4.50-4.54 (m, 1H), 4.37-4.41 (m, 1H), 3.25-3.50 (m, 4H), 3.23-3.24 (m, 4H), 2.90-2.97 (m, 4H), 2.51-2.68 (m, 1H), 2.43-2.46 (m, 1H), 2.02-2.05 (m, 1H).

Example 186

3-(5-(4-(4-acetylpiperazin-1-yl)-6-aminopyridin-2-yl)-1-oxoisoindolin-2-yl)piperidine-2,6-dione (186)

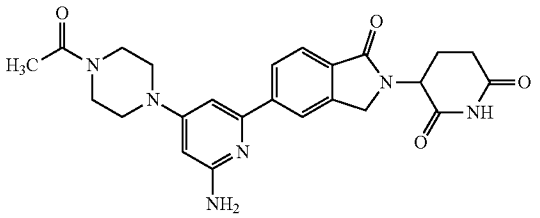

Preparation 186A. 1-(4-(2-chloro-6-((4-methoxybenzyl)amino)pyridin-4-yl)piperazin-1-yl)ethan-1-one 6-Chloro-4-iodo-N-(4-methoxybenzyl)pyridin-2-amine (0.5 g, 1.335 mmol), cesium carbonate (1.305 g, 4.00 mmol) and 1-(piperazin-1-yl)ethan-1-one (0.205 g, 1.602 mmol) was mixed with degassed 1,4-dioxane (10.0 mL) in a sealed tube. The reaction mixture was purged with $N_2$ for 10 min followed by the addition of XPhos Pd G4 (0.053 g, 0.067 mmol). The tube was sealed and heated at 70° C. for 16 h. The reaction vessel was allowed to cool to ambient temperature, diluted with ethyl acetate (20 mL), filtered through a bed of Celite, and concentrated in vacuo to afford the crude product. The crude product obtained was purified by column chromatography (Grace, 25 g snap, dry pack) over silica gel (230-400 mesh) by eluting with 50-100% ethyl acetate petroleum ether. The desired fractions were pooled and concentrated under reduced pressure to afford 1-(4-(2-chloro-6-((4-methoxybenzyl)amino)pyridin-4-yl)piperazin-1-yl)ethan-1-one (0.17 g, 0.351 mmol, 26.3%) as pale brown solid.

Preparation 186B. tert-butyl (S)-4-(5-(4-(4-acetylpiperazin-yl)-6-((4-methoxybenzyl) amino) pyridin-2-yl)-1-oxoisoindolin-2-yl)-5-amino-5-oxopentanoate Into a 10 mL microwave vial containing a well-stirred solution of tert-butyl (S)-5-amino-5-oxo-4-(1-oxo-5-(4,4,5,5-tetramethyl-1,3,2-dioxaborolan-2-yl)isoindolin-2-yl)pentanoate (0.22 g, 0.499 mmol), 1-(4-(2-chloro-6-((4-methoxybenzyl)amino)pyridin-4-yl)piperazin-1-yl)ethan-1-one (0.17 g, 0.453 mmol) in 1,4-dioxane (5 mL) was added potassium phosphate, tribasic (1.209 mL, 3.63 mmol)) in water (1 mL) at ambient temperature under nitrogen atmosphere. The resulting reaction mixture was degassed by bubbling with nitrogen gas into it for 10 minutes. Then XPhos Pd G4 (0.018 g, 0.023 mmol) was added to the reaction mixture and was heated at 70° C. for 16 h. After cooling to room temperature, the reaction mixture was concentrated under reduced pressure to get a crude residue. The residue was purified by silica gel column chromatography (Biotage, eluted with 50% ethyl acetate in petroleum ether) to yield tert-butyl (S)-4-(5-(4-(4-acetylpiperazin-yl)-6-((4methoxybenzyl)amino)pyridin-2-yl)-1-oxoisoindolin-2-yl)-5-amino-5-oxopentanoate (0.25 g, 0.273 mmol, 60.2%) as a pale brown solid.

Example 186

To a stirred solution of tert-butyl (S)-4-(5-(4-(4-acetylpiperazin-1-yl)-6-((4-methoxybenzyl)amino)pyridin-2-yl)-1-oxoisoindolin-2-yl)-5-amino-5-oxopentanoate (0.25 g, 0.381 cmmol) in anhydrous acetonitrile (4.0 mL) in microwave vial under $N_2$ atmosphere was added benzenesulfonic acid (0.06 g, 0.381 mmol). The reaction was sealed and irradiated in the microwave for 1 h at 130° C. After completion of the reaction, the reaction mass was concentrated to provide crude product as off white solid. Purification was done by using preparative HPLC and the fraction was lyophilized to yield 3-(5-(4-(4-acetylpiperazin-1-yl)-6-aminopyridin-2-yl)-1-oxoisoindolin-2-yl)piperidine-2,6-dione (25.0 mg, 0.052 mmol, 13.6%) as a white solid.

Preparative HPLC Method Details: Column: XBridge C18 (250×19) mm, 5 micron, Mobile Phase A: 5 mM Ammonium formate in water, Mobile Phase B: Acetonitrile, Flow rate: 15 mL/min.

LCMS: Column—XBridge C8 (50×4.6 mm) 5 micron, wavelength—220 nm; Mobile Phase—0.1% TFA in water and Acetonitrile. RT=1.21 min. MS (ES): m/z=499.1 $[M+1]^+$.

HPLC: Kinetex Biphenyl C18 (100×4.6) mm, 2.6 μm. Mobile phase A: 0.05% TFA in water; Mobile phase B: ACN; Flow rate: 1.0 mL/min. RT=7.14 min, Purity: 95.69%.

$^1$HNMR: 400 MHZ (DMSO): δ 11.03 (s, 1H), 8.15-8.22 (m, 3H), 7.75 (d, J=8.00 Hz, 1H), 6.86-6.87 (m, 1H), 5.90-5.92 (m, 1H), 5.72-5.74 (m, 2H), 5.12-5.16 (m, 1H), 4.40-4.49 (m, 1H), 4.35 (d, J=8.40 Hz, 1H), 3.48-3.59 (m, 4H), 3.31-3.43 (m, 3H), 2.89-2.97 (m, 1H), 2.60-2.68 (m, 2H), 2.33-2.34 (m, 1H), 2.01-2.06 (m, 4H).

Analytical LCMS Conditions (Examples 187-189)

Method A: ACQUITY UPLC® BEH C18 (3.0×50 mm) 1.7 μm; Mobile Phase A: 95:5 water:acetonitrile with 2.5 mM $NH_4OAc$; Mobile Phase B: 5:95 water:acetonitrile with 2.5 mM $NH_4OAc$; Temperature: 40° C.; Gradient: 20% B to 100% B over 2 min; flow: 0.7 mL/min; Detection: MS and UV (220 nm).

Method B: Column: XBridge BEH XP C18 (50×2.1) mm, 2.5 μm; Mobile Phase A: 95:5 water:acetonitrile with 10 mM $NH_4OAc$; Mobile Phase B: 5:95 water:acetonitrile with 10 mM $NH_4OAc$; Temperature: 50° C.; Gradient: 0% B to 100% B over 3 min; Flow: 1.1 mL/min; Detection: MS and UV (220 nm).

Example 187

3-(5-(4-Methyl-6-(methylamino)pyridin-2-yl)-1-oxoisoindolin-2-yl)piperidine-2,6-dione (187)

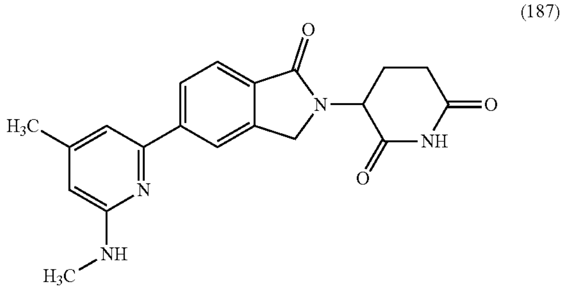 [SMILES: CNc1cc(C)cc(-c2ccc3c(c2)CN(C2CCC(=O)NC2=O)C3=O)n1]

Preparation 187A: 6-Bromo-N,4-dimethylpyridin-2-amine

To stirred suspension of NaH (60% in mineral oil, 21.4 mg, 0.54 mmol) in anhydrous THF (2 mL), 6-bromo-4-methylpyridin-2-amine (100 mg, 0.54 mmol) was added at room temperature. The reaction mixture was stirred for 10 min at room temperature and cooled to 0° C. Methyl iodide (0.067 mL, 1.07 mmol) was added and the reaction mixture was slowly warmed to room temperature and stirred for 16 h. The reaction was quenched with saturated $NH_4Cl$ solution, extracted with EtOAc (5 mL×4) and the combined organic phase was washed with brine, dried over anhydrous $Na_2SO_4$, filtered and concentrated under reduced pressure. The residue obtained was purified by flash chromatography ($SiO_2$, 12 g column, 0-30% EtOAc/pet ether) to give 6-bromo-N,4-dimethylpyridin-2-amine (70 mg, 65% yield). LCMS (Method A): retention time 1.04 min, $[M+H]^+$ 201.1; $^1H$ NMR (300 MHz, CHLOROFORM-d) δ=6.60 (s, 1H), 6.10 (s, 1H), 4.69 (br s, 1H), 2.88 (d, J=5.3 Hz, 3H), 2.22 (s, 3H).

Example 187

To a stirred solution of 6-bromo-N,4-dimethylpyridin-2-amine (70 mg, 0.35 mmol) and tert-butyl (S)-5-amino-5-oxo-4-(1-oxo-5-(4,4,5,5-tetramethyl-1,3,2-dioxaborolan-2-yl)isoindolin-2-yl)pentanoate (186 mg, 0.41 mmol) in dioxane (1.4 mL) and $H_2O$ (0.3 mL), was added potassium carbonate (121 mg, 0.88 mmol). The reaction mixture was purged with argon for five minute and [1,1'-bis(diphenylphosphino) ferrocene]palladium(II) dichloride dichloromethane complex (18 g, 0.022 mmol) was added. The reaction mixture was heated at 100° C. for 2 h, cooled to room temperature, diluted with EtOAc and washed with brine solution. The organic layer was dried over anhydrous $Na_2SO_4$, filtered and concentrated under reduced pressure. The residue was purified by flash chromatography ($SiO_2$, 12 g column, 0-100% EtOAc/DCM) to give tert-butyl (S)-5-amino-4-(5-(4-methyl-6-(methylamino)pyridin-2-yl)-1-oxoisoindolin-2-yl)-5-oxopentanoate (70 mg) as orange oil. This was dissolved in acetonitrile (1.5 mL), added p-TSA monohydrate (46 mg, 0.24 mmol) and heated at 120° C. for 1 h in a microwave reactor. The reaction mixture was concentrated under reduced pressure and purified by reverse phase preparative-LCMS (column: Waters XBridge C18, 19×150 mm, 5-μm particles; mobile phase A: 0.1% trifluoroacetic acid in water; mobile phase B: acetonitrile; gradient: 10-40% B over 20 minutes, then a 5-minute hold at 100% B; flow: 15 mL/min) to give 3-(5-(4-methyl-6-(methylamino)pyridin-2-yl)-1-oxoisoindolin-2-yl)piperidine-2,6-dione (5.3 mg, 4% yield). LCMS (method B): retention time 0.78 min, [M+H]+ 365.2; $^1H$ NMR (400 MHz, DMSO-d6) δ=10.99 (s, 1H), 8.23 (s, 1H), 8.20-8.14 (m, 1H), 7.77 (d, J=8.3 Hz, 1H), 7.04 (s, 1H), 6.52-6.43 (m, 1H), 6.30 (s, 1H), 5.13 (dd, J=5.1, 13.1 Hz, 1H), 4.58-4.47 (m, 1H), 4.44-4.32 (m, 1H), 2.98-2.83 (m, 5H), 2.65-2.57 (m, 1H), 2.42 (dd, J=4.6, 13.1 Hz, 1H), 2.25 (s, 4H), 2.06-1.99 (m, 1H).

General Procedure I (Examples 188 and 189):

A mixture of aryl halide (1 eq.), tert-butyl (S)-5-amino-5-oxo-4-(1-oxo-5-(4,4,5,5-tetramethyl-1,3,2-dioxaborolan-2-yl)isoindolin-2-yl)pentanoate (1.2 eq.), potassium carbonate (2 eq.), dioxane (4 mL/mmol) and water (0.4 mL/mmol) was purged with argon for 5 min at room temperature. [1,1'-bis(diphenylphosphino)ferrocene]palladium(II) dichloride dichloromethane complex (0.05 eq.) was added and the reaction mixture was heated at 100° C. for 2 h. The reaction mixture was cooled to room temperature, diluted with EtOAc and filtered through celite pad. The filtrate was washed with brine solution, dried over anhydrous $Na_2SO_4$, filtered and concentrated under reduced pressure. The residue obtained was purified by flash chromatography. The isolated product was dissolved in acetonitrile, pTSA·$H_2O$ (1.5 eq) was added and the mixture was heated at 120° C. for 1 h in a microwave reactor. The reaction mixture was cooled to room temperature and concentrated under reduced pressure and the crude product was purified by prep-HPLC to afford the desired product.

Example 188

3-(5-(6-(Ethylamino)-4-methylpyridin-2-yl)-1-oxoisoindolin-2-yl)piperidine-2,6-dione (188)

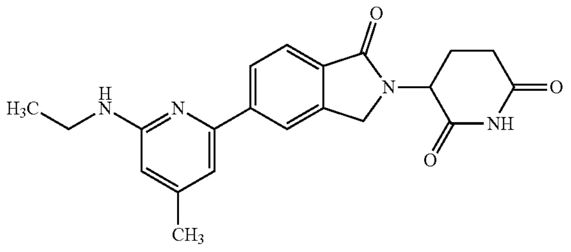

Preparation 188A. 6-Bromo-N-ethyl-4-methylpyridin-2-amine

To stirred suspension of NaH (60% in mineral oil, 141 mg, 3.53 mmol) in anhydrous THF (9 mL), 6-bromo-4-methylpyridin-2-amine (600 mg, 3.21 mmol) was added at room temperature. The reaction mixture was stirred for 10 min at room temperature then cooled to 0° C. Methyl iodide (0.2 mL, 3.21 mmol) was added and the reaction mixture was slowly warmed to room temperature and stirred for 16 h. The reaction was quenched with saturated $NH_4Cl$ solution and extracted with EtOAc (10 mL×4). The combined organic phase was washed with brine, dried over anhydrous $Na_2SO_4$, filtered and concentrated under reduced pressure.

The residue obtained was purified by flash chromatography ($SiO_2$, 24 g column, 0-30% EtOAc/pet ether) to give 6-bromo-N-ethyl-4-methylpyridin-2-amine (550 mg, 80% yield). LCMS (Method A): retention time 1.66 min, [M+H]+ 215.1; $^1$H NMR (300 MHz, CHLOROFORM-d) δ 1.19-1.28 (m, 3H) 2.20 (s, 3H) 3.16-3.30 (m, 2H) 4.56 (br s, 1H) 6.08 (s, 1H) 6.58 (s, 1H).

Example 188

3-(5-(6-(Ethylamino)-4-methylpyridin-2-yl)-1-oxoisoindolin-2-yl)piperidine-2,6-dione was synthesized from 6-bromo-N-ethyl-4-methylpyridin-2-amine using general procedure I. The crude product was purified by preparative LCMS (column: Waters XBridge C18, 19×150 mm, 5-μm particles; mobile phase A: 0.1% trifluoroacetic acid in water; mobile phase B: acetonitrile; gradient: 10-40% B over 20 minutes, then a 5-minute hold at 100% B; flow: 15 mL/min). LCMS (Method B): retention time 1.54 min, $[M+H]^+$ 379.1; $^1$H NMR (400 MHz, DMSO-d6) δ=10.99 (br s, 1H), 8.22 (s, 1H), 8.18 (d, J=8.0 Hz, 1H), 7.77 (d, J=8.0 Hz, 1H), 7.03 (s, 1H), 6.48 (br t, J=5.5 Hz, 1H), 6.30 (s, 1H), 5.14 (dd, J=5.0, 13.6 Hz, 1H), 4.58-4.30 (m, 2H), 3.37 (br dd, J=5.5, 7.0 Hz, 3H), 2.99-2.87 (m, 1H), 2.70-2.58 (m, 1H), 2.47-2.36 (m, 2H), 2.24 (s, 2H), 2.09-1.99 (m, 1H), 1.22-1.17 (m, 2H).

Example 189

3-(5-(4,5-Dimethyl-6-(methylamino)pyridin-2-yl)-1-oxoisoindolin-2-yl)piperidine-2,6-dione (189)

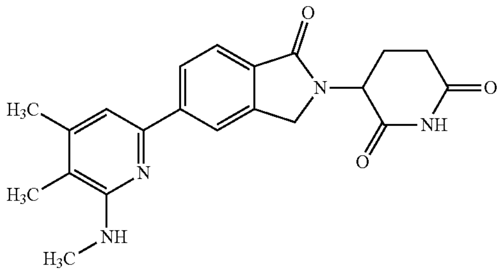

Preparation 189A. 6-Chloro-N,3,4-trimethylpyridin-2-amine

To stirred suspension of NaH (60% in mineral oil, 61 mg, 1.53 mmol) in anhydrous THE (7 mL), 6-chloro-3,4-dimethylpyridin-2-amine (200 mg, 1.28 mmol) was added at room temperature. The reaction mixture was stirred for 10 min at room temperature then cooled to 0° C. Methyl iodide (0.18 mL, 2.81 mmol) was added and the reaction mixture was slowly warmed to room temperature and stirred for 16 h. The reaction was quenched with saturated $NH_4Cl$ solution, extracted with EtOAc (10 mL×4). The combined organic phase was washed with brine, dried over anhydrous $Na_2SO_4$, filtered and concentrated under reduced pressure. The residue obtained was purified by flash chromatography ($SiO_2$, 24 g column, 0-30% EtOAc/pet ether) to give 6-chloro-N,3,4-trimethylpyridin-2-amine (164 mg, 75% yield). LCMS (Method A): retention time 1.47 min, $[M+H]^+$ 170.9; $^1$H NMR (300 MHz, CHLOROFORM-d) δ 6.45 (s, 1H), 4.17-4.34 (m, 1H), 3.02 (d, J=4.91 Hz, 3H), 2.14-2.23 (m, 3H), 1.96 (s, 3H).

Example 189

3-(5-(4,5-Dimethyl-6-(methylamino)pyridin-2-yl)-1-oxoisoindolin-2-yl)piperidine-2,6-dione was synthesized from 6-chloro-N,3,4-trimethylpyridin-2-amine following general procedure I. The crude product was purified by preparative-LCMS (column: Waters XBridge C18, 19×150 mm, 5-μm particles; mobile phase A: 0.1% trifluoroacetic acid in water; mobile phase B: acetonitrile; gradient: 10-40% B over 20 minutes, then a 5-minute hold at 100% B; flow: 15 mL/min). LCMS (Method B): retention time 0.62 min, $[M+H]^+$ 379.1; $^1$H NMR (400 MHz, DMSO-d6) δ 10.97 (br s, 1H), 8.16-8.33 (m, 2H), 7.77 (d, J=8.03 Hz, 1H), 7.12 (s, 1H), 6.03 (br d, J=4.52 Hz, 1H), 5.14 (br dd, J=13.55, 5.02 Hz, 1H), 4.34-4.59 (m, 2H), 2.96 (br d, J=4.02 Hz, 4H), 2.64 (br s, 1H), 2.37-2.46 (m, 1H), 2.25 (s, 3H), 1.96-2.06 (m, 4H).

Biological Assays

The pharmacological properties of the compounds of this invention may be confirmed by a number of biological assays. The exemplified biological assays, which follow, have been carried out with compounds of the invention.

Helios Cellular Degradation Assay

Jurkat cells were plated at 80,000 cells/well in 40 μL RPMI+10% FBS in a 384 well cell culture plate prior to using acoustic dispensing technology for adding compound of interest. Cell cultures were incubated for 72 h at 37° C. and 5% C02. In order to facilitate analysis, cell cultures were spun down at 200 rpm for 5 min and the supernatant was discarded. After shaking the plate to dislodge the cell pellet, cells were resuspended in 50 μL of Fixation Buffer (eBioScience FoxP3 buffer set 00-5523-00) for 60 min at room temperature. After centrifuging and discarding the supernatant, cells were permeabilized with 50 μL of Permeabilization buffer (eBioScience FoxP3 buffer set 00-5523-00) for 10 min at room temperature. Following permeabilization, cells were spun down and the supernatant was replaced with 20 μL fluorescently labelled antibodies against Helios, Ikaros and Aiolos or corresponding Isotype controls in 1× Permeabilization buffer (Ikaros-Alexa488 [Biolegend, Cat #368408, 1:50], Helios-PE [CST, Cat #29360, 1:50], Aiolos-Alexa647 [Biolegend, Cat #371106Biolegend, 1:25]) and staining reactions were incubated for 1 h at room temperature; protected from light. Subsequently, 30 μL of 1× Permeabilization buffer was added prior to centrifuging the cells and discarding the supernatant. Stained cells were resuspended in 25 μL of flow cytometry staining buffer (PBS+0.2% BSA) and analyzed using an Intellicyt Ique Plus flow cytometer.

TABLE 4

| Ex. No. | Helios Jurkat $IC_{50}$ (uM) | Ikaros Jurkat $IC_{50}$ (uM) |
|---|---|---|
| 1 | 0.034 | >20 |
| 2 | 0.37 | 13.7 |
| 3 | 0.036 | >20 |
| 4 | 0.006 | >20 |
| 5 | >20 | >20 |

TABLE 4-continued

| Ex. No. | Helios Jurkat $IC_{50}$ (uM) | Ikaros Jurkat $IC_{50}$ (uM) |
|---|---|---|
| 6 | 0.14 | >20 |
| 7 | 0.073 | >20 |
| 8 | 0.025 | >20 |
| 9 | 0.027 | >20 |
| 10 | 0.10 | >20 |
| 11 | 0.042 | 0.097 |
| 12 | 0.038 | >20 |
| 13 | 0.75 | >20 |
| 14 | 0.40 | >20 |
| 15 | >20 | >20 |
| 16 | 0.030 | >20 |
| 17 | 0.014 | 0.096 |
| 18 | 0.12 | >20 |
| 19 | 0.030 | 0.14 |
| 20 | 0.020 | 0.034 |
| 21 | 0.037 | >20 |
| 22 | 0.008 | >20 |
| 23 | 0.006 | 0.13 |
| 24 | 0.009 | >20 |
| 25 | 0.048 | 8.4 |
| 26 | 0.098 | >20 |
| 27 | 0.025 | >20 |
| 28 | 0.057 | >20 |
| 29 | 0.025 | >20 |
| 30 | >20 | >20 |
| 31 | >20 | >20 |
| 32 | 0.48 | >20 |
| 33 | 0.12 | >20 |
| 34 | 0.070 | >20 |
| 35 | 0.053 | >20 |
| 36 | 0.11 | >20 |
| 37 | 2.4 | >20 |
| 38 | 0.022 | >20 |
| 39 | 0.025 | >20 |
| 40 | 0.019 | >20 |
| 41 | >20 | >20 |
| 42 | 0.11 | 3.6 |
| 43 | >20 | >20 |
| 44 | 0.098 | >20 |
| 45 | 0.43 | >20 |
| 46 | 0.003 | NA |
| 47 | 0.22 | >20 |
| 48 | 0.090 | >20 |
| 49 | 0.037 | >20 |
| 50 | 0.011 | >20 |
| 51 | 0.026 | >20 |
| 52 | 0.21 | >20 |
| 53 | 0.085 | >20 |
| 54 | 0.040 | 5.0 |
| 55 | 1.0 | 8.1 |
| 56 | 0.027 | 0.049 |
| 57 | 0.007 | >20 |
| 58 | 0.001 | 0.009 |
| 59 | 0.024 | NA |
| 60 | 0.015 | 0.16 |
| 61 | 0.007 | NA |
| 62 | >20 | >20 |
| 63 | >20 | >20 |
| 64 | >20 | >20 |
| 65 | >20 | >20 |
| 66 | 0.006 | 0.025 |
| 67 | 0.042 | 3.0 |
| 70 | 0.48 | >20 |
| 71 | 0.075 | >20 |
| 72 | >20 | >20 |
| 73 | 0.067 | 0.45 |
| 74 | 0.032 | 0.034 |
| 75 | 1.2 | >20 |
| 76 | >20 | >20 |
| 77 | >20 | >20 |
| 78 | 2.8 | >20 |
| 79 | >20 | >20 |
| 80 | 0.32 | >20 |
| 81 | 3.9 | >20 |
| 82 | 0.004 | 20 |
| 83 | 0.03 | 20 |
| 84 | 0.003 | 20 |
| 85 | 0.01 | 1.82 |
| 86 | 0.05 | 0.19 |
| 87 | 0.10 | 20 |
| 88 | 0.02 | 20 |
| 89 | 2.2 | 20 |
| 90 | 0.02 | 0.41 |
| 91 | 0.21 | 20 |
| 92 | 1.5 | 20 |
| 93 | 17.11 | 20 |
| 94 | 1.07 | 20 |
| 95 | 0.11 | 0.31 |
| 96 | 0.20 | 20 |
| 97 | 0.09 | |
| 98 | 0.86 | 20 |
| 99 | 0.34 | 20 |
| 100 | 0.21 | 20 |
| 101 | 0.47 | 20 |
| 102 | 0.002 | 20 |
| 103 | 0.01 | 20 |
| 104 | 0.13 | 20 |
| 105 | 0.14 | 20 |
| 106 | 0.02 | 20 |
| 107 | 1.13 | 10 |
| 108 | 0.83 | 10 |
| 109 | 0.61 | 10 |
| 110 | 0.88 | 10 |
| 111 | 0.93 | 10 |
| 112 | 0.42 | 10 |
| 113 | 0.05 | 10 |
| 114 | 1.12 | 10 |
| 115 | 0.10 | 0.16 |
| 116 | 0.17 | 10 |
| 117 | 0.15 | 10 |
| 118 | 0.18 | 10 |
| 119 | 0.24 | 10 |
| 120 | 0.07 | 10 |
| 121 | 0.04 | 1.28 |
| 122 | 0.05 | 20 |
| 123 | 0.08 | 20 |
| 124 | 0.08 | 20 |
| 125 | 0.04 | 20 |
| 126 | 2.99 | 20 |
| 127 | 7.46 | 20 |
| 128 | 2.83 | 20 |
| 129 | 0.01 | 0.09 |
| 130 | 0.45 | 20 |
| 131 | 0.14 | 20 |
| 132 | 0.02 | 20 |
| 133 | 0.01 | 20 |
| 134 | 0.10 | 20 |
| 135 | 0.23 | 10 |
| 136 | 0.29 | 10 |
| 137 | 0.01 | 10 |
| 138 | 0.92 | 10 |
| 139 | 4.16 | 20 |
| 140 | 0.02 | 20 |
| 141 | 0.08 | 20 |
| 142 | 1.35 | 20 |
| 143 | 0.61 | 20 |
| 144 | 0.083 | 20 |
| 145 | 0.01 | 20 |
| 146 | 0.19 | 20 |
| 147 | 0.31 | 10 |
| 148 | 0.01 | 10 |
| 149 | 0.19 | 10 |
| 150 | 0.032 | 10 |
| 151 | 0.01 | 10 |
| 152 | 0.76 | 10 |
| 153 | 0.07 | 10 |
| 154 | 3.98 | 10 |
| 155 | 5.33 | 20 |
| 156 | 0.50 | 20 |
| 157 | 0.11 | 20 |
| 158 | 0.02 | 10 |
| 159 | 0.05 | 0.32 |
| 160 | 0.07 | 20 |
| 161 | 0.02 | 0.09 |

TABLE 4-continued

| Ex. No. | Helios Jurkat $IC_{50}$ (uM) | Ikaros Jurkat $IC_{50}$ (uM) |
|---|---|---|
| 162 | 2.46 | 20 |
| 163 | 0.09 | 20 |
| 164 | 0.04 | 20 |
| 165 | 0.03 | 20 |
| 166 | 0.02 | 20 |
| 167 | 0.05 | >10 |
| 172 | 0.03 | — |
| 173 | 0.12 | 10.00 |
| 174 | 0.35 | — |
| 177 | 0.04 | — |
| 178 | 0.07 | 10.00 |

TABLE 4-continued

| Ex. No. | Helios Jurkat $IC_{50}$ (uM) | Ikaros Jurkat $IC_{50}$ (uM) |
|---|---|---|
| 179 | 10.00 | 10.00 |
| 180 | 0.02 | 10.00 |
| 181 | 0.14 | 10.00 |
| 182 | 0.07 | 10.00 |
| 183 | 0.05 | 10.00 |
| 184 | 10.00 | 10.00 |
| 185 | 6.40 | 10.00 |
| 186 | 10.00 | 10.00 |
| 187 | 0.01 | 10.00 |
| 188 | 0.04 | 10.00 |

What is claimed is:
1. A compound of Formula (I)
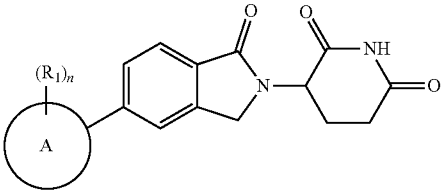
(I)
or a salt thereof, wherein:
Ring A is:
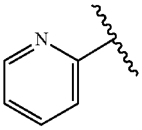
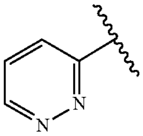
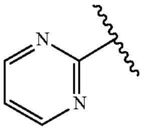
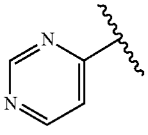
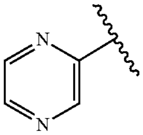
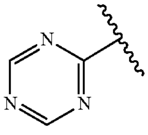
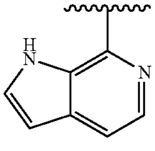
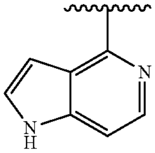
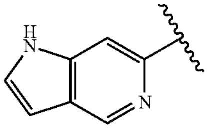
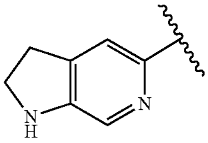
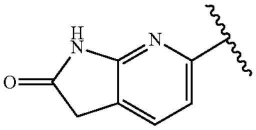
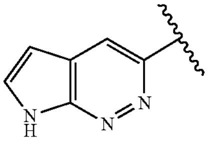
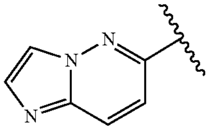
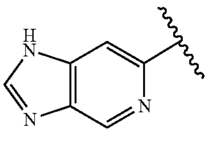
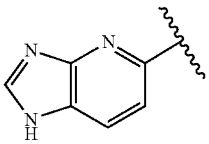
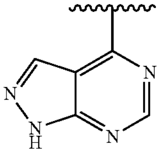
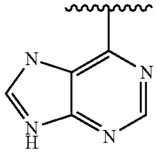
-continued
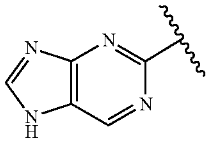
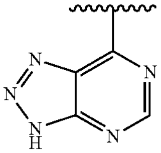
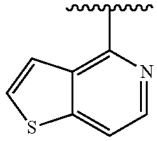
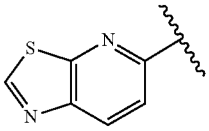
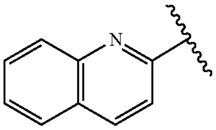
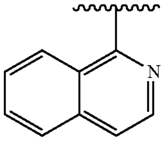
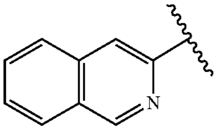
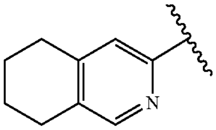
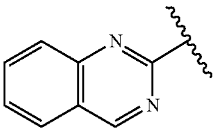
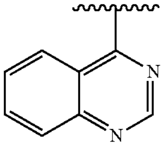
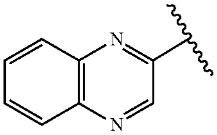
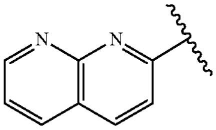
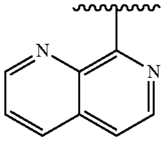
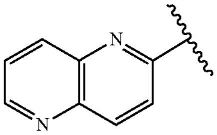
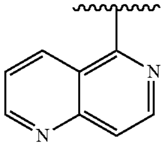
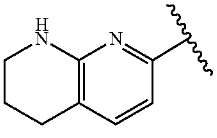
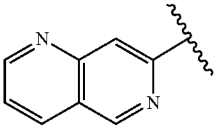
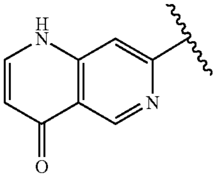

-continued

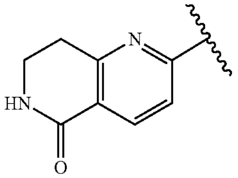
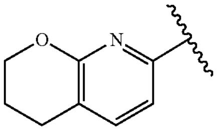
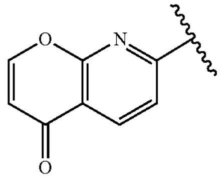
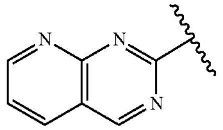
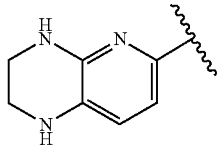
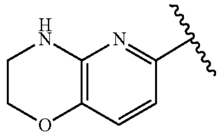
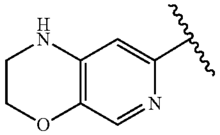
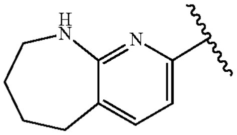
or
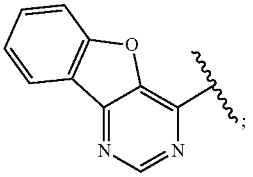 [SMILES: *c1ncnc2c1oc1ccccc12]
;

each $R_1$ is independently F, Cl, Br, —CN, —OH, —$NO_2$, $C_{1-6}$ alkyl substituted with zero to 6 $R_{1a}$, $C_{1-3}$ alkoxy substituted with zero to 6 $R_{1a}$, —$CR_xR_xOCR_xR_x$(phenyl), —$NR_yR_y$, —$NR_xC(O)H$, —$NR_xC(O)(C_{1-2}$ alkyl), —$NR_xC(O)NR_xR_x$, —C(O)H, —C(O)OH, —C(O)O($C_{1-3}$ alkyl), —$C(O)NR_xR_x$, —$C(O)NR_x(C_{3-6}$ cycloalkyl), —OC(O)($C_{1-3}$ alkyl), —$SO_2(C_{1-3}$ alkyl), —NHN($C_{1-2}$ alkyl)$_2$, —$CH_2CH_2Si(CH_3)_3$ or a cyclic group selected from $C_{3-6}$ cycloalkyl, phenyl, pyridinyl, piperidinyl, piperazinyl, pyrrolidinyl, morpholinyl, and dioxidothiomorpholinyl, wherein said cyclic group is substituted with zero to 4 $R_{1b}$;

each $R_{1a}$ is independently F, Cl, —CN, —OH, $C_{1-2}$ alkoxy, $C_{1-2}$ fluoroalkoxy, —$SO_2(C_{1-3}$ alkyl), or phenyl;

each $R_{1b}$ is independently F, Cl, $C_{1-2}$ alkyl, $C_{1-2}$ fluoroalkyl, $C_{1-2}$ alkoxy, $C_{1-2}$ fluoroalkoxy, —C(O)($C_{1-3}$ alkyl), —$SO_2(C_{1-3}$ alkyl), or —$CH_2$(phenyl);

each $R_x$ is independently H or —$CH_3$;

each $R_y$ is independently H or $C_{1-6}$ alkyl; and n is zero, 1, 2, 3, or 4.

2. The compound according to claim 1 or a salt thereof, wherein:

each $R_i$ is independently F, Cl, Br, —CN, —OH, —$NO_2$, $C_{1-5}$ alkyl substituted with zero to 6 $R_{1a}$, $C_{1-2}$ alkoxy substituted with zero to 5 $R_{1a}$, —$CR_xR_xOCH_2$(phenyl), —$NR_yR_y$, —$NR_xC(O)CH_3$, —$NR_xC(O)NR_xR_x$, —C(O)H, —C(O)OH, —C(O)O($C_{1-2}$ alkyl), —$C(O)NR_xR_x$, —$C(O)NR_x$(cyclopropyl), —OC(O)($C_{1-2}$ alkyl), —$SO_2(C_{1-2}$alkyl), —$NHN(CH_3)_2$, —$CH_2CH_2Si(CH_3)_3$, or a cyclic group selected from $C_{3-6}$ cycloalkyl, phenyl, pyridinyl, piperidinyl, piperazinyl, pyrrolidinyl, morpholinyl, and dioxidothiomorpholinyl, wherein said cyclic group is substituted with zero to 3 $R_{1b}$;

each $R_{1b}$ is independently F, Cl, $C_{1-2}$ alkyl, —$CH_2F$, —$CHF_2$, —$CF_3$, $C_{1-2}$ alkoxy, —$OCF_3$, —C(O)($C_{1-2}$ alkyl), or —$SO_2(C_{1-2}$ alkyl); and n is zero, 1, 2, or 3.

3. The compound according to claim 1 or a salt thereof, wherein:

each $R_1$ is independently F, Cl, Br, —CN, —OH, —$NO_2$, —$CH_3$, —$CH_2CH_3$, —$CHCH_2CH_3$, —$CH(CH_3)_2$, —$CH_2C(CH_3)_3$, —$CF_3$, —$CH_2Cl$, —$CH_2CN$, —$CH_2$(phenyl), —$CH_2OH$, —$CH_2OCH_2$(phenyl), —$OCH_3$, —$OCH_2CH_3$, —$OCH_2$(phenyl), —$NH_2$, —$NH(CH_3)$, —$NH(CH_2CH_3)$, —$NH(CH(CH_3)CH_2CH_3)$, —$N(CH_3)_2$, —$N(CH_2CH_3)_2$, —$NHC(O)CH_3$, —$N(CH_3)C(O)CH_3$, —C(O)H, —$C(O)OCH_3$, —C(O)NH(cyclopropyl), —$C(O)NH_2$, —$C(O)N(CH_3)_2$, —$CH_2CH_2Si(CH_3)_3$, —$OC(O)CH_3$, —$NHN(CH_3)_2$, cyclopropyl, phenyl, pyridinyl, (benzyl)morpholinyl, (methylsulfonyl)piperazinyl, or acetylpiperazinyl; and n is zero, 1, 2, or 3.

4. The compound according to claim 1 or a salt thereof, wherein Ring A is:

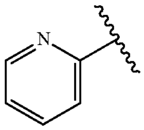
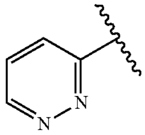
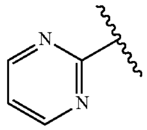
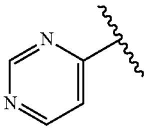
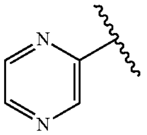
or
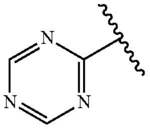
.

5. The compound according to claim 1 or a salt thereof, wherein Ring A is:

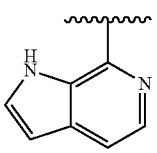
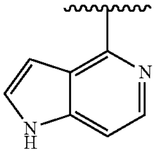
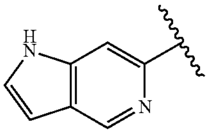
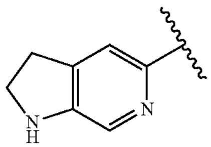
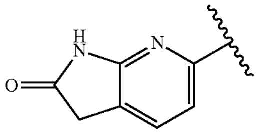
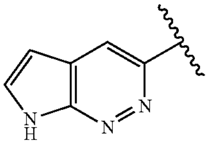
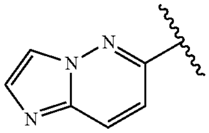
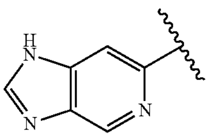
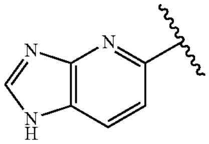

-continued

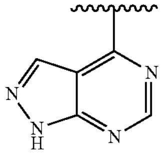

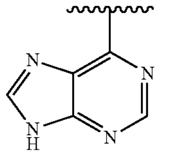

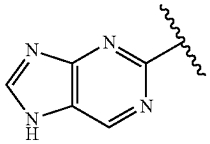

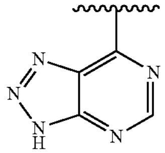

or

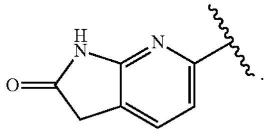

6. The compound according to claim 1 or a salt thereof, wherein

Ring A is:

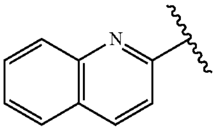

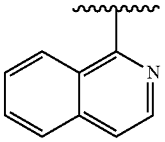

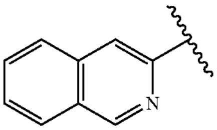

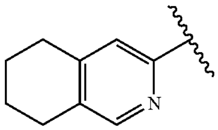

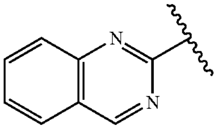

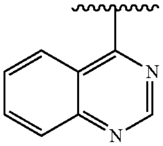

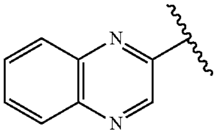

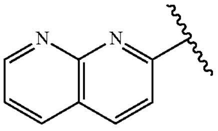

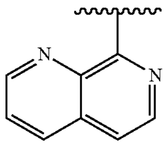

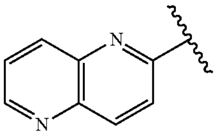

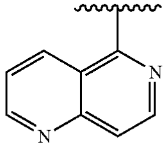

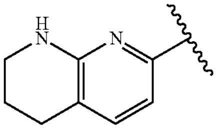

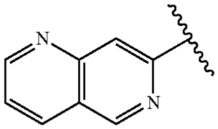

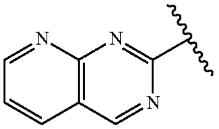

-continued

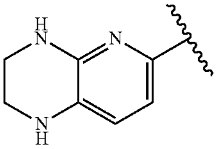

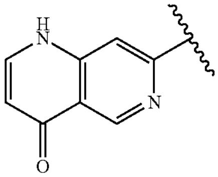

or

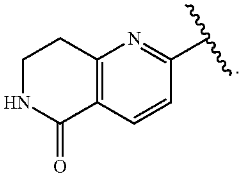

7. The compound according to claim 1 or a salt thereof, wherein:

Ring A is:

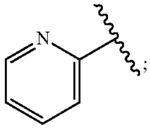 [SMILES: *c1ccccn1]

each $R_1$ is independently F, Cl, Br, —CN, —OH, —$NO_2$, —$CH_3$, —$OCH_3$, —$NH_2$, —$NH(CH_3)$, —$NH(CH_2CH_3)$, —$NHC(O)CH_3$, —$NHN(CH_3)_2$, cyclopropyl, phenyl, (benzyl)morpholinyl, (methylsulfonyl)piperazinyl, or acetylpiperazinyl; and n is zero, 1, 2, or 3.

8. The compound according to claim 1 or a salt thereof, wherein:

A is

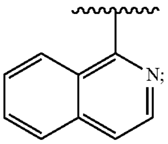 [SMILES: *c1nccc2ccccc12]

each $R_1$ is independently F, Cl, —CN, —OH, —$CH_3$, —$OCH_3$, —$OCH_2$(phenyl), —$NH_2$, —$N(CH_3)_2$, —$CH_2CH_3$, —$CH(CH_3)_2$, —$CH_2C(CH_3)_3$, —$CF_3$, —$CH_2Cl$, —$CH_2CN$, —$CH_2$(phenyl), —$CH_2OH$, —$CH_2OCH_2$(phenyl), —$OCH_2CH_3$, —$NH(CH_3)$, —$NH(CH_2CH_3)$, or —$NHC(O)CH_3$; and n is zero, 1, or 2.

9. The compound according to claim 1 or a salt thereof, wherein:

Ring A is

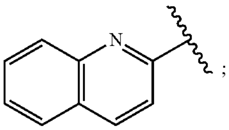 [SMILES: *c1ccc2ccccc2n1]

each $R_1$ is independently F, Cl, —OH, —$CH_3$, —$OCH_3$, —$NH_2$, —$C(O)OCH_3$, —C(O)NH(cyclopropyl), or phenyl; and n is zero, 1, or 2.

10. The compound according to claim 1 or a salt thereof, wherein:

Ring A is:

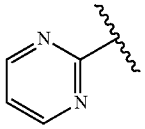 or 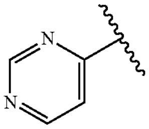 ;

each $R_1$ is independently —CN, —$NH_2$, —C(O)$NH_2$, phenyl, or pyridinyl; and n is zero, 1, or 2.

11. The compound according to claim 1 or a salt thereof, wherein said compound is:

3-[1-oxo-5-(quinolin-2-yl)-2,3-dihydro-1H-isoindol-2-yl]piperidine-2,6-dione (1);

3-[5-(4-aminoisoquinolin-3-yl)-1-oxo-2,3-dihydro-1H-isoindol-2-yl]piperidine-2,6-dione (2);

3-(5-{8-oxa-3,5-diazatricyclo[7.4.0.$0^2$,7]trideca-1(9),2,4,6,10,12-hexaen-6-yl}-1-oxo-2,3-dihydro-1H-isoindol-2-yl)piperidine-2,6-dione (3);

3-[5-(1-aminoisoquinolin-3-yl)-1-oxo-2,3-dihydro-1H-isoindol-2-yl]piperidine-2,6-dione (4);

3-[5-(3-aminoquinoxalin-2-yl)-1-oxo-2,3-dihydro-1H-isoindol-2-yl]piperidine-2,6-dione (5);

3-(1-oxo-5-{7H-pyrrolo[2,3-c]pyridazin-3-yl}-2,3-dihydro-1H-isoindol-2-yl) piperidine-2,6-dione (6);

3-[1-oxo-5-(quinoxalin-2-yl)-2,3-dihydro-1H-isoindol-2-yl]piperidine-2,6-dione (7);

3-[5-(4-aminoquinolin-2-yl)-1-oxo-2,3-dihydro-1H-isoindol-2-yl]piperidine-2,6-dione (8);

3-[1-oxo-5-(quinazolin-2-yl)-2,3-dihydro-1H-isoindol-2-yl]piperidine-2,6-dione (9);

3-(5-{2-[(butan-2-yl)amino]-[1,3]thiazolo[5,4-b]pyridin-5-yl}-1-oxo-2,3-dihydro-1H-isoindol-2-yl)piperidine-2,6-dione (10);

3-(5-{7-fluoro-1H-pyrrolo[3,2-c]pyridin-4-yl}-1-oxo-2,3-dihydro-1H-isoindol-2-yl) piperidine-2,6-dione (11);

3-[5-(4-methoxyquinolin-2-yl)-1-oxo-2,3-dihydro-1H-isoindol-2-yl]piperidine-2,6-dione (12);

3-[1-oxo-5-(4-phenylquinolin-2-yl)-2,3-dihydro-1H-isoindol-2-yl]piperidine-2,6-dione (13);

N-cyclopropyl-2-[2-(2,6-dioxopiperidin-3-yl)-1-oxo-2,3-dihydro-1H-isoindol-5-yl]quinoline-4-carboxamide (14);

3-{5-[6-chloro-4-(diethylamino)quinazolin-2-yl]-1-oxo-2,3-dihydro-1H-isoindol-2-yl}piperidine-2,6-dione (15);

3-[5-(4-amino-6,7-dimethoxyquinazolin-2-yl)-1-oxo-2,3-dihydro-1H-isoindol-2-yl]piperidine-2,6-dione (16);

3-[5-(6-methoxyisoquinolin-1-yl)-1-oxo-2,3-dihydro-1H-isoindol-2-yl]piperidine-2,6-dione (17);

3-[5-(6-chloroquinoxalin-2-yl)-1-oxo-2,3-dihydro-1H-isoindol-2-yl]piperidine-2,6-dione (18);

3-[5-(7-fluoroisoquinolin-1-yl)-1-oxo-2,3-dihydro-1H-isoindol-2-yl]piperidine-2,6-dione (19);

3-[5-(5-fluoroisoquinolin-1-yl)-1-oxo-2,3-dihydro-1H-isoindol-2-yl]piperidine-2,6-dione (20);

3-[5-(1,5-naphthyridin-2-yl)-1-oxo-2,3-dihydro-1H-isoindol-2-yl]piperidine-2,6-dione (21);

3-[5-(4-aminoquinazolin-2-yl)-1-oxo-2,3-dihydro-1H-isoindol-2-yl]piperidine-2,6-dione (22);

3-[5-(6-methylisoquinolin-1-yl)-1-oxo-2,3-dihydro-1H-isoindol-2-yl]piperidine-2,6-dione (23);

3-[5-(4-methylquinolin-2-yl)-1-oxo-2,3-dihydro-1H-isoindol-2-yl]piperidine-2,6-dione (24);

3-[5-(3-aminoisoquinolin-1-yl)-1-oxo-2,3-dihydro-1H-isoindol-2-yl]piperidine-2,6-dione (25);

3-[5-(6-fluoroquinoxalin-2-yl)-1-oxo-2,3-dihydro-1H-isoindol-2-yl]piperidine-2,6-dione (26);

3-[5-(6-chloroquinolin-2-yl)-1-oxo-2,3-dihydro-1H-isoindol-2-yl]piperidine-2,6-dione (27);

3-[5-(7-chloroquinolin-2-yl)-1-oxo-2,3-dihydro-1H-isoindol-2-yl]piperidine-2,6-dione (28);

3-[5-(6-methoxyquinolin-2-yl)-1-oxo-2,3-dihydro-1H-isoindol-2-yl]piperidine-2,6-dione (29);

ethyl 3-[2-(2,6-dioxopiperidin-3-yl)-1-oxo-2,3-dihydro-1H-isoindol-5-yl]quinoxaline-2-carboxylate (30);

methyl 2-[2-(2,6-dioxopiperidin-3-yl)-1-oxo-2,3-dihydro-1H-isoindol-5-yl]quinoline-6-carboxylate (31);

3-[5-(3-methylquinolin-2-yl)-1-oxo-2,3-dihydro-1H-isoindol-2-yl]piperidine-2,6-dione (32);

3-[5-(8-methoxyquinolin-2-yl)-1-oxo-2,3-dihydro-1H-isoindol-2-yl]piperidine-2,6-dione (33);

3-[5-(8-chloroquinolin-2-yl)-1-oxo-2,3-dihydro-1H-isoindol-2-yl]piperidine-2,6-dione (34);

3-[5-(6-fluoroquinazolin-2-yl)-1-oxo-2,3-dihydro-1H-isoindol-2-yl]piperidine-2,6-dione (35);

3-[5-(3-chloroquinolin-2-yl)-1-oxo-2,3-dihydro-1H-isoindol-2-yl]piperidine-2,6-dione (36);

3-[5-(4-hydroxyquinolin-2-yl)-1-oxo-2,3-dihydro-1H-isoindol-2-yl]piperidine-2,6-dione (37);

3-[5-(6-fluoroquinolin-2-yl)-1-oxo-2,3-dihydro-1H-isoindol-2-yl]piperidine-2,6-dione (38);

3-[5-(6-methylquinolin-2-yl)-1-oxo-2,3-dihydro-1H-isoindol-2-yl]piperidine-2,6-dione (39);

3-[5-(6-hydroxyquinolin-2-yl)-1-oxo-2,3-dihydro-1H-isoindol-2-yl]piperidine-2,6-dione (40);

methyl 2-[2-(2,6-dioxopiperidin-3-yl)-1-oxo-2,3-dihydro-1H-isoindol-5-yl]quinazoline-7-carboxylate (41);

3-(5-{5-amino-3-[2-(trimethylsilyl)ethyl]-3H-[1,2,3]triazolo[4,5-d]pyrimidin-7-yl}-1-oxo-2,3-dihydro-1H-isoindol-2-yl)piperidine-2,6-dione (42);

3-[5-(2-amino-9H-purin-6-yl)-1-oxo-2,3-dihydro-1H-isoindol-2-yl]piperidine-2,6-dione (43);

3-[5-(6-amino-7H-purin-2-yl)-1-oxo-2,3-dihydro-1H-isoindol-2-yl]piperidine-2,6-dione (44);

3-(5-{6-amino-1-ethyl-1H-pyrazolo[3,4-d]pyrimidin-4-yl}-1-oxo-2,3-dihydro-1H-isoindol-2-yl)piperidine-2,6-dione (45);

3-{5-[5-amino-1-(2,2-dimethylpropyl)-4-oxo-1,4-dihydro-1,6-naphthyridin-7-yl]-1-oxo-2,3-dihydro-1H-isoindol-2-yl}piperidine-2,6-dione (46);

3-[5-(5-amino-4-oxo-1,4-dihydro-1,6-naphthyridin-7-yl)-1-oxo-2,3-dihydro-1H-isoindol-2-yl]piperidine-2,6-dione (47);

N-{3-[2-(2,6-dioxopiperidin-3-yl)-1-oxo-2,3-dihydro-1H-isoindol-5-yl]isoquinolin-1-yl}acetamide (48);

3-{5-[1-(dimethylamino)isoquinolin-3-yl]-1-oxo-2,3-dihydro-1H-isoindol-2-yl}piperidine-2,6-dione (49);

3-{5-[1-(methylamino)isoquinolin-3-yl]-1-oxo-2,3-dihydro-1H-isoindol-2-yl}piperidine-2,6-dione (50);

3-{5-[5-(methylamino)-1,6-naphthyridin-7-yl]-1-oxo-2,3-dihydro-1H-isoindol-2-yl}piperidine-2,6-dione (51);

N-{3-[2-(2,6-dioxopiperidin-3-yl)-1-oxo-2,3-dihydro-1H-isoindol-5-yl]isoquinolin-1-yl}-N-methylacetamide (52);

3-[5-(6-amino-1,7-naphthyridin-8-yl)-1-oxo-2,3-dihydro-1H-isoindol-2-yl]piperidine-2,6-dione (53);
3-[5-(3-amino-5-methoxyisoquinolin-1-yl)-1-oxo-2,3-dihydro-1H-isoindol-2-yl]piperidine-2,6-dione (54);
3-(5-(4-(4-acetylpiperazin-1-yl)pyrido[2,3-d]pyrimidin-2-yl)-1-oxoisoindolin-2-yl) piperidine-2,6-dione (55);
3-(5-{4-bromo-1H-pyrrolo[2,3-c]pyridin-7-yl}-1-oxo-2,3-dihydro-1H-isoindol-2-yl) piperidine-2,6-dione (56);
3-[5-(5-amino-1,6-naphthyridin-7-yl)-1-oxo-2,3-dihydro-1H-isoindol-2-yl]piperidine-2,6-dione (57);
3-[5-(3,6-dimethoxyisoquinolin-1-yl)-1-oxo-2,3-dihydro-1H-isoindol-2-yl]piperidine-2,6-dione (58);
1-[2-(2,6-dioxopiperidin-3-yl)-1-oxo-2,3-dihydro-1H-isoindol-5-yl]isoquinoline-3-carbonitrile (59);
4-[2-(2,6-dioxopiperidin-3-yl)-1-oxo-2,3-dihydro-1H-isoindol-5-yl]thieno[3,2-c]pyridine-2-carbaldehyde (60);
3-{5-[1-methyl-4-(methylamino)-1H-imidazo[4,5-c]pyridin-6-yl]-1-oxo-2,3-dihydro-1H-isoindol-2-yl}piperidine-2,6-dione (61);
3-(5-{2-methyl-4-oxo-4H-pyrano[2,3-b]pyridin-7-yl}-1-oxo-2,3-dihydro-1H-isoindol-2-yl)piperidine-2,6-dione (62);
3-{5-[5,7-dichloro-3-(dimethylamino)isoquinolin-1-yl]-1-oxo-2,3-dihydro-1H-isoindol-2-yl}piperidine-2,6-dione (63);
3-[5-(1,7-naphthyridin-8-yl)-1-oxo-2,3-dihydro-1H-isoindol-2-yl]piperidine-2,6-dione (64);
3-(5-{2-aminoimidazo[1,2-b]pyridazin-6-yl}-1-oxo-2,3-dihydro-1H-isoindol-2-yl) piperidine-2,6-dione (65);
3-[5-(isoquinolin-1-yl)-1-oxo-2,3-dihydro-1H-isoindol-2-yl]piperidine-2,6-dione (66);
3-[5-(isoquinolin-3-yl)-1-oxo-2,3-dihydro-1H-isoindol-2-yl]piperidine-2,6-dione (67);
3-(5-(2-amino-6-methoxypyrimidin-4-yl)-1-oxoisoindolin-2-yl)piperidine-2,6-dione (68);
3-(5-(6-aminopyridin-2-yl)-1-oxoisoindolin-2-yl)piperidine-2,6-dione (69);
3-(5-(2-aminopyrimidin-4-yl)-1-oxoisoindolin-2-yl)piperidine-2,6-dione (70);
3-(1-oxo-5-(4-phenylpyrimidin-2-yl)isoindolin-2-yl)piperidine-2,6-dione (71);
3-(1-oxo-5-(4-(pyridin-3-yl)pyrimidin-2-yl)isoindolin-2-yl)piperidine-2,6-dione (72);
3-(5-(4-amino-6-phenyl-1,3,5-triazin-2-yl)-1-oxoisoindolin-2-yl)piperidine-2,6-dione (73);
3-(1-oxo-5-(4-phenylpyridin-2-yl)isoindolin-2-yl)piperidine-2,6-dione (74);
3-(1-oxo-5-(4-(pyridin-2-yl)pyrimidin-2-yl)isoindolin-2-yl)piperidine-2,6-dione (75);
3-(2-(2,6-dioxopiperidin-3-yl)-1-oxoisoindolin-5-yl) pyridazine-4-carbonitrile (76);
6-[2-(2,6-dioxopiperidin-3-yl)-1-oxo-2,3-dihydro-1H-isoindol-5-yl]pyridazine-3-carbonitrile (77);
6-[2-(2,6-dioxopiperidin-3-yl)-1-oxo-2,3-dihydro-1H-isoindol-5-yl]pyridazine-3-carboxamide (78);
3-[5-(6-amino-3-nitropyridin-2-yl)-1-oxo-2,3-dihydro-1H-isoindol-2-yl]piperidine-2,6-dione (79);
4-amino-2-[2-(2,6-dioxopiperidin-3-yl)-1-oxo-2,3-dihydro-1H-isoindol-5-yl]pyrimidine-5-carbonitrile (80);
4-amino-2-[2-(2,6-dioxopiperidin-3-yl)-1-oxo-2,3-dihydro-1H-isoindol-5-yl]pyrimidine-5-carboxamide (81);
(3S)-3-[5-(1-aminoisoquinolin-3-yl)-1-oxo-2,3-dihydro-1H-isoindol-2-yl]piperidine-2,6-dione (82);
(3R)-3-[5-(1-aminoisoquinolin-3-yl)-1-oxo-2,3-dihydro-1H-isoindol-2-yl]piperidine-2,6-dione (83);
(3S)-3-[5-(1-amino-4-ethoxyisoquinolin-3-yl)-1-oxo-2,3-dihydro-1H-isoindol-2-yl]piperidine-2,6-dione (84);
3-(5-(4-ethoxyisoquinolin-3-yl)-1-oxoisoindolin-2-yl)piperidine-2,6-dione (85);
3-(5-(1-chloro-4-ethoxyisoquinolin-3-yl)-1-oxoisoindolin-2-yl)piperidine-2,6-dione (86);
3-(5-(2,3-dihydro-1H-pyrido[3,4-b][1,4]oxazin-7-yl)-1-oxoisoindolin-2-yl)piperidine-2,6-dione (87);
3-(5-(1-methylisoquinolin-3-yl)-1-oxoisoindolin-2-yl)piperidine-2,6-dione (88);
3-(5-(1-cyclopropylisoquinolin-3-yl)-1-oxoisoindolin-2-yl)piperidine-2,6-dione (89);
1-(2-(2,6-dioxopiperidin-3-yl)-1-oxoisoindolin-5-yl)isoquinoline-4-carbonitrile (90);
3-(1-oxo-5-(quinazolin-4-yl)isoindolin-2-yl)piperidine-2,6-dione (91);
3-(5-(6-methyl-5-oxo-5,6,7,8-tetrahydro-1,6-naphthyridin-2-yl)-1-oxoisoindolin-2-yl)piperidine-2,6-dione (92);
3-(5-(3-chloroquinoxalin-2-yl)-1-oxoisoindolin-2-yl)piperidine-2,6-dione (93);
3-(5-(3-methoxyquinoxalin-2-yl)-1-oxoisoindolin-2-yl) piperidine-2,6-dione (94);
3-(5-(3-(ethylamino)quinoxalin-2-yl)-1-oxoisoindolin-2-yl)piperidine-2,6-dione (95);
3-(5-(3-hydroxyquinoxalin-2-yl)-1-oxoisoindolin-2-yl) piperidine-2,6-dione (96);
3-(5-(3-cyclopropylquinoxalin-2-yl)-1-oxoisoindolin-2-yl)piperidine-2,6-dione (97);
3-(5-(3-isopropylquinoxalin-2-yl)-1-oxoisoindolin-2-yl) piperidine-2,6-dione (98);
3-(1-oxo-5-(3-phenylquinoxalin-2-yl)isoindolin-2-yl)piperidine-2,6-dione (99);
3-(5-(1,6-naphthyridin-5-yl)-1-oxoisoindolin-2-yl)piperidine-2,6-dione (100);
3-(5-(6-amino-3-bromopyridin-2-yl)-1-oxoisoindolin-2-yl)piperidine-2,6-dione (101);
3-(5-(6-aminoisoquinolin-3-yl)-1-oxoisoindolin-2-yl)piperidine-2,6-dione (102);
3-(5-(4-methoxyisoquinolin-1-yl)-1-oxoisoindolin-2-yl) piperidine-2,6-dione (103);
3-(5-(3-methoxypyridin-2-yl)-1-oxoisoindolin-2-yl)piperidine-2,6-dione (104);
3-(5-(4-(benzyloxy)isoquinolin-1-yl)-1-oxoisoindolin-2-yl)piperidine-2,6-dione (105);
3-(5-(6-amino-3-methoxypyridin-2-yl)-1-oxoisoindolin-2-yl)piperidine-2,6-dione (106);
3-(5-(3-(hydroxymethyl)pyridin-2-yl)-1-oxoisoindolin-2-yl)piperidine-2,6-dione (107);
3-(5-(4-(hydroxymethyl)pyridin-2-yl)-1-oxoisoindolin-2-yl)piperidine-2,6-dione (108);
3-(1-oxo-5-(pyridin-2-yl)isoindolin-2-yl)piperidine-2,6-dione (109);
2-(2-(2,6-dioxopiperidin-3-yl)-1-oxoisoindolin-5-yl) isonicotinonitrile (110);
2-(2-(2-(2,6-dioxopiperidin-3-yl)-1-oxoisoindolin-5-yl) pyridin-4-yl)acetonitrile (111);
3-(5-(6-amino-4-(hydroxymethyl)pyridin-2-yl)-1-oxoisoindolin-2-yl)piperidine-2,6-dione (112);
3-(5-(2,3-dihydro-1H-pyrrolo[2,3-c]pyridin-5-yl)-1-oxoisoindolin-2-yl)piperidine-2,6-dione (113);
3-(1-oxo-5-(2-oxo-2,3-dihydro-1H-pyrrolo[2,3-b]pyridin-6-yl)isoindolin-2-yl) piperidine-2,6-dione (114);
3-(1-oxo-5-(5,6,7,8-tetrahydroisoquinolin-3-yl)isoindolin-2-yl)piperidine-2,6-dione (115);

3-(5-(6-amino-5-methylpyridin-2-yl)-1-oxoisoindolin-2-yl)piperidine-2,6-dione (116);
3-(5-(5,6-diaminopyridin-2-yl)-1-oxoisoindolin-2-yl)piperidine-2,6-dione (117);
3-(1-oxo-5-(1,2,3,4-tetrahydropyrido[2,3-b]pyrazin-6-yl)isoindolin-2-yl)piperidine-2,6-dione (118);
3-(5-(5-amino-4,6-dimethylpyridin-2-yl)-1-oxoisoindolin-2-yl)piperidine-2,6-dione (119);
3-(5-(6-amino-4-(trifluoromethyl)pyridin-2-yl)-1-oxoisoindolin-2-yl)piperidine-2,6-dione (120);
3-(5-(4,5-dimethylpyridin-2-yl)-1-oxoisoindolin-2-yl)piperidine-2,6-dione (121);
(3S)-3-[5-(1,8-naphthyridin-2-yl)-1-oxo-2,3-dihydro-1H-isoindol-2-yl]piperidine-2,6-dione (122);
(S)-3-(5-(3-aminoisoquinolin-1-yl)-1-oxoisoindolin-2-yl)piperidine-2,6-dione (123);
(S)—N-(1-(2-(2,6-dioxopiperidin-3-yl)-1-oxoisoindolin-5-yl)isoquinolin-3-yl) acetamide (124);
3-{2-[(3S)-2,6-dioxopiperidin-3-yl]-1-oxo-2,3-dihydro-1H-isoindol-5-yl}isoquinoline-1-carbonitrile (125);
3-{2-[(3S)-2,6-dioxopiperidin-3-yl]-1-oxo-2,3-dihydro-1H-isoindol-5-yl}isoquinoline-1-carboxamide (126);
(4S)-7-{2-[(3S)-2,6-dioxopiperidin-3-yl]-1-oxo-2,3-dihydro-1H-isoindol-5-yl}-2H,3H,4H-pyrano[2,3-b]pyridin-4-yl acetate (127);
(4R)-7-{2-[(3S)-2,6-dioxopiperidin-3-yl]-1-oxo-2,3-dihydro-1H-isoindol-5-yl}-2H,3H,4H-pyrano[2,3-b]pyridin-4-yl acetate (128);
3-{5-[7-chloro-4-(dimethylamino)isoquinolin-1-yl]-1-oxo-2,3-dihydro-1H-isoindol-2-yl}piperidine-2,6-dione (129);
1-amino-3-[2-(2,6-dioxopiperidin-3-yl)-1-oxo-2,3-dihydro-1H-isoindol-5-yl]-N,N-dimethylisoquinoline-4-carboxamide (130);
3-[5-(1-amino-4-methylisoquinolin-3-yl)-1-oxo-2,3-dihydro-1H-isoindol-2-yl]piperidine-2,6-dione (131);
3-[5-(6-amino-3-cyclopropylpyridin-2-yl)-1-oxo-2,3-dihydro-1H-isoindol-2-yl]piperidine-2,6-dione (132);
3-[5-(6-aminoisoquinolin-1-yl)-1-oxo-2,3-dihydro-1H-isoindol-2-yl]piperidine-2,6-dione (133);
N-{1-[2-(2,6-dioxopiperidin-3-yl)-1-oxo-2,3-dihydro-1H-isoindol-5-yl]isoquinolin-6-yl}acetamide (134);
3-{5-[6-amino-4-(chloromethyl)pyridin-2-yl]-1-oxo-2,3-dihydro-1H-isoindol-2-yl}piperidine-2,6-dione (135);
3-(1-oxo-5-{5H,6H,7H,8H,9H-pyrido[2,3-b]azepin-2-yl}-2,3-dihydro-1H-isoindol-2-yl)piperidine-2,6-dione (136);
3-[1-oxo-5-(5,6,7,8-tetrahydro-1,8-naphthyridin-2-yl)-2,3-dihydro-1H-isoindol-2-yl]piperidine-2,6-dione (137);
3-{5-[6-(2,2-dimethylhydrazin-1-yl)pyridin-2-yl]-1-oxo-2,3-dihydro-1H-isoindol-2-yl}piperidine-2,6-dione (138);
3-(5-(1H-imidazo[4,5-b]pyridin-5-yl)-1-oxoisoindolin-2-yl)piperidine-2,6-dione (139);
3-(5-(6-amino-4-methylpyridin-2-yl)-1-oxoisoindolin-2-yl)piperidine-2,6-dione (140);
3-(5-(3,4-dihydro-2H-pyrido[3,2-b][1,4]oxazin-6-yl)-1-oxoisoindolin-2-yl)piperidine-2,6-dione (141);
3-(5-(6-aminopyrazin-2-yl)-1-oxoisoindolin-2-yl)piperidine-2,6-dione (142);
3-(5-(2-amino-6-methylpyrimidin-4-yl)-1-oxoisoindolin-2-yl)piperidine-2,6-dione (143);
3-(5-(4,6-dimethylpyridin-2-yl)-1-oxoisoindolin-2-yl)piperidine-2,6-dione (144);
3-(5-(5-chloro-3-hydroxyisoquinolin-1-yl)-1-oxoisoindolin-2-yl)piperidine-2,6-dione (145);
3-(5-(6-methoxy-4-methylpyridin-2-yl)-1-oxoisoindolin-2-yl)piperidine-2,6-dione (146);
3-(5-(6-hydroxy-4-methylpyridin-2-yl)-1-oxoisoindolin-2-yl)piperidine-2,6-dione (147);
2-amino-6-(2-(2,6-dioxopiperidin-3-yl)-1-oxoisoindolin-5-yl)-4-methylnicotinonitrile (148);
2-amino-6-(2-(2,6-dioxopiperidin-3-yl)-1-oxoisoindolin-5-yl)isonicotinonitrile (149);
3-(5-(1-amino-5,6,7,8-tetrahydroisoquinolin-3-yl)-1-oxoisoindolin-2-yl)piperidine-2,6-dione (150);
3-(5-(6-amino-4,5-dimethylpyridin-2-yl)-1-oxoisoindolin-2-yl)piperidine-2,6-dione (151);
6-(2-(2,6-dioxopiperidin-3-yl)-1-oxoisoindolin-5-yl)-4-methylnicotinonitrile (152);
3-(5-(6-amino-5-methoxy-4-methylpyridin-2-yl)-1-oxoisoindolin-2-yl)piperidine-2,6-dione (153);
3-(5-(6-amino-5-methoxy-4-methylpyridin-2-yl)-1-oxoisoindolin-2-yl)piperidine-2,6-dione (154);
3-[5-(6-methoxypyridin-2-yl)-1-oxo-2,3-dihydro-1H-isoindol-2-yl]piperidine-2,6-dione (155);
3-[5-(1-methoxyisoquinolin-3-yl)-1-oxo-2,3-dihydro-1H-isoindol-2-yl]piperidine-2,6-dione (156);
3-[1-oxo-5-(1-oxo-1,2-dihydroisoquinolin-3-yl)-2,3-dihydro-1H-isoindol-2-yl]piperidine-2,6-dione (157);
3-(5-{1-Benzyl-1H-pyrrolo[3,2-c]pyridin-6-yl}-1-oxo-2,3-dihydro-1H-isoindol-2-yl) piperidine-2,6-dione (158);
3-(1-oxo-5-(1H-pyrrolo[3,2-c]pyridin-6-yl)isoindolin-2-yl)piperidine-2,6-dione (159);
3-(1-oxo-5-(1H-pyrrolo[3,2-c]pyridin-4-yl)isoindolin-2-yl)piperidine-2,6-dione (160);
3-(5-(1-benzyl-1H-pyrrolo[3,2-c]pyridin-4-yl)-1-oxoisoindolin-2-yl)piperidine-2,6-dione (161);
6-(2-(2,6-dioxopiperidin-3-yl)-1-oxoisoindolin-5-yl)picolinonitrile (162);
3-(5-(6-amino-4-(trifluoromethyl)pyridin-2-yl)-1-oxoisoindolin-2-yl)piperidine-2,6-dione (163);
3-(5-(6-amino-4-methoxypyridin-2-yl)-1-oxoisoindolin-2-yl)piperidine-2,6-dione (164);
3-(5-(6-amino-4-chloropyridin-2-yl)-1-oxoisoindolin-2-yl)piperidine-2,6-dione (165);
2-amino-6-(2-(2,6-dioxopiperidin-3-yl)-1-oxoisoindolin-5-yl)nicotinonitrile (166);
2-amino-6-(2-(2,6-dioxopiperidin-3-yl)-1-oxoisoindolin-5-yl)pyridine-3,5-dicarbonitrile (168);
2-amino-6-(2-(2,6-dioxopiperidin-3-yl)-1-oxoisoindolin-5-yl)-5-fluoronicotinonitrile (169);
3-(5-(6-amino-4-phenylpyridin-2-yl)-1-oxoisoindolin-2-yl)piperidine-2,6-dione (170);
6-amino-2-(2-(2,6-dioxopiperidin-3-yl)-1-oxoisoindolin-5-yl)-4-(trifluoromethyl) nicotine-nitrile (171);
2-amino-6-(2-(2,6-dioxopiperidin-3-yl)-1-oxoisoindolin-5-yl)-4-propylnicotinonitrile (172);
6-amino-2-(2-(2,6-dioxopiperidin-3-yl)-1-oxoisoindolin-5-yl)-4-propylnicotinonitrile (173);
6-amino-4-(difluoromethyl)-2-(2-(2,6-dioxopiperidin-3-yl)-1-oxoisoindolin-5-yl) nicotinonitrile (174);
2-amino-6-(2-(2,6-dioxopiperidin-3-yl)-1-oxoisoindolin-5-yl)-5-(trifluoromethyl) nicotine-nitrile (175);
2-amino-4-(difluoromethyl)-6-(2-(2,6-dioxopiperidin-3-yl)-1-oxoisoindolin-5-yl) nicotinonitrile (176);
2-amino-6-(2-(2,6-dioxopiperidin-3-yl)-1-oxoisoindolin-5-yl)-4-(trifluoromethyl) nicotine-nitrile (177);
2-amino-6-(2-(2,6-dioxopiperidin-3-yl)-1-oxoisoindolin-5-yl)-4-isopropylnicotinonitrile (178);
6-amino-2-(2-(2,6-dioxopiperidin-3-yl)-1-oxoisoindolin-5-yl)-4-isopropylnicotinonitrile (179);

6-amino-2-(2-(2,6-dioxopiperidin-3-yl)-1-oxoisoindolin-5-yl)-5-methylnicotinonitrile (180);
2-amino-6-(2-(2,6-dioxopiperidin-3-yl)-1-oxoisoindolin-5-yl)-5-methoxynicotinonitrile (181);
6-amino-5-cyclopropyl-2-(2-(2,6-dioxopiperidin-3-yl)-1-oxoisoindolin-5-yl) nicotinonitrile (182);
2-amino-5-cyclopropyl-6-(2-(2,6-dioxopiperidin-3-yl)-1-oxoisoindolin-5-yl) nicotinonitrile (183);
3-(5-(6-amino-4-(4-benzylpiperazin-1-yl) pyridin-2-yl)-1-oxoisoindolin-2-yl) piperidine-2,6-dione (184);
3-(5-(6-amino-4-(4-(methylsulfonyl)piperazin-1-yl)pyridin-2-yl)-1-oxoisoindolin-2-yl)piperidine-2,6-dione (185);
3-(5-(4-(4-acetylpiperazin-1-yl)-6-aminopyridin-2-yl)-1-oxoisoindolin-2-yl) piperidine-2,6-dione (186);
3-(5-(4-methyl-6-(methylamino)pyridin-2-yl)-1-oxoisoindolin-2-yl)piperidine-2,6-dione (187);
3-(5-(6-(ethylamino)-4-methylpyridin-2-yl)-1-oxoisoindolin-2-yl)piperidine-2,6-dione (188); or
3-(5-(4,5-dimethyl-6-(methylamino)pyridin-2-yl)-1-oxoisoindolin-2-yl) piperidine-2,6-dione (189).

12. A pharmaceutical composition comprising a compound according to claim 1 or a pharmaceutically-acceptable salt thereof, and a pharmaceutically acceptable carrier.

13. A method for the treatment of cancer, in a patient comprising administering to said patient a therapeutically effective amount of a compound and/or pharmaceutically acceptable salt thereof according to claim 1.

14. The method according to claim 13, wherein said cancer is selected from cancer of the colon, gastric, pancreatic cancer, breast cancer, prostate cancer, lung cancer, ovarian cancer, cervical cancer, renal cancer, cancer of the head and neck, lymphoma, leukemia and melanoma.

15. A method of decreasing Helios protein levels, Helios activity level, or Helios expression level in the cells comprising contacting said Helios protein with a compound according to claim 1, or a pharmaceutically acceptable salt thereof.

16. The method according to claim 15, wherein Helios protein is the amino acid sequence encoded by SEQ ID NOs: 1, 2, 3, 4, or 5.

17. A method of decreasing Eos protein levels, Eos activity level, or Eos expression level in the cells comprising contacting said Eos protein with a compound according to claim 1, or a pharmaceutically acceptable salt thereof.

18. The method according to claim 17, wherein Eos protein is the amino acid sequence encoded by SEQ ID NOs: 7 or 8.

* * * * *